(12) United States Patent
Cheu et al.

(10) Patent No.: US 7,786,119 B2
(45) Date of Patent: Aug. 31, 2010

(54) DRUG CONJUGATES OF ION CHANNEL MODULATING COMPOUNDS

(75) Inventors: Elizabeth L. S. Cheu, Halifax (CA); Lewis Siu Leung Choi, Burnaby (CA); Doug Ta Hung Chou, Vancouver (CA); Allen W. Davidoff, Calgary (CA); Alan M. Ezrin, Miami, FL (US); Grace Jung, New Westminster (CA); Bertrand M. C. Plouvier, Vancouver (CA); Aregahegn S. Yifru, Somerville, MA (US)

(73) Assignee: Cardiome Pharma Corp., Vancouver (CA)

( * ) Notice: Subject to any disclaimer, the term of this patent is extended or adjusted under 35 U.S.C. 154(b) by 232 days.

(21) Appl. No.: 11/547,419

(22) PCT Filed: Mar. 31, 2005

(86) PCT No.: PCT/US2005/011124

§ 371 (c)(1),
(2), (4) Date: Sep. 14, 2007

(87) PCT Pub. No.: WO2005/094897

PCT Pub. Date: Oct. 13, 2005

(65) Prior Publication Data

US 2008/0021005 A1 Jan. 24, 2008

Related U.S. Application Data

(60) Provisional application No. 60/586,992, filed on Jul. 8, 2004, provisional application No. 60/559,405, filed on Apr. 1, 2004.

(51) Int. Cl.
*A61K 31/501* (2006.01)

(52) U.S. Cl. .......................... 514/252.03; 514/254.01; 514/262.1; 514/369; 514/406; 514/422; 514/424; 548/541; 548/544; 548/364.1; 548/182; 548/187; 544/238; 544/372; 540/521

(58) Field of Classification Search ............ 514/252.03, 514/254.01, 262.1, 369, 406, 422, 424; 540/521; 544/238, 372; 548/187, 182, 364.1, 444, 548/541
See application file for complete search history.

(56) References Cited

U.S. PATENT DOCUMENTS

| | | | |
|---|---|---|---|
| 4,859,698 A | 8/1989 | Cavazza et al. | 514/445 |
| 5,455,027 A | 10/1995 | Zalipsky et al. | 424/78.17 |
| 5,681,811 A | 10/1997 | Ekwuribe | 514/8 |
| 5,846,514 A | 12/1998 | Foster et al. | 424/1.81 |
| 6,191,105 B1 | 2/2001 | Ekwuribe et al. | 514/3 |
| 6,214,966 B1 | 4/2001 | Harris | 528/322 |
| 6,217,869 B1 | 4/2001 | Meyer et al. | 424/178.1 |
| 6,503,921 B2 | 1/2003 | Naicker et al. | 514/291 |
| 6,515,017 B1 | 2/2003 | Li et al. | 514/449 |
| 6,517,824 B1 | 2/2003 | Kohn et al. | 424/78.06 |
| 6,613,739 B1 | 9/2003 | Naicker et al. | 514/11 |
| 6,623,729 B2 | 9/2003 | Park et al. | 424/78.17 |
| 2001/0021763 A1 | 9/2001 | Harris | 528/75 |
| 2003/0000447 A1 | 1/2003 | Fontenot et al. | 114/322 |
| 2003/0017131 A1 | 1/2003 | Park et al. | 424/78.17 |
| 2003/0026764 A1 | 2/2003 | Griffiths | 424/9.34 |
| 2003/0044845 A1 | 3/2003 | Jenkins et al. | 435/7.1 |
| 2003/0073617 A1 | 4/2003 | Li et al. | 514/2 |
| 2003/0130170 A1 | 7/2003 | Li et al. | 514/2 |
| 2003/0186869 A1 | 10/2003 | Poiani et al. | 514/12 |
| 2003/0229006 A1 | 12/2003 | Ekwuribe | 514/2 |
| 2003/0229010 A1 | 12/2003 | Ekwuribe | 514/3 |
| 2004/0018960 A1 | 1/2004 | Li et al. | 514/2 |
| 2005/0002693 A1 | 1/2005 | Pak et al. | 399/165 |
| 2007/0015924 A1 | 1/2007 | Jung et al. | 548/541 |
| 2007/0088075 A1 | 4/2007 | Chou et al. | 514/424 |

FOREIGN PATENT DOCUMENTS

| | | |
|---|---|---|
| EP | 0014263 B1 | 5/1982 |
| EP | 0317780 B1 | 5/1992 |
| EP | 0544620 A1 | 6/1993 |
| EP | 0884325 A1 | 12/1998 |
| JP | 2002-105067 A | 4/2002 |
| JP | 2003-113084 | 4/2003 |
| WO | WO 94/03481 A1 | 2/1994 |
| WO | WO 94/28901 A1 | 12/1994 |
| WO | WO 97/33552 A1 | 9/1997 |
| WO | WO 98/19682 A1 | 5/1998 |

(Continued)

OTHER PUBLICATIONS

Vippagunta et al, "Crystalline Solids", Advanced Drug Delivery Reviews, vol. 48, pp. 3-26 (2001).*

(Continued)

*Primary Examiner*—Kamal A Saeed
*Assistant Examiner*—Valerie Rodriguez-Garcia
(74) *Attorney, Agent, or Firm*—Seed IP Law Group PLLC

(57) ABSTRACT

This invention is directed to drug conjugates of certain ion channel modulating compounds having the following formula:

(DC-I)

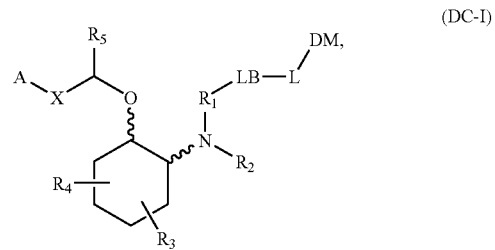

wherein A, X, $R_1$, $R_2$, $R_3$, $R_4$, $R_5$, LB, L and DM are defined herein, including isolated enantiomeric and diastereomeric isomers thereof, and mixtures thereof. Pharmaceutical compositions and methods of use are also disclosed.

6 Claims, No Drawings

FOREIGN PATENT DOCUMENTS

| WO | WO99/50225 | * | 10/1999 |
|---|---|---|---|
| WO | WO 99/50225 A1 | | 10/1999 |
| WO | WO 00/23023 A1 | | 4/2000 |
| WO | WO 00/47547 A2 | | 8/2000 |
| WO | WO 00/66110 A1 | | 11/2000 |
| WO | WO 01/96335 A1 | | 12/2001 |
| WO | WO 02/28412 A1 | | 4/2002 |
| WO | WO 03/064374 A1 | | 8/2003 |
| WO | WO 03/104200 A1 | | 12/2003 |
| WO | WO 2004/014973 A2 | | 2/2004 |
| WO | WO 2004/082585 A2 | | 9/2004 |
| WO | WO 2004/098525 A2 | | 11/2004 |
| WO | WO 2004/099137 A1 | | 11/2004 |
| WO | WO2004/099137 A1 | * | 11/2004 |
| WO | WO 2005/018635 A2 | | 3/2005 |
| WO | WO 2005/079861 A2 | | 9/2005 |
| WO | WO 2005/097203 A2 | | 10/2005 |
| WO | WO 2005/113011 A2 | | 12/2005 |

OTHER PUBLICATIONS

Gavezzotti, "Are Crystal Structures Predictable?", Accounts of Chemical Research, vol. 27, pp. 309-314 (1994).*
Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
Jordan, V. C. Nature Reviews: Drug Discovery, 2, 2003, p. 205-213.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Balser et al., [small beta, Greek]-Adrenergic Blockade Accelerates Conversion of Postoperative Supraventricular Tachyarrhythmias [Clinical Investigations] *Anesthesiology* 89(5): 1052-1059, Nov. 1998.
Bansal et al., *N*-Hydroxymethyl Derivatives of Nitrogen Heterocycles as Possible Prodrugs II: Possible Prodrugs of Allopurinol, Glutethimide, and Phenobarbital, *J. of Pharma. Sci.* 70(8): 855-857, Aug. 1981.
Bhadra et al., "Pegnology: a review of PEG-ylated systems," *Pharmazie* 57: 5-29, 2002.
Bogatskii et al., "Effect of Polymethylene- and Polyhydroxyethylene-bis-(2-Amino-1,3-Diazepinium) Iodides on Cell and Model Membranes," *Byulleten' Eksperimental'noi Biologii i Meditsiny* 94(8): 52-54, Aug. 1982 [English translation included from the Department of Chemistry of Macrocyclic Complexnes, Physicochemical Institute, Academy of Sciences of the Ukrainian SSR, Odessa, pp. 1071-1074.].
Booth and Philp, "Efficient recognition-induced acceleration of a [3+2] dipolar cycloaddition reaction," *Tetrahedron Letters* 39: 6987-6990, 1998.
Carmeliet and Mubagwa, "Antiarrhythmic drugs and cardiac ion channels: mechanisms of action," *Progress in Biophysics & Molecular Biology* 70: 1-72, 1998.
Chiu et al., "Molecular dynamics computations and solid state nuclear magnetic resonance of the gramicidin cation channel," *Biophys. J.* 60: 974-978, Oct. 1991.
Davies et al., "Radical-Induced Damage to Bovine Serum Albumin: Role of the Cysteine Residue," *Free Rad. Res. Comms.* 18(6): 353-367, 1993.
Greenwald et al., "Drug Delivery Systems: Water Soluble Taxol 2'-Poly(ethylene glycol) Ester Prodrugs—Design and in Vivo Effectiveness," *J. Med. Chem.* 39(2): 424-431, 1996.
Greenwald et al., "Effective drug delivery by PEGylated drug conjugates," *Advanced Drug Delivery Reviews* 55: 217-250, 2003.
Greenwald, "PEG drugs: an overview," *J. of Controlled Release* 74: 159-171, 2001.
Higuchi and Shiobara, "Quantitative Determination of Nifedipine in Human Plasma by Selected Ion Monitoring," *Biomedical Mass Spectrometry* 5(3): 220-223, 1978.
Hino et al., "Investigation on SCH00013, a Novel Cardiotonic Agent with $Ca^{++}$ Sensitizing Action," *Arzneim.-Forsh./Drug Res.* 49(I)(5): 398-406, 1999.
Hou et al., "Synthesis of novel and enantiomerically pure epoxypropylamine: a divergent route to the chiral β-adrenergic blocking agents," *Tetrahedron: Asymmetry* 10: 2319-2326, 1999.
Howard and Walker, "Electrical Stimulation Studies with Quinacainol, a Putative 1C Agent, in the Anaesthetised Rat," *Proc. West. Pharmacol. Soc.* 33: 123-127, 1990.
Iida et al., "Synthesis of $^{13}$ C-Labelled Compounds having a Urea Unit, and Observation of $^{13}$C-Isotope Effect in Their Infrared Spectra," *J. Labelled Cpd. Radiopharm.* XXXIX(1): 69-77, 1997.
Johansen et al., "Synthesis of carbon-14 and stable isotope labelled NN414: a potent potassium channel opener," *J. Labelled Cpd. Radiopharm.* 47: 127-138, 2004.
Kahl et al., "Radioimmunoassay for the Calcium Release Channel Agonist Ryanodine," *Analytical Biochemistry* 218: 55-62, 1994.
Kepler et al., "Synthesis of 5,5-Diphenylhydantoin-2,4,5-$^{13}C_3$," *J. Labelled Cpd.* X(4): 683-687, 1974.
Kowey et al., "Electrophysiology of Beta Blockers in Supraventricular Arrhythmias," *The American Journal of Cardiology* 60: 32D-38D, Aug. 31, 1987.
Luurtsema et al., "Synthesis and PET-Studies of (R)- and (S)-[$^{11}$C]Verapamil for Measuring PGP function in MDR1A(+/+)/B(+/+) and MDR1A(−/−)/B(−/−) Mice," *J. Labelled Cpd. Radiopharm.* 44(Suppl. I): S313-S315, 2001.
Minin and Walton, "Radical Ring Closures of 4-Isocyanato Carbon-Centered Radicals," *J. Org. Chem.* 68: 2960-2963, 2003.
Molineux, "Pegylation: Engineering Improved Biopharmaceuticals for Oncology," *Pharmacotherapy* 23(8 Pt 2): 3S-8S, 2003.
Moustafa et al., "Comparative Study on the para-Metabolic Oxidation of Phenytoin and Decadeuteriophenytoin," *Arzneim.-Forsch/Drug Res.* 40(11), Nr. 10: 1076-1078, 1990.
Ohtaka and Kajiwara, "Synthesis of [$^{13}C_2$]nifedipine," *J. Labelled Cpd. Radiopharm.* 46: 1177-1179, 2003.
Page, "Beta-Blockers for Atrial Fibrillation: Must We Consider Asymptomatic Arrhythmias?," *Journal of the American College of Cardiology* 36(1): 147-150, Jul. 2000.
Rampe et al., "Deuterated analogs of verapamil and nifedipine. Synthesis and biological activity," *Eur. J. Med. Chem.* 28: 259-263, 1993.
Rich et al., "Alkylating Derivatives of Amino Acids and Peptides. Synthesis of *N*-Maleoylamino Acids, [1-(*N*-Maleoylglycyl)cysteinyl]oxytocin, and [1-(*N*-Maleoyl-11-aminoundecanoyl)cysteinyl]oxytocin. Effects on Vasopressin-Stimulated Water Loss from Isolated Toad Bladder," *Journal of Medicinal Chemistry* 18(10): 1004-1010, 1975.
Roberts et al., "Chemistry for peptide and protein PEGylation," *Advanced Drug Delivery Reviews* 54: 459-476, 2002.
Soriani et al, "Antioxidant Potential of Anaerobic Human Plasma: Role of Serum Albumin and Thiols as Scavengers of Carbon Radicals," *Archives of Biochemistry and Biophysics* 312(1): 180-188, Jul. 1994.
Steck et al., "Quinolines VI. Some 4-Aminoquinoline Derivatives," *J. Am. Chemical Society* 70(12): 4063-4065, Dec. 1948.
Stoschitzky et al., "Racemic beta-blockers—fixed combinations of different drugs," *J. Clin. Bas. Cardiology* 1: 14-18, 1998.
Sugio et al., "Crystal structure of human serum albumin at 2.5 Å resolution," *Protein Engineering* 12(6): 439-446, 1999.
Sung et al., "Beta-adrenoceptor blockade: Electrophysiology and antiarrhythmic mechanisms," *Am. Heart J.* 108(4 Part 2): 1115-1120, Oct. 1984.
Tuck et al., "A simple Procedure for the Deuteriation of Phenols," *J. Labelled Cpd. Radiopharm.* 43: 817-823, 2000.
Van Gelder et al., "A Comparison of Rate Control and Rhythm Control in Patients with Recurrent Persistent Atrial Fibrillation," *N. Engl. J. Med.* 347(23): 1834-1840, Dec. 5, 2002.
Van Noord et al., "Verdict: The Verapamil versus Digoxin Cardioversion Trial: A Randomized Study on the Role of Calcium Lowering for Maintenance of Sinus Rhythm after Cardioversion of Persistent Atrial Fibrillation," *J. Cardiovasc. Electrophysiol.* 12: 766-769, Jul. 2001.
Veronese and Morpurgo, "Bioconjugation in pharmaceutical chemistry," *Il Farmaco* 54: 497-516, 1999.

Waldo et al., "Effect of *d*-sotalol on mortality in patients with left ventricular dysfunction after recent and remove myocardial infarction," *The Lancet 348*: 7-12, Jul. 6, 1996.

Yahalom et al., "Beta-Adrenergic Blockade as Adjunctive Oral Therapy in Patients with Chronic Atrial Fibrillation," *Chest 71*: 592-596, May 1977.

Zalipsky, "Chemistry of polyethylene glycol conjugates with biologically active molecules," *Advanced Drug Delivery Reviews 16*: 157-182, 1995.

* cited by examiner

DRUG CONJUGATES OF ION CHANNEL MODULATING COMPOUNDS

FIELD OF THE INVENTION

The field of the compounds and methods described in this patent application is generally ion channel modulating compounds and their uses, and includes, but is not limited, to ion channel modulating compounds and their uses as antiarrhythmics, particularly for the treatment and/or prevention of atrial fibrillation (AF) and for the treatment and/or prevention of atrial flutter.

BACKGROUND OF THE INVENTION

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

For example, cardiac ion channels are proteins that reside in the cell membrane and control the electrical activity of cardiac tissue. In response to external stimuli, such as changes in potential across the cell membrane, these ion channels can form a pore through the cell membrane, and allow movement of specific ions into or out of the cell. The integrated behavior of thousands of ion channels in a single cell results in an ionic current, and the integrated behavior of many of these ionic currents makes up the characteristic cardiac action potential.

Arrhythmia is a variation from the normal rhythm of the heart beat and generally represents the end product of abnormal ion-channel structure, number or function. Both atrial arrhythmias and ventricular arrhythmias are known. The major cause of fatalities resulting from cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these cases will be first heart attacks and 450,000 of these will be recurrent attacks. About one-third of individuals experiencing these attacks will die as a result. At least 250,000 people a year die of coronary heart disease within 1 hour of the onset of symptoms and before they reach adequate medical aid. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., *N. Engl. J. Med.* 327(14):1031 Oct. 1, 1992, discussion 1031-2; Kannel and Wolf, *Am. Heart J.* 123(1):264-7 January 1992). The prevalence of AF is likely to increase as the population ages and it is estimated that 3-5% of patients over the age of 60 years have AF (Kannel W. B., Abbot R. D., Savage D. D., McNamara P. M., *N. Engl. J. Med.* 306(17):1018-22, 1982; Wolf P. A., Abbot R. D., Kannel W. B., *Stroke* 22(8):983-8, 1991). While AF is rarely fatal, it can impair cardiac function and is a major cause of stroke (Hinton R. C., Kistler J. P., Fallon J. T., Friedlich A. L., Fisher C. M., *Am. J. Cardiol.* 40(4):509-13, 1977; Wolf P. A., Abbot R. D., Kannel W. B., *Arch. Intern. Med.* 147(9):1561-4, 1987; Wolf P. A., Abbot R. D., Kannel W. B., *Stroke* 22(8):983-8, 1991; Cabin H. S., Clubb K. S., Hall C., Perlmutter R. A., Feinstein A. R., *Am. J. Cardiol.* 65(16):1112-6, 1990).

Antiarrhythmic agents have been developed to prevent or alleviate cardiac arrhythmia. For example, Class I antiarrhythmic compounds have been used to treat supraventricular arrhythmias and ventricular arrhythmias. Treatment of ventricular arrhythmia is very important since such an arrhythmia can be fatal. Serious ventricular arrhythmias (ventricular tachycardia and ventricular fibrillation) occur most often in the presence of myocardial ischemia and/or infarction. Ventricular fibrillation often occurs in the setting of acute myocardial ischemia, before infarction fully develops. At present, there is no satisfactory pharmacotherapy for the treatment and/or prevention of ventricular fibrillation during acute ischemia. In fact, many Class I antiarrhythmic compounds may actually increase mortality in patients who have had a myocardial infarction.

Class Ia, Ic and III antiarrhythmic drugs have been used to convert recent onset AF to sinus rhythm and prevent recurrence of the arrhythmia (Fuch and Podrid, 1992; Nattel S., Hadjis T., Talajic M., *Drugs* 48(3):345-71, 1994). However, drug therapy is often limited by adverse effects, including the possibility of increased mortality, and inadequate efficacy (Feld G. K., *Circulation* 83(6):2248-50, 1990; Coplen S. E., Antman E. M., Berlin J. A., Hewitt P., Chalmers T. C., *Circulation* 1991; 83(2):714 and *Circulation* 82(4):1106-16, 1990; Flaker G. C., Blackshear J. L., McBride R., Kronmal R. A., Halperin J. L., Hart R. G., *J. Am. Coll. Cardiol.* 20(3):527-32, 1992; CAST, *N. Engl. J. Med.* 321:406, 1989; Nattel S., *Cardiovasc. Res.* 37(3):567-77, 1998). Conversion rates for Class I antiarrhythmics range between 50-90% (Nattel S., Hadjis T., Talajic M., *Drugs* 48(3):345-71, 1994; Steinbeck G., Remp T., Hoffmann E., *J. Cardiovasc. Electrophysiol.* 9(8 Suppl):S104-8, 1998). Class III antiarrhythmics appear to be more effective for terminating atrial flutter than for AF and are generally regarded as less effective than Class I drugs for terminating of AF (Nattel S., Hadjis T., Talajic M., *Drugs* 48(3):345-71, 1994; Capucci A., Aschieri D., Villani G. Q., *Drugs Aging* 13(1):51-70, 1998). Examples of such drugs include ibutilide, dofetilide and sotalol. Conversion rates for these drugs range between 30-50% for recent onset AF (Capucci A., Aschieri D., Villani G. Q., *Drugs Aging* 13(1):51-70, 1998), and they are also associated with a risk of the induction of Torsades de Pointes ventricular tachyarrhythmias. For ibutilide, the risk of ventricular proarrhythmia is estimated at ~4.4%, with ~1.7% of patients requiring cardioversion for refractory ventricular arrhythmias (Kowey P. R., VanderLugt J. T., Luderer J. R., *Am. J. Cardiol.* 78(8A):46-52, 1996). Such events are particularly tragic in the case of AF as this arrhythmia is rarely a fatal in and of itself.

There remains a need in the art to identify new antiarrhythmic treatments, for both ventricular arrhythmias as well as for atrial arrhythmias. The present invention fulfills this need, and further provides other related advantages.

Related Literature

Certain ion channel modulating compounds of interest to the present invention are disclosed and described in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US2005002693, the disclosures of which are incorporated in full by reference herein.

SUMMARY OF THE INVENTION

In one aspect, this invention is directed to PEGylated derivatives of an ion channel modulating compound comprising one or more PEG moieties attached to an ion channel modulating compound.

In another aspect, this invention is directed to pharmaceutical compositions comprising a PEGylated derivative of the invention and a pharmaceutically acceptable excipient.

In another aspect, this invention is directed to methods of treating arrhythmia in a subject in need thereof, wherein the methods comprise administering to the subject a therapeutically effective amount of a PEGylated derivative of the invention or a pharmaceutical composition comprising a PEGylated derivative of the invention.

In another aspect, this invention is directed to methods for modulating ion channel activity in a subject, wherein the methods comprise administering to the subject a therapeutically effective amount of a PEGylated derivative of the invention or a pharmaceutical composition comprising a PEGylated derivative of the invention.

In another aspect, this invention is directed to methods for modulating ion channel activity in vitro, wherein the methods comprise utilizing a PEGylated derivative of the invention.

In another aspect, this invention is directed to drug conjugates comprising an ion channel modulating compound and an additional drug moiety.

In another aspect, this invention is directed to pharmaceutical compositions comprising a drug conjugate of the invention and a pharmaceutically acceptable excipient.

In another aspect, this invention is directed to methods of treating arrhythmia in a subject in need thereof, wherein the methods comprise administering to the subject a therapeutically effective amount of a drug conjugate of the invention or a pharmaceutical composition comprising a drug conjugate of the invention.

In another aspect, this invention is directed to methods for modulating ion channel activity in a subject, wherein the methods comprise administering to the subject an effective amount of a drug conjugate of the invention or a pharmaceutical composition comprising a drug conjugate of the invention.

In another aspect, this invention is directed to methods for modulating ion channel activity in vitro, wherein the methods comprise utilizing a drug conjugate of the invention.

In another aspect, this invention is directed to isotopic ion channel modulating compounds comprising an ion channel modulating compound wherein at least one atom of the ion channel modulating compound is substituted with a stable isotope thereof.

DETAILED DESCRIPTION OF THE INVENTION

As disclosed within the present invention, a variety of cardiac pathological conditions may be treated and/or prevented by the use of one or more of the compounds disclosed herein that, either singly or together with one or more additional therapeutic agents, are able to selectively inhibit certain combination of cardiac ionic currents. More specifically, the cardiac currents referred to above are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{SUS}$. A second calcium dependent transient outward current ($I_{to2}$) has also been described.

The cardiac pathological conditions that may be treated and/or prevented by the compounds of the present invention may include, but are not limited to, arrhythmias such as the various types of atrial and ventricular arrhythmias.

Of particular interest to the present invention are the ion channel modulating compounds disclosed in PCT Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US2005002693; the disclosures of which are incorporated in full herein by reference in their entireties.

A. Definitions

In accordance with the present invention and as used herein, the following terms are defined to have the following meanings, unless explicitly stated otherwise:

"Acyl" refers to branched or unbranched hydrocarbon fragments terminated by a carbonyl —(C=O)— group containing the specified number of carbon atoms. Examples include acetyl [$CH_3(C=O)$—, a $C_2$acyl] and propionyl [$CH_3CH_2(C=O)$—, a $C_3$acyl].

"Alkanoyloxy" refers to an ester substituent wherein the ether oxygen is the point of attachment to the molecule. Examples include propanoyloxy [($CH_3CH_2(C=O)$—O—, a $C_3$alkanoyloxy] and ethanoyloxy [$CH_3(C=O)$—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to an alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2O(C=O)$—, a $C_3$alkoxycarbonyl] and methoxycarbonyl [$CH_3O(C=O)$—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds, where phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing a hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S$—, a $C_1$thioalkyl).

"Modulating" in connection with the activity of an ion channel means that the activity of the ion channel may be either increased or decreased in response to administration of a compound or composition or method described herein. Thus, the ion channel may be activated, so as to transport more ions, or may be blocked, so that fewer or no ions are transported by the channel.

As used in this patent application, a "subject" may generally be any human or non-human animal that would benefit from the methods described in this application. In one version of the methods, a subject is a human subject. In some versions of the methods, a subject is a warm-blooded animal. In some versions of the methods, a subject is a mammal. In some versions, the subject is any domestic animal, including, but not limited to dogs and cats. In some versions, the subject is any livestock animal, including but not limited to horses, pigs and cattle. In some versions, the subject is any zoo animal, including but not limited to Bengal tigers.

As used in this patent application, unless the context makes clear otherwise, "treatment," and similar word such as "treated," "treating" etc., is an approach for obtaining beneficial or desired results, including and preferably clinical results. Treatment can involve optionally either the amelioration of symptoms of the disease or condition, or the delaying of the progression of the disease or condition.

As used in this patent application, unless the context makes clear otherwise, "prevention," and similar word such as "prevented," "preventing" etc., is an approach for preventing the onset of a disease or condition or preventing the occurrence of the symptoms of a disease or condition, or optionally an approach for delaying the onset of a disease or condition or delaying the occurrence of the symptoms of a disease or condition. As used herein, "prevention" and similar words also includes reducing the intensity, effect, symptoms and/or burden of a disease or condition prior to onset of the disease or condition.

As used in this patent application, an "effective amount" or a "therapeutically effective amount" of a substance is that amount sufficient to affect a desired biological effect, such as beneficial results, including clinical results.

As used in this patent application, unless the context makes clear otherwise, "inhibition" and similar words such as "inhibit" of any ion channel means any decrease in current through that channel. When "inhibition" is used in the context of a specified concentration, it is determined by the $IC_{50}$. For example, an ion channel modulating compound which inhibits an ion channel at a concentration of 1 µM, the ion channel may be said to have an $IC_{50}$ of 1 µM for that ion channel modulating compound. This example is for illustrative purposes only and is in no way intended to be limiting.

As used in this patent application, unless the context makes clear otherwise, "$IC_{50}$" or "$IC_{50}$ concentration" means a drug concentration at which the specified current amplitude (peak or steady-state, or integrated current) is inhibited by 50%.

As used in this patent application, unless the context makes clear otherwise, "blocking" or "block" of an ion channel means any block or inhibition of current through that ion channel.

As used in this patent application, unless the context makes clear otherwise, "recovery time constant of inhibition" refers to a time constant at which recovery of current amplitude occurs, presumed to reflect dissociation of a drug from its binding site, as for example, a sodium channel when the stimulus rate is decreased from 10 Hz to 1 Hz.

"Pharmaceutically acceptable carriers" for therapeutic use are well known in the pharmaceutical art, and are described, for example, in *Remington's Pharmaceutical Sciences*, Mack Publishing Co. (current edition). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

"Pharmaceutically acceptable salt" refers to salts of a compound of the invention derived from the combination of such compounds and an organic or inorganic acid (acid addition salts) or an organic or inorganic base (base addition salts) which retain the biological effectiveness and properties of the compounds of the present invention and which are not biologically or otherwise undesirable. The compounds of the invention described herein may be used in either the free base or salt forms, with both forms being considered as being within the scope intended herein. Pharmaceutically-acceptable salts of the compounds of the invention include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochloride and sulfates; and salts of organic acids, such as but not limited to acetates, lactates, malates, tartrates, citrates, ascorbates, succinates, butyrates, valerates and fumarates. Other examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

"Prodrug" refers to a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

When the compounds described herein contain olefinic double bonds or other centers of geometric asymmetry, and unless specified otherwise, it is intended that the compounds include both E and Z geometric isomers. Likewise, all tautomeric forms are also intended to be included.

It is also to be understood that the compounds described herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

For purposes of this invention, when a bond is indicated in a formula as a wavy line, such as the bond between the oxygen atom and cyclopentyl moiety in compound of formula (IA), it is meant to indicate a bond which can give rise to either R or S stereochemistry.

Following the standard chemical literature description practice and as used in this patent, a full wedge bond means above the ring plane, and a dashed wedge bond means below the ring plane; one full bond and one dashed bond (i.e., - - - ) means a trans configuration, whereas two full bonds or two dashed bonds means a cis configuration.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position.

Optically active (+) and (−), (R)- and (S)-, or (D)- and (L)-isomers may be prepared using chiral synthons or chiral reagents, or resolved using conventional techniques, such as reverse phase HPLC.

Thus, in the description of the compounds of formulae (I), (IA) and (IX) and Compound A, as described herein, all enantiomeric and diastereomeric forms of the compounds are intended. Pure stereoisomers, mixtures of enantiomers and/or diastereomers, and mixtures of different ion channel modulating compounds are described. The compounds of of formulae (I), (IA) and (IX) may therefore occur as racemates, racemic mixtures and as individual diastereomers or enantiomers with all isomeric forms being included in the present invention. A racemate or racemic mixture does not imply a 50:50 mixture of stereoisomers. Where a given structural formula or chemical name is presented for a compound of formulae (I), (IA) and (IX) it is intended that all possible solvates, pharmaceutically acceptable salts, esters, amides, complexes, chelates, stereoisomers, geometric isomers, crystalline or amorphous forms, metabolites, metabolic precursors or prodrugs of the compound are also separately described by the chemical structural formula or chemical name.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

The compounds of the invention may contain an "aminocycloalkyl ether moiety", i.e., the following moiety:

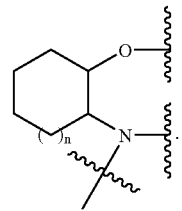

where n is 0, 1, 2, or 3. As used herein, the term "aminocycloalkyl ether moiety" includes compounds wherein the cycloalkyl group is a cyclohexyl group, such as in compounds of formula (I), formula (IA) and Compound A disclosed herein, and includes compounds wherein the cycloalkyl group is a cyclopentyl, cycloheptyl or cyclooctyl group, such as in compounds of formula (IX) disclosed herein.

As used in this patent application, "equivalently inhibits" and "equivalently inhibited" means equally inhibits or equally inhibited. In one version, equivalently inhibits means that there is no statistically significant difference in inhibition of currents resulting from application of an ion channel modulating compound. For example, the early and sustained sodium currents are equivalently inhibited if there is no statistically significant difference in the effect of an ion channel modulating compound on early and sustained sodium currents.

As used in this patent application, "rapidly associated and dissociated" means that a compound has blocking and unblocking kinetics of the 'fast-on, fast-off' form such as the 'fast-on, fast-off' kinetics defined by Carmeliet and Mubagwa (Prog. Biophys. Molec. Biol. 70, 1-72, 1998). For example, an ion channel modulating compound rapidly associates and dissociates from sodium channels where the ion channel modulating compound has 'fast-on, fast-off' kinetics as defined by Carmeliet and Mubagwa.

As used in this patent application, "rate-independent and use-independent" inhibition means inhibition that is predominantly heart rate and/or stimulus rate and use-independent such that there is no statistically significant effect of steady-state or transient changes in heart rate or stimulus rate with respect to the inhibition. For example, an ion channel modulating compound that inhibits Kv1 channels in a "rate-independent and use-independent" manner means that there is no influence of the heart rate or stimulus rate on the amount of inhibition produced by the ion channel modulating compound on Kv1 channels.

As used in this patent application, "affects atrial repolarizing currents" means "has a statistically significant effect on atrial repolarizing current amplitudes."

As used in this patent application, "prolongs atrial refractoriness" means "has a statistically significant prolonging effect on atrial refractoriness."

As used in this patent application, "has substantially no effect on ventricular tissue" means "has no statistically significant effect on normal human ventricular action potential duration or refractoriness." Any apparent difference in effect, therefore, is attributed to intrinsic variability, such as in one aspect, less than a 10% difference.

As used in this patent application, "does not substantially slow conduction" means "has no statistically significant effect on slowing conduction in the ventricles." As such, any apparent difference in effect, therefore, is attributed to intrinsic variability. In one aspect, the ion channel modulating compound has no statistically significant effect on the slowing of conduction wherein the compound produces less than a 15%, preferably less than a 10%, increase in cardiac QRS duration at physiological heart rates.

As used in this patent application, "rate-dependent inhibition" of an ion channel means that the level of inhibition of the ion channel changes with the frequency of stimulation.

The term "QT interval" is used as is known in the art; for example, the QT interval as measured from an electrocardiogram. As used herein, unless the context makes clear otherwise, the term "prolongs" or "prolong" generally means extends or lengthens as in duration.

The term "antiarrhythmic" is used as is known in the art; for example, as a compound which prevents or alleviates irregularities in heart rate.

The term "induces" as used herein, unless the context indicates otherwise, generally means to stimulate the occurrence of.

The term "chemically induced" or "chemically induces" is used as is known in the art. As used herein, unless the context makes clear otherwise, the term "terminating" or "terminates" generally means to bring to an end or to halt.

B. Compounds of formula (I), (IA), (IX) and Compound A

The present invention utilizes ion channel modulating compounds. Generally, any compound that modulates ion channel activity may by an ion channel modulating compound. A compound that modulates ion channel activity may be a compound that increases or decreases ion channel activity. An ion channel modulating compound that decreases ion channel activity may be a compound that blocks ion channel activity completely or partially.

In another version, any compound that either singly or together with one or more additional compounds selectively inhibit certain combination of cardiac ionic currents is an ion channel modulating compound. The cardiac currents may be the sodium currents and early repolarizing currents. Ion channel modulating compounds may block cardiac currents from extracellular loci. Such compounds act on an external locus of the ion channel that is accessible from the extracellular surface. This facilitates access to the ion channel and provides rapid onset kinetics and exhibits frequency dependent blockade of currents. Such properties are all beneficial for compounds used to treat arrhythmias. An ion channel modulating compound may selectively inhibit cardiac early repolarizing currents and cardiac sodium currents. Ion channel modulating compounds may be used to selectively inhibit cardiac early repolarizing currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation. An ion channel modulating compound may be an atrial selective agent. An ion channel modulating compound may treat or prevent ventricular arrhythmia. An ion channel modulating compound may block cardiac sodium currents or cardiac early repolarizing currents. An ion channel modulating compound may inhibit multiple cardiac ionic currents. An ion channel modulating compound may be used to treat or prevent arrhythmic, including ventricular or atrial arrhythmia, particularly atrial fibrillation.

The ion channel modulating compounds may block the cardiac ion channels responsible for early repolarizing currents and sodium currents; and/or block cardiac early repolarizing currents and cardiac sodium currents under conditions where an arrhythmogenic substrate is present in the heart; and/or block the cardiac ion channels responsible for early repolarizing currents and sodium currents under conditions where an arrhythmogenic substrate is present in the heart; and/or block cardiac early repolarizing currents and cardiac sodium currents from extracellular loci in cardiac cells.

In one variation, the cardiac early repolarizing currents referred to above comprise ionic currents which activate rapidly after depolarization of membrane voltage and which effect repolarization of the cell. The early repolarizing currents may comprise the cardiac transient outward potassium current ($I_{to}$) and/or the ultrarapid delay rectifier current ($I_{Kur}$). The cardiac transient outward potassium current ($I_{to}$) and/or the ultrarapid delay rectifier current ($I_{Kur}$) may comprise at least one of the Kv4.2, Kv4.3, Kv2.1, Kv1.4 and Kv1.5 currents.

Ion channel modulating compounds may generally have any pKa, however ion channel modulating compounds typically have pKa values of between 4-9, and may have pKa values that are less than 8, including pKa values between 5-7.5. Methods to determine pKa values are well known in the art (see, e.g., Perrin, "Dissociation Constants of Organic Bases in Aqueous Solution", Butterworth, London, 1972). For ion channel modulating compounds with the specific ranges of pKa described above, the fraction of the charged (protonated) species will be increased under the pathological conditions such as cardiac arrhythmias and the presence of an arrhythmogenic substrate in the heart as described above due to the increase in cardiac milieu acidity. Where the charged form of a compound is active, its potency increases under conditions associated with an increase in cardiac milieu acidity.

Particular ion channel modulating compounds have structural characteristics that may be determined by various physical methods, such as single crystal X-ray crystallography. For instance, some ion channel modulating compounds comprise a cycloalkane ring and substituents J and K as shown below in structure T, wherein the relative positions of J and K provide a "C" shaped angle and wherein n=1, 2, 3 or 4.

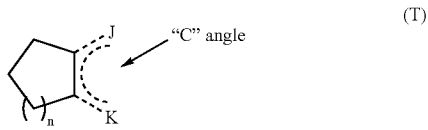

(T)

Typically, one of J and K comprises a hydrophobic moiety, such as but not limited to a moiety comprising alkyl and/or aryl moieties. In one variation, one of J and K comprises a hydrophobic aromatic moiety, which may be attached to the cycloalkane ring of structure T via an ether bond. Typically, one of J and K comprises a hydrophilic moiety, such as a heteroatom containing moiety, including but not limited to a nitrogen containing moiety that is available to form a quaternary salt and/or a hydroxyl moiety. In one variation, one of J and K comprises a nitrogen containing moiety substituted with a hydroxyl moiety or the like, such as a pyrrolidinyl moiety. In a particular variation of structure T, n=2, J comprises an aromatic moiety and K comprises a nitrogen containing moiety substituted with a hydroxyl moiety or the like. The cycloalkane ring may be optionally substituted. In one version, the cycloalkane ring may be replaced by a structural moiety imparting rigidity to the relative positions of the J and K groups. For example if the J and K groups are attached to atoms L and M that are directly bonded to each other, any group that does not allow substantial rotation about the bond between atoms L and M can impart rigidity to the relative positions of the J and K groups. For example, the ion channel modulating compound may be a compound of formula

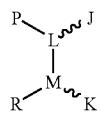

where J and K are as described above and groups P and R are moieties such that there is not substantial rotation about the L-M bond. In one example P and R are taken together form a cyclic moiety that prevents substantial rotation about the L-M bond.

In one version, the ion channel modulating compound comprises an amino substituted 5, 6, 7 or 8-membered ring, which may be a 5, 6, 7, or 8-membered substituted or unsubstituted cycloalkyl ring. The amino substituted cycloalkane ring may be an aminocyclohexyl ring and may be further substituted with one or more additional moieties. In one version, the amino substituted cycloalkane ring is further substituted with an ether moiety. In some instances, the ion channel modulating compound comprises an aminocyclohexyl ring that is further substituted with an ether moiety.

In another, the ion channel modulating compound is a protonated version of any of the ion channel modulating compounds described herein. That is, for each ion channel modulating compound described herein, the quaternary protonated amine form of the compound may also be considered as an amino ion channel modulating compound. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

In one aspect, the present invention utilizes ion channel modulating compounds of formula (I), or solvates or pharmaceutically acceptable salts thereof:

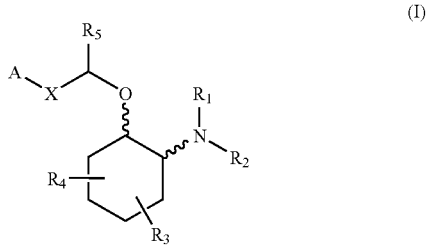

(I)

wherein, independently at each occurrence,

X is selected from a direct bond, —C($R_6,R_{14}$)—Y— and —C($R_{13}$)=CH—, with the proviso that when X is a direct bond and A is formula (III), then at least one of $R_7$, $R_8$ and $R_9$ is not hydrogen;

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (I), form a ring denoted by formula (II):

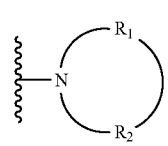

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

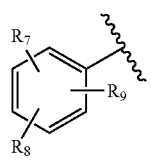

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$,$R_{16}$) where $R_{15}$ and $R_{16}$ are independently selected from hydrogen, acetyl, methanesulfonyl and $C_1$-$C_6$alkyl;

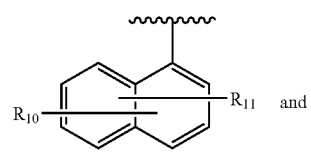

(IV)

and

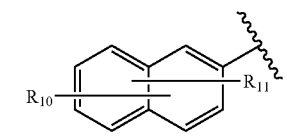

(V)

where $R_{10}$ and $R_{11}$, are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$,$R_{16}$) where $R_{15}$ and $R_{16}$ are independently selected from hydrogen, acetyl, methanesulfonyl, and $C_1$-$C_6$alkyl;

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$,$R_{16}$) where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

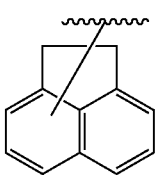

(VII)

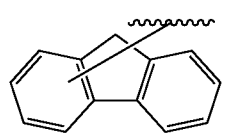

(VIII)

including isolated enantiomeric, diastereomeric and geometric isomers thereof, and mixtures thereof.

Of particular interest are compounds of formula (I) selected from the group consisting of the following:

(1R,2R)/(1S,2S)-[2-(4-morpholinyl)-1-(2-naphthenethoxy)] cyclohexane;

(1R,2R)/(1S,2S)-[2-(4-morpholinyl)-1-(1-naphthenethoxy)] cyclohexane;

(1R,2R)/(1S,2S)-[2-(4-morpholinyl)-1-(4-bromophenethoxy)]cyclohexane;
(1R,2R)/(1S,2S)-[2-(4-morpholinyl)-1-[2-(2-naphthoxy)ethoxy]]cyclohexane;
(1R,2R)/(1S,2S)-[2-(4-morpholinyl)-1-[2-(4-bromophenoxy)ethoxy]]cyclohexane;
(1R,2R)/(1S,2S)-[2-(4-morpholinyl)-1-(3,4-dimethoxyphenethoxy)]cyclohexane;
(1R,2R)/(1S,2S)-[2-(1-pyrrolidinyl)-1-(1-naphthenethoxy)]cyclohexane;
(1R,2R)/(1S,2S)-[2-(4-morpholinyl)-1-(2-(benzo[b]thiophen-3-yl)]cyclohexane;
(1R,2R)/(1S,2S)-[2-(4-morpholinyl)-1-(2-(benzo[b]thiophen-4-yl)]cyclohexane;
(1R,2R)/(1S,2S)-[2-(4-morpholinyl)-1-(3-bromophenethoxy)]cyclohexane;
(1R,2R)/(1S,2S)-[2-(4-morpholinyl)-1-(2-bromophenethoxy)]cyclohexane;
(1R,2R)/(1S,2S)-[2-(4-morpholinyl)-1-(3-(3,4-dimethoxyphenyl)propoxy)]cyclohexane;
(1R,2R)/(1S,2S)-[2-[bis(2-methoxyethyl)aminyl]-1-(2-naphthenethoxy)]cyclohexane;
(1R,2R)/(1S,2S)-2-(4-morpholinyl)-1-(3,4-dichlorophenethoxy)cyclohexane;
(1R,2R)/(1S,2S)-2-(3-ketopyrrolidinyl)-1-(1-naphthenethoxy)cyclohexane;
(1R,2R)/(1S,2S)-2-(1-acetylpiperazinyl)-1-(2-naphthenethoxy)cyclohexane;
(1R,2R)/(1S,2S)-2-(3-ketopyrrolidinyl)-1-(2,6-dichlorophenethoxy)cyclohexane;
(1R,2R)/(1S,2S)-2-[1,4-dioxa-7-azaspiro[4.4]non-7-yl]-1-(1-naphthenethoxy)cyclohexane;
(1R,2S)/(1S,2R)-2-(4-morpholinyl)-1-[(2-trifluoromethyl)phenethoxy]cyclohexane monohydrochloride;
(1R,2R)/(1S,2S)-2-(3-ketopyrrolidinyl)-1-[3-(cyclohexyl)propoxy]cyclohexane monohydrochloride;
(1R,2R)/(1S,2S)-2-(3-acetoxypyrrolidinyl)-1-(1-naphthenethoxy)cyclohexane monohydrochloride;
(1R,2R)/(1S,2S)-2-(4-morpholinyl)-1-[(2,6-dichlorophenyl)methoxy]cyclohexane monohydrochloride;
(1R,2R)/(1S,2S)-2-(3-ketopyrrolidinyl)-1-[(2,6-dichlorophenyl)methoxy]cyclohexane monohydrochloride;
(1R,2R)/(1S,2S)-2-(3-hydroxypyrrolidinyl)-1-(2,6-dichlorophenethoxy)cyclohexane monohydrochloride;
(1R,2R)/(1S,2S)-2-(3-ketopyrrolidinyl)-1-(2,2-diphenylethoxy)cyclohexane monohydrochloride;
(1R,2R)/(1S,2S)-2-(3-thiazolidinyl)-1-(2,6-dichlorophenethoxy)cyclohexane monohydrochloride;
(1R,2S)/(1S,2R)-2-(3-ketopyrrolidinyl)-1-(1-naphthenethoxy)cyclohexane monohydrochloride; and
(1R,2R)/(1S,2S)-2-(3-hydroxypyrrolidinyl)-1-(3,4-dimethoxyphenethoxy)cyclohexane monohydrochloride.

In another aspect, the present invention utilizes ion channel modulating compounds of formula (IA), or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof:

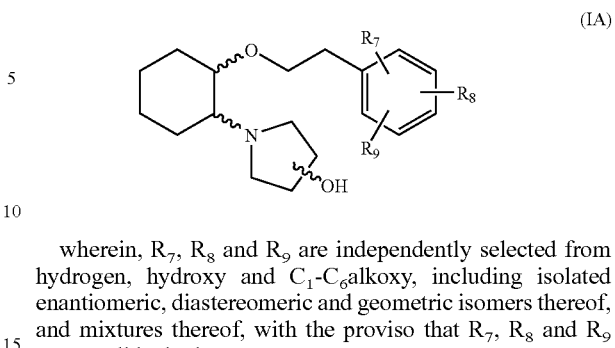

(IA)

wherein, $R_7$, $R_8$ and $R_9$ are independently selected from hydrogen, hydroxy and $C_1$-$C_6$alkoxy, including isolated enantiomeric, diastereomeric and geometric isomers thereof, and mixtures thereof, with the proviso that $R_7$, $R_8$ and $R_9$ cannot all be hydrogen.

Of particular interest are compounds of formula (IA) selected from the group consisting of the following:
(1R,2R)/(1S,2S)-2-[(3R)/(3S)-hydroxypyrrolidinyl]-1-(3,4-dimethoxyphenethoxy)-cyclohexane;
(1R,2R)/(1S,2S)-2-[(3R)-hydroxypyrrolidinyl]-1-(3,4-dimethoxyphenethoxy)-cyclohexane;
(1R,2R)/(1S,2S)-2-[(3S)-hydroxypyrrolidinyl]-1-(3,4-dimethoxyphenethoxy)-cyclohexane;
(1R,2R)-2-[(3R)-hydroxypyrrolidinyl]-1-(3,4-dimethoxyphenethoxy)-cyclohexane;
(1R,2R)-2-[(3S)-hydroxypyrrolidinyl]-1-(3,4-dimethoxyphenethoxy)-cyclohexane;
(1R,2S)-2-[(3R)-hydroxypyrrolidinyl]-1-(3,4-dimethoxyphenethoxy)-cyclohexane;
(1R,2S)-2-[(3S)-hydroxypyrrolidinyl]-1-(3,4-dimethoxyphenethoxy)-cyclohexane;
(1S,2R)-2-[(3R)-hydroxypyrrolidinyl]-1-(3,4-dimethoxyphenethoxy)-cyclohexane;
(1S,2R)-2-[(3S)-hydroxypyrrolidinyl]-1-(3,4-dimethoxyphenethoxy)-cyclohexane;
(1S,2S)-2-[(3R)-hydroxypyrrolidinyl]-1-(3,4-dimethoxyphenethoxy)-cyclohexane;
(1S,2S)-2-[(3S)-hydroxypyrrolidinyl]-1-(3,4-dimethoxyphenethoxy)-cyclohexane; and
(1R,2S)/(1S,2R)-2-[(3R)/(3S)-hydroxypyrrolidinyl]-1-(3,4-dimethoxyphenethoxy)-cyclohexane.

In another aspect, the present invention utilizes ion channel modulating compounds of formula (IX), or solvates or pharmaceutically acceptable salts thereof:

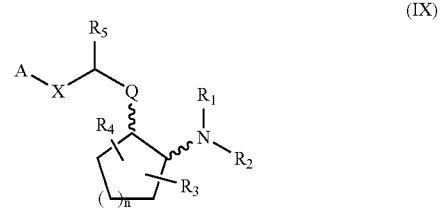

(IX)

wherein, independently at each occurrence,
n is selected from 1, 3 and 4;
Q is either O (oxygen) or —O—C(O);
X is selected from a direct bond, —C($R_6$,$R_{14}$)—Y—, and —C($R_{13}$)=CH—;
Y is selected from a direct bond, O, S, and $C_1$-$C_4$alkylene;
$R_{13}$ is selected from hydrogen, $C_1$-$C_6$alkyl, $C_3$-$C_8$cycloalkyl, aryl, and benzyl;
$R_1$ and $R_2$ are independently selected from hydrogen, $C_1$-$C_8$alkyl, $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached in formula (IX), form a ring denoted by formula (II):

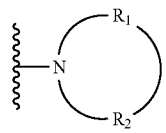

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached in formula (IX), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

$R_3$ and $R_4$ are independently attached to the cyclohexane ring shown in formula (IX) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

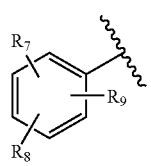

(III)

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and $N(R_{15},R_{16})$ where $R_{15}$ and $R_{16}$ are independently selected from hydrogen, acetyl, methanesulfonyl and $C_1$-$C_6$alkyl;

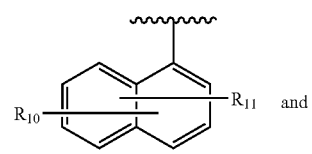

(IV)

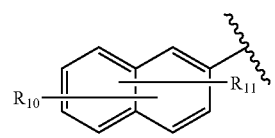

(V)

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl;

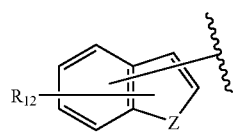

(VI)

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (IX) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

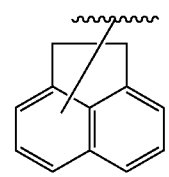

(VII)

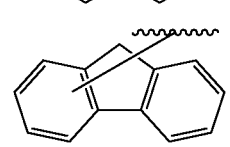

(VIII)

including isolated enantiomeric, diastereomeric and geometric isomers thereof, and mixtures thereof.

Of particular interest are compounds of formula (IX) selected from the group consisting of the following:

(1R,2R)/(1S,2S)-2-(4-morpholinyl)-1-(2-naphthalenethoxy) cyclopentane monohydrochloride; and (1R,2R)/(1S,2S)-2-(3-ketopyrrolidinyl)-1-(2,6-dichlorophenethoxy)cyclopentane monohydrochloride.

Of particular interest to the invention described herein is a compound of formula (IA) having the following formula:

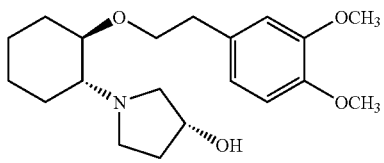

This compound has the chemical name of (1R,2R)-2-[(3R)-hydroxypyrrolidinyl]-1-(3,4-dimethoxyphenethoxy)cyclohexane and is referred to herein as "Compound A". For purposes of this invention, the term "Compound A" is intended to include this compound and its pharmaceutically acceptable salts, solvates, esters, amides, complexes, chelates, stereoisomers, stereoisomeric mixtures, geometric isomers, crystalline or amorphous forms, metabolites, metabolic precursors or prodrugs thereof.

B. Preparation of the Compounds of Formula (I), (IA), (IX) and Compound A

The compounds of formulae (I), (IA) and/or (IX) and/or Compound A used in the present invention may be prepared as described in PCT Published Patent Application No. WO 1999/50225; PCT Published Patent Application No. WO 2000/047547; PCT Published Patent Application No. WO 2004/098525; PCT Published Patent Application No. 2004/099137; PCT Published Patent Application No. 2005/018635; and U.S. Published Patent Application No. 2005002693; or may be prepared by methods known to one skilled in the art.

C. Preparation of Polyethylene Glycol Derivatives of Ion Channel Modulating Compounds It is well known in the art that polyalkylene glycols, such as polyethylene glycol (PEG), may be attached to a therapeutic agent. Polyalkylene glycolated (PAGylated) therapeutic agents, and in particular, PEGylated therapeutic agents, have been reported to increase solubility, circulating life, safety, decrease renal excretion, and decrease immunogenicity thus potentially providing a method of improved drug delivery. A PEGylated therapeutic agent may exhibit: (a) increased plasma circulatory half lives in vivo compared to the corresponding non-PEGylated compound, (b) enhanced therapeutic indices compared to the corresponding non-PEGylated compounds and (c) increased solubility compared to the corresponding non-PEGylated compounds, effecting possible improved drug delivery.

Examples in which PEGylation has been used to effect drug delivery are disclosed, for example, in U.S. Pat. No. 6,623,729; U.S. Pat. No. 6,517,824; U.S. Pat. No. 6,515,017; U.S. Pat. No. 6,217,869; U.S. Pat. No. 6,191,105; U.S. Pat. No. 5,681,811; U.S. Pat. No. 5,455,027; U.S. Published Patent Application No. 20040018960; U.S. Published Patent Application No. 20030229010; U.S. Published Patent Application No. 20030229006; U.S. Published Patent Application No. 20030186869; U.S. Published Patent Application No. 20030026764; and U.S. Published Patent Application No. 20030017131. U.S. Pat. No. 6,214,966, U.S. Published Patent Application No. 2003000447, and U.S. Published Patent Application No. 2001021763 describe soluble, degradable poly(ethylene glycol) derivatives for controlled release of bound molecules into solution.

Recent reviews on PEGylation are provided in, for example, Greenwald R. B., Choe Y. H., McGuire J., Conover C. D. Adv. Drug Del. Rev. 2003, 55, 217, Molineux G. Pharmacotherapy 2003, (8 Pt 2), 3S-8S, Roberts M. J., Bentley, M. D., Harris J. M. Adv. Drug Deliv. Rev. 2002, 54, 459, Bhadra D., Bhadra S., Jain P., Jain N. K. Pharmazie 2002, 57, 5, Greenwald R. B. J. Controlled Release 2001, 74, 159, Veronese F. M., Morpurgo M. Farmaco. 1999, 54, 497 and Zalipsky S. Adv. Drug Deliv. Rev. 1995, 16, 157.

Ion channel modulating compounds, particularly the compounds of formulae (I), (IA) and (IX) and Compound A, as described above, may be PEGylated as described below.

Attachment of a PEG moiety (known as "PEGylation") to an ion channel modulating compound may be accomplished by known chemical synthesis techniques, which are described in more detail below. Any moiety comprising PEG may be attached to an ion channel modulating compound to provide a PEGylated derivative of an ion channel modulating compound. In general, a PEGylated derivative of an ion channel modulating compound comprises a PEG moiety attached to an ion channel modulating compound at any site on the compound amenable thereto.

A PEGylated derivative may comprise more than one ion channel modulating compound. A PEGylated derivative comprising more than one ion channel modulating compound may comprise one or more than one type of ion channel modulating compound. An ion channel modulating compound type is determined by its chemical structure, such that ion channel modulating compounds with different chemical structures are of different types. As such, high loading of a single ion channel modulating compound in a PEGylated derivative may be achieved by attaching more than one of the same ion channel modulating compound to a single PEG moiety. Alternatively, different ion channel modulating compounds may be attached to a single PEG moiety, such that a single PEGylated derivative may comprise different ion channel modulating compounds.

A PEGylated derivative may contain ion channel modulating compounds in any amount that is allowed by the loading capacity of the PEG moiety. The loading capacity of the PEG moiety refers to the number of ion channel modulating compounds that may be attached to the PEG moiety. The loading capacity may be determined by the number of available functional groups (i.e., "attachment sites") on the PEG moiety, which will be readily apparent to one of skill in the art. For instance, a bifunctional PEG moiety with available functional groups on each terminus of the PEG moiety will have a loading capacity of 2, provided that no other sites on the PEG moiety are available as attachment sites. Although usually present at the termini of a PEG moiety, an attachment site may be any functional group on the PEG moiety that allows attachment of an ion channel modulating compound. A PEGylated derivative as described herein contains at least one ion channel modulating compound and may contain any number of additional ion channel modulating compounds up to an including the maximum number that is determined by the loading capacity of the PEG moiety.

In other instances, more than one PEG moiety may be attached to a single ion channel modulating compound. For instance, a PEGylated derivative may comprise an ion channel modulating compound with 2 PEG moieties attached to different sites on the ion channel modulating compound. In another instance, a PEGylated derivative comprises 3 or more PEG moieties attached to an ion channel modulating compound. A PEG moiety may be attached to any site on an ion channel modulating compound that is amenable to such attachment, as detailed in the "attachment site" section below.

In some variations, the PEGylated derivative comprises an ion channel modulating compound and a PEG moiety in a 1:1 molar ratio of ion channel modulating compound:PEG moiety. In other variations, the PEGylated derivative comprises an ion channel modulating compound and a PEG moiety in a 2:1 molar ratio of ion channel modulating compound:PEG moiety. In still other variations, the PEGylated derivative comprises an ion channel modulating compound and a PEG moiety in a molar ratio of ion channel modulating compound:PEG moiety of from about 1:1,000 to about 1,000:1; or, in yet another variation, in a molar ratio of from about 1:100 to about 100:1; or, in still a further variation, in a molar ratio of from about 1:10 to about 10:1.

A PEGylated derivative comprising two or more types of ion channel modulating compounds may have the ion channel modulating compounds present in the PEGylated derivative in any molar ratio of a first ion channel modulating compound to a second ion channel modulating compound, wherein the first and second ion channel modulating compounds are not the same. In some instances, the PEGylated derivative will comprise two different ion channel modulating compounds in a 1:1 molar ratio of a first ion channel modulating compound to a second ion channel modulating compound. In other instances, a PEGylated derivative may comprise two different ion channel modulating compounds, wherein a first ion channel modulating compound is about twice as abundant in the PEGylated derivative than the second ion channel modulating compound.

The PEG moiety of the PEGylated derivative may be any size or length. As used herein, the size of the PEG moiety refers to the overall molecular weight of the PEG moiety. As used herein, the length of the PEG moiety refers to the number of ethylene glycol units from which the PEG moiety is derived. The PEG moiety is described in more detail below in the section entitled, "PEG moiety".

Examples of PEGylated derivatives of ion channel modulating compounds may be found in the sections that follow.

A PEG moiety of a PEGylated derivative may be any moiety that comprises at least two ethylene glycol units (i.e. a —$OCH_2CH_2OCH_2CH_2O$— moiety). The PEG moiety may be solely comprised of PEG, or may be part of a larger structure, such as polyoxyethylated glycerol ("POG") and other polyoxyethylated polyols such as polyoxyethylated sorbitol or polyoxyethylated glucose.

The PEG moiety may be further substituted with one or more additional functional groups, including but not limited to: an alkane, an alkene, an alkyne, an arene, a halide, an alcohol, an ether, an amine, a nitrile, a nitro, a sulfide, a sulfoxide, a sulfone, a thiol, a carbonyl, an aldehyde, a ketone, a carboxylic acid, an ester, an amide, a carboxylic acid chloride, a carboxylic acid anhydride and the like, or any combination of the foregoing.

The PEG moiety may be present as a polymer of two or more ethylene glycol monomer units, and can be a homopolymer or a heteropolymer, either of which may be a straight chain or branched, substituted or unsubstituted polymer. If the PEG moiety is part of a heteropolymer, it may be present in a random or block copolymer.

The PEG moiety can be of any length or molecular weight, and these characteristics can affect the biological properties of the PEGylated derivative. PEG moiety average molecular weights which may be useful for decreasing clearance rates in vivo are generally in the range of 2,000 to 35,000 daltons. In addition, if two ion channel modulating compounds are linked to a bifunctional PEG moiety, for instance one at each terminus, the length of the PEG moiety can impact upon the effective distance, and other spatial relationships, between the two ion channel modulating compounds. Thus, one skilled in the art can vary the length of the PEG moiety to optimize or confer the desired biological activity.

The length of the PEG moiety, represented by $(Z)_n$, where Z is the monomeric ethylene glycol unit, may be such that n is any positive integer greater than 1. These lengths include variations where n is selected from a range of from about 2 to about 1000; in another instance, n is selected from a range of from about 50 to about 500; in another instance, n is selected from a range of from about 400 to 600, in another instance, n is selected from a range of from about 500 to about 1,000; in yet another instance, n is selected from a range of from about 50 to about 250; in still another instance, n is selected from a range of from about 2 to about 50. In certain instances, n is greater than 10 and in other instances, n is greater than 10. In still another instance, n is an integer from about 1,000 to about 5,000.

Attachment of a PEG moiety to an ion channel modulating compound may be by any means, including but not limited to a direct bond or via a linker as detailed in the "linker" section below. The PEG moiety may be attached to an ion channel modulating compound, either directly or via a linker from any site on the PEG moiety that is amenable to such attachment.

Typically, the attachment sites on a PEG moiety will be a reactive site at the terminus of a PEG polymer chain. Reactive sites are functional groups that may be utilized in the attachment of a PEG moiety to an ion channel modulating compound or linker. Examples of reactive sites include esters, alcohols and isocyanates. PEG moieties embedded within bifunctional groups may be used for the attachment of two ion channel modulating compounds to a single PEG moiety.

As described above, any ion channel modulating compound may be modified to form a PEGylated derivative of the ion channel modulating compound. The ion channel modulating compound to be modified to a PEGylated derivative may increase or decrease ion channel activity. In some instances, the ion channel modulating compound may be used in the treatment of arrhythmia. In still other instances, the ion channel modulating compound may be used in the treatment of atrial fibrillation. Specific ion channel modulating compounds for use in a PEGylated derivative are compounds of formula (I), (IA) and (IX) and Compound A, as described above.

In one variation, a compound of formula (I), as described above, is attached to a PEG moiety or linker by the substitution of any valency of a compound of formula (I) with a bond to the PEG moiety or to a linker that in turn is bound to the PEG moiety.

In another variation, a compound of formula (IA), as described above, is attached to a PEG moiety or linker by the substitution of any valency of a compound of formula (IA) with a bond to the PEG moiety or to a linker that in turn is bound to the PEG moiety. In one instance, a PEGylated derivative is provided, wherein the compound of formula (IA) is attached to the PEG moiety by the substitution of the valency occupied by hydrogen in the ⌇⌇OH moiety with a bond to the PEG moiety or to a linker that in turn is bound to the PEG moiety.

In another variation, a compound of formula (IX), as described above, is attached to a PEG moiety or linker by the substitution of any valency of a compound of formula (IX) with a bond to the PEG moiety or to a linker that in turn is bound to the PEG moiety.

In still another variation, Compound A, as described above, is attached to a PEG moiety or linker by the substitution of any valency of the compound with a bond to a PEG moiety or to a linker that in turn is bound to the PEG moiety. In one instance, a PEGylated derivative is provided, wherein Compound A is attached to a PEG moiety by the substitution of the valency occupied by hydrogen in the ⋯⋯⋯OH moiety with a bond to the PEG moiety or to a linker that in turn is bound to the PEG moiety. In still another variation on this variation, a second PEG moiety is attached to Compound A by the substitution of the valency occupied by one of the methyl groups of the —OMe groups with a bond to the second PEG moiety.

As noted above, an ion channel modulating compound may be attached to a PEG moiety or a linker that is in turn attached to a PEG moiety from any site on the ion channel modulating compound that is amenable to such attachment. That is, any atom or atoms on the ion channel modulating compound may be replaced with a covalent bond to a PEG moiety or a linker. For instance, a hydroxyl group or an amino group on the ion channel modulating compound may be modified to attach the ion channel modulating compound to the PEG moiety or linker. In another variation, an alkoxy group on the ion channel modulating compound is modified such that the oxygen containing functionality is used in the attachment of the ion channel modulating compound to the PEG moiety.

In general, when an ion channel modulating compound is modified to form a PEGylated derivative, at least one valency of the ion channel modulating compound is substituted with a bond to a PEG moiety or with a bond to a linker that is in turn bound to the PEG moiety. When a valency is said to be substituted with a bond, it is meant that any atom, unpaired electron, lone pair of electrons, or empty electron orbital present in the ion channel modulating compound may be replaced with a bond to the PEG moiety or to a linker. For instance, an ion channel modulating compound comprising a hydroxyl functional group may form a PEGylated derivative by the replacement of the hydrogen atom of an O—H moiety with a bond to a PEG moiety. Accordingly, a PEGylated derivative with an O—PEG moiety is provided.

An ion channel modulating compound may be attached to a PEG moiety by any method that is amenable thereto. By attached to the PEG moiety, it is meant that the ion channel modulating compound is attached either via a direct bond to the PEG moiety or via a linker that is in turn bound to the PEG moiety. An ion channel modulating compound may be attached to a linker or to a PEG moiety by any means, including but not limited to a covalent, ionic, hydrogen, dative, van der Waals, or other chemical bonding or any combination of chemical bonding. In a particular version, the ion channel modulating compound is attached to the PEG moiety via a covalent bond.

Mutually reactive groups on the PEG moiety and the ion channel modulating may be used to effect attachment thereof. Mutually reactive groups are recognized by those of skill in the art and examples of mutually reactive groups are described herein, in particular, in the Examples section below.

As noted above, the ion channel modulating compound may be attached to a PEG moiety either directly (i.e. by a direct bond) or via a linker. Typically, the ion channel modulating compound is bound to the PEG moiety or linker via a linkage group, including but not limited to an ester, ether, amide, carbamate, urea, N-hydroxyimide or boronate linkage group. If additional atoms are required to form the linkage group, a linker may be used, wherein the linker may be used to facilitate the formation of the linkage group.

A linker may be of any size, from a small moiety that is only used to facilitate the formation of the linkage bond, to a larger group which is employed as a connector and/or spacer group. These groups are collectively referred to as "linkers." In one variation, the linker comprises a group selected from an alkyl, aryl or alkoxy group.

A linker may be used as a spacer molecule to create a separation between the ion channel modulating compound and the PEG moiety, and/or to avoid undesired steric interactions. The spatial separation may be desired for modified, enhanced, or optimal function of the PEGylated derivative. The linkers may also facilitate the preparation or use of the PEGylated derivative.

Alternatively, the PEG moiety may be embedded in the linker, such that a PEG moiety is not the terminal group of the PEGylated derivative. Examples of embedded PEG moieties may be linkers comprising a terminal functional group including but not limited to an alkyl, substituted alkyl, alkene, substituted alkene or wherein the PEG embedded linker comprises an additional terminal group, such as a serum protein, including human serum albumin.

The linker may be primarily hydrophobic in nature or may be primarily hydrophilic in nature and may thus contribute to the overall hydrophobicity or hydrophilicity of the conjugate.

The linker may be cleavable or noncleavable. A cleavable linker comprises a bond that may be cleaved in vivo including but not limited to cleavage via enzymatic, non-enzymatic, or hydrolytic cleavage. An example of a cleavable linker includes a linker that includes an ester bond.

In synthesizing a PEGylated derivative comprising a linker, it may be useful to employ a linker that has at least two functional groups, one for bonding of the linker to the ion channel modulating compound and one for bonding of the linker to the PEG moiety.

In one variation, the linker molecule is a bifunctional linker molecule. A bifunctional linker molecule comprises two reactive termini, one of which is available for linkage to the ion channel modulating compound and one of which is available for linkage to the PEG moiety. The functional groups on the reactive termini may be the same or different.

In particular variations, a PEGylated derivative is provided, whereby the use of a linker, including linkers where the PEG moiety is embedded therein, gives rise to a PEG moiety in the PEGylated derivative selected from the group consisting of:

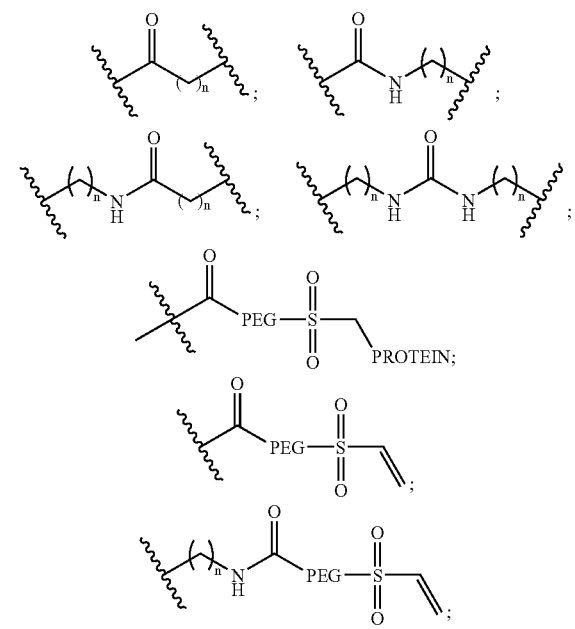

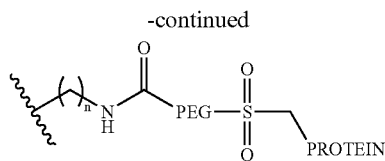

wherein each n is 1 to 10 and the symbol ∿∿∿ indicates a point of attachment to an ion channel modulating compound if the symbol is present only once in a structure above, and if the symbol ∿∿∿ is present twice in a structure above, it indicates one point of attachment to a PEG moiety and another point of attachment to an ion channel modulating compound.

In one variation of the formulae above, PEG is $(CH_2CH_2O)_n$ wherein n is an integer selected from any one of the ranges 1 to 1,000,000; 1 to 100,000; 1 to 10,000; 1 to 1000; 1 to 100; 1 to 10; 100 to 1,000; 100 to 10,000; 200 to 500; 200 to 800; 500 to 800; 800 to 1,000; 500 to 1,000; 500 to 10,000; 5,000 to 10,000; 5,000 to 100,000; 100 to 100,000; 1 to 8; 1 to 5; 2 to 10 and 4 to 10. In another variation, the PEG moiety of the formulas above is about 20 K in molecular weight. In another variation, the PEG moiety of the formulas above is about 10 K in molecular weight. In another variation, the PEG moiety of the formulas about is about 5 K in molecular weight.

Although any ion channel modulating compound may be modified to a PEGylated derivative thereof, examples of PEGylated compounds of formulae (I), (IA) and (IX) are provided below, as well as PEGylated Compound A.

Thus, in one aspect, PEGylated derivatives of compounds of formula (I) (PEGI), or a solvate or pharmaceutically acceptable salt thereof, is provided:

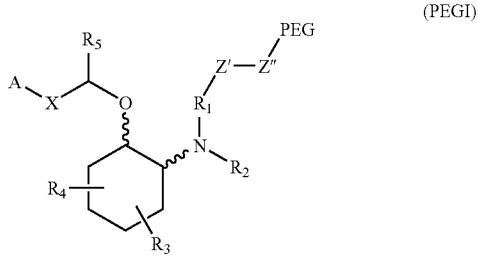

(PEGI)

wherein:

$R_1$ and $R_2$ are independently selected from hydrogen, $C_1$-$C_6$alkyl, $C_3$-$C_8$alkoxyalkyl, $C_1$-$C_8$hydroxyalkyl, and $C_7$-$C_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$ are taken together with the nitrogen atom to which they are directly attached in formula (PEGI), form a ring denoted by formula (PEG-Z-II):

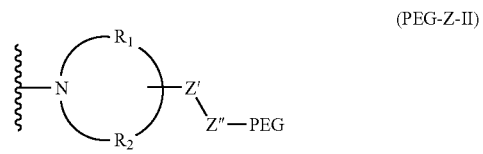

(PEG-Z-II)

wherein the ring of formula (PEG-Z-II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together with the nitrogen atom to which they are directly attached in formula (PEGI), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl, wherein the bicyclic ring is substituted with —Z'—Z"-PEG;

Z' is a linkage group;

Z" is an optional linker;

$R_3$ and $R_4$ are independently attached to the cyclohexane ring shown in formula (PEGI) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

X, Y, $R_5$, $R_6$, $R_{14}$ and A are as described above for compounds of formula (I); including isolated enantiomeric, diastereomeric and geometric isomers thereof, and mixtures thereof.

It is understood, for purposes of this invention, that the —Z'—Z"-PEG radical may be attached to the compound of formula (I) by the substitution of any valency of the compound of formula (I) to prepare compounds of formula (PEGI) and that the specific formulae depicted herein with the —Z'—Z"-PEG radical are for illustration purposes only and are not intended to provide a limitation to the scope of the invention.

In another aspect, other PEGylated derivatives of compounds of formula (I) (PEGII), or a solvate or pharmaceutically acceptable salt thereof, is provided:

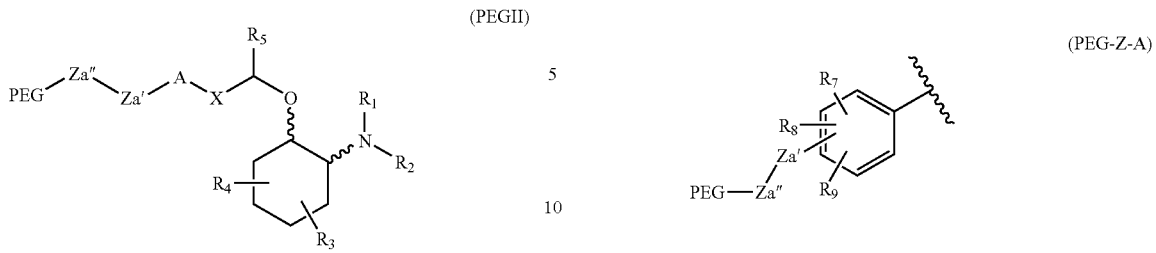

wherein:

X is selected from a direct bond, —C(R$_6$,R$_{11}$)—Y— and —C(R$_{13}$)=CH—;

Y is selected from a direct bond, O, S and C$_1$-C$_4$alkylene;

R$_{13}$ is selected from hydrogen, C$_1$-C$_6$alkyl, C$_3$-C$_8$cycloalkyl, aryl and benzyl;

R$_1$ and R$_2$ are independently selected from hydrogen, C$_1$-C$_6$alkyl, C$_3$-C$_8$alkoxyalkyl, C$_1$-C$_8$hydroxyalkyl, and C$_7$-C$_{12}$aralkyl; or R$_1$ and R$_2$ are independently selected from C$_3$-C$_8$alkoxyalkyl, C$_1$-C$_8$hydroxyalkyl, and C$_7$-C$_{12}$aralkyl; or R$_1$ and R$_2$ are taken together with the nitrogen atom to which they are directly attached in formula (PEGII), form a ring denoted by formula (II):

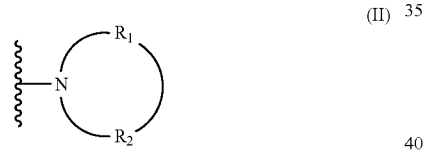

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, C$_1$-C$_3$hydroxyalkyl, oxo, C$_2$-C$_4$acyl, C$_1$-C$_3$alkyl, C$_2$-C$_4$alkylcarboxy, C$_1$-C$_3$alkoxy, C$_1$-C$_{20}$alkanoyloxy, or may be substituted to form a spiro five- or six-membered heterocyclic ring containing one or two heteroatoms selected from oxygen and sulfur; and any two adjacent additional carbon ring atoms may be fused to a C$_3$-C$_8$carbocyclic ring, and any one or more of the additional nitrogen ring atoms may be substituted with substituents selected from hydrogen, C$_1$-C$_6$alkyl, C$_2$-C$_4$acyl, C$_2$-C$_4$hydroxyalkyl and C$_3$-C$_8$alkoxyalkyl; or R$_1$ and R$_2$ are taken together with the nitrogen atom to which they are directly attached in formula (PEGII), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

A is selected from formulae (PEG-Z-A):

(PEG-Z-A)

where R$_7$ and R$_9$ are independently selected from bromine, chlorine, fluorine, carboxy, hydrogen, hydroxy, hydroxymethyl, methanesulfonamido, nitro, sulfamyl, trifluoromethyl, C$_2$-C$_7$alkanoyloxy, C$_1$-C$_6$alkyl, C$_1$-C$_6$alkoxy, C$_2$-C$_7$alkoxycarbonyl, where R$_8$ is hydroxy, hydroxymethyl or carboxy;

Za' is a linkage group;

Za" is an optional linker;

including isolated enantiomeric, diastereomeric and geometric isomers thereof, and mixtures thereof.

It is understood, for purposes of this invention, that the -Za'-Za"-PEG radical may be attached to the compound of formula (I) by the substitution of any valency of the compound of formula (I) to prepare compounds of formula (PEGII) and that the specific formulae depicted herein with the -Za"-Za"-PEG radical are for illustration purposes only and are not intended to provide a limitation to the scope of the invention.

In another aspect, still other PEGylated derivatives of compounds of formula (I) (PEGIII), or a solvate or pharmaceutically acceptable salt thereof, is provided:

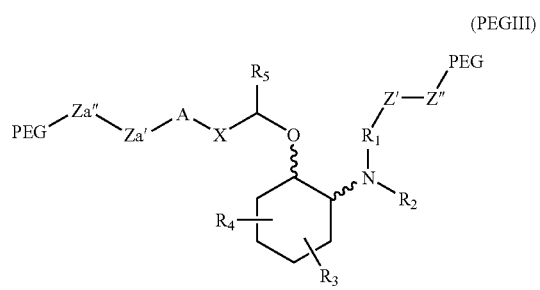

wherein:

X is selected from a direct bond, —C(R$_6$,R$_{14}$)—Y— and —C(R$_{13}$)=CH—;

Y is selected from a direct bond, O, S and C$_1$-C$_4$alkylene;

R$_{13}$ is selected from hydrogen, C$_1$-C$_6$alkyl, C$_3$-C$_8$cycloalkyl, aryl and benzyl;

R$_1$ and R$_2$ are independently selected from hydrogen, C$_1$-C$_6$alkyl, C$_3$-C$_8$alkoxyalkyl, C$_1$-C$_8$hydroxyalkyl, and C$_7$-C$_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$ are taken together with the nitrogen atom to which they are directly attached in formula (PEGIII), form a ring denoted by formula (PEG-Z-II):

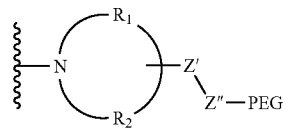

(PEG-Z-II)

wherein the ring of formula (PEG-Z-II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together with the nitrogen atom to which they are directly attached in formula (PEGIII), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl, wherein the bicyclic ring is substituted with —Z'—Z"-PEG;

Z' is a linkage group;

Z" is an optional linker;

$R_3$ and $R_4$ are independently attached to the cyclohexane ring shown in formula (PEGIII) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from formulae (PEG-Z-A):

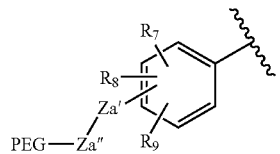

(PEG-Z-A)

where $R_7$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, and where $R_8$ is hydroxy, hydroxymethyl or carboxy;

Za' is a linkage group; and

Za" is an optional linker;

including isolated enantiomeric, diastereomeric and geometric isomers thereof, and mixtures thereof.

It is understood, for purposes of this invention, that the —Z'—Z"-PEG radical or the -Za'-Za"-PEG radical may be attached to the compound of formula (I) by the substitution of any valency of the compound of formula (I) to form a compound of formula (PEGIII) and that the specific formulae depicted herein containing both the —Z'—Z"-PEG radical and -Za'-Za"-PEG radical are for illustration purposes only and are not intended to provide a limitation to the scope of the invention.

Various methods of attaching a PEG moiety to a compound are well known in the art and would be readily recognized by one of skill in the art. Examples of such methods may be found in the examples below.

A PEG moiety may be attached directly to an ion channel modulating compound, whereby a linkage group, or bond, is formed. If a linker is used, the linker may be attached to the ion channel modulating compound via a linkage group, followed by addition of the PEG moiety to the linker. This step-wise fashion may take place by known synthetic methods. Alternatively, a PEG moiety may be attached to a linker and then attached to the ion channel modulating compound as a PEG moiety-linker compound.

In one variation, attachment of a PEG moiety to an ion channel modulating compound comprising an aminocycloalkyl ether moiety, such as an aminocyclcohexyl ether moiety, is provided via a linkage group (Z') and an optional linker, (Z"). A PEGylated derivative, such as the compounds (PEGI), (PEGII) or (PEGIII) as described above and as prepared as described below in General Reaction Scheme PEG-1 below, are provided. In general, a PEGylated derivative may be provided by conjugation of an ion channel modulating compound to a PEG moiety via a linkage group, and optionally, with the use of a linker. The scheme below is generally applicable to ion channel modulating compounds comprising an aminocycloalkyl ether moiety as set forth in the compounds of formulae (I), (IA) and (IX) and Compound A. In the scheme below, Z' and Za' represent a linkage group that may be formed upon reacting an ion channel modulating compound with a PEG moiety or with a linker/PEG moiety complex (i.e, Z"-PEG and Za"-PEG).

General Reaction Scheme PEG-1 Synthesis of PEGylated Derivatives

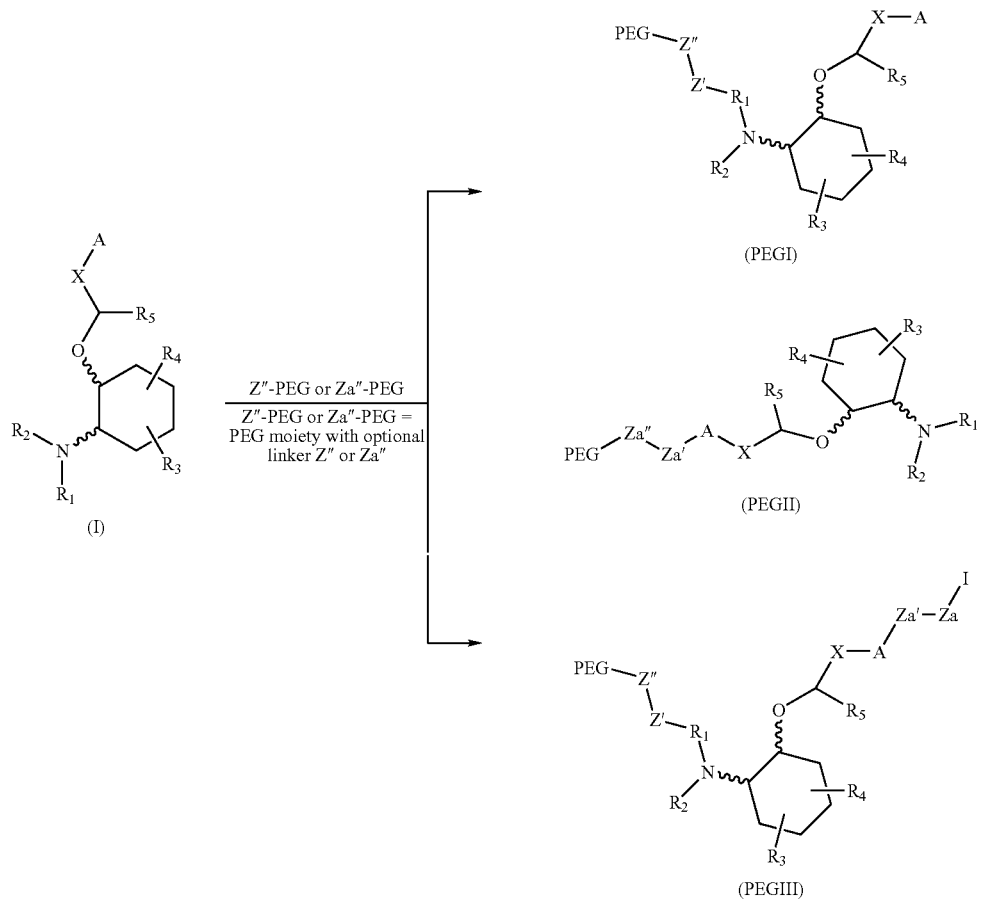

Further methods for preparing PEGylated derivatives may be found according to the following specific Examples P1-P8.

The following examples describe methods for preparing PEGylated derivatives as described herein. The reaction steps as described below may be used in the preparation of the derivatives, or alternate reaction steps may be used. Alternate reaction steps would be readily recognized by one of skill in the art and include the reaction steps described "Comprehensive Organic Transformations: A Guide to Functional Group Preparations", Richard C. Larock, Wiley-VCH: 1999 and in "March's Advanced Organic Chemistry: Reactions, Mechanisms and Structure", Jerry March & Michael Smith, John Wiley & Sons Inc: 2001.

Commercially available PEGs of many different types and molecular weights can be obtained from Nektar Therapeutics, SunBio, Serva (Crescent Chemical Co.) and Fluka (Sigma-Aldrich) and include examples such as but not limited to activated PEG-NHS ester reagents and NHS PEG vinyl sulfone. These activated PEG reagent examples may be used to conjugate directly with the aminocycloalkyl ether compounds. Polypure AS, Norway, supplies monodisperse PEG and PEG derivatives that are consisted of substantially one oligomer only. Where appropriate, these monodisperse PEG and PEG derivatives may be advantageously utilized to form more well defined PEG derivatives of the present invention.

PEG derivatives of the present invention may also be synthesized by standard methods from commercially available starting materials. For example, PEG (40 kDa) dicarboxylic acid may be synthesized from the commercially available PEG diol. In a typical reaction, a solution of PEG diol in a suitable solvent (e.g., toluene) may be azeotroped with the removal of a pre-determined amount of distillate. The reaction mixture may be allowed to cooled to 30° C. followed by addition of 1 M potassium tert-butoxide in tert-butyl alcohol. The resulting mixture may be stirred at ambient temperature for approximately 1 h followed by addition of ethyl bromoacetate. The solution may be heated to reflux and stirred at ambient temperature for 18 h. The reaction mixture may then be filtered and solvent removed. The resulting residue may be purified/recrystallized to yield the pure PEG (40 kDa) dicarboxylic acid (see, e.g., Greenwald R. B., Gilbert C. W., Pendri A., Conover C. D., Xia J., Martinez J. Med. Chem. 1996, 39, 424).

The following examples are illustrative of the PEGylated derivatives of the invention wherein Compound A is indicated as compound (A) in the reaction schemes:

Example P1

Synthesis of the PEG-Compound A Derivative (P3) from Compound A and (P2)

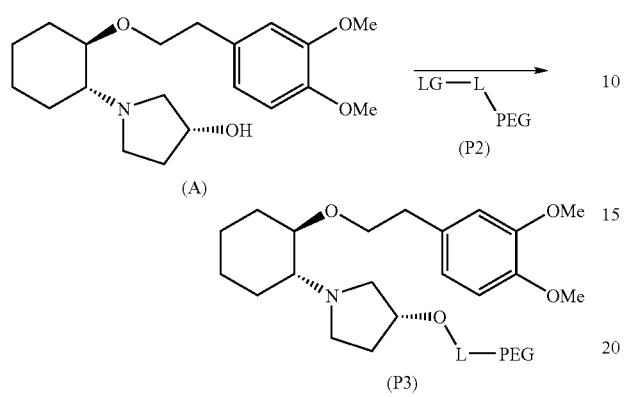

LG = good leaving group on reaction with hydroxy function
L = optional linker group In a typical reaction, to a solution of PEG linker (P2) in a suitable solvent (e.g., anhydrous DMF) may be added COMPOUND A and DMAP, and the mixture may be stirred for about 12 h at a suitable temperature. Ethyl ether may then be added to the reaction solution with stirring to effect the precipitation of PEG derivative (P3). The mixture may be stored at about −20° C. for about 12 h and the crude solid collected by filtration. The product may be further purified by re-crystallization to yield (P3).

Example P2

Synthesis of an Ester-Linked PEG-Compound A Derivative (P5) from Compound A and (P4) (MPEG-Succinimidyl Propionate; MW 2K, 20K)

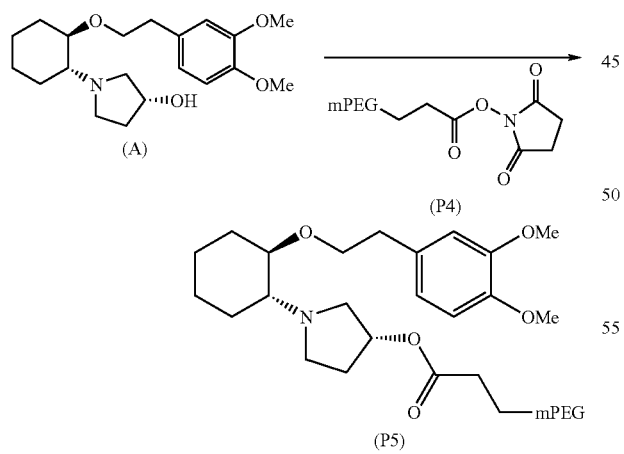

In a typical reaction, to a solution of PEG linker (P4) in a suitable solvent (e.g., anhydrous DMF) may be added COMPOUND A and DMAP, and the mixture may be stirred for 12 h at ambient temperature Ethyl ether may then be added to the reaction solution with stirring to effect the precipitation of PEG derivative (P5). The mixture may be stored at about −20° C. for about 12 h and the crude solid collected by filtration. The product may be further purified by re-crystallization to yield (P5).

Example P3

Synthesis of an Ester Linked PEG-Compound A Derivative (P7) from Compound A and (P6) (MPEG-Succinic Acid MW 2K, 20K) (DIPC=Diisopropylcarbodiimide and DMAP=Dimethylaminopyridine)

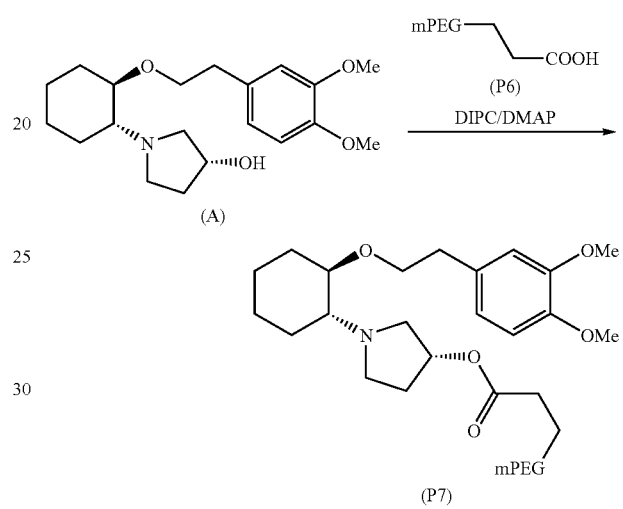

In a typical reaction, to a solution of PEG linker (P6) in a suitable solvent (e.g., anhydrous DMF) may be added COMPOUND A and DMAP, and the mixture may be stirred for 12 h at ambient temperature. Ethyl ether may then be added to the reaction solution with stirring to effect the precipitation of PEG derivative (P7). The mixture may be stored at about −20° C. for about 12 h and the crude solid collected by filtration. The product may be further purified by re-crystallization to yield (P7).

Example P4

Synthesis of a Carbamate Linked PEG-Compound A Derivative (P9) from Compound A and (P8) (MPEG-Isocyanate MW 2K, 20K)

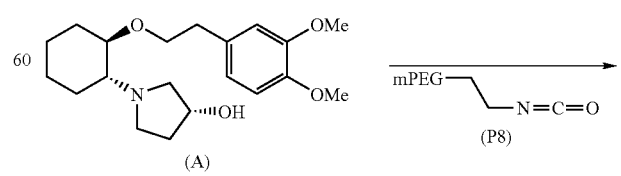

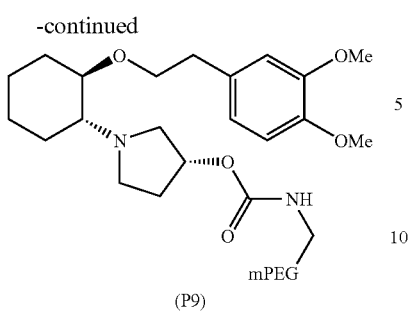

(P9)

In a typical reaction, to a solution of PEG linker (P8) in a suitable solvent (e.g., anhydrous DMF) may be added COMPOUND A and DMAP, and the mixture may be stirred for 12 h at ambient temperature. Ethyl ether may then be added to the reaction solution with stirring to effect the precipitation of PEG derivative (P9). The mixture may be stored at about −20° C. for about 12 h and the crude solid collected by filtration. The product may be further purified by re-crystallization to yield (P9).

Example P5

Synthesis of Ester Linked PEG-Dicompound A Derivative (P11) from Compound A and (P10) (PEG-(Succinic Acid)$_2$ MW 10K)

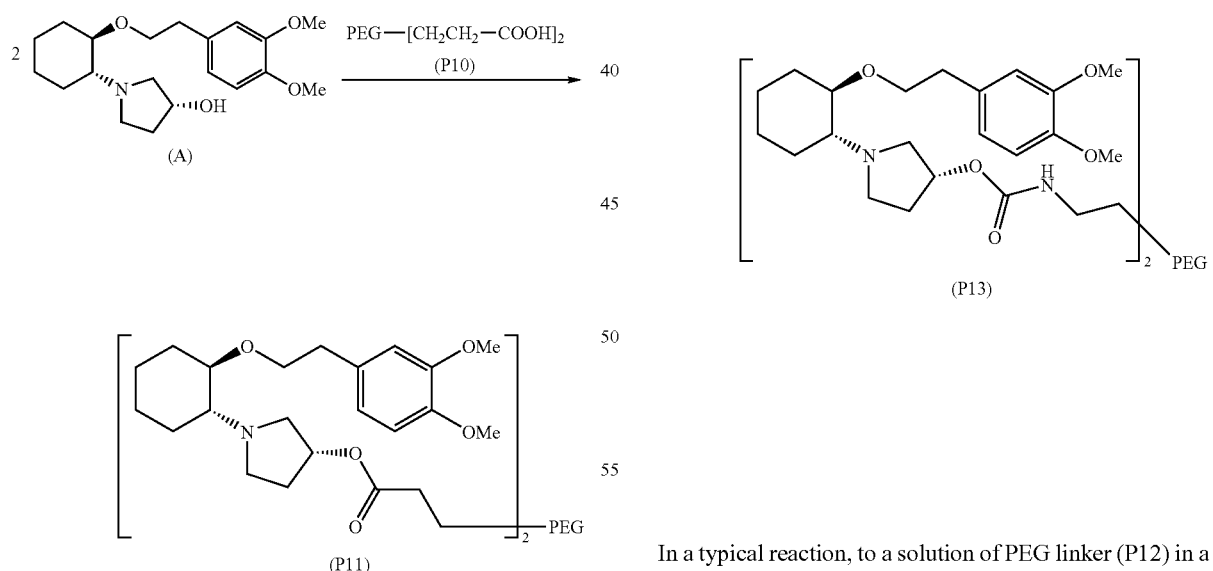

In a typical reaction, to a solution of PEG linker (P10) in a suitable solvent (e.g., anhydrous DMF) may be added COMPOUND A and DMAP, and the mixture may be stirred for 12 h at ambient temperature. Ethyl ether may be then added to the reaction solution with stirring to effect the precipitation of PEG derivative (P11). The mixture may be stored at about −20° C. for about 12 h and the crude solid collected by filtration. The product may be further purified by re-crystallization to yield (P11).

Example P6

Synthesis of Carbamate Linked PEG-Dicompound A Derivative (P13) from Compound A and (P12) (PEG-(Isocyanate)$_2$ MW 10K)

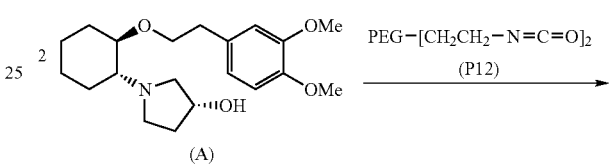

In a typical reaction, to a solution of PEG linker (P12) in a suitable solvent (e.g., anhydrous DMF) may be added COMPOUND A and DMAP, and the mixture may be stirred for 12 h at ambient temperature. Ethyl ether is then added to the reaction solution with stirring to effect the precipitation of PEG derivative (P13). The mixture may be stored at about −20° C. for about 12 h and the crude solid collected by filtration. The product may be further purified by re-crystallization to yield (P13).

Example P7

Synthesis of Ester Linked PEG-Thiol-Reactive Derivative (P15) from Compound A and (P14) (NHS Vinyl Sulfone NHS PEG VS.)

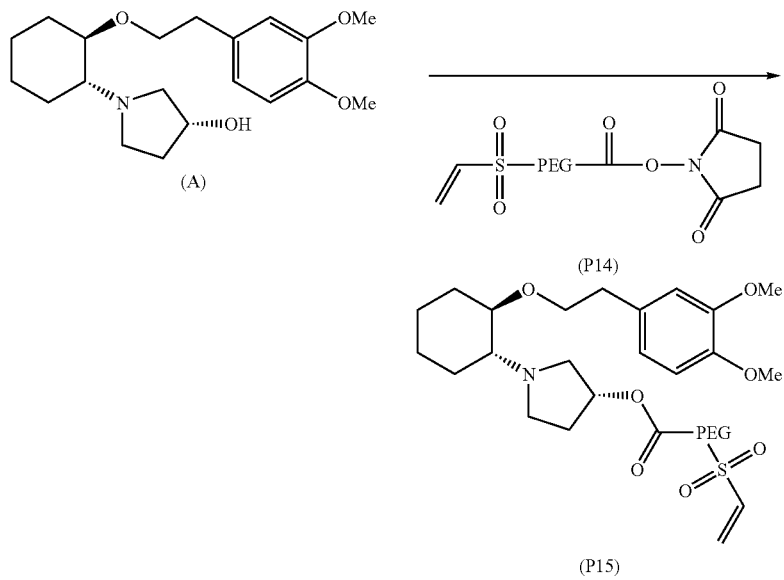

In a typical reaction, to a solution of PEG linker (P14) in a suitable solvent (e.g., anhydrous DMF) may be added COMPOUND A and DMAP, and the mixture may be stirred for 12 h at ambient temperature. Ethyl ether may then be added to the reaction solution with stirring to effect the precipitation of PEG derivative (P15). The mixture may be stored at about −20° C. for about 12 h and the crude solid collected by filtration. The product may be further purified by re-crystallization to yield (P15).

Example P8

Conjugation of PEG-Thiol-Reactive Derivative (P15) with Thiol Function of Albumin to Generate the PEG-Compound A-Albumin Derivative (P16)

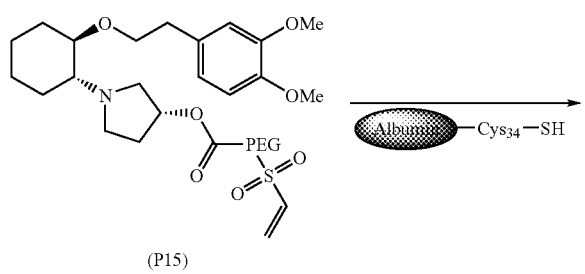

The conjugation of thiol-reactive derivative (P15) with the thiol functionality of albumin to generate the albumin derivative (P16). The single free thiol group of albumin, highly conserved among species, is located at amino acid residue $Cys_{34}$. It has been demonstrated recently that the $Cys_{34}$ of albumin has an increased reactivity relative to free thiols on other free thiol-containing proteins. This is due in part to the very low pKa value of 5.5 for the $Cys_{34}$ of albumin. This is much lower than typical pK values for cysteine residues in general, which are typically about 8. Owing to this low pK, under normal physiological conditions, $Cys_{34}$ of albumin is predominantly in the ionized form, which dramatically increases its reactivity. In addition to the low pK value of $Cys_{34}$, another factor which enhances the reactivity of $Cys_{34}$ is its location, which is in a crevice close to the surface of one loop of region V of albumin (see, e.g., Sugio S., Kashima A., Mochizuki S., Noda M., Kobayashi K., Prot. Eng. 1999, 12, 439 and references therein). This location makes $Cys_{34}$ accessible to ligands of all kinds, and is an important factor in the biological roles of Cys$_{34}$ as a free radical trap (e.g., Davies M. J., Gilbert B. C., Haywood R. M., Free Radic. Res. Commun. 1993, 18, 353) and free thiol scavenger (e.g., Soriani M., Pietraforte D., Minetti M., Arch. Biochem. Biophys. 1994, 312, 180). As a result, the reaction rate acceleration can be as much as 1000-fold relative to rates of reaction with other free-thiol containing proteins.

In another variation, methods are provided for preparing PEG-aminocycloalkyl ether compounds comprising the following reaction steps according to General Reaction Schemes PEG2 and PEG3 and Examples P9-P14.

The aminoethers described in the present invention may be prepared from aminoalcohols and alcohols by following the general methods and specific experimental procedures described below.

General Reaction Scheme PEG-2 Preparation of Compounds 21(a) and 21(a)

The Williamson ether synthesis (see, e.g., Feuer, H.; Hooz, J. Methods of Formation of the Ether Linkage, In *Patai*, Wiley: New York, 1967; pp 445-492) between the activated chloride form (37a) of aminoalcohol (18a) and the alkoxide of the appropriate phenethyl alcohol (19a) or (19b) in a polar solvent such as DME (General Reaction Scheme PEG2) provide the corresponding aminoether in high yield. Subsequent hydrogenolysis of (20a) or (20b) provide (21a) or (21b).

Reaction of benzyl alcohol with 2-bromoethyl isocyanate or 4-bromobutyl isocyanate (see Minin, Patricia L. and Walton, John C. *J. Org. Chem.* 2003, 68, 2960-2963) in dichloromethane at ambient temperature gives intermediates (17a) and (17b), respectively (General Reaction Scheme PEG-2). Subsequent reaction of homovanillyl alcohol with intermediates (17a) and (17b) in the presence of sodium carbonate and in a polar solvent such as DMF give precursors (19a) and (19b), respectively.

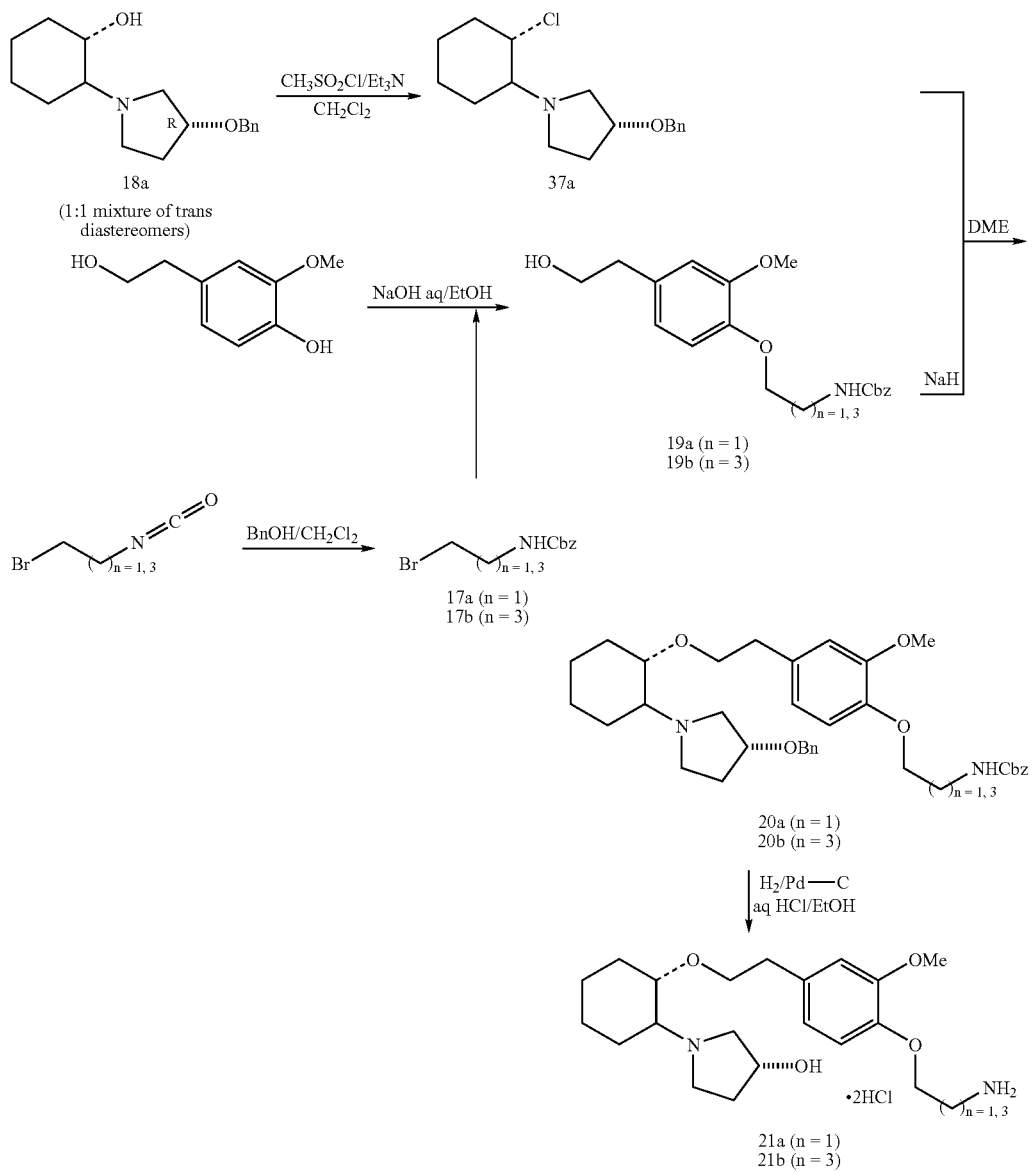

The following example provides specific details on the preparation of Compound (37a).

(1R,2R)/(1S,2S)-1-[(3R)-benzyloxypyrrolidinyl]-2-chlorocyclohexane (37a)

A recent study has established that activation of 18a with methanesulfonyl chloride gives the corresponding chloride 37a. To a chilled (0° C.) solution of 18a (16.151 g, 58.7 mmol) and Et$_3$N (1.25 eq., 10.2 mL, 73.4 mmol) in anhydrous CH$_2$Cl$_2$ (250 mL) was added dropwise neat methanesulfonyl chloride (5.65 mL, 73.4 mmol). The reaction mixture was stirred at 0° C. for 30 min and then at ambient temperature for 20 h. The reaction mixture was concentrated in vacuo, and the resulting residue was partitioned between a mixture of H$_2$O-2M NaHCO$_3$ aq (1:1, v/v, 150 mL) and diethyl ether (150 mL). The aqueous layer was separated and extracted twice more with diethyl ether (2×150 mL). The organic extracts were combined and dried over anhydrous magnesium sulfate. Concentration of the organic layer in vacuo and further removal of residual volatile materials under high vacuum yielded the crude chloride 37a as a viscous oil (15.25 g). R$_f$ 0.81 (EtOAc-iPrNH$_2$, 95:5, v/v); $^1$H NMR (300 MHz, CDCl$_3$) δ 7.36-7.22 (m, 5H, Ar), 4.53-4.41 (m, 2H, AB coupling), 4.19-4.02 (m, 2H), 3.14-2.97 (m, 1H), 2.92-2.53 (m, 4H), 2.38-2.18 (m, 1H), 2.18-1.80 (m, 3H), 1.79-1.60 (m, 3H), 1.52-1.20 (m, 3H); $^{13}$C NMR (75 MHz, CDCl$_3$, APT) δ 138.36(+), 128.26(−), 127.54(−), 127.44(−), 77.81/77.70(−), 70.92/70.83(+), 65.04/64.91(−), 61.32/61.16(−) 56.39/56.29 (+), 54.96(+), 48.86(+), 47.54/47.36(+), 33.36/33.18(+), 31.21(+), 24.76/24.68(+), 23.19/23.06(+), 22.48/22.40(+); MS (ES) [M+H, Cl$^{35}$]$^+$ 294.0 [M+H, Cl$^{37}$]$^+$ 296.0

General Reaction Scheme PEG-3 Preparation of Compound 18(a)

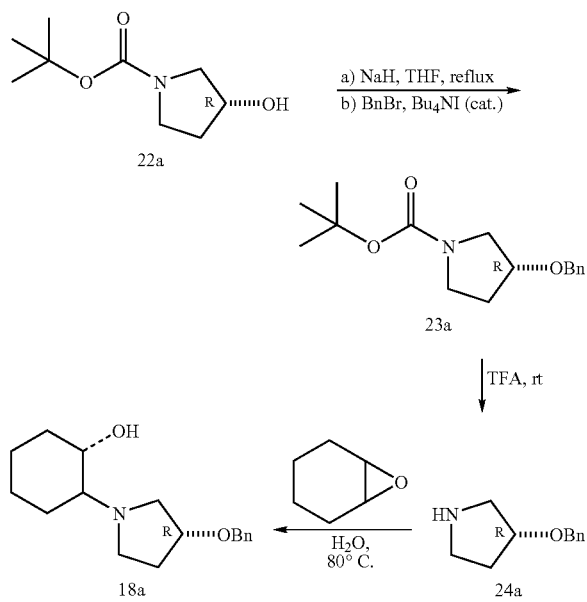

Aminoalcohols used in General Reaction Scheme PEG-2 were prepared by typical S$_N$2 cyclohexene oxide opening with the secondary amine of choice in the presence of water which provides aminoalcohols with an anti relationship relative to the cyclohexane ring. More specifically, aminoalcohol (18a) (General Reaction Scheme PEG-3) required the preparation of amine (24a). N-Boc-3-(R)-pyrrolidinol (22a) was benzylated with benzyl bromide to give (23a), hydrolysis of the carbamate protecting group in the presence of trifluoroacetic acid provided (24a). Cyclohexene oxide ring opening with (24a) in water gave aminoalcohol (18a).

The following examples provide specific details on the preparation of Compounds (23a), (24a), and (18a).

N-tert-Butoxycarbonyl-3R-benzyloxypyrrolidine (23a)

A suspension of sodium hydride (8.08 g, 269 mmol, 80%) in anhydrous THF (100 mL) was stirred, allowed to settle and the supernatant was discarded. The grey residue was washed with THF (2×50 mL) and then re-suspended in THF (700 mL). To the cold (0° C.), stirred suspension of sodium hydride was added dropwise a solution of 22a (41.7 g, 223 mmol) in THF (200 mL) and the resultant mixture was refluxed for 1 h. After the reaction mixture had cooled to ambient temperature, benzyl bromide (26.5 mL, 223 mmol) and tetrabutylammonium iodide (8.20 g, 22.3 mmol) were successively added. The mixture was stirred at ambient temperature for 18 h and then concentrated under reduced pressure. To the residue was added brine (300 mL) and water (50 mL), and the pH of the resultant mixture was adjusted to neutrality with 1M aq HCl. This mixture was extracted with hexane (100 mL), and the hexane extract was dried (MgSO$_4$ anhydr) and concentrated under reduced pressure to give 64.3 g (>98% yield) of a yellow oil, which was shown by GC analysis to consist almost exclusively of the desired product. A small amount of the oil was subjected to flash column chromatography on silica gel eluted with hexane-ethyl acetate (3:1) to give 23a as a colourless oil, which crystallized on standing. R$_f$ 0.58 (CHCl$_3$-MeOH, 4:1, v/v), $^1$H NMR (400 MHz, CDCl$_3$) δ 7.35-7.25 (m, 5H), 4.58-4.47 (m, 2H), 4.12 (br s, 1H), 3.55-3.40 (m, 4H), 2.10-2.00 (m, 1H), 2.00-1.90 (m, 1H), 1.48 (s, 9H); $^{13}$C NMR (75 MHz, CDCl$_3$) δ 154.5, 138.0, 128.3, 127.6, 79.1, 77.7, 76.8, 70.8, 51.4, 50.7, 44.0, 43.6, 31.4, 30.4, 28.4; IR (film) 2975, 1691, 1410 cm$^{-1}$; HRMS m/z calcd for C$_{16}$H$_{23}$NO$_3$ (M$^+$) 277.16779, found 277.16790.

3R-Benzyloxypyrrolidine (24a)

A mixture of trifluoroacetic acid (50 mL) and 23a (20 g, 72 mmol) was stirred at ambient temperature for 1 h and then concentrated under reduced pressure. The residue was taken up in water (250 mL) and the resultant acidic aqueous solution was extracted with Et$_2$O (2×150 mL). To the acidic aqueous layer was carefully added in portions solid NaHCO$_3$ until saturation. The basic aqueous solution was then extracted with CH$_2$Cl$_2$ (2×150 mL) and the combined organic extracts were dried (Na$_2$SO$_4$ anhydr). Evaporation of the solvent in vacuo yielded 8.0 g of 24a (62% yield). R$_f$ 0.24 (CHCl$_3$-MeOH, 9:1, v/v), $^1$H NMR (400 MHz, CDCl$_3$) δ 7.40-7.17 (m, 5H), 4.43 (s, 2H), 4.09-4.03 (m, 1H), 3.10-2.98 (m, 2H), 2.85-2.70 (m, 2H), 2.46 (s, 1H), 1.90-1.78 (m, 2H); IR (film) 3400, 1452, 1100, 1068 cm$^{-1}$.

(1R,2R)-1-(1S,2S)-1-[(3R)-benzyloxypyrrolidinyl]cyclohexan-2-ol (18a)

A mixture of cyclohexene oxide (12.5 mL, 120.9 mmol), 24a (14.3 g, 80.6 mmol) and water (6 mL) was heated at 80° C. for 9.5 h, after which GC analysis revealed complete consumption of 24a. The reaction mixture was allowed to cool to ambient temperature and diluted with water (140 mL).

By the addition of 1M aq HCl (55 mL), the pH was adjusted to 4.6 and the mixture was extracted with Et$_2$O (2×200 mL). After the aqueous layer was adjusted to pH 12.5 by the addition of 40% aq NaOH (NaCl may be added to effect separation into 2 clear layers), it was extracted with Et$_2$O (1×400 mL, 1×200 mL). The combined Et$_2$O extracts (from basic aqueous layer) were dried (Na$_2$SO$_4$ anhydr), and concentrated under reduced pressure and then in vacuo at 55° C. with stirring, to give 18a as an orange oil (15.9 g, 72%) of 96% purity (GC). R$_f$ 0.24 (EtOAc-iPrNH$_2$, 98:2, v/v); $^1$H NMR (200 MHz, CDCl$_3$) δ 7.4-7.2 (m, 5H), 4.5 (s, 2H), 4.2-4.0 (m, 1H), 3.9 (br s, 1H), 3.4-3.2 (m, 1H), 3.0-2.5 (m, 4H), 2.4 (t, J 10 Hz, 1H), 2.2-1.9 (m, 2H), 1.9-1.6 (m, 4H), 1.3-1.1 (m, 4H); $^{13}$C NMR (75 MHz, CDCl$_3$) δ 138.30, 128.35, 127.61, 127.55, 77.98, 77.71, 71.07, 71.01, 70.52, 70.45, 64.96, 64.89, 54.16, 52.74, 46.83, 45.43, 33.24, 31.53, 31.34, 25.20, 24.13, 21.40, 21.33; IR (film) 3450 (broad) cm$^{-1}$.

Derivatized COMPOUND A (46a,b) may be preferred for the preparation of compounds (25a,b-30a,b). An alternate route is exemplified below in General Reaction Schemes PEG4 and PEG5.

In the following Reaction Schemes PEG4 and PEG5, the Williamson ether synthesis between the chloride (44) and the alkoxide of the appropriate phenethyl alcohol (19a) or (19b) in a polar solvent such as DME (General Reaction Scheme PEG4) provide the corresponding aminoether in high yield. Subsequent hydrogenolysis of (45a) or (45b) provide (46a) or (46b).

Aminoalcohol (43) (General Reaction Scheme PEG5) requires the preparation of amine (42). N-Benzyl-3-(R)-pyrrolidinol (40) is silylated with tert-butyldimethylsilyl chloride and imidazole in DMF to give (41), hydrogenolysis of the benzyl protecting group provides (42). Cyclohexene oxide ring opening with (42) in water gives aminoalcohol (43).

In a typical reaction, to a solution of PEG linker (General Reaction Scheme PEG-4) in a suitable solvent (e.g., anhydrous CH$_2$Cl$_2$) is added derivatized COMPOUND A (46a,b) and Et$_3$N, and the mixture is stirred for 12 h at ambient temperature. Ethyl ether is then added to the reaction solution with stirring to effect the precipitation of the silylated protected intermediate. Subsequent deprotection of the silyl group with tetra-butyl ammonium fluoride (TBAF) provide PEG derivative (25a,b). The mixture is stored at about −20° C. for about 12 h and the crude solid collected by filtration. The product may be further purified by recrystallization to yield pure (25a,b).

General Reaction Scheme PEG-4 Preparation of Compounds 46(a) and 46(b)

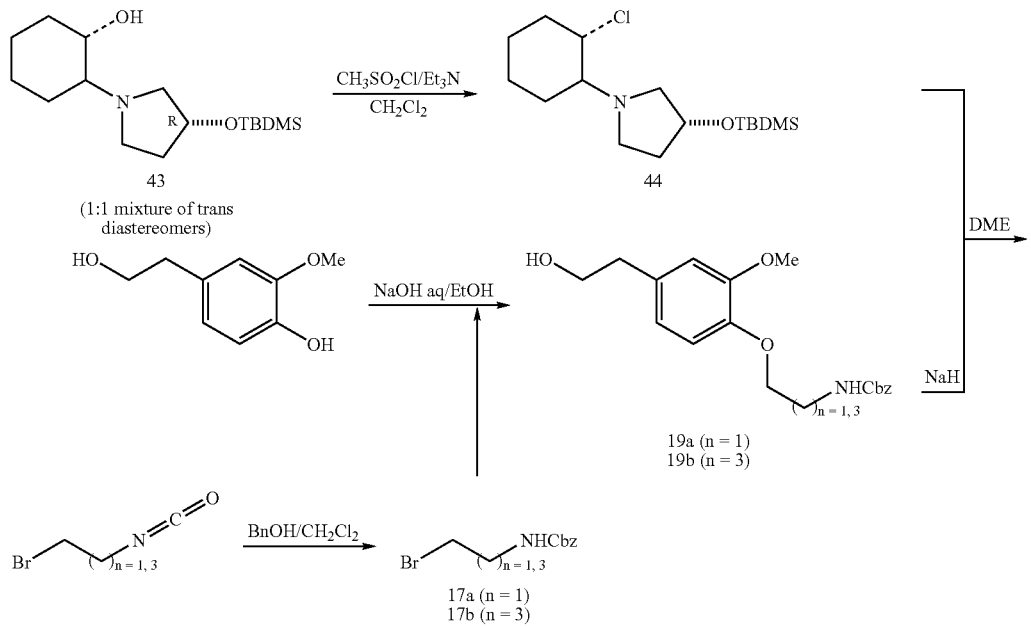

-continued
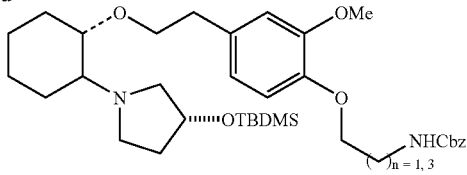
45a (n = 1)
45b (n = 3)
↓ H₂/Pd—C/EtOH
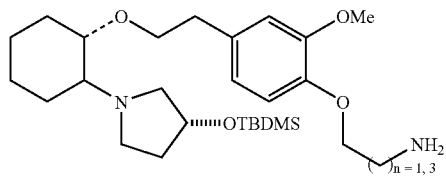
46a (n = 1)
46b (n = 3)
General Reaction Scheme PEG-5 Preparation of Compound 43
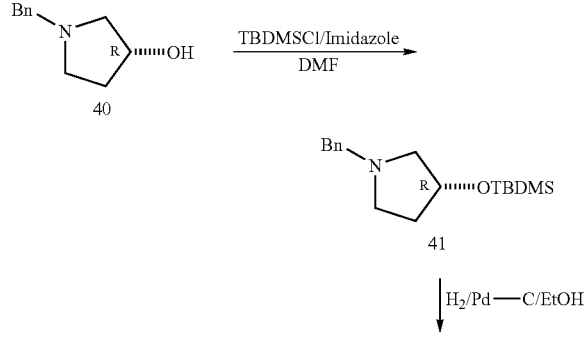
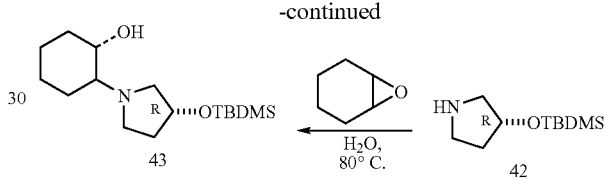
The following examples provide specific details on the preparation of PEGylated derivatives of the invention.
Example P9
Synthesis of an Amide Linked PEG-Compound A Derivative (25a,b) from Derivative Compound A (21a,b) and (P4) (MPEG-Succinimidyl Propionate MW 2K, 20K)
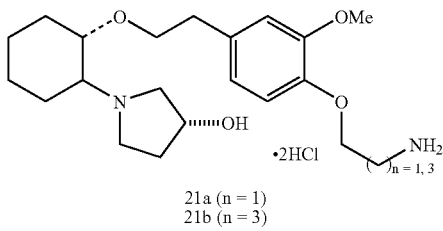
21a (n = 1)
21b (n = 3)
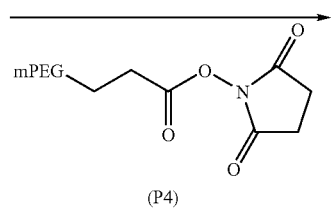
(P4)

-continued

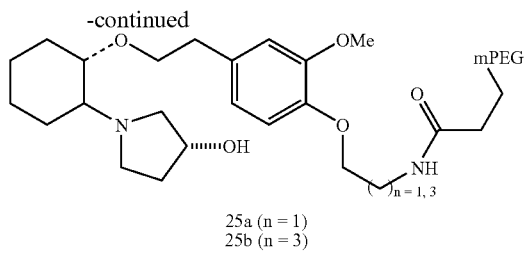

25a (n = 1)
25b (n = 3)

In a typical reaction, to a solution of PEG linker (P4) in a suitable solvent (e.g., anhydrous $CH_2Cl_2$) may be added to derivatized COMPOUND A (21a,b) and $Et_3N$, and the mixture may be stirred for 12 h at ambient temperature. Ethyl ether may then be added to the reaction solution with stirring to effect the precipitation of PEG derivative (25a,b). The mixture may be stored at about −20° C. for about 12 h and the crude solid collected by filtration. The product may be further purified by re-crystallization to yield (25a,b).

Example P10

Synthesis of an Amide Linked PEG-Compound A Derivative (26a,b) from Derivative Compound A (21a,b) and (P6) (MPEG-Succinic Acid MW 2K, 20K) (DIPC=Diisopropylcarbodiimide and DMAP=Dimethylaminopyridine)

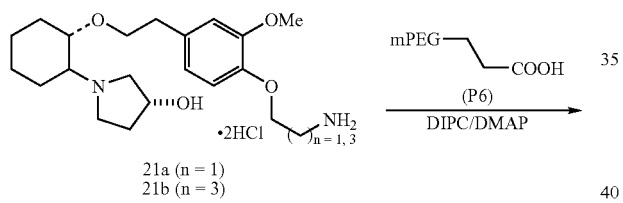

21a (n = 1)
21b (n = 3)

-continued

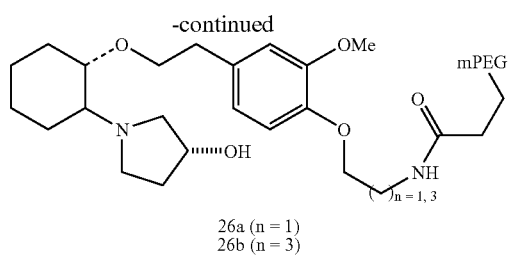

26a (n = 1)
26b (n = 3)

In a typical reaction, to a solution of PEG linker (P6) in a suitable solvent (e.g., anhydrous $CH_2Cl_2$) may be added to derivatized COMPOUND A (21a,b) and DIPC/DMAP, and the mixture may be stirred for 12 h at ambient temperature. Ethyl ether may then be added to the reaction solution with stirring to effect the precipitation of PEG derivative (26a,b). The mixture may be stored at about −20° C. for about 12 h and the crude solid collected by filtration. The product may be further purified by re-crystallization to yield (26a,b).

Example P11

Synthesis of an Urea Linked PEG-Compound A Derivative (27a,b) from Derivatized Compound A (21a,b) and (P8) (MPEG-Isocyanate MW 2K, 20K)

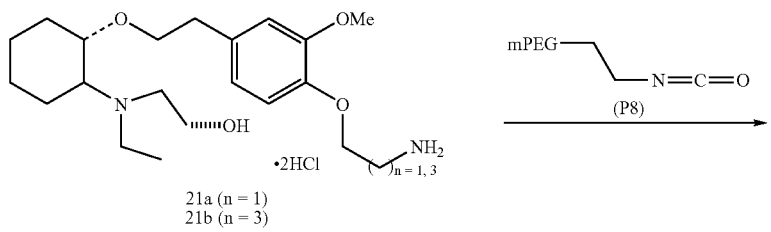

21a (n = 1)
21b (n = 3)

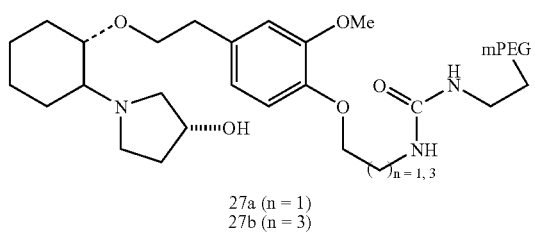

27a (n = 1)
27b (n = 3)

In a typical reaction, to a solution of PEG linker (P8) in a suitable solvent (e.g., anhydrous $CH_2Cl_2$) may be added to derivatized COMPOUND A (21a,b) and $Et_3N$, and the mixture may be stirred for 12 h at ambient temperature. Ethyl ether may then be added to the reaction solution with stirring to effect the precipitation of PEG derivative (27a,b). The mixture may be stored at about −20° C. for about 12 h and the crude solid collected by filtration. The product may be further purified by re-crystallization to yield (27a,b).

Example P12

Synthesis of Amide Linked PEG-Dicompound A Derivative (28a,b) from Derivatized Compound A (21a,b) and (P10) (PEG-(Succinic Acid)$_2$ MW 10K)

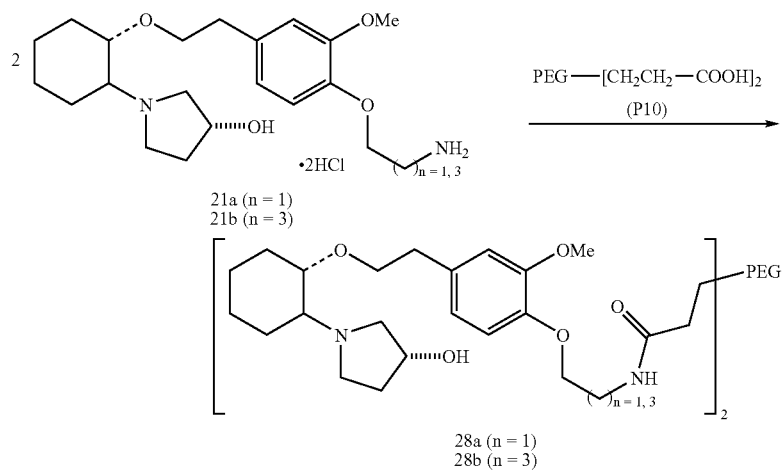

In a typical reaction, to a solution of PEG linker (P10) in a suitable solvent (e.g., anhydrous $CH_2Cl_2$) may be added to derivatized COMPOUND A (21a,b) and $Et_3N$, and the mixture may be stirred for 12 h at ambient temperature. Ethyl ether may then be added to the reaction solution with stirring to effect the precipitation of PEG derivative (28a,b). The mixture may be stored at about −20° C. for about 12 h and the crude solid collected by filtration. The product may be further purified by re-crystallization to yield (28a,b).

Example P13

Synthesis of Urea Linked PEG-Dicompound A Derivative (29a,b) from Derivatized Compound A (21a,b) and (P12) (PEG-(Isocyanate)$_2$ MW 10K)

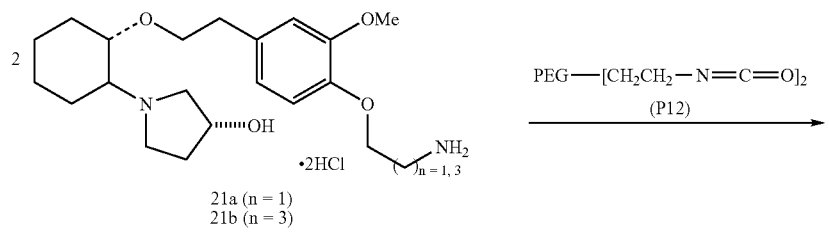

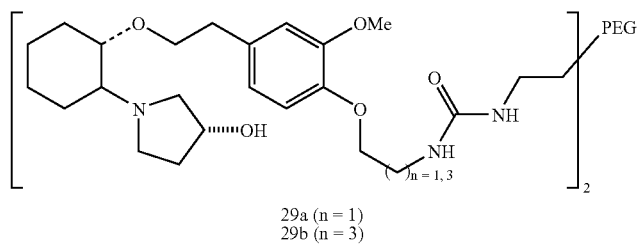

29a (n = 1)
29b (n = 3)

In a typical reaction, to a solution of PEG linker (P12) in a suitable solvent (e.g., anhydrous CH$_2$Cl$_2$) may be added to derivatized COMPOUND A (21a,b) and Et$_3$N, and the mixture may be stirred for 12 h at ambient temperature. Ethyl ether may then be added to the reaction solution with stirring to effect the precipitation of PEG derivative (29a,b). The mixture may be stored at about −20° C. for about 12 h and the crude solid collected by filtration. The product may be further purified by re-crystallization to yield (29a,b).

Example P14

Synthesis of Amide Linked PEG-Thiol-Reactive Derivative (30a,b) from Derivatized Compound A (21a,b) and (P14) (NHS Vinyl Sulfone NHS PEG VS.)

In a typical reaction, to a solution of PEG linker (P14) in a suitable solvent (e.g., anhydrous CH$_2$Cl$_2$) may be added to derivatized COMPOUND A (21a,b) and Et$_3$N, and the mixture may be stirred for 12 h at ambient temperature. Ethyl ether may then be added to the reaction solution with stirring to effect the precipitation of PEG derivative (30a,b). The mixture may be stored at about −20° C. for about 12 h and the crude solid collected by filtration. The product may be further purified by re-crystallization to yield (30a,b).

In another variation, the present invention provides methods for preparing PEG-aminocycloalkyl ether compounds comprising the following reaction steps according to Examples P15-P20.

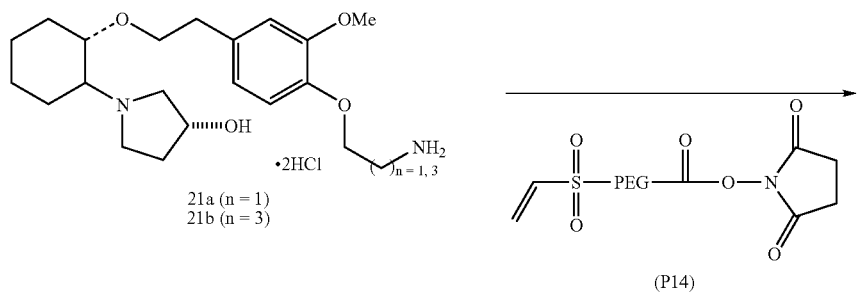

21a (n = 1)
21b (n = 3)

(P14)

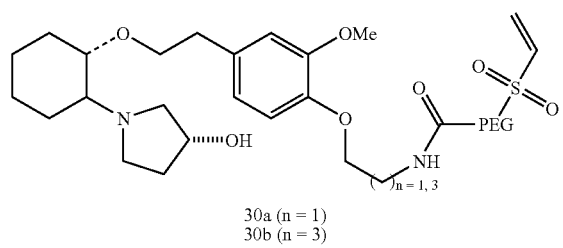

30a (n = 1)
30b (n = 3)

Example P15

Synthesis of a Di-PEG-Compound A Derivative (31a,b) from Derivatized Compound A (21a,b) and an Excess of (P4) (MPEG-Succinimidyl Propionate MW 2K, 20K)

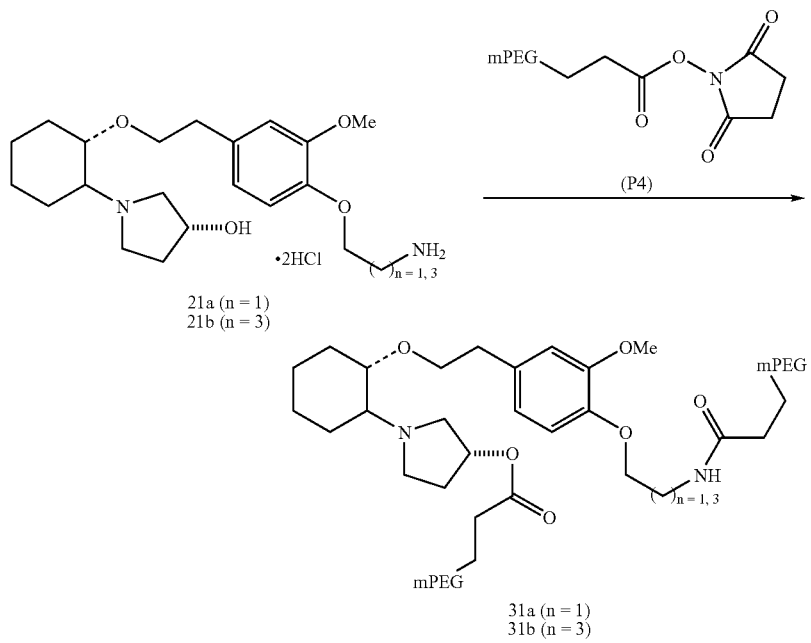

In a typical reaction, to a solution of excess PEG linker (P4) in a suitable solvent (e.g., anhydrous CH$_2$Cl$_2$) may be added to derivatized COMPOUND A (21a,b) and Et$_3$N, and the mixture may be stirred for 12 h at ambient temperature. Ethyl ether may then be added to the reaction solution with stirring to effect the precipitation of PEG derivative (31a,b). The mixture may be stored at about −20° C. for about 12 h and the crude solid collected by filtration. The product may be further purified by re-crystallization to yield (31a,b).

Example P16

Synthesis of Di-PEG-Compound A Derivative (32a, b) from Derivatized Compound A (21a,b) and an Excess of (P6) (MPEG-Succinic Acid MW 2K, 20K) (DIPC=Diisopropylcarbodiimide and DMAP=Dimethylaminopyridine)

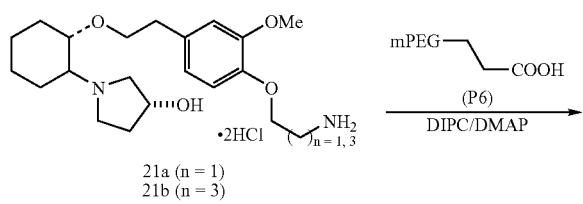

-continued

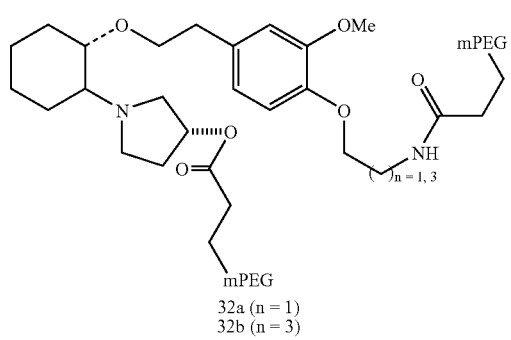

In a typical reaction, to a solution of excess PEG linker (P6) in a suitable solvent (e.g., anhydrous CH$_2$Cl$_2$) may be added to derivatized Compound A (21a,b) and DIPC/DMAP, and the mixture may be stirred for 12 h at ambient temperature. Ethyl ether may then be added to the reaction solution with stirring to effect the precipitation of PEG derivative (32a,b). The mixture may be stored at about −20° C. for about 12 h and the crude solid collected by filtration. The product may be further purified by re-crystallization to yield (32a,b).

Example P17

Synthesis of Di-PEG-Compound A Derivative (33a, b) from Derivatized Compound A (21a,b) and an Excess of (P8) (MPEG-Isocyanate MW 2K, 20K)

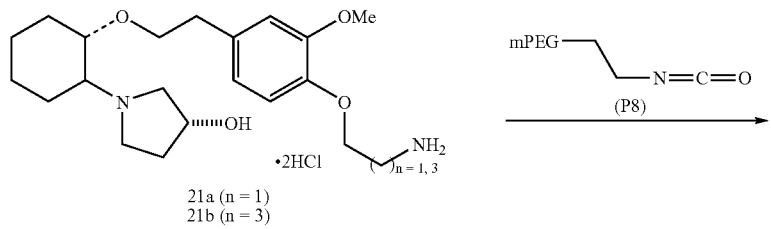

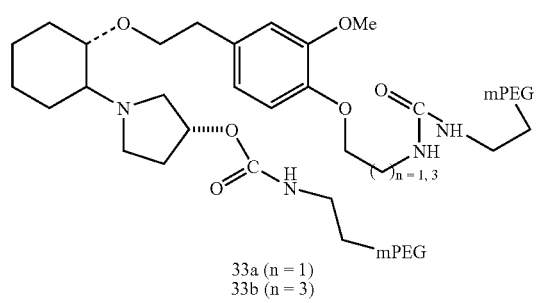

In a typical reaction, to a solution of excess PEG linker (P8) in a suitable solvent (e.g., anhydrous $CH_2Cl_2$) may be added to derivatized Compound A (21a,b) and $Et_3N$, and the mixture may be stirred for 12 h at ambient temperature. Ethyl ether may then be added to the reaction solution with stirring to effect the precipitation of PEG derivative (33a,b). The mixture may be stored at about −20° C. for about 12 h and the crude solid collected by filtration. The product may be further purified by re-crystallization to yield (33a,b).

Example P18

Synthesis of Di-PEG-Dicompound A Derivative (34a,b) from Derivatized Compound A (21a,b) and an Excess of (P10) (PEG-(Succinic Acid)$_2$ MW 10K)

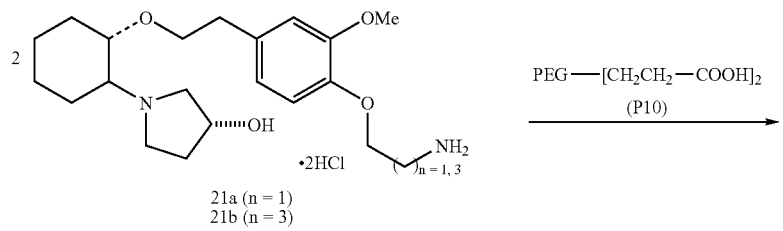

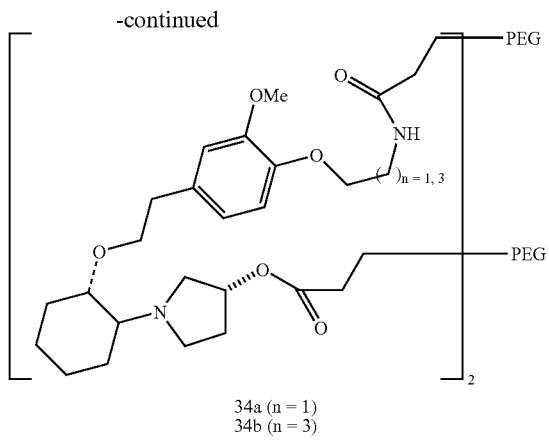

34a (n = 1)
34b (n = 3)

In a typical reaction, to a solution of excess PEG linker (P10) in a suitable solvent (e.g., anhydrous $CH_2Cl_2$) may be added to derivatized Compound A (21a,b) and $Et_3N$, and the mixture may be stirred for 12 h at ambient temperature. Ethyl ether may then be added to the reaction solution with stirring to effect the precipitation of PEG derivative (34a,b). The mixture may be stored at about −20° C. for about 12 h and the crude solid collected by filtration. The product may be further purified by re-crystallization to yield (34a,b).

Example P19

Synthesis of Di-PEG-Dicompound A Derivative (35a,b) from Derivatized Compound A (21a,b) and (P12) (PEG-(Isocyanate)$_2$ MW 10K)

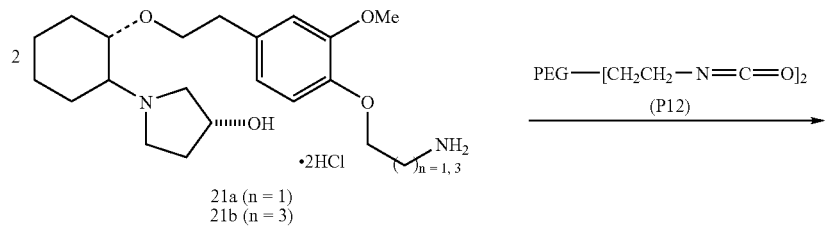

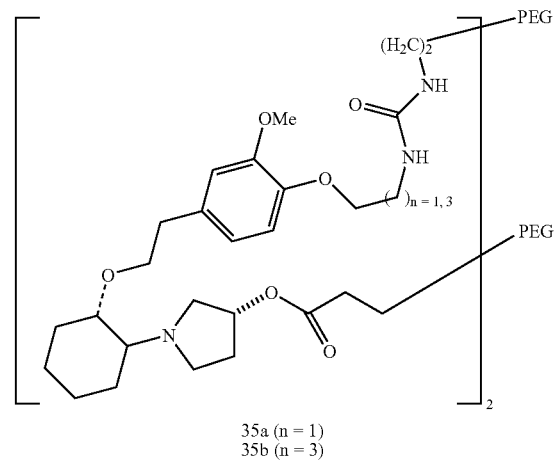

35a (n = 1)
35b (n = 3)

In a typical reaction, to a solution of excess PEG linker (P12) in a suitable solvent (e.g., anhydrous $CH_2Cl_2$) may be added to derivatized Compound A (21a,b) and $Et_3N$, and the mixture may be stirred for 12 h at ambient temperature. Ethyl ether may then be added to the reaction solution with stirring to effect the precipitation of PEG derivative (35a,b). The mixture may be stored at about −20° C. for about 12 h and the crude solid collected by filtration. The product may be further purified by re-crystallization to yield (35a,b).

Example P20

Synthesis of Di-PEG-Thiol-Reactive Derivative (36a, b) from Derivatized Compound A (21a,b) and (P14) (NHS Vinyl Sulfone NHS PEG VS)

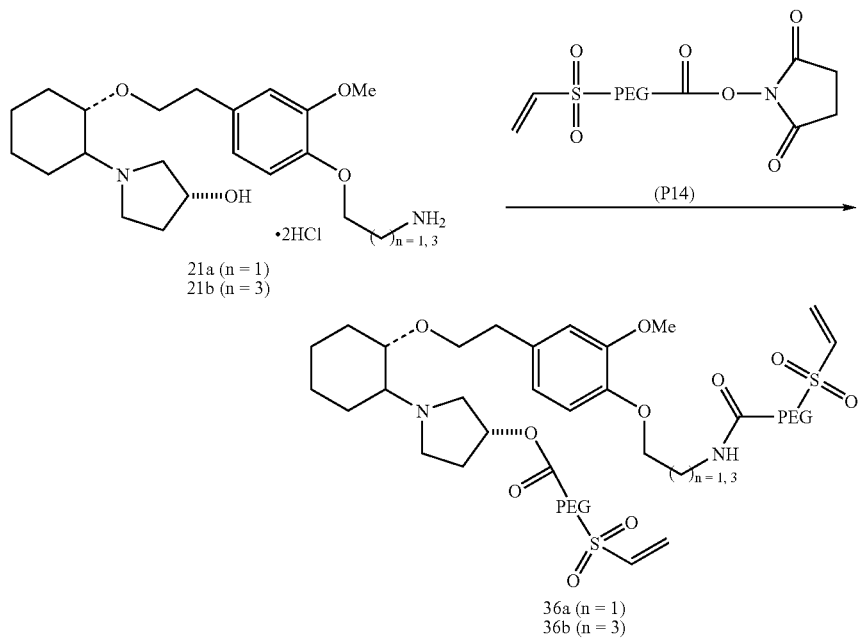

36a (n = 1)
36b (n = 3)

In a typical reaction, to a solution of excess PEG linker (P14) in a suitable solvent (e.g., anhydrous $CH_2Cl_2$) may be added to derivatized Compound A (21a,b) and $Et_3N$, and the mixture may be stirred for 12 h at ambient temperature. Ethyl ether may then be added to the reaction solution with stirring to effect the precipitation of PEG derivative (36a,b). The mixture may be stored at about −20° C. for about 12 h and the crude solid collected by filtration. The product may be further purified by re-crystallization to yield (36a,b).

D. Ion Channel Modulating Compounds Conjugated to Additional Drug Moieties

The descriptions in this section are generally directed towards drug conjugates of ion channel modulating compounds, particularly compounds of formula (I), (IA) or (IX) and Compound A, and additional drug moieties (known herein as "drug conjugates"). Generally, the drug conjugates described herein comprise an ion channel modulating compound and at least one additional drug moiety, wherein the additional drug moiety is attached to the ion channel modulating compound either directly or via a linker and wherein the ion channel modulating compound and the additional drug moiety may demonstrate the same or different biological and/or therapeutic effects. For instance, ion channel modulating compounds of formula (I), (IA) or (IX) and Compound A may be conjugated to additional drug moieties, such as cardiovascular agents, beta-blockers, ACE inhibitors, antihypertensives, diuretics, antipsychotics, anticoagulants (antiplatelets), antidepressants, inotropes, Ca sensitizers, Ca Channel blockers, Adrenergic blocking agents, Angiotensin II receptor antagonists, Xanthine Oxidase Inhibitors (XOIs), Natriuretic Peptides such as an atrial natriuretic peptide (ANP), metabolic modulators, lipid/cholesterol modulating agents, anti-inflammatory agents, vasodilators, anti-convulsants, antioxidants, antilipids, digitalis glycosides, rate control drugs, antihistamines, antispasmodics, antibiotics, anti-rejection drugs, immunomodulators, chemotherapeutics, and antiarrhythmics. The conjugation of an additional drug moiety to an ion channel modulating compound may take place either directly (via a direct bond from the additional drug moiety to the ion channel modulating compound) or by the use of a linker, including but not limited to the linkers described in the "linker" section below. A drug conjugate comprises at least one additional drug moiety, and may in some variations comprise more than one additional drug moiety. If more than one additional drug moiety is present in a drug conjugate, the additional drug moieties may be the same or different or may exhibit similar or different biological activity. In one variation, a drug conjugate is provided, comprising an ion channel modulating compound and more than one additional drug moieties in a 2:1 molar ratio of additional drug moieties:ion channel modulating compound; in yet another variation, this molar ratio is from about 2:1 to about 5:1; in still another variation, this molar ratio is from about 5:1 to about 10:1; in still a further variation, this molar ratio is greater than 10:1.

Also provided herein are methods for the attachment of an ion channel modulating compound to an additional drug moiety. Methods for the therapeutic use of the conjugates are also described, such as their use in the treatment and/or prevention of arrhythmia and/or other conditions such as hypertension.

Any ion channel modulating compound may be attached to an additional drug moiety to provide a drug conjugate thereof. The ion channel modulating compound for use in a drug conjugate may increase or decrease ion channel activity. In some instances, the ion channel modulating compound may be used in the treatment of arrhythmia. In still other instances, the ion channel modulating compound may be used in the treatment of atrial fibrillation. Specific ion channel modulating compounds for use in a drug conjugate are described throughout this patent, such as those compounds of formula (I), (IA), (IX) and Compound A, as described above.

In one variation, a compound of formula (I), as described above, is used in a drug conjugate wherein the compound of formula (I) is attached to an additional drug moiety or linker by the substitution of any valency of the compound of formula (I) with a bond to the additional drug moiety or to a linker that in turn is bound to the additional drug moiety.

In another variation, a compound of formula (IA), as described above, is used in a drug conjugate wherein the compound of formula (IA) is attached to an additional drug moiety or linker by the substitution of any valency of the compound of formula (IA) with a bond to the additional drug moiety or to a linker that in turn is bound to the additional drug moiety. In one instance, a drug conjugate is provided, wherein the compound of formula (IA) is attached to the additional drug moiety by the substitution of the valency occupied by hydrogen in the ∼∼∼OH moiety with a bond to the additional drug moiety or to a linker that in turn is bound to the additional drug moiety.

In another variation, a compound of formula (IX), as described above, is used in a drug conjugate wherein the compound of formula (IX) is attached to an additional drug moiety or linker by the substitution of any valency of the compound of formula (IX) with a bond to the additional drug moiety or to a linker that in turn is bound to the additional drug moiety.

In another variation, Compound A, as described above, is used in a drug conjugate wherein Compound A is attached to an additional drug moiety or linker by the substitution of any valency of Compound A with a bond to the additional drug moiety or to a linker that in turn is bound to the additional drug moiety. In one variation, Compound A is attached to the additional drug moiety by the substitution of the valency occupied by hydrogen in the ╌╌╌OH moiety with a bond to the additional drug moiety.

The depiction herein of the conjugation of the additional drug moiety to the compounds of formulae (I), (IA) and (IX) and Compound A is not intended to limit the scope of the invention. It is understood that the additional drug moiety may be attached to the rest of the molecule by substitution of any valency of the compound of interest.

Additional Drug Moiety Attachment Site on Ion Channel Modulating Compound

If an ion channel modulating compound is modified to form a drug conjugate, at least one valency of the ion channel modulating compound is substituted with a bond to an additional drug moiety or with a bond to a linker that is in turn bound to an additional drug moiety. That is, any valency of an ion channel modulating compound occupied by an atom, lone pair of electrons, or an empty orbital may be substituted with a bond to an additional drug moiety or a bond to a linker that is in turn bound to an additional drug moiety.

The additional drug moiety or linker may generally be attached to the ion channel modulating compound at any site on the ion channel modulating compound that allows for such attachment.

In one version, a functional group on the ion channel modulating compound may be used as an attachment site for an additional drug moiety or linker. The attachment site may be modified by amenable chemistry to facilitate the attachment of an additional drug moiety or linker. The modification may be the conversion of a first functional group to a second or further functional group, wherein the second or further functional group is used as an attachment site for the additional drug moiety or linker. An attachment site may be reacted with a functional group on the linker or additional drug moiety to form a linkage bond that attaches the ion channel modulating compound to the additional drug moiety or linker. Attachment sites on an ion channel modulating compound are typically sufficiently reactive to undergo addition or substitution reactions. Illustrative examples of functional groups that may be used to facilitate the attachment of an additional drug moiety or linker include but are not limited to amino, hydroxyl, mercapto, carboxy, alkenyl, nitrile, allyl, vinyl, amido, halo, urea, oxiranyl, aziridinyl, oxazolinyl, imidazolinyl, sulfonato, phosphonato, bipyridines, and isocyanato groups.

In synthesizing the conjugate, the attachment of the additional drug moiety to an ion channel modulating compound may take place in a step-wise fashion. That is, the attachment may be performed in sequential reactive steps starting with the intact ion channel modulating compound. The step-wise synthesis may include a first attachment of the ion channel modulating compound to a linker and a second attachment of the ion channel modulating compound/linker complex to the additional drug moiety. These steps may be altered, for example, by first attaching the additional drug moiety to a linker and then attaching the additional drug moiety/linker complex to the ion channel modulating compound. The step-wise synthesis may be a single reaction or a series of reactions by which the additional drug moiety is directly associated with an intact ion channel modulating compound. The attachment of an additional drug moiety to an ion channel modulating compound may also take place during the synthesis of the ion channel modulating compound itself, either by direct attachment of the additional drug moiety or via the use of a linker. The synthesis may be a "one-pot" procedure, or may take place over a series of different synthetic steps, wherein the intermediate compounds are isolated, purified, extracted, crystallized, or otherwise removed from the reaction media.

Synthetic protocols for attaching an additional drug moiety to an ion channel modulating compound will depend on the nature of the ion channel modulating compound, additional drug moiety and optional use of a linker. Specific protocols would be readily recognized by one of skill in the art upon the selection of conjugate components.

In general, an additional drug moiety or linker is bound to an ion channel modulating compound by reacting two complementary functional groups, thereby forming a linkage bond, wherein a first functional group is present on the additional drug moiety or linker and wherein a second functional group is present on the ion channel modulating compound. Complementary reactive functional groups on the ion channel modulating compound and the additional moiety or linker are readily recognized by those of skill in the art. Examples of complementary reactive functional groups include but are not limited to those depicted in Table 1 below, entitled "Complementary Reactive Functional Groups." The first or second functional groups in the table below may be present on the ion channel modulating compound or on the additional drug moiety or linker, so long as one of the foregoing comprises a first functional group and another comprises a complementary second functional group. These and other functional groups may be present on the ion channel modulating compound, additional drug moiety or linker or may be introduced to any of the foregoing using known synthetic techniques. See, for example, "Comprehensive Organic Transformations: A Guide to Functional Group Preparations", Richard C. Larock, Wiley-VCH: 1999 or in "March's Advanced Organic Chemistry: Reactions, Mechanisms and Structure", Jerry March & Michael Smith, John Wiley & Sons Inc: 2001.

TABLE 1

Complementary Reactive Functional Groups

| $1^{st}$ reactive group | $2^{nd}$ reactive group | Linkage Bond Formed |
|---|---|---|
| hydroxyl | Isocyanate | urethane |
| amine | Epoxide | β-hydroxyamine |
| sulfonyl halide | Amine | sulfonamide |
| carboxyl acid | Amine | amide |
| hydroxyl | alkyl/aryl halide | ether |
| aldehyde | amine/NaCNBH$_4$ | amine |
| ketone | amine/NaCNBH$_4$ | amine |
| amine | isocyanate | urea |
| amine | NHS-ester | amide |

Various functional groups on the ion channel modulating compound may be modified to facilitate attachment of a linker or the additional drug moiety. For example, a hydroxyl group on the ion channel modulating compound may be modified to facilitate attachment. The modified hydroxyl group may be part of a larger structural feature of the ion channel modulating compound, such as a hydroxycycloalkyl or hydroxyheterocycloalkyl ring. In some variations, the modified hydroxyl group is the hydroxyl portion of a 3-hydroxyl-pyrrolidinyl moiety. In some variations, an alkoxy group is modified to facilitate attachment. The modified alkoxy group may be a $C_1$-$C_6$ alkoxy group. In some variations, the modified alkoxy group is methoxy. The modified alkoxy group may be part of a larger structural feature of the ion channel modulating compounds, such as the alkoxy group of any one of an alkoxyaryl, alkoxyphenyl or substituted derivative of the foregoing. In some variations, the modified alkoxy group is the methoxy group of a substituted or unsubstituted methoxybenzene moiety. The modified alkoxy group may be the 4-methoxy group of a 3,4-dimethoxy benzene moiety on the ion channel modulating compound.

Linkage Bonds for Drug Conjugates

When a functional group on the ion channel modulating compound reacts with a complementary functional group on a linker or an additional drug moiety, a linkage bond is formed. The bond that is formed between the ion channel modulating compound and the linker or additional drug moiety depends on the functional group that is used as the attachment site on the ion channel modulating compound and on the complementary functional group on the linker or additional moiety. In some variations, the linkage bond is a cleavable covalent bond. A cleavable covalent bond is usually cleaved by enzymatic or hydrolytic cleavage. In some variations, a reaction between the functional group on the ion channel modulating compound and a complementary functional group on the linker or additional drug moiety forms a linkage bond as listed in Table 1 above. In one variation, the linkage bond may be selected from an amide, carbamate, carbonate, urea, disulfide, sulfonamide, sulfonate, thio-sulfonate, thio-ether, thio-ester, ether, ester, and amine bond. In another variation, the linkage bond is selected from an ester, ether, or amide bond. In another variation, a urethane bond is formed. Typically, the bond that is formed between the ion channel modulating compound and the linker or additional moiety is cleavable.

Additional Drug Moieties for Drug Conjugates

A drug conjugate of an ion channel modulating compound and an additional drug moiety may comprise any drug moiety as the additional drug moiety. An additional drug moiety may be a drug that can be prescribed in tandem with an ion channel modulating compound. An "additional drug moiety" as used herein may be an entire drug or may be any portion of an additional drug, wherein the portion of the additional drug contains the pharmacophore thereof. Illustrative examples of additional drug moieties include drug moieties such as cardiovascular agents, beta-blockers, ACE inhibitors, antihypertensives, diuretics, antipsychotics, anticoagulants (antiplatelets), antidepressants, inotropes, Ca sensitizers, Ca Channel blockers, Adrenergic blocking agents, Angiotensin II receptor antagonists, Xanthine Oxidase Inhibitors (XOIs), Natriuretic Peptides such as an atrial natriuretic peptide (ANP), metabolic modulators, lipid/cholesterol modulating agents, anti-inflammatory agents, vasodilators, anti-convulsants, antioxidants, antilipids, digitalis glycosides, rate control drugs, antihistamines, antispasmodics, antibiotics, antirejection drugs, immunomodulators, chemotherapeutics, and anti-arrhythmics.

Linkers for Drug Conjugates

The attachment of an ion channel modulating compound to an additional drug moiety may employ one or more linker, connector and/or spacer groups. These groups are collectively referred to as "linkers." The linkers may be used as a spacer molecule to create a separation between the ion channel modulating compound and the additional drug moiety, and/or to avoid undesired steric interactions. The spatial separation may be desired for modified, enhanced, or optimal function of the conjugate. The linkers may also facilitate the preparation or use of the conjugate.

The linker may be primarily hydrophobic in nature or may be primarily hydrophilic in nature and may thus contribute to the overall hydrophobicity or hydrophilicity of the conjugate. A single linker may also comprise both hydrophobic regions and hydrophilic regions.

The linker may be cleavable or non-cleavable. A cleavable linker comprises or will form a linkage bond to an ion channel modulating compound that may be cleaved in vivo or ex vivo including but not limited to cleavage via enzymatic, non-enzymatic, or hydrolytic cleavage. An example of a cleavable linker includes a linker that will comprise or will form an ester bond upon attachment to an ion channel modulating compound. In one version, a drug conjugate comprises a linker that forms an ester or amide linkage bond between the ion channel modulating compound and the linker.

In synthesizing a drug conjugate comprising a linker, it may be useful to employ a linker that has at least two functional groups, one for bonding of the linker to the ion channel modulating compound and one for bonding of the linker to the additional drug moiety. A linker functional group will usually be chosen to complement the functional groups on the ion channel modulating compound and the additional drug moiety. In one version, a drug conjugate comprises a bifunctional linker molecule. A bi-functional linker molecule has two reactive termini, one of which is available for linkage to the ion channel modulating compound and one of which is available for linkage to the additional drug moiety. The functional groups on the reactive termini may be the same or different.

Suitable bifunctional linkers are reported extensively but not exhaustively by U.S. Published Patent Application US 2003/0044845 (Jenkins et al.).

Linkers may be selected from, but are not limited to, bi-functional linkers, hetero-bi-functional linkers and/or multi-functional linkers. As used herein, "hetero-bi-functional linkers" are linkers with two different functional groups (e.g., SIAB, SPDP etc.) that may be used in a more selective conjugation of an ion channel modulating compound to an additional drug moiety. As used herein, "multi-functional linkers" are linkers with more than two functional groups (homo- or hetero-) and can be used to link an ion channel modulating compound to two or more additional drug moieties. Commercial and non-commercial examples of linkers are described below and in the Experimental section.

Commercially available hetero-bi-functional linkers can be obtained from Interchim or Nektar Therapeutics and include but are not limited to N-succinimidyl-3-(2-pyridylthio)proprionate and NHS PEG vinyl sulfone. Thiol-reactive linkers are available from Biotium, Inc. Bi-functional linkers include but are not limited to amine-reactive linkers, thiol reactive linkers or both amine and thiol reactive linkers. By amine reactive, it is meant that the linker comprises a functional group that can form a linkage bond with a compound (ion channel modulating compound or additional drug moiety) comprising an amine moiety. By thiol reactive, it is meant that the linker comprises a functional group that can form a linkage bond with a compound (ion channel modulating compound or additional drug moiety) comprising a thiol moiety. By both amino and thiol reactive, it is meant that the linker comprises at least one thiol reactive group and at least one amino reactive group. Functional groups that are thiol reactive include haloacetyls, such as bromoacetyls and iodoacetyls, and maleimides. An example of a linker that is both amino and thiol reactive is N-succinimidyl(4-iodoacetyl)aminobenzoate (SIAB), which has amine-reactive and sulfhydryl-reactive ends. The NHS ester of SIAB can couple to amine-containing molecules, forming stable amide linkages. The iodoacetyl group creates stable thioether bonds. SIAB is water-insoluble and it must be first dissolved in organic solvent (such as DMSO and DMF) prior to addition to an aqueous reaction medium. Alternatively, water soluble derivatives of water insoluble linkers, such as SIAB, may be provided by the attachment of water soluble functional groups to the water insoluble linkers, such as provided by a sulfonate salt derivative of a water insoluble linker. In one variation, a bifunctional linker comprises two carboxylic acid moieties separated by alkylene units, wherein either or both of the carboxylic acid groups may be optionally converted to an ester, including the N-succinic ester derivative. Illustrative bifunctional linkers include but are not limited to succinic acid, sebacic acid bis(N-succinimidyl)ester, pimelic acid, β-alanine and 1,4-diisocyanato-butane from Sigma-Aldrich, and the linkers shown in the figures below.

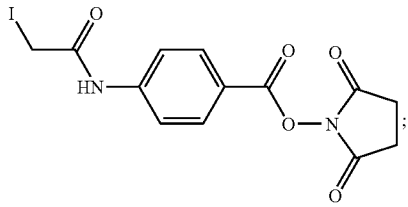

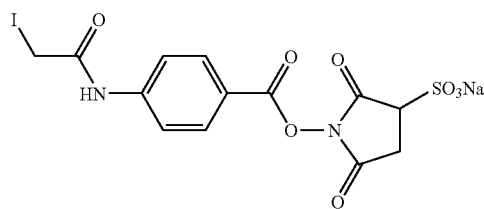

SIAB: Succinimidyl-4-iodoacetyl-aminobenzoate or the Water-Soluble Sulfonate Salt Thereof.

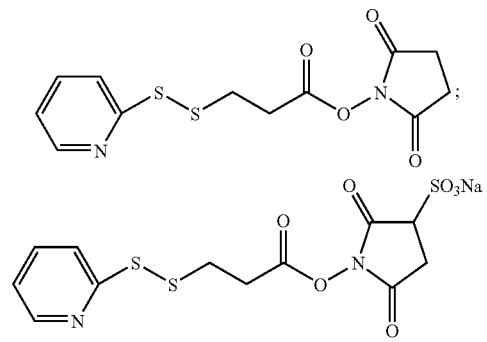

SPDP: N-succinimidyl-3-(2-pyridylthio)propionate or the Water-Soluble Sulfonate Salt Thereof

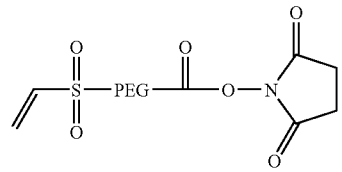

NHS Vinyl Sulfone (NHS PEG VS)

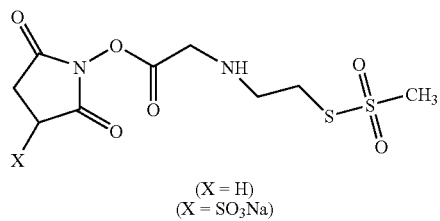

(X = H)
(X = SO₃Na)

Succinic Acid

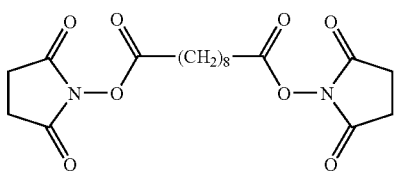

Sebacic Acid bis(N-succinimidyl)ester

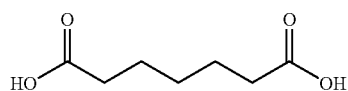

Pimelic Acid

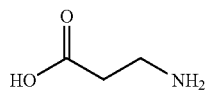

β-alanine

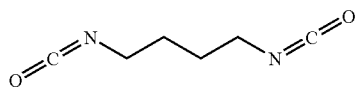

1,4-diisocyanato-butane

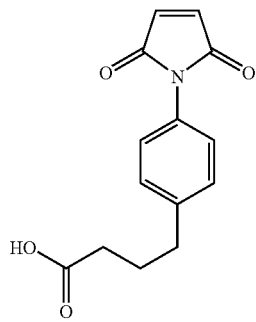

4-[4-(2,5-Dioxo-2,5-dihydropyrrol-1-yl)phenyl]butyric Acid

Specific drug conjugates comprising an ion channel modulating compound and an additional drug moiety are provided herein. For instance, drug conjugates comprising the ion channel modulating compounds of formula (I), (IA), (IX) and Compound A, as described above, are provided.

In one variation, a drug conjugate comprising compounds of formula (I) (DC-I), or a solvate or pharmaceutically acceptable salt thereof, is provided:

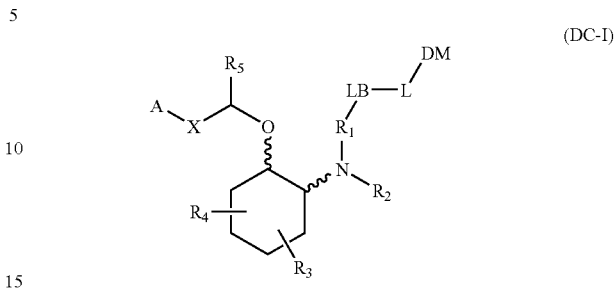

wherein:

$R_1$ and $R_2$ are independently selected from hydrogen, $C_1$-$C_6$alkyl, $C_3$-$C_8$alkoxyalkyl, $C_1$-$C_8$hydroxyalkyl, and $C_7$-$C_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$ are taken together with the nitrogen atom to which they are directly attached in formula (DC-I), form a ring denoted by formula (DC-II-Z):

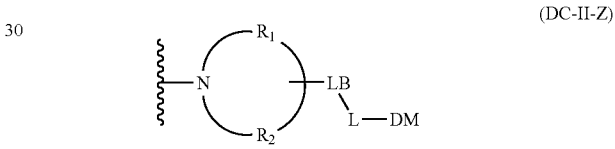

wherein the ring of formula (DC-II-Z) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together with the nitrogen atom to which they are directly attached in formula (DC-I), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl, wherein the bicyclic ring is substituted with -LB-L-DM;

LB is a linkage group;

L is an optional linker;

DM is an additional drug moiety;

$R_3$ and $R_4$ are independently attached to the cyclohexane ring shown in formula (DC-I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

X, Y, $R_5$, $R_6$, $R_{14}$ and A are as described above for compounds of formula (I); including isolated enantiomeric, diastereomeric and geometric isomers thereof, and mixtures thereof.

It is understood, for purposes of this invention, that the -LB-L-DM radical may be attached to the compound of formula (I) by the substitution of any valency of the compound of formula (I) to prepare compounds of formula (DC-I) and that the specific formulae depicted herein with the -LB-L-DM radical are for illustration purposes only and are not intended to provide a limitation to the scope of the invention.

In another aspect, other drug conjugates of compounds of formula (I) (DC-III), or a solvate or pharmaceutically acceptable salt thereof, is provided:

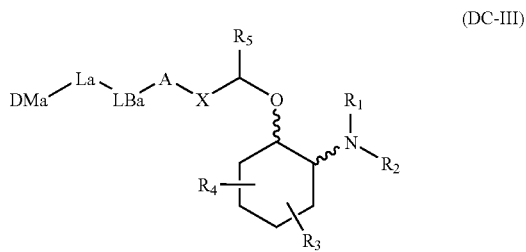

(DC-III)

wherein:

X is selected from a direct bond, —C($R_6$,$R_{11}$)—Y— and —C($R_{13}$)=CH—;

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_6$alkyl, $C_3$-$C_8$alkoxyalkyl, $C_1$-$C_8$hydroxyalkyl, and $C_7$-$C_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$ are taken together with the nitrogen atom to which they are directly attached in formula (DC-III), form a ring denoted by formula (II):

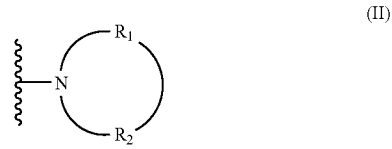

(II)

wherein the ring of formula (II) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together with the nitrogen atom to which they are directly attached in formula (DC-III), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl;

A is selected from formula (DC-A-Z):

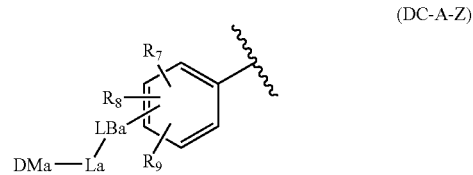

(DC-A-Z)

where $R_7$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, where $R_8$ is hydroxy, hydroxymethyl or carboxy;

LBa is a linkage group;

La is an optional linker; and

DMa is an additional drug moiety;

including isolated enantiomeric, diastereomeric and geometric isomers thereof, and mixtures thereof.

It is understood, for purposes of this invention, that the -LBa—La-DMa radical may be attached to the compound of formula (I) by the substitution of any valency of the compound of formula (I) to prepare compounds of formula (DC-III) and that the specific formulae depicted herein with the -LBa—La-DMa radical are for illustration purposes only and are not intended to provide a limitation to the scope of the invention.

In another aspect, drug conjugates of compounds of formula (I) (DC-IV) are provided, or a solvate or pharmaceutically acceptable salt thereof:

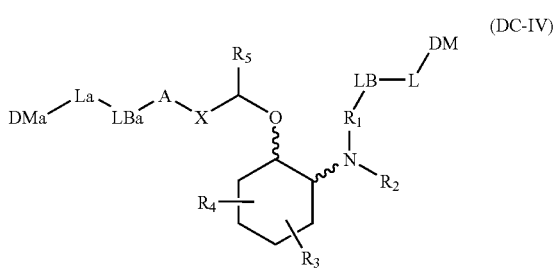

wherein:

X is selected from a direct bond, —C($R_6$,$R_{14}$)—Y— and —C($R_{13}$)=CH—;

Y is selected from a direct bond, O, S and $C_1$-$C_4$alkylene;

$R_{13}$ is selected from hydrogen, $C_1$-$C_6$alkyl, $C_3$-$C_8$cycloalkyl, aryl and benzyl;

$R_1$ and $R_2$ are independently selected from hydrogen, $C_1$-$C_6$alkyl, $C_3$-$C_8$alkoxyalkyl, $C_1$-$C_8$hydroxyalkyl, and $C_7$-$C_{12}$aralkyl; or $R_1$ and $R_2$ are independently selected from $C_3$-$C_8$alkoxyalkyl, $C_1$-$C_8$hydroxyalkyl, and $C_7$-$C_{12}$aralkyl; or $R_1$ and $R_2$ are taken together with the nitrogen atom to which they are directly attached in formula (DC-IV), form a ring denoted by formula (DC-II-Z):

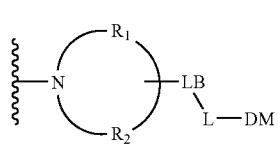

wherein the ring of formula (DC-II-Z) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$ are taken together with the nitrogen atom to which they are directly attached in formula (DC-IV), may form a bicyclic ring system selected from 3-azabicyclo[3.2.2]nonan-3-yl, 2-azabicyclo[2.2.2]octan-2-yl, 3-azabicyclo[3.1.0]hexan-3-yl and 3-azabicyclo[3.2.0]heptan-3-yl, wherein the bicyclic ring is substituted with -LB-L-DM;

LB is a linkage bond;

L is an optional linker;

DM is an additional drug moiety;

$R_3$ and $R_4$ are independently attached to the cyclohexane ring shown in formula (DC-IV) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from formula (DC-A-Z):

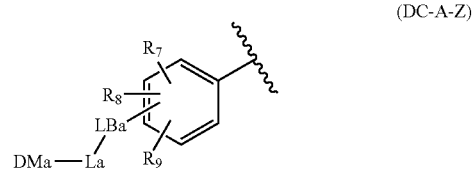

where $R_7$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, where $R_8$ is hydroxy, hydroxymethyl or carboxy;

LBa is a linkage group;

La is an optional linker; and

DMa is an additional drug moiety;

including isolated enantiomeric, diastereomeric and geometric isomers thereof, and mixtures thereof.

It is understood, for purposes of this invention, that the -LB-L-DM radical and the LBa—La-DMa radical may be attached to the compound of formula (I) by the substitution of any valency of the compound of formula (I) to prepare compounds of formula (DC-IV) and that the specific formulae depicted herein with the -LB-L-DM and the -LBa—La-DMa radical are for illustration purposes only and are not intended to provide a limitation to the scope of the invention.

In another aspect, methods for preparing drug conjugates, such as those of formulas (DC-I), (DC-III) and (DC-IV), are provided as illustrated in Reaction Scheme DC-1 and in the Examples section below. The methods may comprise of conjugation of an ion channel modulating compound to an additional drug moiety via a linker. The scheme below is generally applicable to ion channel modulating compounds comprising an aminocycloalkyl ether moiety, such as the compounds of formula (I), (IA), (IX) and Compound A, as described herein. In the scheme below, LB and LBa represent a linkage bond that may form upon reacting an ion channel modulating compound with a bifunctional linker/additional drug moiety complex (i.e., L-DM and La-DMa).

Reaction Scheme DC-1

Synthesis of the Amino-Linked (DC-I), Aromatic-Linked (DC-III) or the Amino and Aromatic Linked (DC-IV) Drug Conjugate Aminocycloalkyl Ether with N-hydroxysuccinimide bromoacetate or the optionally water soluble sulfonate derivative to form the thiol-reactive heterobifunctional linker or the water-soluble derivative. The resultant thiol-reactive heterobifunctional linker is isolated and purified using standard work-up procedures.

Hetero-bi-functional linkers may also be synthesized by standard methods known in the art from commercially available starting materials. For example, 4-[4-(2,5-dioxo-2,5-dihydro-pyrrol-1-yl)-phenyl]-butyric acid is condensed from

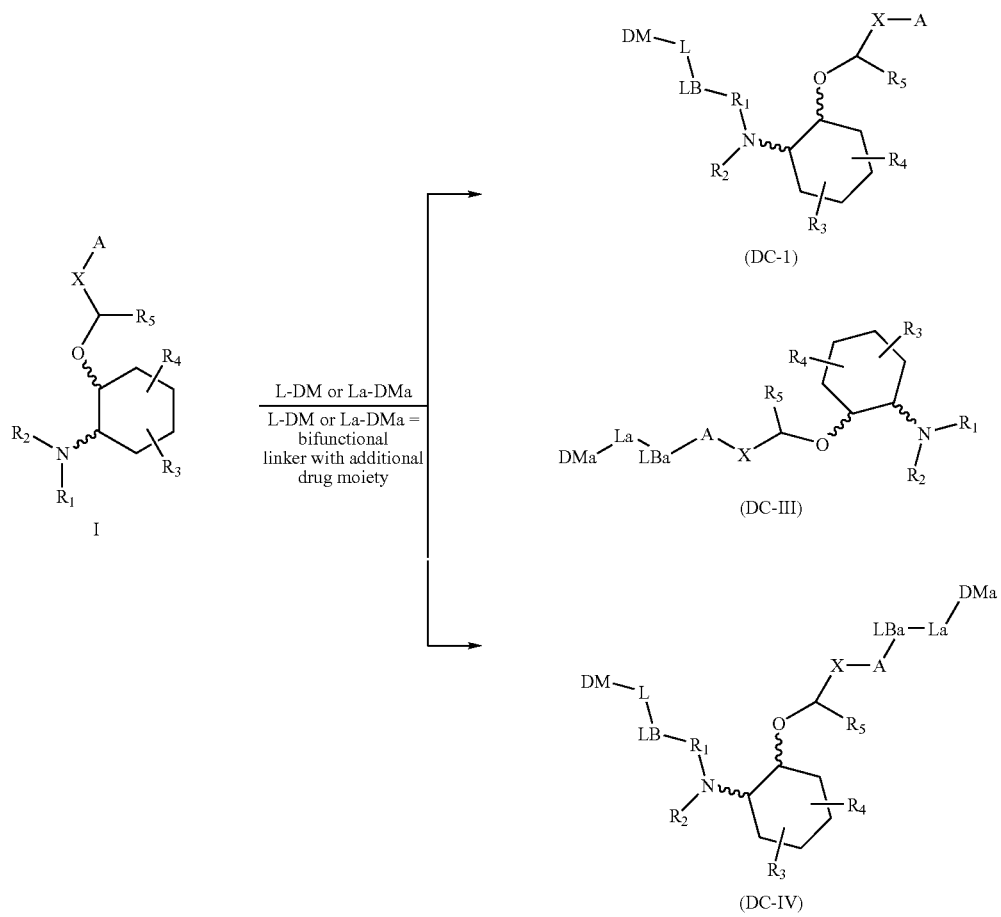

Scheme DC-1 illustrates the syntheses of the amino-linked (DC-I), aromatic-linked (DC-III) or the amino and aromatic linked (DC-IV) drug conjugate aminocycloalkyl ether.

Examples of drug conjugates of aminocycloalkyl ether compounds of formula (DC-I), (DC-III) and (DC-IV) and the methods for their preparation are further illustrated in the following reaction schemes DC-2 to DC-33. The reaction schemes are generally applicable to ion channel modulating compounds comprising an aminocycloalkyl ether moiety.

Commercially available hetero-bi-functional linkers may be obtained from Interchim or Nektar Therapeutics and include examples such as but not limited to N-succinimidyl-3-(2-pyridylthio)proprionate and NHS PEG vinyl sulfone. Thiol-reactive linkers are also available from Biotium, Inc. Sebacic acid bis(N-succinimidyl)ester and pimelic acid are obtained from Sigma-Aldrich.

In a typical reaction, 2-(aminoethyl)methane thiosulfonate hydrobromide is dissolved in a suitable solvent and reacted the commercially available 4-(4-aminophenyl)butyric acid and maleic anhydride (e.g., Booth C. A. and Philp D. Tetrahedron Lett. 1998, 39, 6987 and Rich D. H., Gesellchen P. D., Tong A., Cheung A., Buckner C. K. J. Med. Chem. 1975, 18, 1004).

1-Bromo-4-isocyanato-butane may be synthesized from the corresponding 4-isocyanato-butylamine hydrobromide and phosgene or phosgene equivalent.

The aminocycloalkyl ether compounds used in the following reaction schemes and examples are compounds of formula (I), (IA), (IX) or Compound A, as described herein.

An example of an ACE inhibitor is described in PCT published patent application WO-03104200, an antihypertensive is described in PCT published patent application WO-09403481, a selective water diuresis agent is described in PCT published patent application WO-00228412, a glycine cleavage system inhibitor (GCS) compound for psychotic disorders is described in PCT published patent application WO-00066110, an anticoagulant compound is described in EP-00884325, an antidepressant is described in PCT published patent application WO-03064374, an inotropic agent is described in U.S. Pat. No. 4,859,698, a calcium channel sensitizer is described in PCT published patent application WO-09819682, a xanthine oxidase inhibitor is described in Japanese patent application, JP-2002105067, a ANP modulator is described in PCT published patent application WO-09428901 and a vasodilator is described in EP-00544620.

REACTION SCHEME DC-2

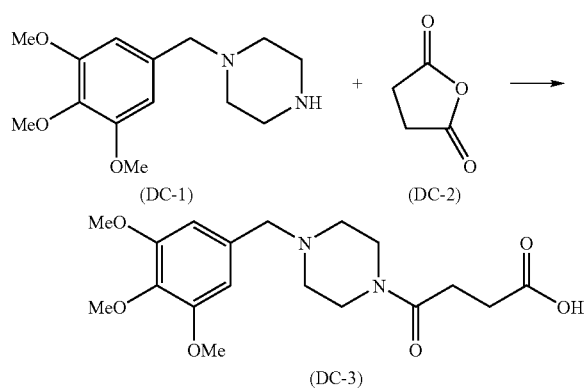

(DC-1)    (DC-2)

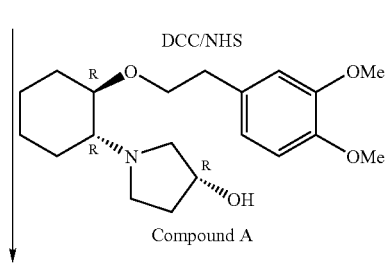

(DC-3)

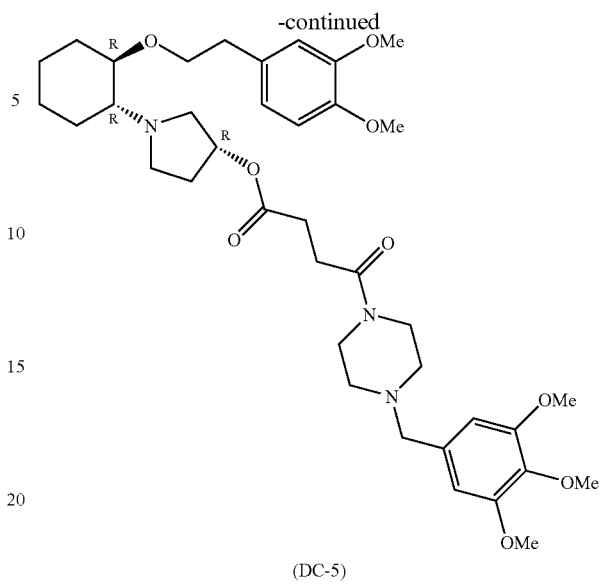

(DC-5)

Reaction Scheme DC-2 illustrates the synthesis of drug conjugate (DC-5) from trimetazidine (DC-1) and (1R,2R)-2-[(3R)-hydroxypyrrolidinyl]-1-(3,4-dimethoxyphenethoxy)cyclohexane (Compound A).

In a typical reaction, trimetazidine (TMZ) may be dissolved in a suitable solvent (e.g $CH_2Cl_2$) and may be reacted with succinic anhydride, DCC/NHS to generate the succinic acid derivative of TMZ. The intermediate (DC-3) may be isolated and purified and subsequently dissolved in a suitable solvent (e.g., $CH_2Cl_2$) and reacted with (1R,2R)-2-[(3R)-hydroxypyrrolidinyl]-1-(3,4-dimethoxyphenethoxy)cyclohexane (Compound A) to generate the drug conjugate (DC-5). The drug conjugate (DC-5) may then be isolated and purified by known standard methods.

REACTION SCHEME DC-3

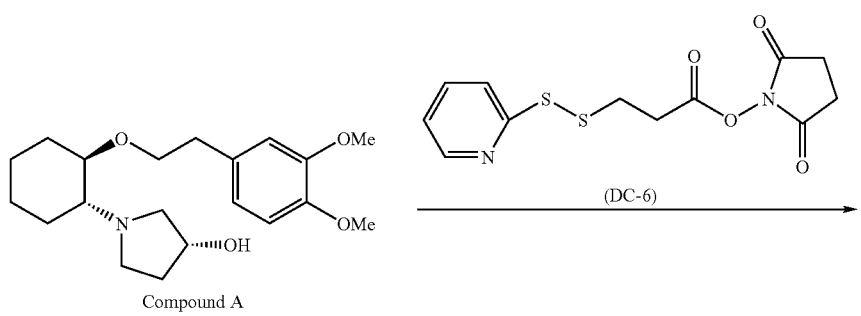

-continued

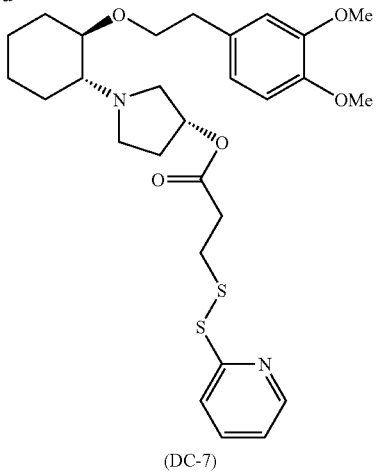

(DC-7)

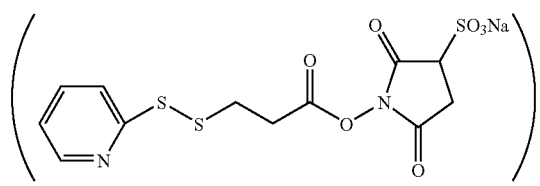

(DC-6a)

Reaction Scheme DC-3 illustrates the derivatization of (1R,2R)-2-[(3R)-hydroxypyrrolidinyl]-1-(3,4-dimethoxyphenethoxy)cyclohexane (Compound A) with a bifunctional linker 3-(pyridine-2-yldisulfanyl)-propionic acid 2,5-dioxo-pyrrolidin-1-yl ester (or N-succinimidyl-3-(2-pyridylthio)proprionate) (DC-6) (Interchim) or a water-soluble sulfonate derivative (DC-6a) of the bifunctional linker to form a thiol-reactive derivative (DC-7).

In a typical reaction, (1R,2R)-2-[(3R)-hydroxypyrrolidinyl]-1-(3,4-dimethoxyphenethoxy)cyclohexane (1 equiv) (Compound A) may be dissolved in a suitable solvent (e.g., DMF) and reacted with 3-(pyridine-2-yldisulfanyl)-propionic acid 2,5-dioxo-pyrrolidin-1-yl ester (or N-succinimidyl-3-(2-pyridylthio)proprionate) (1 equiv) (DC-6) or a water-soluble sulfonate derivative (DC-6a) in a standard coupling reaction. The resultant thiol-reactive aminocycloalkyl ether (DC-7) may be isolated and purified using standard work-up procedures.

REACTION SCHEME DC-4

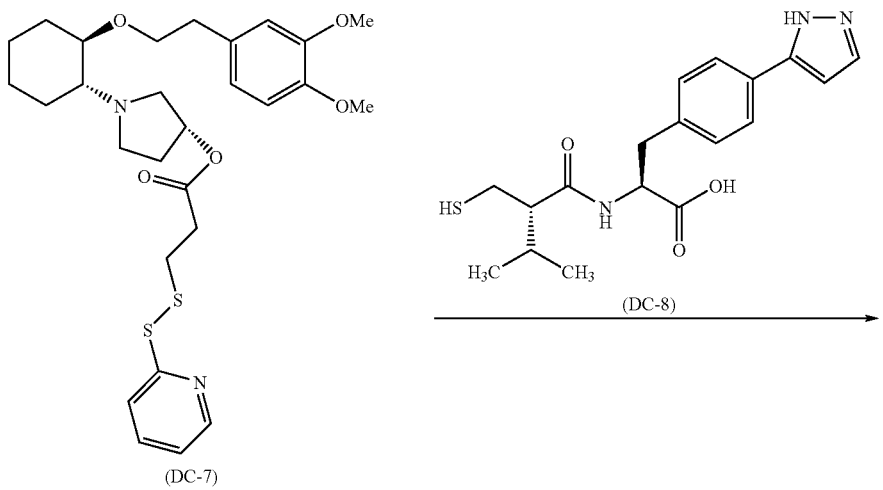

-continued

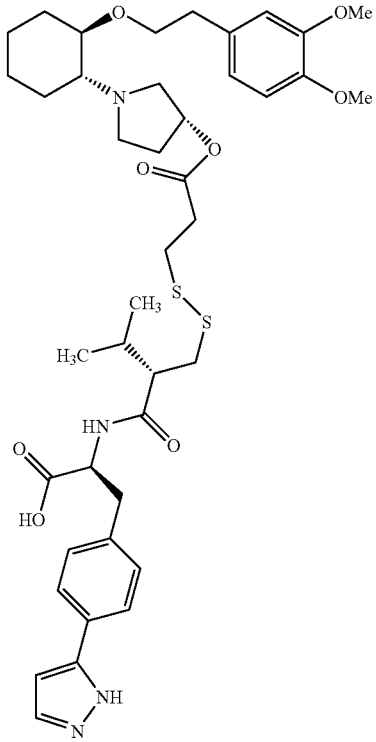

(DC-9)

Reaction Scheme DC-4 illustrates the synthesis of drug conjugate (DC-9) from the thiol-reactive derivative (DC-7) and ACE inhibitor, a derivative of N-(3-mercapto-2-alkylpropionyl)-4-heteroaryl-L-phenylalanine (DC-8). (REF. WO-03104200 18 Dec. 2003, Glaxo Group Ltd.)

In a typical reaction, the thiol-reactive intermediate (DC-7) may be dissolved in a suitable solvent (e.g., $CH_2Cl_2$) and reacted with a derivative of N-(3-mercapto-2-alkylpropionyl)-4-heteroaryl-L-phenylalanine (DC-8) to generate the drug conjugate (DC-9). The drug conjugate (DC-9) may then be isolated and purified by known standard methods.

REACTION SCHEME DC-5

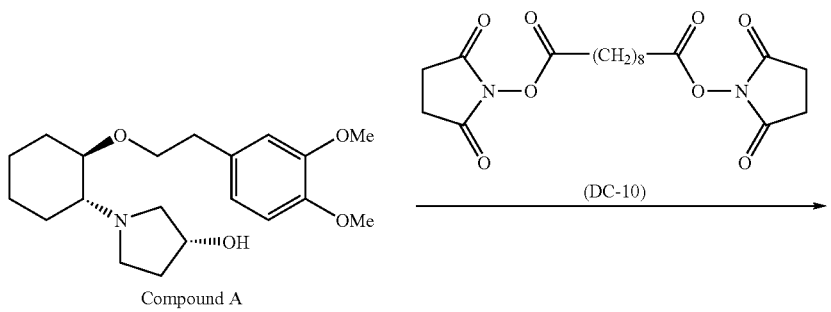

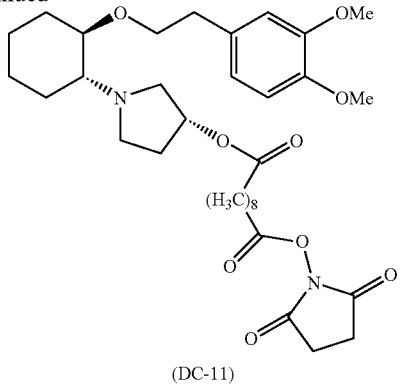

(DC-11)

Reaction Scheme DC-5 illustrates the synthesis of the amine reactive derivative (DC-11) from sebacic acid bis(N-succinimidyl)ester (DC-10) (Sigma-Aldrich) and (1R,2R)-2-[(3R)-hydroxypyrrolidinyl]-1-(3,4-dimethoxyphenethoxy)cyclohexane (Compound A).

In a typical reaction, (1R,2R)-2-[(3R)-hydroxypyrrolidinyl]-1-(3,4-dimethoxyphenethoxy)cyclohexane (Compound A) may be dissolved in a suitable solvent (e.g., $CH_2Cl_2$) and reacted with sebacic acid bis(N-succinimidyl) ester to generate the amine reactive intermediate (DC-11). This intermediate (DC-11) may be isolated and purified by known standard methods.

REACTION SCHEME DC-6

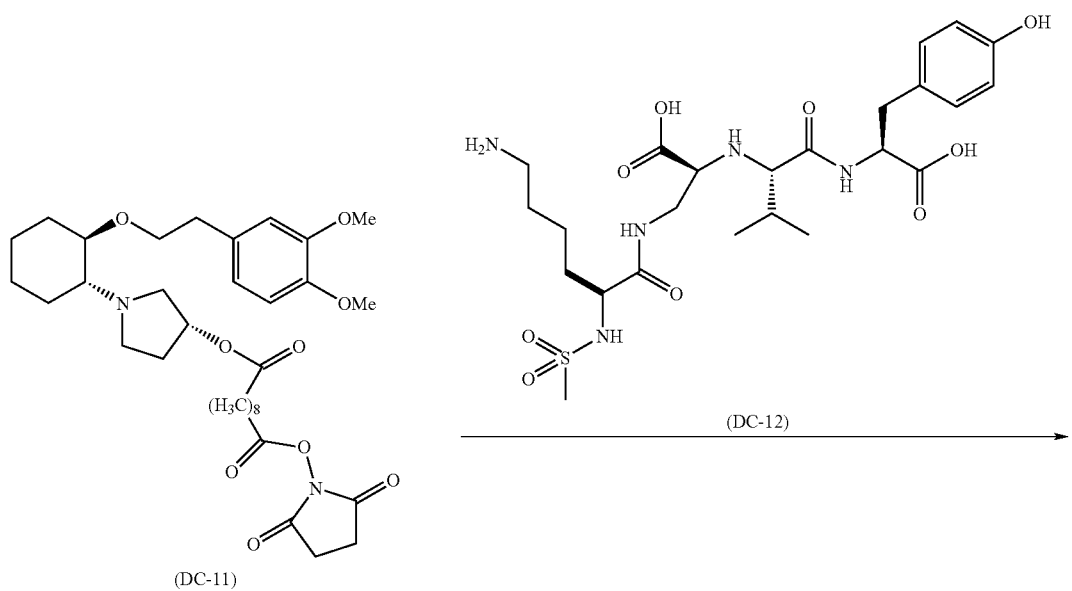

-continued

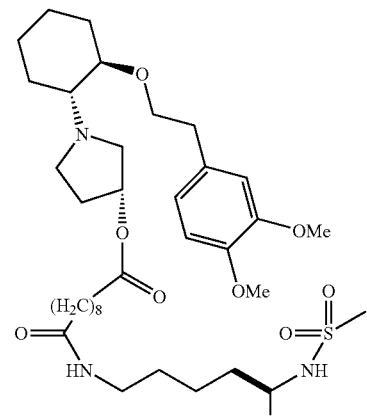

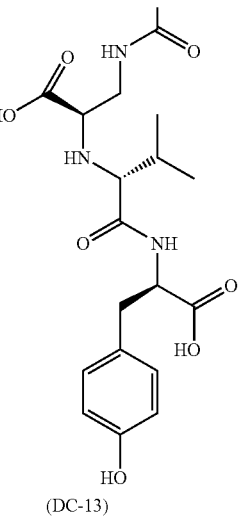

(DC-13)

Reaction Scheme DC-6 illustrates the synthesis of drug conjugate (DC-13) from amine reactive derivative (DC-11) and antihypertensive agent (DC-12). (Ref. WO-09403481 17 Feb. 1994, SCHERING CORPORATION).

In a typical reaction, the amine-reactive intermediate (DC-11) may be dissolved in a suitable solvent (e.g., $CH_2Cl_2$) and reacted with the antihypertensive agent (DC-12) to generate the drug conjugate (DC-13). The drug conjugate (DC-13) may then be isolated and purified by known standard methods.

REACTION SCHEME DC-7
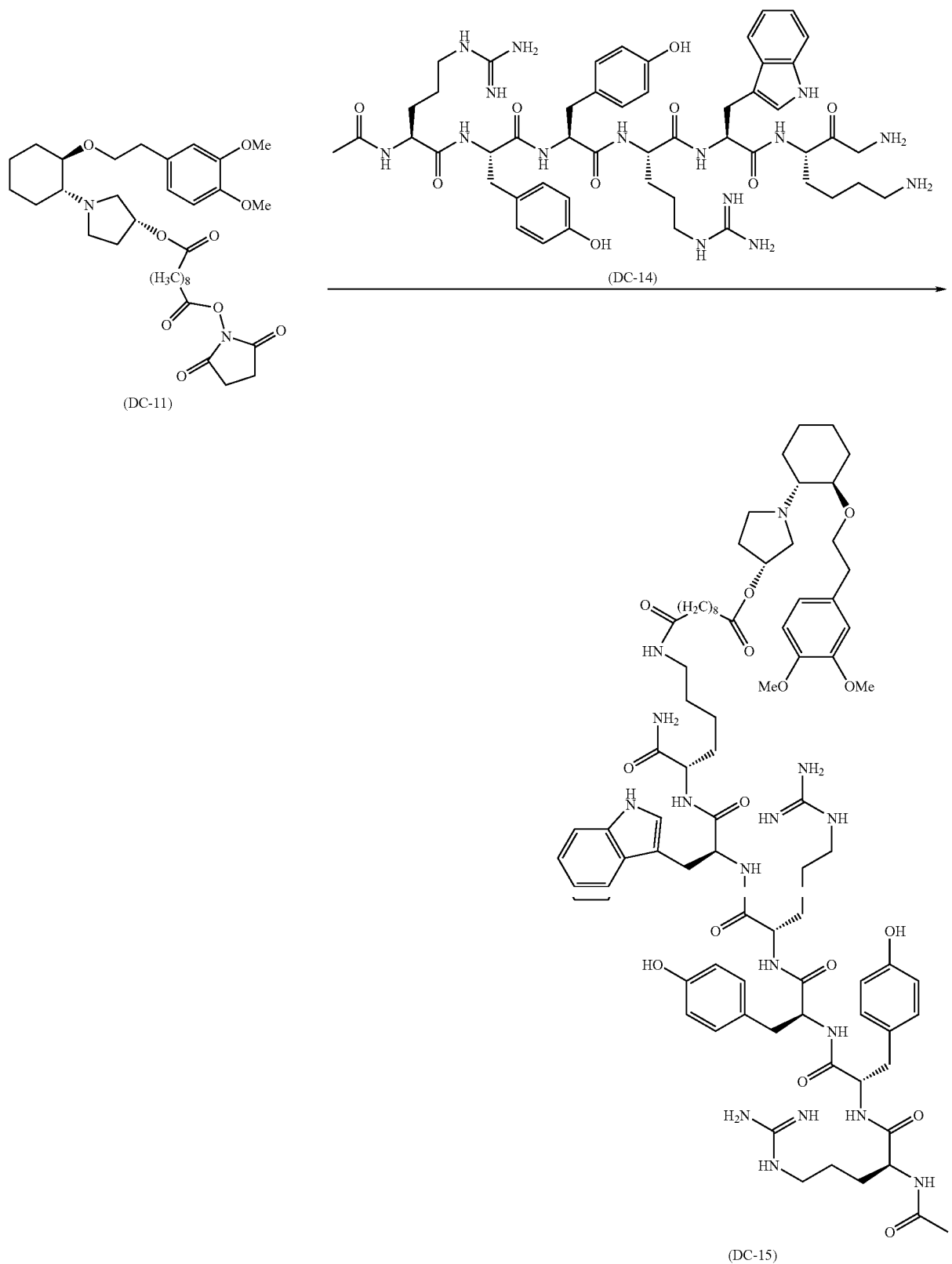

Reaction Scheme DC-7 illustrates the synthesis of drug conjugate (DC-15) from the amine reactive derivative (DC-11) and the selective water diuresis agent (DC-14). (Ref. WO-00228412 11 Apr. 2002, Zealand Pharmaceuticals A/S).

In a typical reaction, the amine-reactive intermediate (DC-11) may be dissolved in a suitable solvent (e.g., $CH_2Cl_2$) and reacted with the selective water diuresis agent (DC-14) to generate the drug conjugate (DC-15). The drug conjugate (DC-15) may then be isolated and purified by known standard methods.

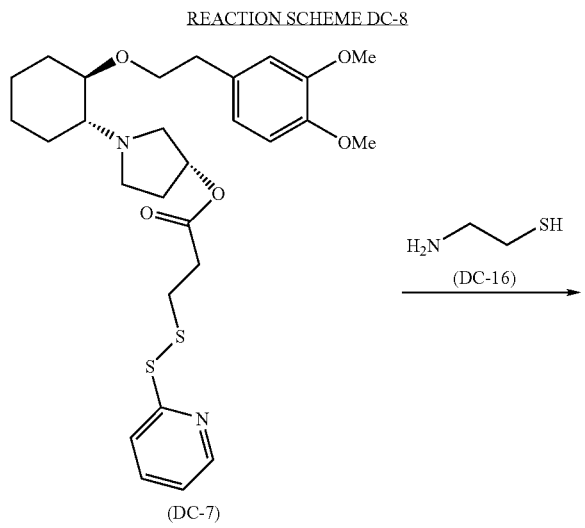

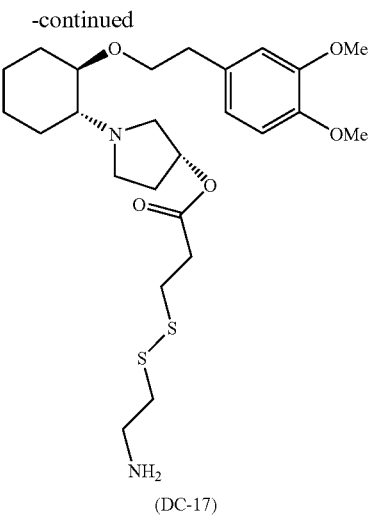

Reaction Scheme DC-8 illustrates the synthesis of drug conjugate (DC-17) from thiol-reactive derivative (DC-7) and a glycine cleavage system inhibitor (GCS) compound for psychotic disorders (DC-16). (Ref. WO-0006611 9 Nov. 2000, MERCK PATENT GMBH).

In a typical reaction, the thiol-reactive intermediate (DC-7) may be dissolved in a suitable solvent (e.g., $CH_2Cl_2$) and reacted with glycine cleavage system inhibitor (GCS) compound for psychotic disorders (DC-16) to generate the drug conjugate (DC-17). The drug conjugate (DC-17) may then be isolated and purified by known standard methods.

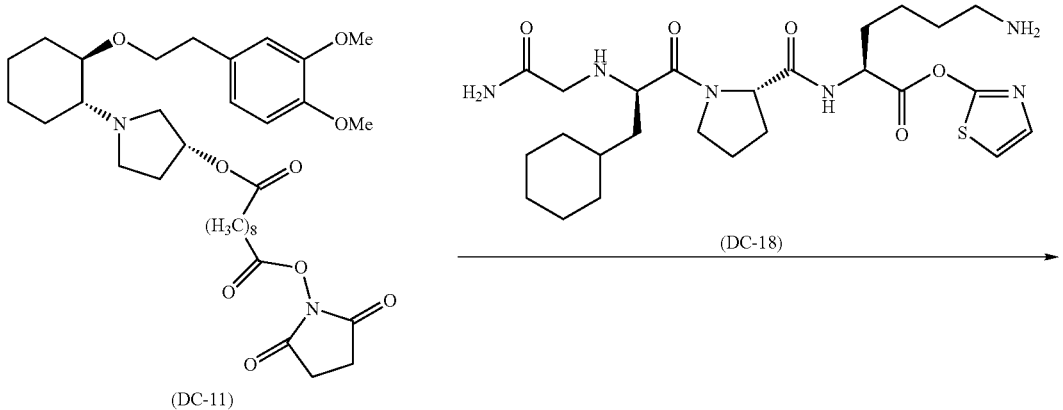

-continued

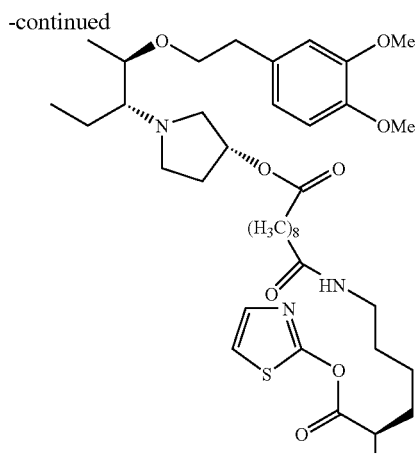

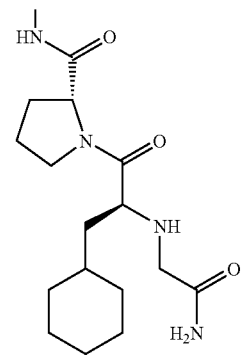

(DC-19)

Reaction Scheme DC-9 illustrates the synthesis of drug conjugate (DC-19) from the amine reactive derivative (DC-11) and the anticoagulant compound (DC-18). (Ref. EP-00884325 16 Dec. 1998, AKZO NOBEL N.V.).

In a typical reaction, the amine-reactive intermediate (DC-11) may be dissolved in a suitable solvent (e.g., $CH_2Cl_2$) and reacted with the anticoagulant compound (DC-18) to generate the drug conjugate (DC-19). The drug conjugate (DC-19) may then be isolated and purified by known standard methods.

REACTION SCHEME DC-10

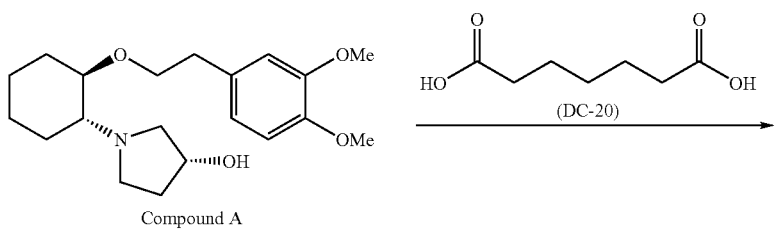

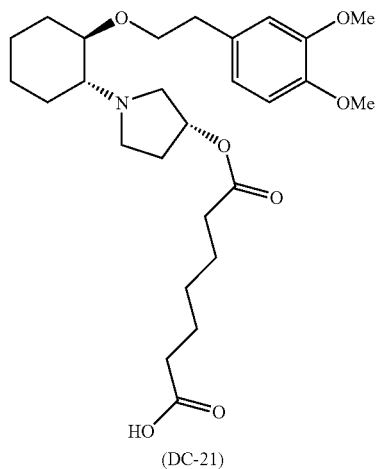

(DC-21)

Reaction Scheme DC-10 illustrates the synthesis of the alcohol reactive derivative (DC-21) from (1R,2R)-2-[(3R)-hydroxypyrrolidinyl]-1-(3,4-dimethoxyphenethoxy)cyclohexane (Compound A) and pimelic acid (DC-20) (Sigma-Aldrich).

In a typical reaction, (1R,2R)-2-[(3R)-hydroxypyrrolidinyl]-1-(3,4-dimethoxyphenethoxy)cyclohexane (1 equiv) (Compound A) may be dissolved in a suitable solvent (e.g., DMF) and reacted with pimelic acid (1 equiv) (DC-20). The resultant alcohol-reactive aminocycloalkyl ether (DC-21) may be isolated and purified using standard work-up procedures.

REACTION SCHEME DC-11

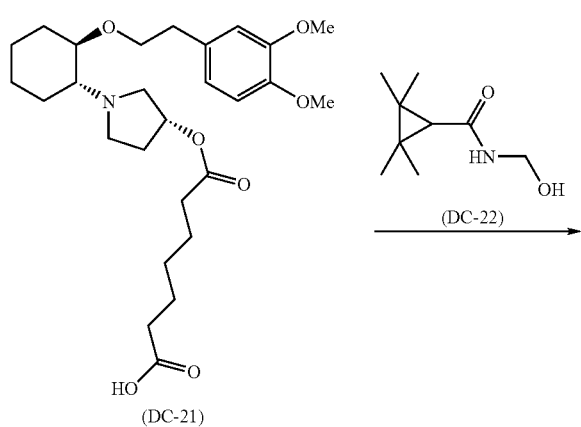

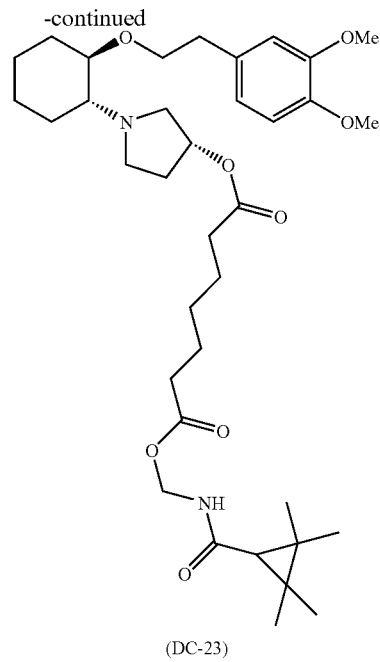

(DC-23)

Reaction Scheme DC-11 illustrates the synthesis of drug conjugate (DC-23) from the alcohol derivative (DC-21) and the N-hydroxyalkyl-tetramethylcyclopropane-carboxamide derivative (DC-22) for treatment of antidepression. (Ref. WO-03064374 7 Aug. 2003, Yissum Research Development Company of The Hebrew University Of Jerusalem).

In a typical reaction, the alcohol-reactive intermediate (DC-21) may be dissolved in a suitable solvent (e.g., $CH_2Cl_2$) and reacted with the anticoagulant compound (DC-22) to generate the drug conjugate (DC-23). The drug conjugate (DC-23) may then be isolated and purified by known standard methods.

REACTION SCHEME DC-12

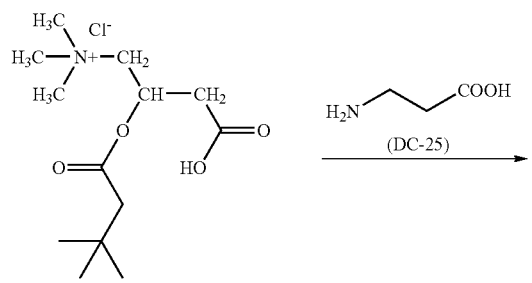

(DC-24)

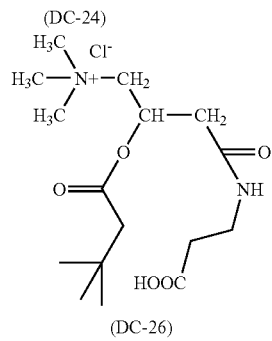

(DC-26)

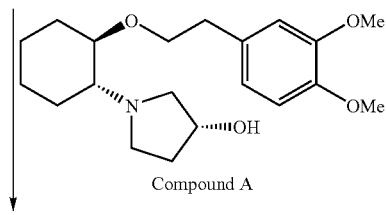

Compound A

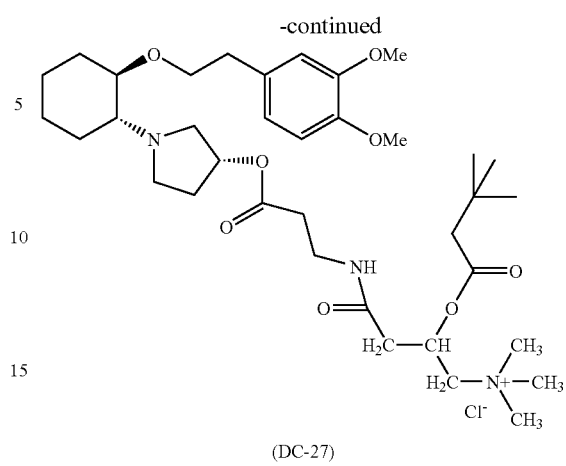

(DC-27)

Reaction Scheme DC-12 illustrates the synthesis of drug conjugate (DC-27) from the inotropic agent (DC-24), a suitable linker and (1R,2R)-2-[(3R)-hydroxypyrrolidinyl]-1-(3,4-dimethoxyphenethoxy)cyclohexane (Compound A). (Ref. U.S. Pat. No. 4,859,698 22 Aug. 1989, SIGMA-TAU INDUSTRIE FARMACEUTICHE RIUNITE S.P.A.).

In a typical reaction, the inotropic agent may be reacted with β-alanine and a coupling agent (e.g., tetramethyl uronium salts) to generate the alcohol reactive inotropic intermediate (DC-26). This intermediate may be isolated, purified by known standard methods and subsequently dissolved in a suitable solvent (e.g., $CH_2Cl_2$) and reacted with (1R,2R)-2-[(3R)-hydroxypyrrolidinyl]-1-(3,4-dimethoxyphenethoxy)cyclohexane (Compound A) to generate the drug conjugate (DC-27).

REACTION SCHEME DC-13

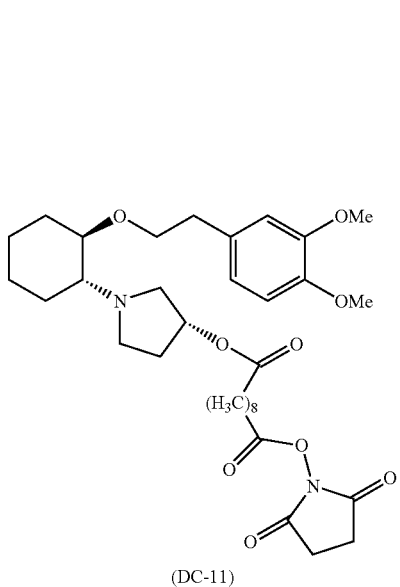

(DC-11)

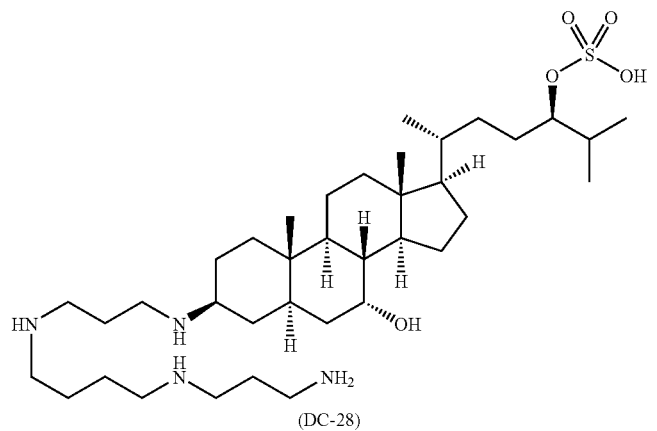

(DC-28)

-continued

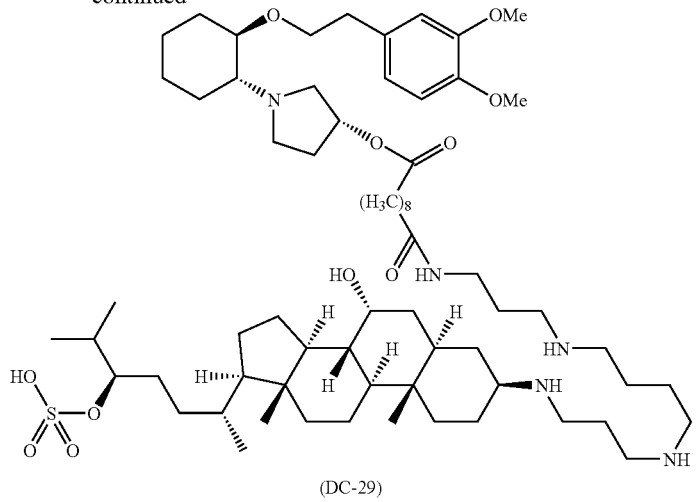

(DC-29)

Reaction Scheme DC-13 illustrates the synthesis of drug conjugate (DC-29) from the amine reactive derivative (DC-11) and the calcium channel sensitizer (DC-28). (Ref. WO-09819682 14 May 1998, MAGAININ PHARMACEUTICALS INC.).

In a typical reaction, the amine-reactive intermediate (DC-11) may be dissolved in a suitable solvent (e.g., $CH_2Cl_2$) and reacted with the calcium channel sensitizer (DC-28) to generate the drug conjugate (DC-29). The drug conjugate (DC-29) may then be isolated and purified by known standard methods.

REACTION SCHEME DC-14

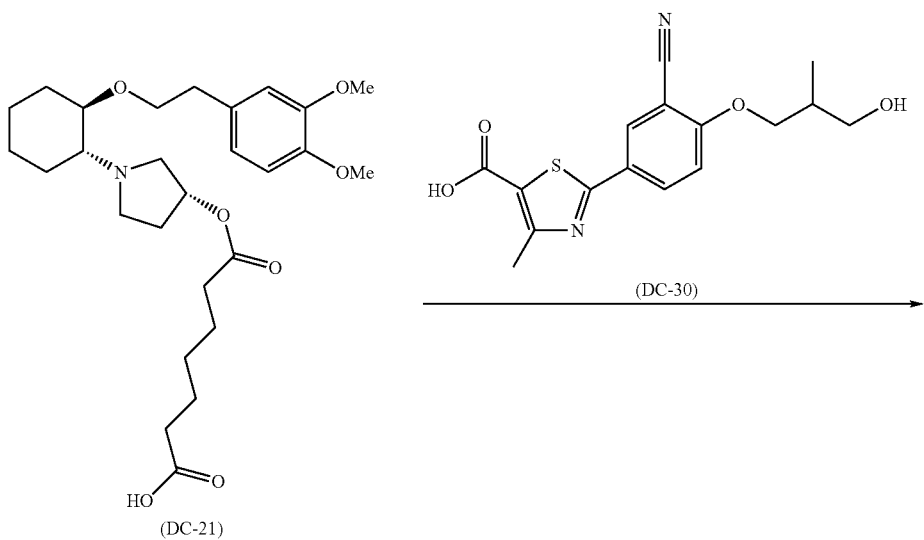

(DC-21)  (DC-30)

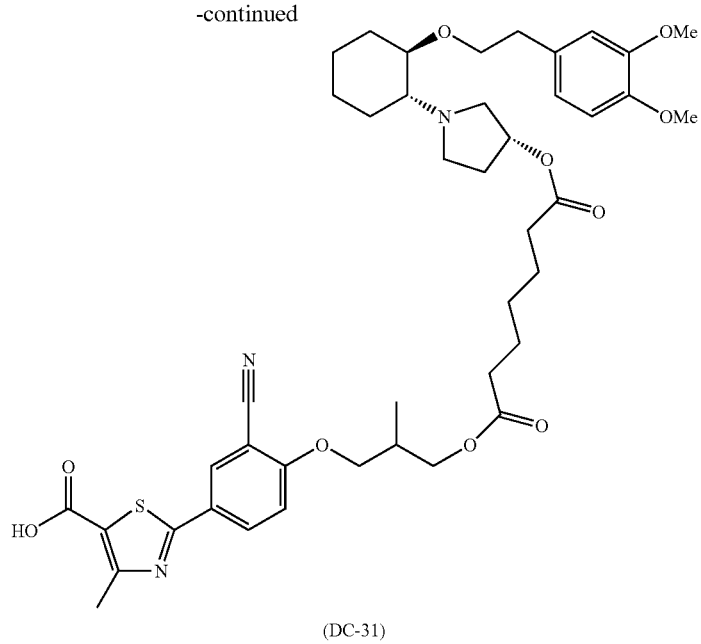

(DC-31)

Reaction Scheme DC-14 illustrates the synthesis of drug conjugate (DC-31) from the alcohol reactive derivative (DC-21) and the xanthine oxidase inhibitor (DC-30). (Ref. JP-2002105067 10 Apr. 2002, Ijin Ltd.).

In a typical reaction, the alcohol-reactive intermediate (DC-21) may be dissolved in a suitable solvent (e.g., $CH_2Cl_2$) and reacted with the xanthine oxidase inhibitor (DC-30) to generate the drug conjugate (DC-31). The drug conjugate (DC-31) may then be isolated and purified by known standard methods.

REACTION SCHEME DC-15

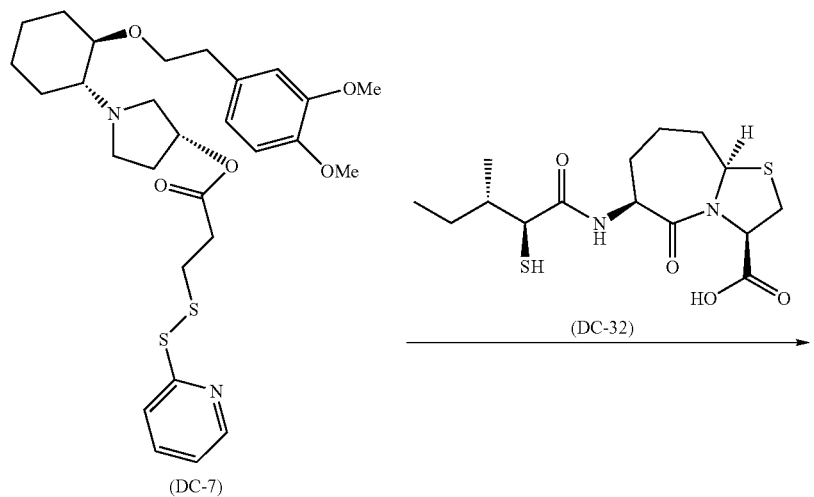

-continued

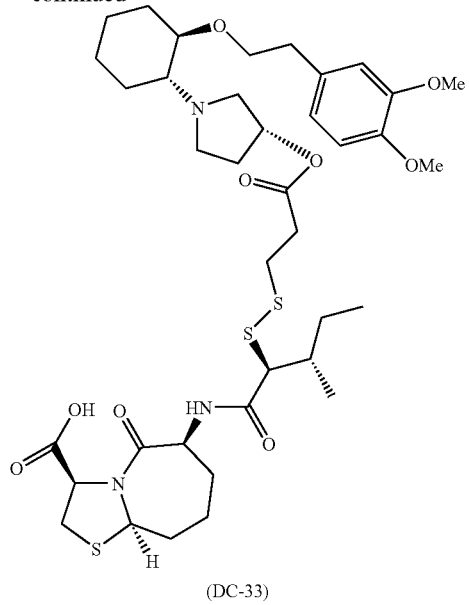

(DC-33)

Reaction Scheme DC-15 illustrates the synthesis of drug conjugate (DC-33) from the thiol reactive derivative (DC-7) and the ANP modulator (DC-32). (Ref. WO-09428901 22 Dec. 1994, EISAI CO., LTD.).

In a typical reaction, the thiol-reactive intermediate (DC-7) may be dissolved in a suitable solvent (e.g., $CH_2Cl_2$) and reacted with the ANP modulator (DC-32) to generate the drug conjugate (DC-33). The drug conjugate (DC-33) may then be isolated and purified by known standard methods.

Reaction Scheme DC-16 illustrates the synthesis of the alcohol reactive derivative (DC-35) from (1R,2R)-2-[(3R)-hydroxypyrrolidinyl]-1-(3,4-dimethoxyphenethoxy)cyclohexane (Compound A) and 1,4-diisocynatobutane (DC-34) (Sigma-Aldrich).

In a typical reaction, reaction of (Compound A) with an excess (at least 2 equiv.) of 1,4-diisocyanatobutane (DC-34) in dichloromethane at ambient temperature may give, after standard work-up well known in the art, alcohol-reactive intermediate (DC-35).

REACTION SCHEME DC-16

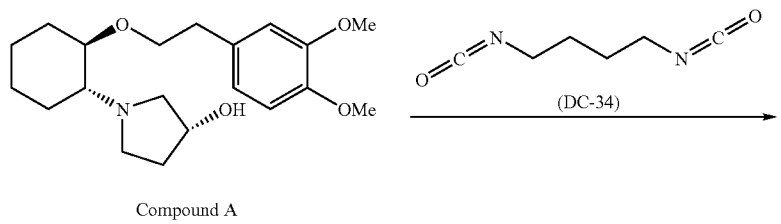

Compound A

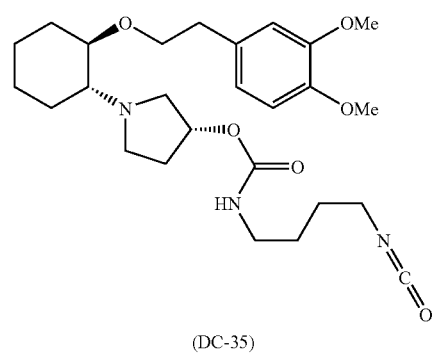

(DC-35)

REACTION SCHEME DC-17

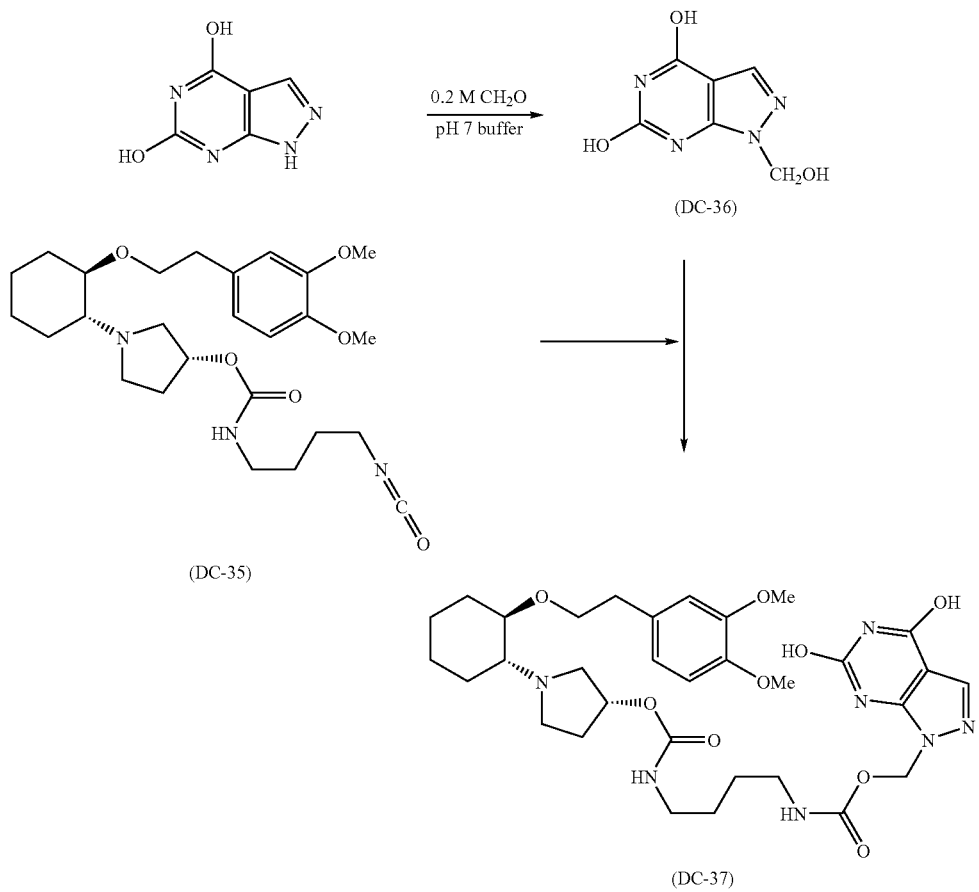

Reaction Scheme DC-17 illustrates the synthesis of the drug conjugate (DC-37) from the alcohol reactive derivative (DC-35) and xanthine oxidase inhibitor derivative 1-hydroxymethyloxypurinol (DC-36).

In a typical reaction, 1-hydroxymethyloxypurinol (DC-36) may be prepared from commercially available oxypurinol (4,6-dihydropyrazolo[3,4-d]pyrimidine, Lancaster) following an adapted procedure of Bansal, P. C.; Pitman, I H.; Higuchi, T. N-Hydroxymethyl derivatives of nitrogen heterocycles as possible pro-drugs II: Possible prodrugs of Allopurinol, Glutethimide, and Phenobarbital. *J. Pharm. Sci.* 1981, 70 (8), 855-857. More specifically, oxypurinol may be treated with 0.2M solution of formaldehyde in buffer pH7 to yield the desired hydroxymethylated product (DC-36). The alcohol-reactive intermediate (DC-35) may then be reacted with (DC-36) to give drug conjugate (DC-37), which can be isolated and purified by known standard methods.

REACTION SCHEME DC-18

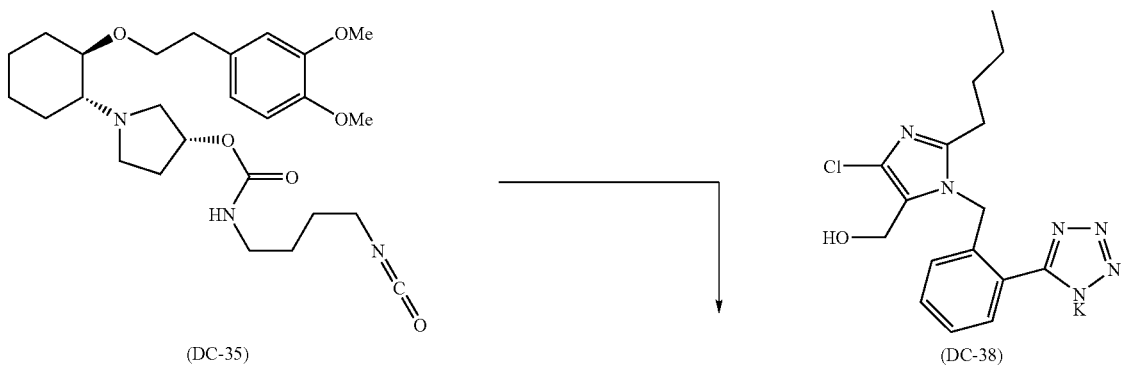

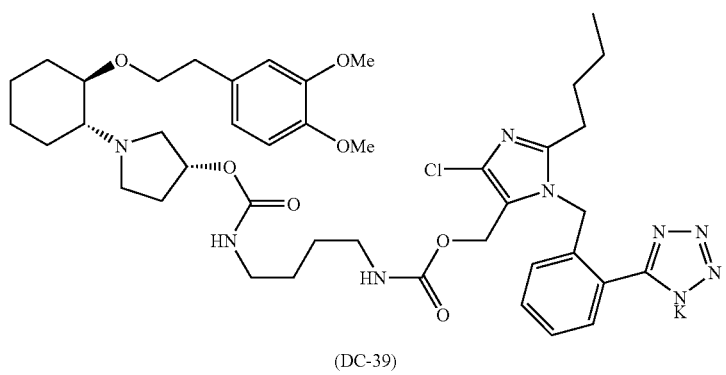

(DC-39)

Reaction Scheme DC-18 illustrates the synthesis of the drug conjugate (DC-39) from the alcohol reactive derivative (DC-35) and antihypertensive 2-butyl-4-chloro-1-[p-(o-1H-tetrazol-5-ylphenyl)benzyl]imidazole-5-methanol, monopotassium salt (DC-38).

In a typical reaction, the reaction between alcohol reactive derivative (DC-35) and antihypertensive 2-butyl-4-chloro-1-[p-(o-1H-tetrazol-5-ylphenyl)benzyl]imidazole-5-methanol, monopotassium salt (DC-38) in a suitable solvent such as dimethylformamide at a suitable temperature may give, after standard work-up procedures well known in the art, drug conjugate (DC-39).

REACTION SCHEME DC-19

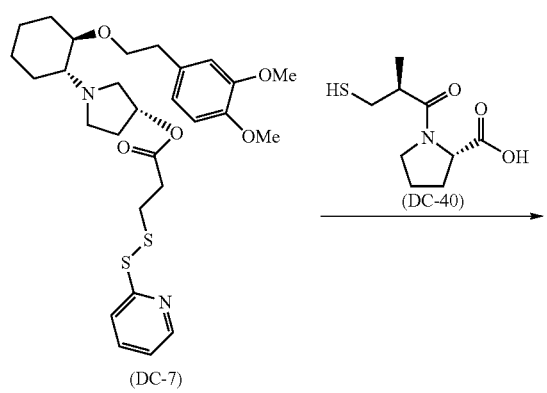

(DC-7)

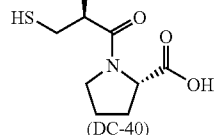

(DC-40)

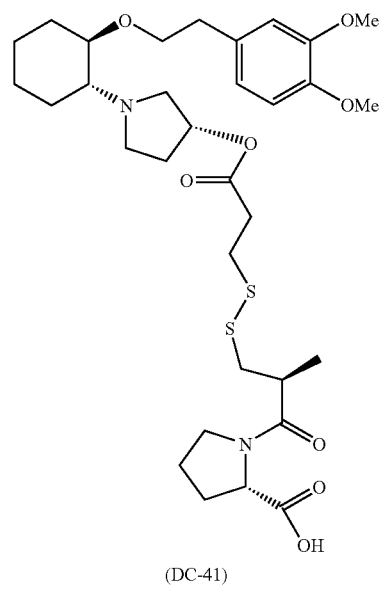

(DC-41)

Reaction Scheme DC-19 illustrates the synthesis of the drug conjugate (DC41) from the thiol reactive derivative (DC-7) and ACE inhibitor captopril, 1-[(2S)-3-mercapto-2-methylpropionyl]-L-proline (DC-40).

In a typical reaction, reaction of the thiol reactive derivative (DC-7) and ACE inhibitor captopril, 1-[(2S)-3-mercapto-2-methylpropionyl]-L-proline (DC-40) in a suitable solvent such as dimethylformamide at a suitable temperature may give, after standard work-up well known in the art, drug conjugate (DC-41).

REACTION SCHEME DC-20

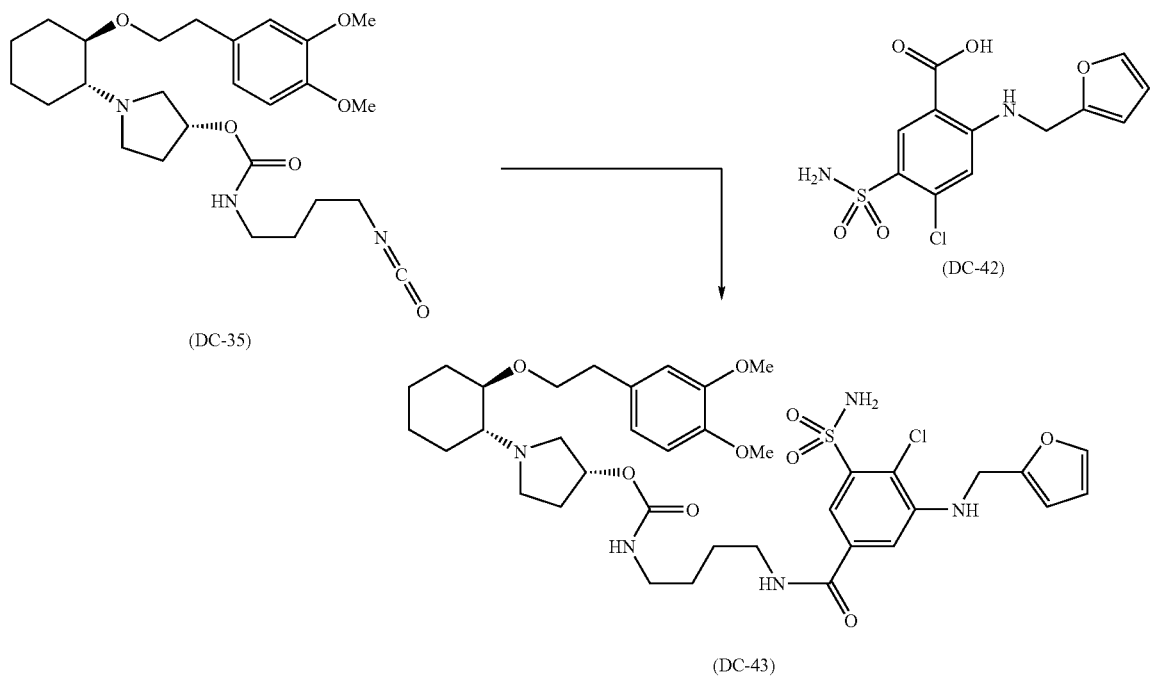

Reaction Scheme DC-20 illustrates the synthesis of the drug conjugate (DC-43) from the alcohol reactive derivative (DC-35) and diuretic furosemide 4-chloroN-furfuryl-5-sulfamoylanthranilic acid (DC-42).

In a typical reaction, the alcohol reactive derivative (DC-35) may be reacted with diuretic furosemide 4-chloroN-furfuryl-5-sulfamoylanthranilic acid (DC-42) in a suitable solvent such as dimethylformamide at a suitable temperature to give, after standard work-up procedures well known in the art, drug conjugate (DC43).

REACTION SCHEME DC-21

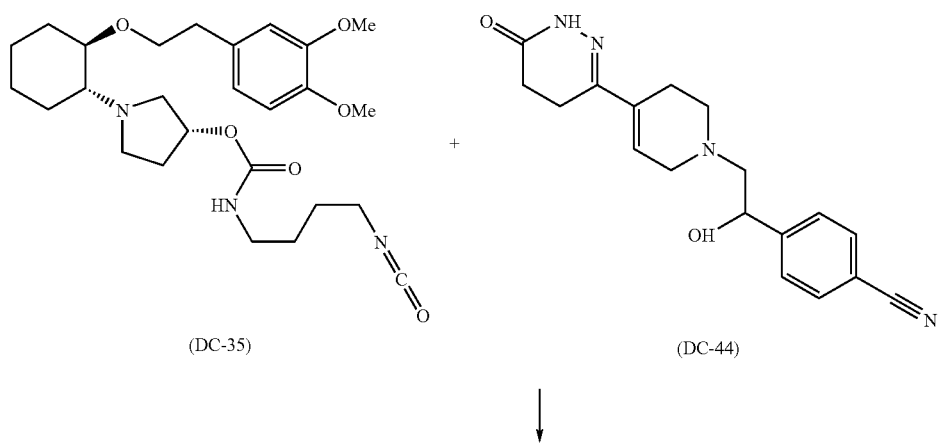

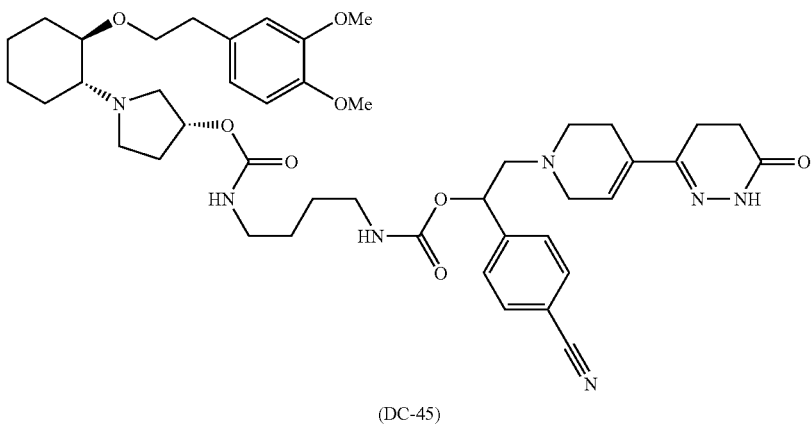

(DC-45)

Reaction Scheme DC-21 illustrates the synthesis of the drug conjugate (DC-45) from the alcohol reactive derivative (DC-35) and calcium sensitizer, SCH00013 (4,5-dihydro-6-[1-[2-hydroxy-2-(4-cyanophenyl)ethyl]-1,2,5,6-tetrahydro-pyrido-4-yl]pyridazin-3(2H)-one) (DC-44) (see Hino, M. et al., Arzneimittel-Forschung (1999), 49(5), 398-406).

In a typical reaction, the alcohol reactive derivative (DC-35) may be reacted with calcium sensitizer 4,5-dihydro-6-[1-[2-hydroxy-2-(4-cyanophenyl)ethyl]-1,2,5,6-tetrahydropyrido-4-yl]pyridazin-3(2H)-one (DC-44) in a suitable solvent such as dimethylformamide at a suitable temperature to give drug conjugate (DC-45).

REACTION SCHEME DC-22

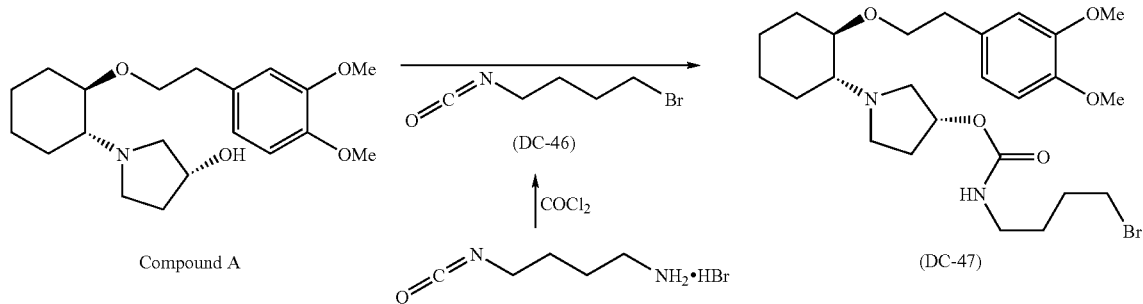

Reaction Scheme DC-22 illustrates the synthesis of the amino reactive derivative (DC-47) from (1R,2R)-2-[(3R)-hydroxypyrrolidinyl]-1-(3,4-dimethoxyphenethoxy)cyclohexane (Compound A) and 4-bromobutylisocyanate (DC-46).

In a typical reaction, (1R,2R)-2-[(3R)-hydroxypyrrolidinyl]-1-(3,4-dimethoxyphenethoxy)cyclohexane (Compound A) may be reacted with 4-bromobutylisocyanate (DC-46) (see, Minin, P. et al., *J. Org. Chem.* (2003), Vol. 68, pp. 2960-2963) in a suitable solvent such as dichloromethane at a suitable temperature to give amino-reactive derivative (DC-47).

REACTION SCHEME DC-23

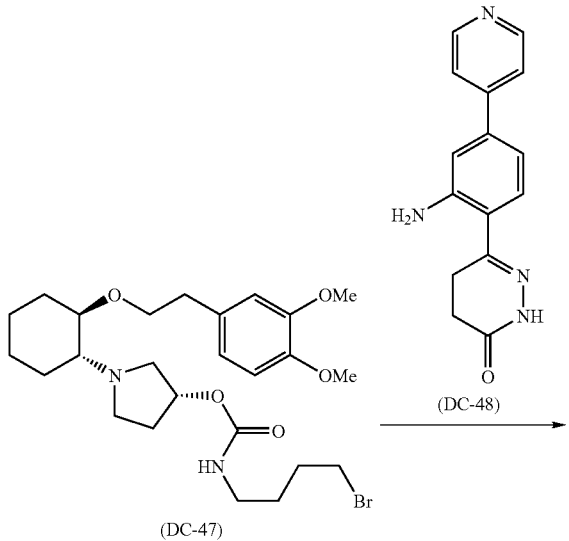

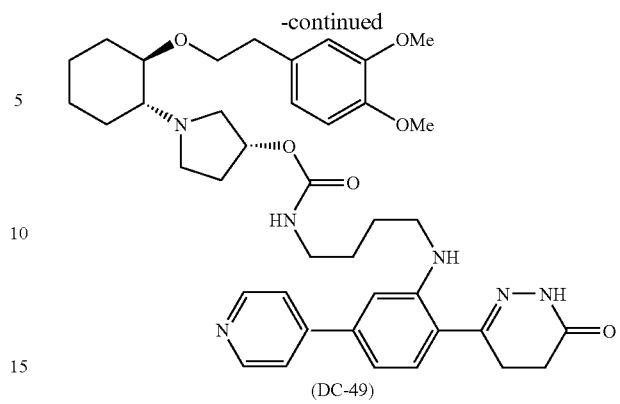

Reaction Scheme DC-23 illustrates the synthesis of the drug conjugate (DC-49) from the amino reactive derivative (DC-47) and calcium sensitizer MCl-154 6-[4-(4'-pyridyl) aminophenyl]-4,5-dihydro-3(2H)-pyridazinone (DC-48). (JP 2003113084; Mitsubishi Welpharma Co., Japan)

In a typical reaction, the amino reactive derivative (DC-47) and 6-[4-(4'-pyridyl) aminophenyl]-4,5-dihydro-3(2H)-pyridazinone (DC-48) may be reacted in a suitable solvent such as dimethylformamide at a suitable temperature to give, after standard work-up procedure, drug conjugate (DC-49).

REACTION SCHEME DC-24

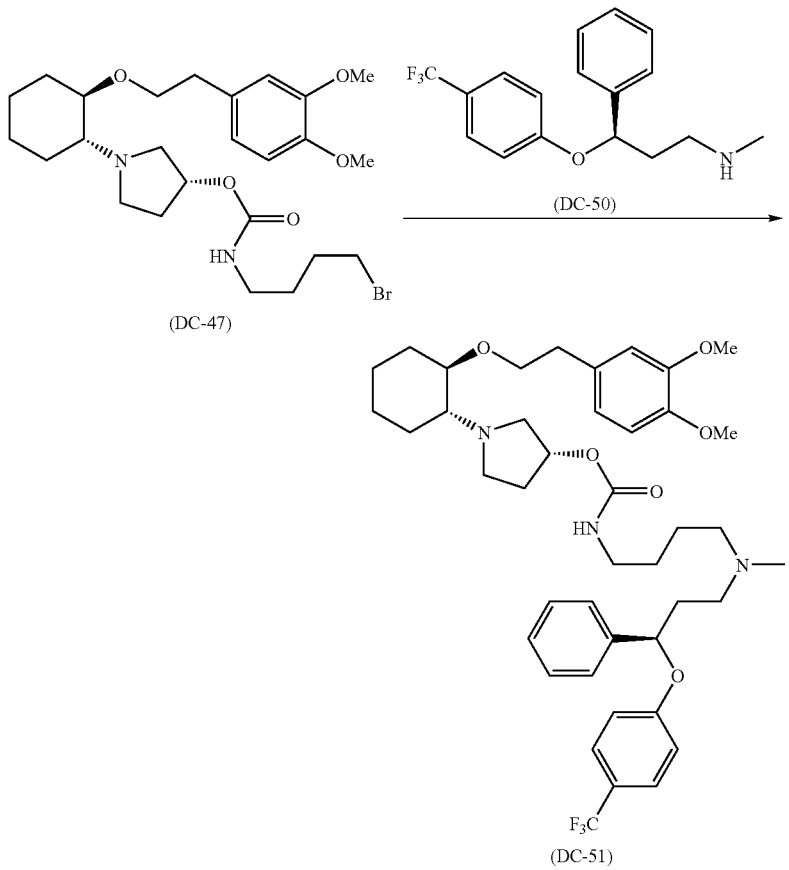

Reaction Scheme DC-24 illustrates the synthesis of the drug conjugate (DC-51) from the amino reactive derivative (DC-47) and antidepressant fluoxetine (±)-N-methyl-3-phenyl-3-[(α,α,α-trifluoro-p-tolyl)oxy]propylamine (DC-50).

In a typical reaction, reaction of the amino reactive derivative (DC-47) and (±)-N-methyl-3-phenyl-3-[(α,α,α-trifluoro-p-tolyl)oxy]propylamine (DC-50) in a solvent such as dimethylformamide at a suitable temperature may give drug conjugate (DC-51).

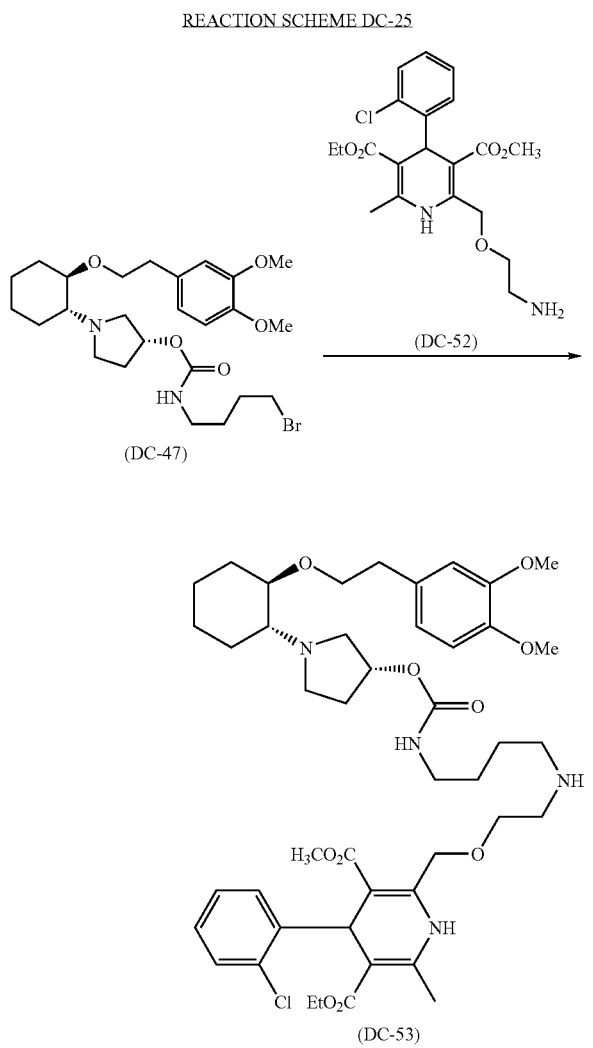

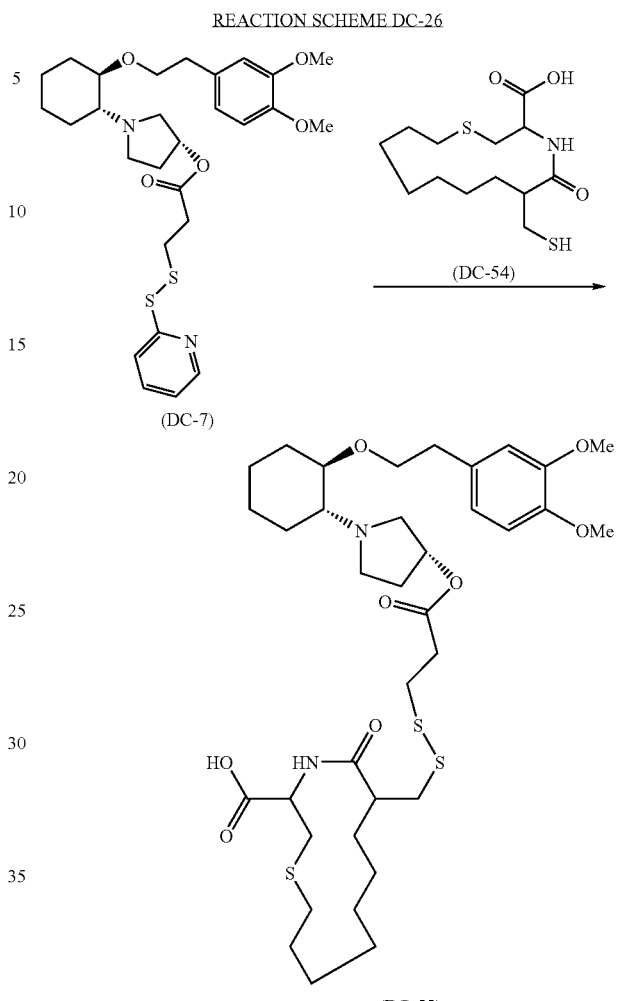

Reaction Scheme DC-25 illustrates the synthesis of the drug conjugate (DC-53) from the amino reactive derivative (DC-47) and antihypertensive/antianginal amlodipine 3-ethyl-5-methyl(±)-2-[(2-aminoethoxy)methyl]-4-(o-chlorophenyl)-1,4-dihydro-6-methyl-3,5-pyridinedicarboxylate (DC-52).

In a typical reaction, the amino reactive derivative (DC-47) and 3-ethyl-5-methyl(±)-2-[(2-aminoethoxy)methyl]4-(o-chlorophenyl)-1,4-dihydro-6-methyl-3,5-pyridinedicarboxylate (DC-52) may be reacted in a suitable solvent such as dimethylformamide to give, after isolation and purification by known methods, drug conjugate (DC-53).

Reaction Scheme DC-26 illustrates the synthesis of drug conjugate (DC-55) from thiol-reactive derivative (DC-7) and a vasodilator (DC-54). (Ref. EP-00544620 Jun. 2, 1993, CIBA-GEIGY AG).

In a typical reaction, the thiol-reactive intermediate (DC-7) may be dissolved in a suitable solvent (e.g., $CH_2Cl_2$) and reacted with the vasodilator (DC-54) to generate the drug conjugate (DC-55). The drug conjugate (DC-55) may then be isolated and purified by known standard methods.

Preparation of Drug Conjugates for $\beta_1$-Blockade

In one aspect, the additional drug moiety set forth above is a beta-blocker. Additional drug moieties may also be selected from any of the drug moiety described in this patent application, for example, the additional drug moieties described in the PCT Published Patent Application No. WO 2005/018635.

In another aspect, the additional drug moiety may be a drug or a pharmacophore with $\beta_1$-blocking activity. A drug or a pharmacophore with $\beta_1$-blocking activity is said to be a "cardioselective beta-blocker".

Metoprolol as an Additional Drug Moiety

Atrial fibrillation (AF) can be divided into three groups based on the duration of the AF episode and the refractoriness to cardioversion. The three groups are; paroxysmal, persistent and permanent, in decreasing order of receptivity to treatment. Permanent AF is resistant to any form of pharmacological treatment and cardioversion, and therefore patients with permanent AF may be considered candidates for therapies such as the MAZE procedure and can be treated with either calcium channel blockers or β-blockers to control ventricular rate.

In the remaining two categories of paroxysmal and persistent AF, treatment has a dual intent. Firstly, if a patient is in AF, physicians may wish to restore normal sinus rhythm (AF conversion). Secondly, after the patient has successfully attained sinus rhythm the physician will attempt to maintain sinus rhythm and prevent recurrence of AF.

If a patient is in AF, the physician may elect to restore sinus rhythm by the use of pharmacological rhythm control agents such as Compound A, or alternatively, to allow AF to continue, and ensure that ventricular rate is controlled (correcting tachycardia-induced cardiomyopathy).

The AFFIRM (Atrial Fibrillation Follow-up Investigation in Rhythm Management, 2001) trial and RACE (Rate Control Equal to Rhythm Control) trial examined comparative efficacy and mortality rates between AF patient groups using either rhythm control or rate control drugs. Results of these studies indicated that rate and rhythm control are equivalent in efficacy in relatively asymptomatic patients with atrial fibrillation. The AFFIRM trial randomized patients to medical therapy either to restore atrial rhythm or to control ventricular heart rate, whereas RACE compared medical therapy to control heart rate with electrocardioversion of rhythm. The primary study endpoint of the AFFIRM trial, total mortality, was slightly lower in the rate-control arm, although the trend was not statistically significant. Outcomes were approximately the same for the two groups in the secondary endpoint, ischemic stroke. In the RACE study, the difference between primary endpoints was also small. It was reported that patients with hypertension in particular did not do well with electrocardioversion for rhythm control. The rate of mortality, thromboembolism, or other severe complications was approximately 19 percent for rate-control therapy vs. approximately 31 percent for rhythm control.

There are two classes of antiarrhythmic agents that restore and maintain sinus rhythm through rhythm control; Class I and Class III antiarrhythmics. A summary of their ion channel blocking profiles and mechanism of action is as follows:

| | |
|---|---|
| Class IA: | Sodium channel blockers that prolong ventricular repolarization, including quinidine, procainamide, disopyramide |
| Class IB: | Sodium channel blockers that shorten ventricular repolarization including lidocaine, mexiletine, tocainide, phenytoin |
| Class IC: | Sodium channel blockers with little effect on ventricular repolarization, including encainide, flecainide, propafenone |
| Class III: | Potassium channel blockers that primarily prolong ventricular repolarization, including amiodarone, bretylium, d,l-sotalol, ibutilide, azimilide |

The SWORD study (see, Waldo, A L et al. Effect of d-sotalol on mortality in patients with left ventricular dysfunction after recent and remote myocardial infarction. *Lancet* 1996, 348, 7-12) has shown that optically pure d-sotalol increased mortality by 65% compared to placebo. In light of those results, K. Stoschitzky et al. (see, Stoschitzky, K. et al. Racemic beta-blockers—fixed combinations of different drugs. *J. Clin. Cardiol.* 1998, 1, 14-18) suggest to replace the currently used racemic mixtures with the optically pure I-enantiomers.

There are two classes of antiarrhythmic agents that restore and maintain sinus rhythm through rate control; Class II and IV antiarrhythmics. A summary of their ion channel profiles and mechanism is as follows:

| | |
|---|---|
| Class II: | β-adrenergic blocking drugs that indirectly reduce $I_{Ca-L}$ current in SA and AV nodes, including propranolol, atenolol, metoprolol, esmolol, timolol |
| Class IV: | Calcium channel blockers that block $I_{Ca-L}$ current, thus slowing conduction in SA and AV nodes and depressing contractility in all heart myocytes, including verapamil, diltiazem |

The VERDICT (Verapamil versus Digoxin Cardioversion Trial) (see, Van Noord, T. et al. VERDICT: The Verapamil versus Digoxin Cardioversion Trial: A Randomized Study on the Role of Calcium Lowering for Maintenance of Sinus Rhythm after Cardioversion of Persistent Atrial Fibrillation. *J. Cardiovasc. Electrophysiol.* 2001, 12, 766-769) has shown that the use of calcium-lowering drugs alone initiated pre-ECV (electrical cardioversion) and continued post-ECV seems to be insufficient to prevent subacute relapses.

AF patients are commonly treated with agents, such as β-blockers, to control ventricular rate (see, e.g., Van Gelder, I. C. et al. A comparison of Rate Control and Rhythm Control in Patients with Recurrent Persistent Atrial Fibrillation. *N. Engl. J. Med.* 2002, 347 (23), 1834-1840; Basler, J. R. et al. β-Adrenergic Blockade Accelerates Conversion of Postoperative Supraventricular Tachyarrhythmias. *Anesthesiology* 1998, 89 (5), 1052-1059; and Yahalom, J. Beta-Adrenergic Blockade as Adjunctive Oral Therapy in Patients with Chronic Atrial Fibrillation. *Chest,* 1977, 71 (5), 592-596). β-adrenoceptor-blocking agents depress sinus node automaticity and inhibit atrioventricular nodal function by prolonging refractoriness and slowing conduction (see, Sung, R. J. et al. Beta-Adrenoceptor Blockade: Electrophysiology and Antiarrhythmic Mechanisms. *Am. Heart J.* 1984, 108, 1115-1120; and Kowey, P. R. et al. Electrophysiology of Beta Blockers in Supraventricular Arrhythmias. *Am. J. Cardiol.* 1987, 60, 32D-38D). Rather than using multiple drugs, the pharmacophores for antiarrhythmic activity and β₁-blockade may be combined in a single drug molecule. Hence, such an agent may be derived by attaching metoprolol, a β₁-selective antagonist (cardioselective), to (1S,2S)-2-[(3R)-hydroxypyrrolidinyl]-1-(3,4-dimethoxyphenethoxy)cyclohexane or (1R,2R)-2-[(3R)-hydroxypyrrolidinyl]-1-(3,4-dimethoxyphenethoxy)cyclohexane.

In one variation, the ion channel modulating compound is (1R,2R)-2-[(3R)-hydroxypyrrolidinyl]-1-(3,4-dimethoxyphenethoxy)cyclohexane monohydrochloride (Compound A) and the additional drug moiety is a β1-blocker that may have the S configuration.

Metoprolol may be used for the treatment of AF (see, Page, R. L. Beta-Blockers for Atrial Fibrillation: Must We Consider Asymptomatic Arrhythmias? *J. Am Coll. Cardiol.* 2000, 36 (1), 147-150). However, other cardioselective β-adrenoceptor-blocking agents could be selected from the pharmacopea following the type of pharmacological profile targeted (i.e. short-acting vs. long-acting, potency vs. selectivity) for the use in a drug conjugate (for example: Esmolol, Acebutolol, Practolol, Atenolol, Celiprolol, Betaxolol, Cetamolol, Bisoprolol and Bevantolol)

Examples of conjugates of ion channel modulating compounds and Metoprolol include, but are not limited to, covalently linking (1R,2R)/(1S,2S)-2-[(3R)-hydroxypyrrolidinyl]-1-(3,4-dimethoxyphenethoxy)cyclohexane to Metoprolol via a linker with complementary functionalities for the ion channel modulating compound and the additional drug moiety such that the drug conjugates of Table 2 are provided (i.e., Compounds DC-67, DC-69, DC-72 and DC-73).

each case, the divalent linker is reacted with a complementary functionality on the ligand to form a linkage bond. Such complementary functionality is well known in the art and is exemplified by compounds DC-67, DC-69, DC-72 and

TABLE 2

STRUCTURE OF METOPROLOL, COMPOUND A AND DRUG CONJUGATES C-67, DC-69, DC-72, DC-73

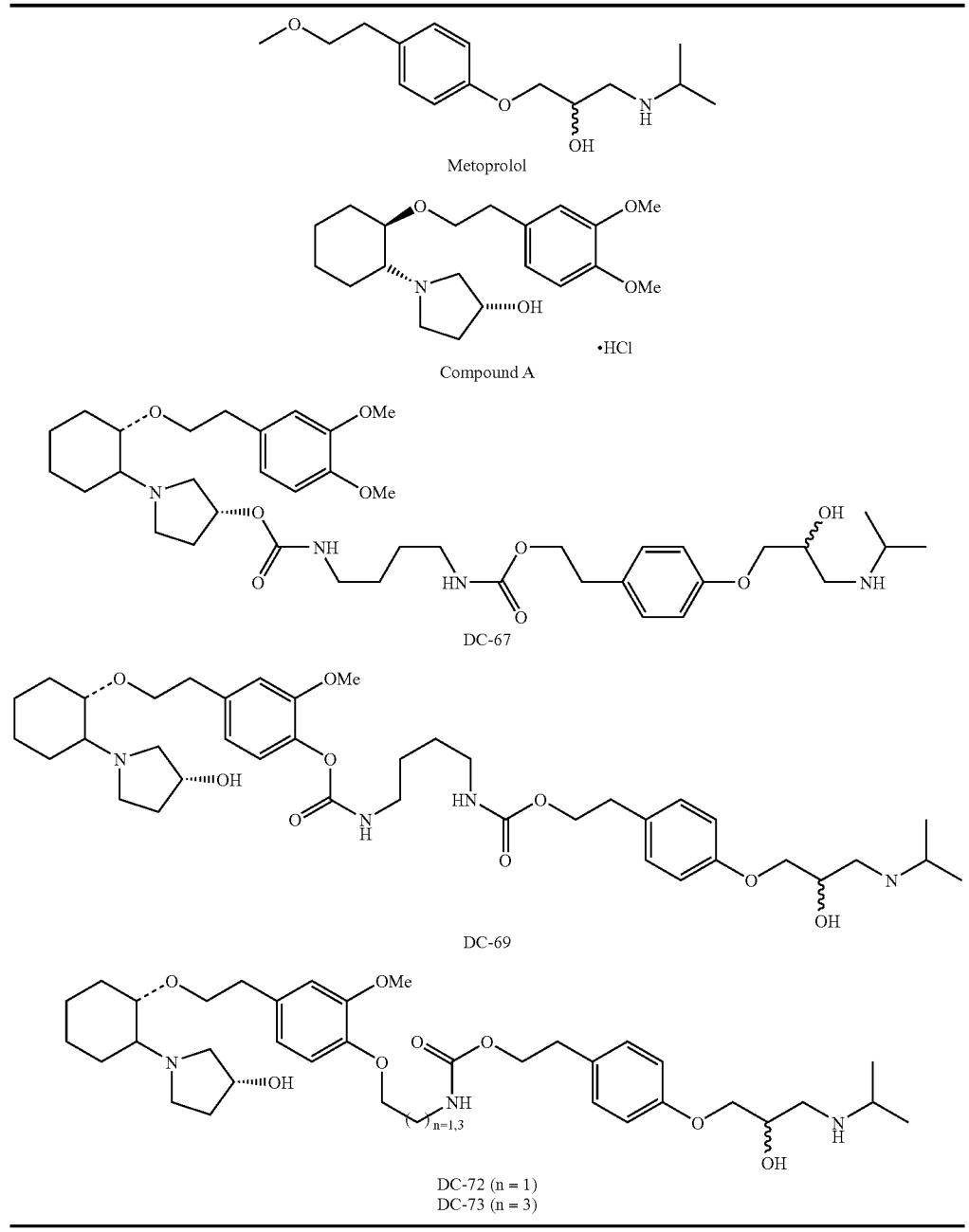

Compounds DC-67, DC-69, DC-72 and DC-73 are prepared using chemical reactions as illustrated in more detail below in Reaction Schemes DC-27 to DC-31. Diastereomeric mixtures or pure enantiomeric forms of the compounds can be prepared by methods known in the art.

Suitable divalent linkers include, by way of compound only, those derived from dihalides and diisocyanates or mixtures of halides and isocyanates, as exemplified in Table 2. In DC-73. Metoprolol (Log $D_{pH7.4}$=−0.60 (Pallas 2.1)) is covalently linked to the pyrrolidinol ring of Compound A (Log $D_{pH7.4}$=1.87 (Pallas 2.1)) (DC-67, Log $D_{pH7.4}$=1.80, Pallas 2.1) via 1,4-diisocyanatobutane. The same divalent linker is used to attach Metoprolol in 4-position of the phenyl ring of Compound A (DC-69, Log $D_{pH7.4}$=0.37, Pallas 2.1). Alternatively, the use of a mixed divalent linker, such as 2-bromoethyl isocyanate or 4-bromobutyl isocyanate, provide compounds DC-72 (Log $D_{pH7.4}$=0.34, Pallas 2.1) and DC-73 (Log $D_{pH7.4}$=1.19, Pallas 2.1), respectively.

Reaction Schemes DC-27 to DC-31 illustrate the synthesis of drug conjugates (DC-67), (DC-69), (DC-72) and (DC-73) which links the $\beta_1$-blocker metoprolol with (1R,2R)/(1S,2S)-2-[(3R)-hydroxypyrrolidinyl]-1-(3,4-dimethoxyphenethoxy)cyclohexane.

The aminocycloalkyl ethers described in the present patent application could be prepared from aminoalcohols and alcohols by following the general methods and specific experimental procedures described in the references cited above and the reaction schemes and examples shown below.

the alkoxide of (DC-61) to provide (DC-62). Hydrogenolysis of (DC-62) in the presence concentrated HCl gives (DC-63), whereas partial hydrogenolysis in neutral conditions gives (DC-64).

The following examples provide specific details on the preparation of Compounds (DC-61, DC-62, and DC-63).

4-Benzyloxy-3-methoxyphenethyl alcohol (DC-61)

A mixture of homovanillyl alcohol (100 mmol, 17.0 g), benzyl bromide (105 mmol, 18.33 g) and 5M aqueous NaOH (24 mL) in ethanol (200 mL) was refluxed for 6 h. The organic

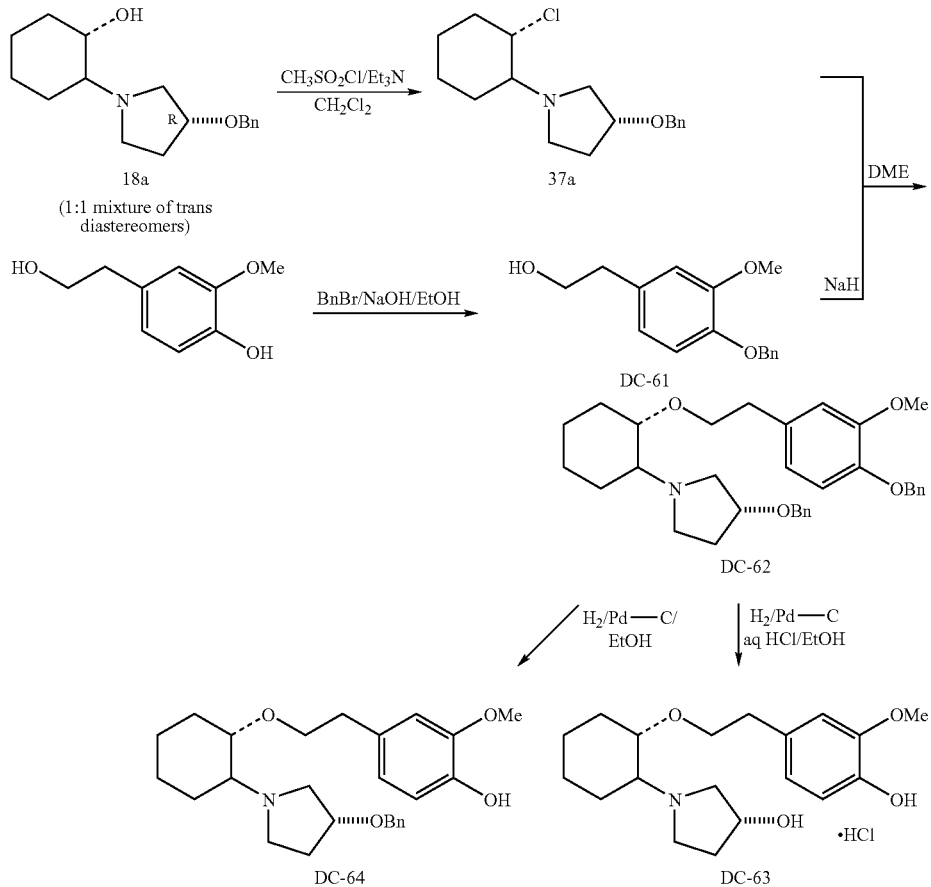

REACTION SCHEME DC-27

The Williamson ether synthesis (Feuer, H.; Hooz, J. Methods of Formation of the Ether Linkage. In Patai, Wiley: New York, 1967; pp 445-492) between an activated form (37a) of aminoalcohol (18a) with the alkoxide of the appropriate phenethyl alcohol (DC-61) in a polar solvent such as ethylene glycol dimethyl ether (DME) (Reaction Scheme DC-27) provide the corresponding aminoether in high yield. Subsequent hydrogenolysis of (DC-62) in the presence of Pd—C provides compound (DC-63) in strongly acidic conditions and compound (DC-64) in neutral conditions, respectively.

Compound (DC-61) was prepared as follows: homovanillyl alcohol was reacted with benzyl bromide in the presence of NaOH aqueous in EtOH to provide intermediate (DC-61). Activation of (18a) via mesylation to give chloride (37a), as previously described herein, was followed by reaction with solvent was evaporated in vacuo. The residue was partitioned between brine (200 mL) and diethyl ether (200 mL). The aqueous layer was separated from the organic layer and extracted again with ether. The combined organic layers were dried over $MgSO_4$ and the solvent was evaporated in vacuo. Purification by dry-column chromatography with mixtures of ethyl acetate-hexanes (1:4, 1:3, v/v) yielded 20.66 g (80% yield) of (DC-61) as pale yellow oil. $R_f$ 0.25 (EtOAc-hexanes, 1:1, v/v); $^1$H-NMR (300 MHz, $CDCl_3$) δ 7.44-7.25 (m, 5H, Ar), 6.84-6.67 (m, 3H, Ar), 5.12 (s, 2H, $PhCH_2O$), 3.88 (s, 3H, $CH_3O$), 3.81 (t, 2H, $CH_2CH_2OH$), 2.79 (t, 2H, $CH_2CH_2OH$), 1.54 (s, 1H, OH); $^{13}$C-NMR (75 MHz, $CDCl_3$, APT) δ 149.63 (+), 146.75 (+), 137.21 (+), 131.60 (+), 128.43 (−), 127.70 (−), 127.17 (−), 120.84 (−), 114.25 (−), 112.74 (−), 71.07 (+), 63.58 (+), 55.90 (−), 38.67 (+).

(1R,2R)/(1S,2S)-1-(4-Benzyloxy-3-methoxyphenethoxy)-2-[(3R)-benzyloxypyrrolidinyl]cyclohexane (DC-62)

To a suspension of NaH (2.07 g, 80% dispersion in mineral oil, 69 mmol) in anhydrous ethylene glycol dimethyl ether (100 mL) was added a solution of 4-benzyloxy-3-methoxyphenethyl alcohol (DC-61) (17.05 g, 66 mmol) in ethylene glycol dimethyl ether (100 mL). The resultant mixture was then stirred at room temperature for 30 min to complete formation of the sodium alkoxide.

The chloride (37a) (19.4 g, 66 mmol) in anhydrous ethylene glycol dimethyl ether (50 mL) was added quickly to the mixture containing the alkoxide of (DC-61) and the resultant mixture was refluxed under argon for 16 h. The reaction mixture was allowed to cool to room temperature and then quenched with water (250 mL), followed by concentration under reduced pressure. The resultant aqueous solution was adjusted to pH0.6 by the addition of 37% aqueous HCl (22 mL) diluted with $H_2O$ (28 mL). To remove unreacted 4-benzyloxy-3-methoxyphenethyl alcohol (DC-61), the acidic aqueous layer was extracted with ether (3×300 mL, 350 mL). The aqueous solution was then adjusted to pH13 by the addition of 40% aqueous NaOH (24 mL) and extracted with ether (2×300 mL). The ether extracts at pH13 were combined and dried ($Na_2SO_4$ anhydr). Removal of solvent in vacuo yielded 25.7 g (83% yield) of the compound (DC-62) as an orange oil. $R_f$ 0.44 (EtOAc-iPrNH$_2$, 98:2, v/v); $^1$H NMR (300 MHz, CDCl$_3$) δ 7.43-7.24 (m, 10H, Ar), 6.79-6.66 (m, 3H, Ar), 5.10 (s, 2H, PhCH$_2$O), 4.45 (d, 2H, PhCH$_2$O), 4.05 (m, 1H), 3.85 (s, 3H, CH$_3$O), 3.75-1.18 (m, 20H); $^{13}$C NMR (75 MHz, CDCl$_3$, APT) δ 149.45 (+), 146.53 (+), 138.56 (+), 137.41 (+), 132.72 (+), 128.46 (−), 128.32 (−), 127.70 (−), 127.63 (−), 127.46 (−), 127.24 (−), 120.80 (−), 114.20 (−), 112.99 (−), 79.26 (−), 77.88 (−), 71.18 (+), 70.95 (+), 70.89 (+), 69.74 (+), 64.00 (−), 57.57 (+), 56.94 (+), 55.96 (−), 49.88 (+), 49.26 (+), 36.52 (+), 31.29 (+), 28.73 (+), 27.02 (+), 23.16 (+), 22.82 (+).

(1R,2R)/(1S,2S)-1-(4-Hydroxy-3-methoxyphenethoxy)-2-[(3R)-hydroxypyrrolidinyl]cyclohexane monohydrochloride (DC-63)

(a) To a 100 mL Schlenk-flask charged with a solution of (DC-62) (1.25 g, 2.42 mmol) in ethanol (12 mL) was added Pd—C catalyst (400 mg) and aqueous 6M hydrochloric acid (0.8 mL). The reaction mixture was stirred vigorously overnight (20 h) at room temperature under a positive pressure of $H_2$. TLC and GC analysis indicated total consumption of substrate and clean conversion into the desired product. The reaction mixture was filtered through a syringe filter (PTFE, pore size: 0.2 μm; diameter: 25 mm. VWR# 28195-868) and rinsed with methanol.

(b) The acidic alcoholic solution was concentrated under reduced pressure to yield the title compound as a hygroscopic solid (840 mg, 93% yield). Further trituration of 0.38 g of compound (DC-63) in diethyl ether yielded 0.34 g of non-hygroscopic white solid. $R_f$ 0.10 (EtOAc-iPrNH$_2$, 98:2, v/v); $^1$H NMR (free amine, 300 MHz, CDCl$_3$) δ 6.81-6.66 (m, 3H, Ar), 4.21-4.17 (m, 1H, OH), 3.84 (s, 3H, CH$_3$), 3.75-1.18 (m, 20H); $^{13}$C NMR (free amine, 75 MHz, APT, CDCl$_3$) δ 146.28 (+), 143.95 (+), 131.24 (+), 121.49 (−), 114.17 (−), 111.67 (−), 79.42/79.18 (−), 71.27/71.03 (−), 69.80/69.65 (+), 63.28 (−), 59.79/59.28 (+), 55.89 (−), 48.63/48.33 (+), 36.55 (+), 34.43/34.27 (+), 28.93 (+), 27.36/27.14 (+), 23.43/23.35 (+), 23.04/22.98 (+); MS (ESI) [M+H]+336.4 (100).

In the following Reaction Scheme DC-29 and DC-30, compounds (DC-67) and (DC-69) require the same isocyanate intermediate (DC-65), which is obtained from reaction between 1,4-diisocyanatobutane and 4-benzyloxyphenethyl alcohol in dichloromethane at room temperature.

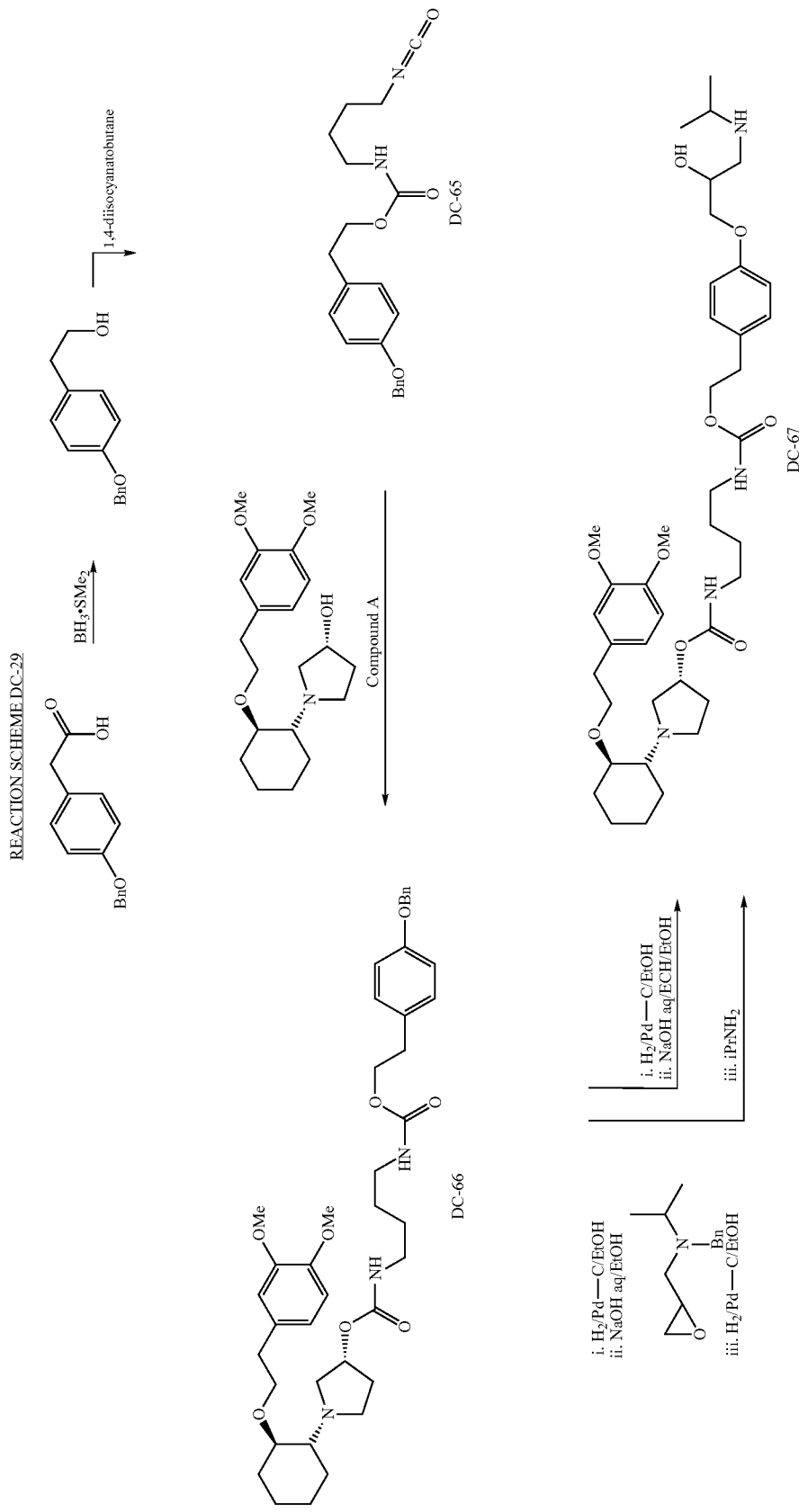

Reaction of intermediate (DC-65) in Reaction Scheme DC-29 with (1R,2R)-2-[(3R)-hydroxypyrrolidinyl]-1-(3,4-dimethoxyphenethoxy)cyclohexane monohydrochloride (Compound A) in dichloromethane at room temperature provides (DC-66). Hydrogenolysis of the benzyloxy group in the presence of palladium charcoal in EtOH was followed by appendage of the oxypropanolamine side-chain (Reaction Scheme DC-29). In one aspect of the invention, elaboration of the propanolamine side-chain was achieved by reacting epichlorohydrin (ECH) with the hydrogenolyzed product from (DC-66) in the presence of NaOH aqueous in EtOH. After removal of the excess epichlorohydrin, the crude material was refluxed in isopropylamine for 18 hours to provide compound (DC-67). In another aspect of the invention, the propanolamine side-chain is appended using N-benzyl-N-isopropyl-2,3-epoxypropylamine. Once the reaction is judged complete by TLC analysis, a final hydrogenolytic step is carried out to provide compound (DC-67). N-Benzyl-N-isopropyl-2,3-epoxypropylamine is prepared by heating to 70° C. N-benzyl-N-isopropylamine with epichlorhydrin as described by Steck et al. (see, Steck Edgar A., Hallock Louis L. and Suter C. M. Quinolines VI. Some 4-Aminoquinoline Derivatives. *J. Am. Chem. Soc.* 1948, 70, 4063-4065). Alternatively, N-benzyl-N-isopropyl-2,3-epoxypropylamine is prepared by alkylation of N-benzyl-N-isopropylamine with allyl bromide followed by epoxidation according to Hou et al. (see, Xue-Long Hou, Bin-Feng Li and Li-Xin Dai Synthesis of novel and enantiomerically pure epoxypropylamine: a divergent route to chiral β-adrenergic blocking agents. *Tetrahedron: Asymmetry* 1999, 10, 2319-2326).

REACTION SCHEME DC-30
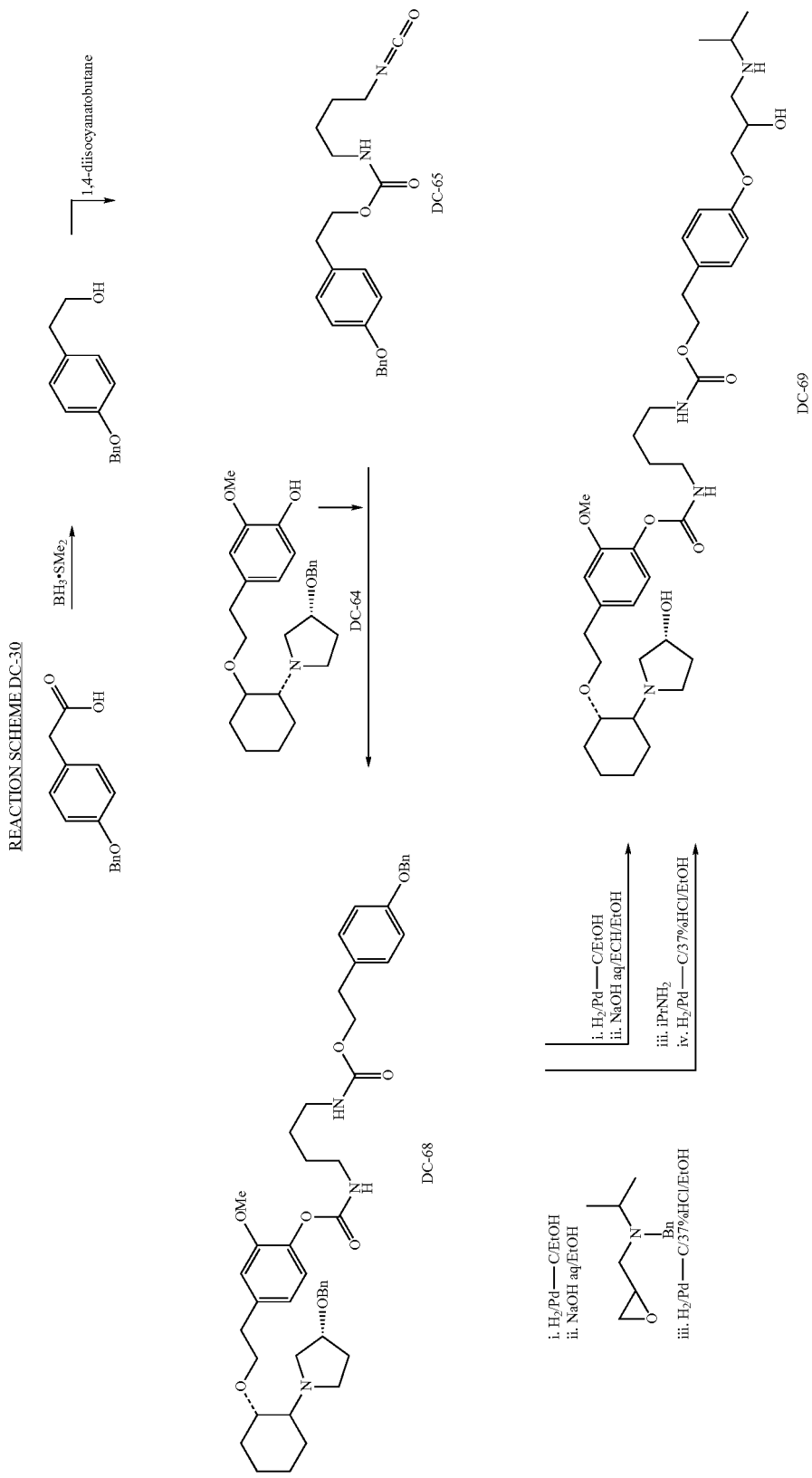

The preparation of compound (DC-69) (Reaction Scheme DC-30) is achieved by reacting intermediates (DC-64) and (DC-65) in similar conditions as the ones described for compound (DC-67). Elaboration of the propanolamine side-chain from (DC-68) was preferably achieved by using N-benzyl-N-isopropyl-2,3-epoxypropylamine.

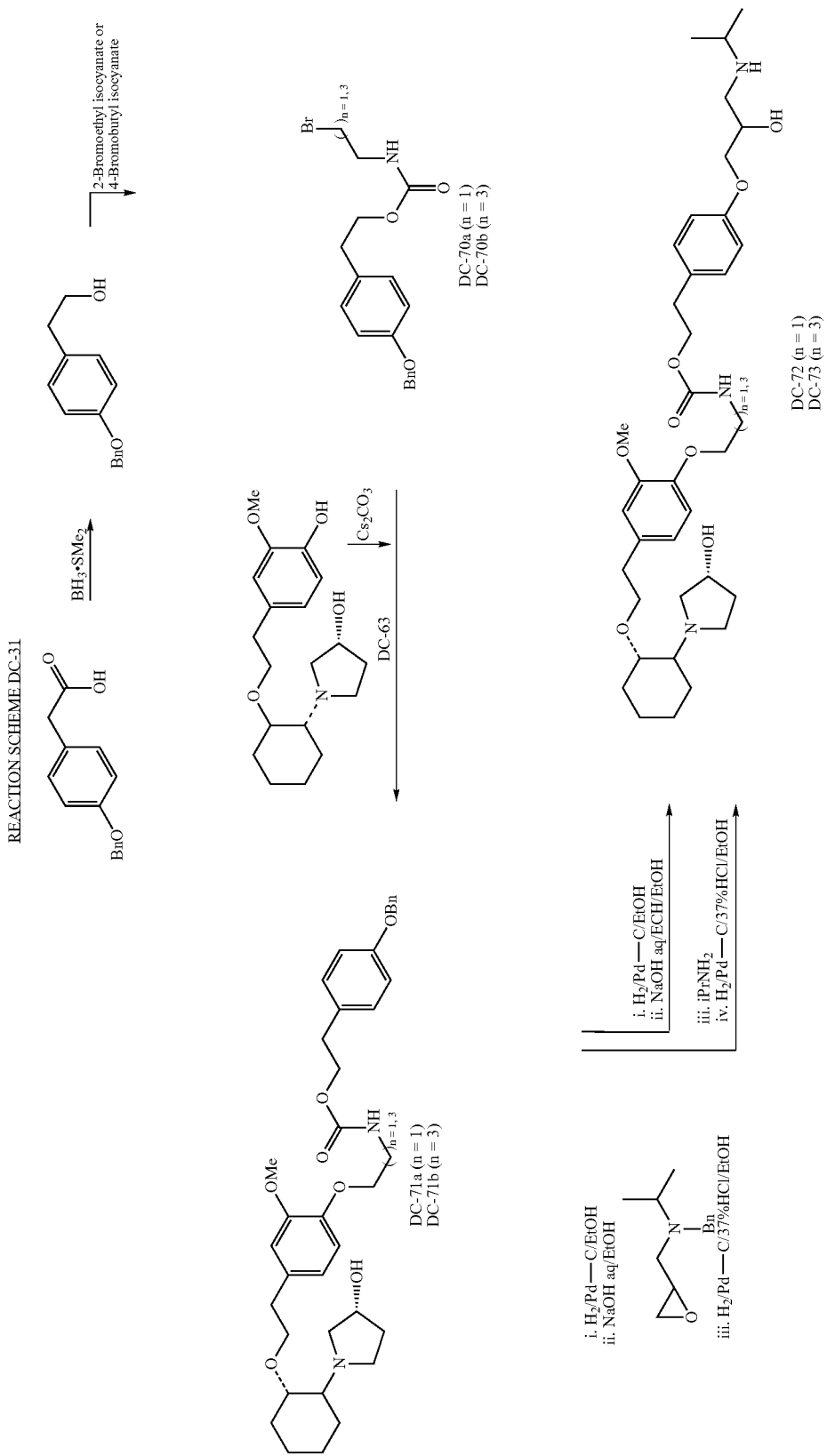

Compounds (DC-72) and (DC-73) require the reaction of 4-benzyloxyphenethyl alcohol with 2-bromoethyl isocyanate or 4-bromobutyl isocyanate (see, Minin, Patricia L. and Walton, John C. *J. Org. Chem.* 2003, 68, 2960-2963) in dichloromethane at ambient temperature to form (DC-70a) and (DC-70b), respectively (Reaction Scheme DC-31). Intermediates (DC-70a) and (DC-70b) react with (DC-63) in the presence of sodium carbonate in a polar solvent such as DMF to give precursors (DC-71a) and (DC-71b), respectively. Finally, the propanolamine side-chain was elaborated preferably using N-benzyl-N-isopropyl-2,3-epoxypropylamine as reported for compounds (DC-72) and (DC-73).

In addition to the foregoing drug conjugates of the invention, the following drug conjugates may be prepared as set forth in Reaction Schemes DC-32-38.

REACTION SCHEME DC-32

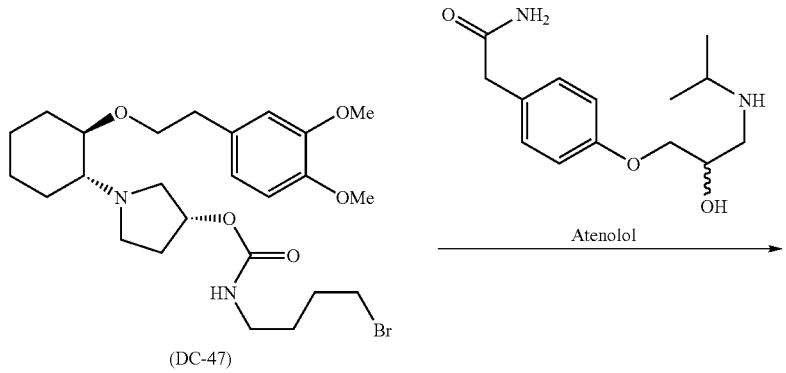

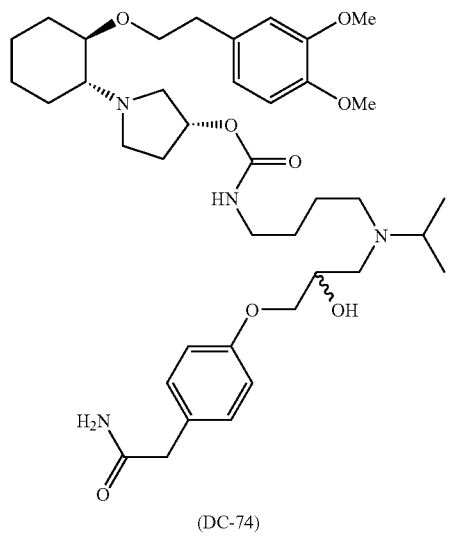

Reaction Scheme DC-32 illustrates the synthesis of the drug conjugate (DC-74) from the amino reactive derivative (DC-47) and beta-blocker atenolol.

In a typical reaction, the alcohol reactive derivative (DC-47) may be reacted with atenolol in a suitable solvent such as dimethylformamide at a suitable temperature to give drug conjugate (DC-74) which can be isolated and purified by general standard methods known in the art.

REACTION SCHEME DC-33

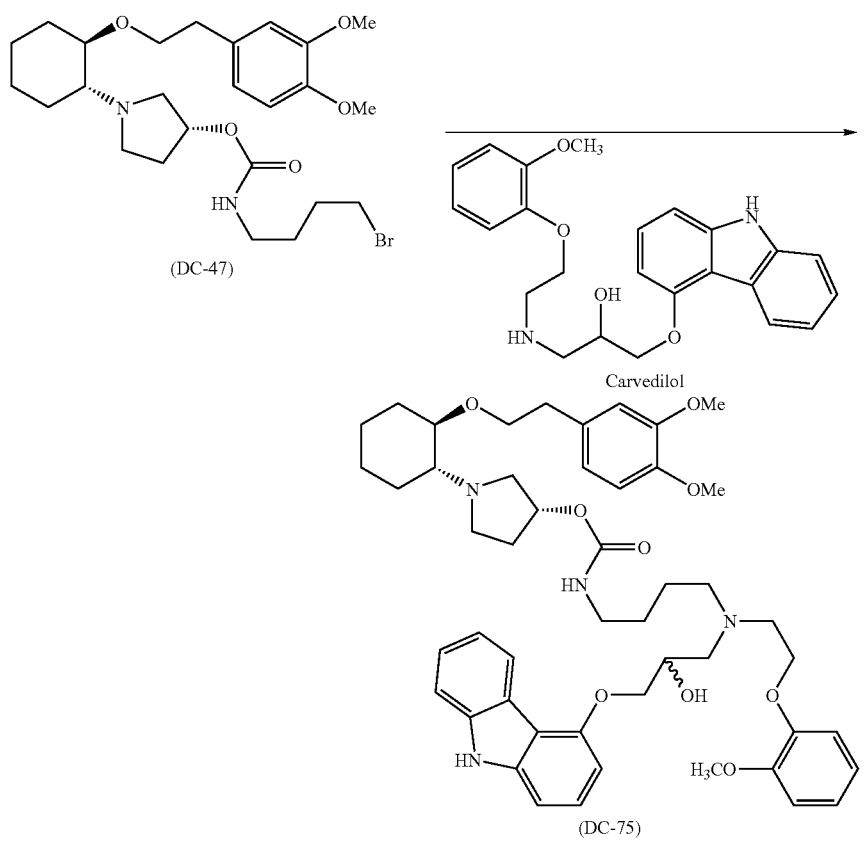

Reaction Scheme DC-33 illustrates the synthesis of the drug conjugate (DC-75) from the amino reactive derivative (DC-47) and beta-blocker carvedilol.

In the typical reaction, the alcohol reactive derivative (DC-47) may be reacted with carvedilol in a suitable solvent such as dimethylformamide at a suitable temperature to give drug conjugate (DC-75) which can be isolated and purified by general standard methods known in the art.

REACTION SCHEME DC-34

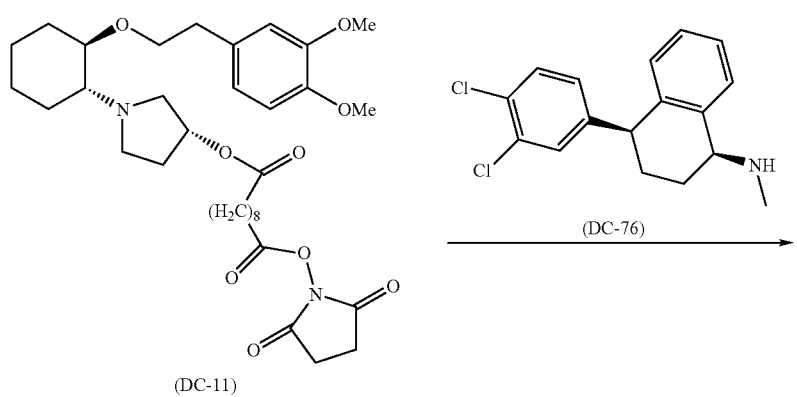

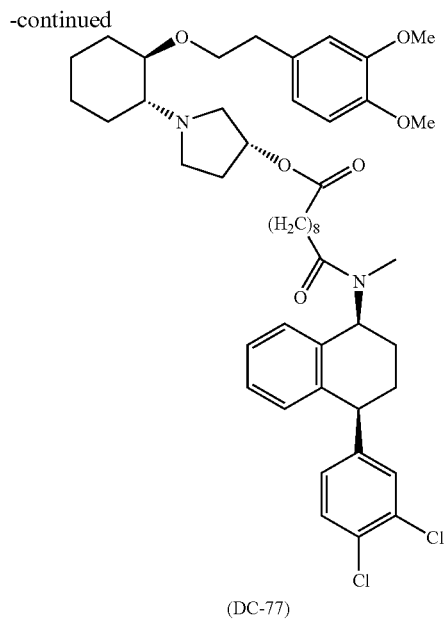

(DC-77)

Reaction Scheme DC-34 illustrates the synthesis of drug conjugate (DC-77) from the amine reactive derivative (DC-11) and the zoloft (DC-76) (antidepressant).

In a typical reaction, the amine-reactive intermediate (DC-11) is dissolved in a suitable solvent (e.g., CH$_2$Cl$_2$) and reacted with zoloft (DC-76) (antidepressant) to generate the drug conjugate (DC-77). The drug conjugate (DC-77) is then isolated and purified by known standard methods.

REACTION SCHEME DC-35

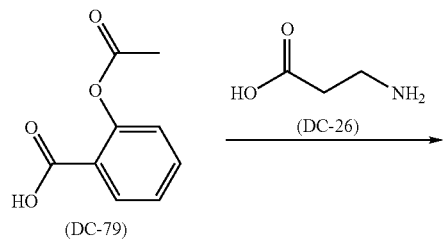
(DC-79)    (DC-26)

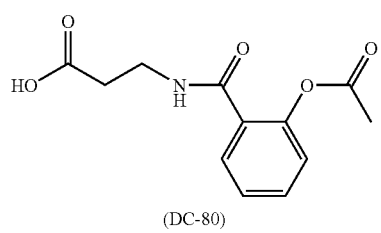
(DC-80)

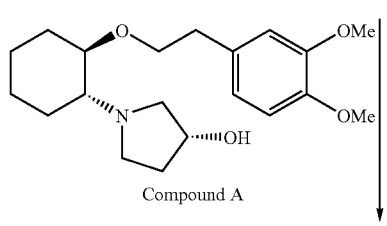
Compound A

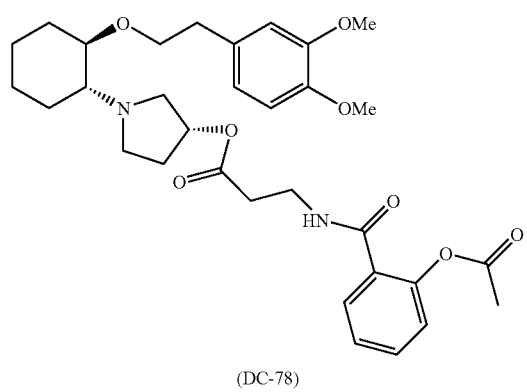
(DC-78)

Reaction Scheme DC-35 illustrates the synthesis of drug conjugate (DC-78) from acetylsalicylic acid (DC-79), a suitable linker and (1R,2R)-2-[(3R)-hydroxypyrrolidinyl]-1-(3,4-dimethoxyphenethoxy)cyclohexane (Compound A).

In a typical reaction, acetylsalicylic acid is reacted with β-alanine (DC-26) and a coupling agent (e.g., tetramethyl uronium salts) to generate the alcohol reactive intermediate (DC-80). This intermediate is isolated, purified by known standard methods and subsequently dissolved in a suitable solvent (e.g., CH$_2$Cl$_2$) and reacted with (1R,2R)-2-[(3R)-hydroxypyrrolidinyl]-1-(3,4-dimethoxyphenethoxy)cyclohexane (Compound A) to generate the drug conjugate (DC-78).

REACTION SCHEME DC-36

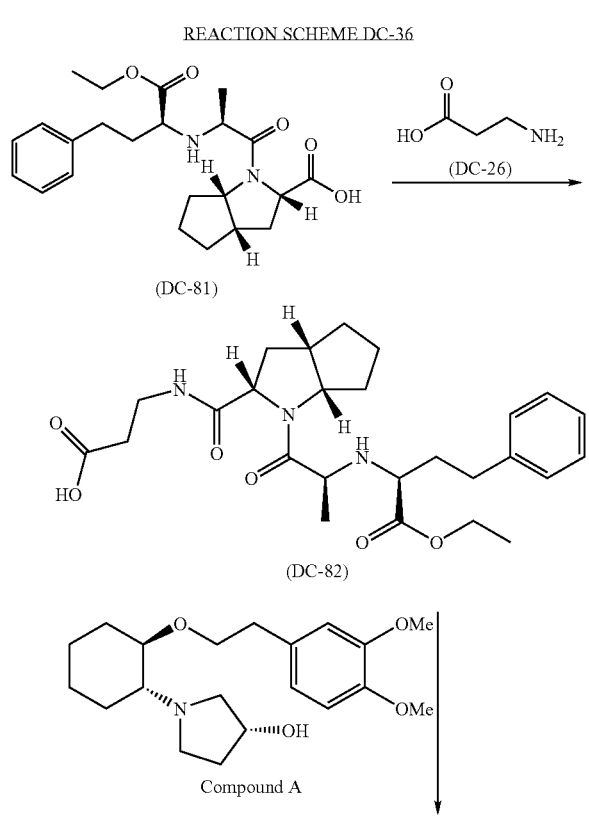

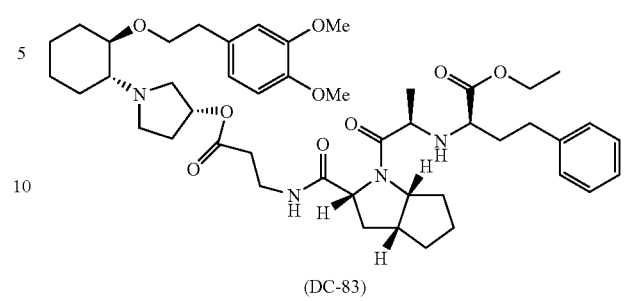

Reaction Scheme DC-36 illustrates the synthesis of drug conjugate (DC-83) from ramipril (DC-81), a suitable linker and (1R,2R)-2-[(3R)-hydroxypyrrolidinyl]-1-(3,4-dimethoxyphenethoxy)cyclohexane (Compound A).

In a typical reaction, ramipril (DC-81) is reacted with β-alanine (DC-26) and a coupling agent (e.g., tetramethyl uronium salts) to generate the alcohol reactive intermediate (DC-82). This intermediate is isolated, purified by known standard methods and subsequently dissolved in a suitable solvent (e.g., $CH_2Cl_2$) and reacted with (1R,2R)-2-[(3R)-hydroxypyrrolidinyl]-1-(3,4-dimethoxyphenethoxy)cyclohexane (Compound A) to form the drug conjugate (DC-83).

REACTION SCHEME DC-37

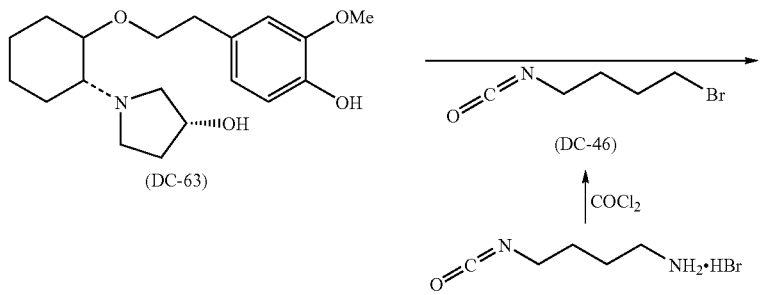

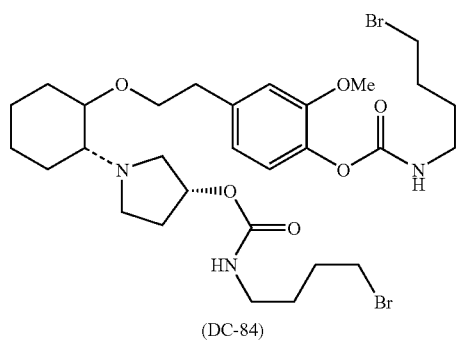

Reaction Scheme DC-37 illustrates the synthesis of the amino reactive derivative (DC-84) from compound (DC-63) and 4-bromobutylisocyanate (DC-46).

In a typical reaction, amino reactive derivative (DC-84) may be prepared by reaction of compound (63) with 4-bromobutylisocyanate (DC-46) in a suitable solvent such as dichloromethane at a suitable temperature. The product may be isolated and purified by standard methods known to those skilled in the art.

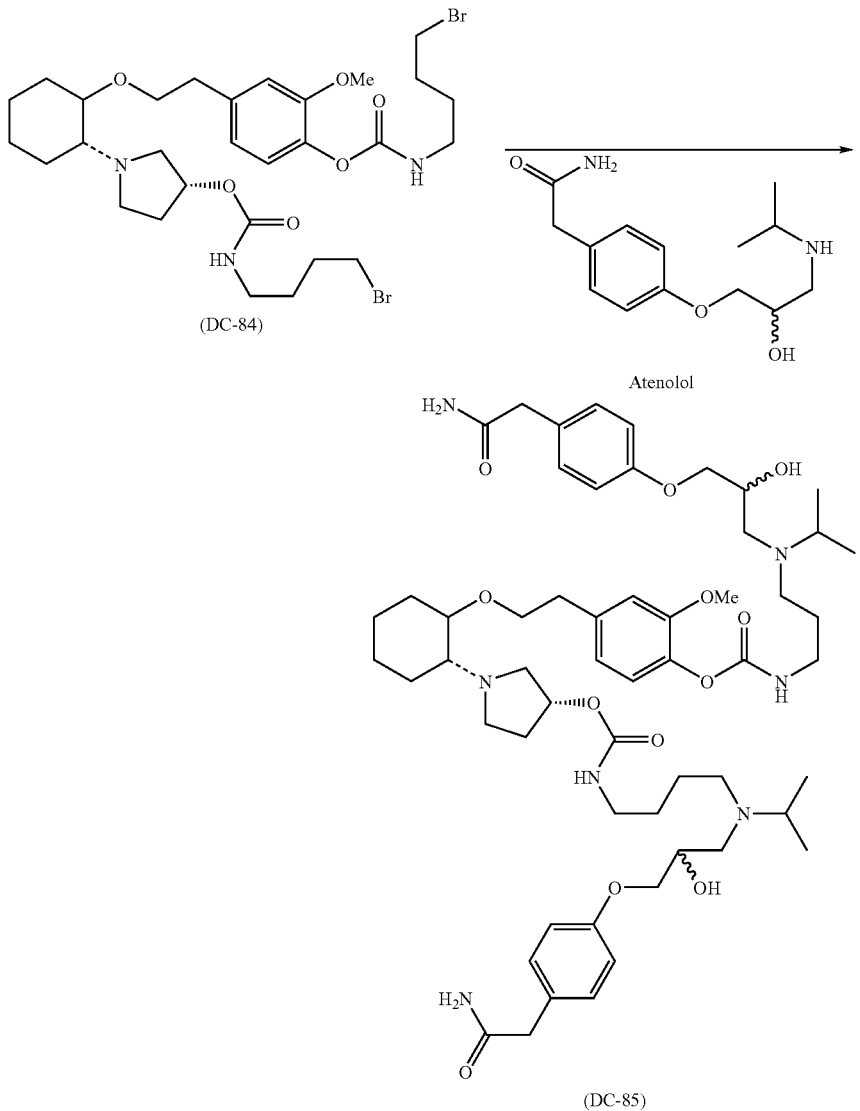

Reaction Scheme DC-38 illustrates the synthesis of drug conjugate (DC-85) from the amino reactive derivative (DC-84) and atenolol.

In a typical reaction, drug conjugate (DC-85) may be prepared by reaction of the amino reactive derivative (DC-84) with excess atenolol in a suitable solvent such as dichloromethane at a suitable temperature. The product may be isolated and purified by standard methods known to those skilled in the art.

REACTION SCHEME DC-39

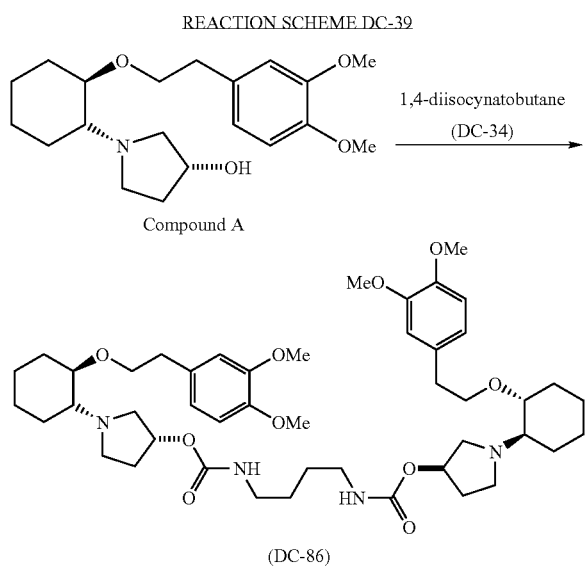

Reaction Scheme DC-39 illustrates the synthesis of the drug conjugate (DC-86) from (1R,2R)-2-[(3R)-hydroxypyrrolidinyl]-1-(3,4-dimethoxyphenethoxy)cyclohexane (Compound A) and 1,4-diisocynatobutane (DC-34) (Sigma-Aldrich).

In a typical reaction, drug conjugate (DC-86) may be prepared by reaction of 1-[(1R,2R)/(1S,2S)-2-[2-(3,4-dimethoxyphenyl)ethoxy]cyclohexyl]-3-pyrrolidinyl, hydrochloride (0.59 g, 1.53 mmol) and triethylamine (223 μL, 1.6 mmol) in dichloromethane (5 mL) to which was added 1,4-diisocyanatobutane (100 μL, 0.76 mmol). The resultant mixture was then refluxed for 18 hours. The cooled reaction mixture was concentrated in vacuo and the residue was partitioned between 1M HCl aq (30 mL) and diethyl ether (2×30 mL). The aqueous layer was then collected and extracted with dichloromethane (2×30 mL). The combined organic layers were then washed with 2M NaHCO$_3$ aq (50 mL), dried over anhydrous MgSO$_4$ and concentrated in vacuo to give the crude material as the free base. Purification by column chromatography using a mixture of EtOAc-iPrNH$_2$ (98:2, v/v) provided 0.52 g of purified material. The material was then partitioned between 1M HCl (20 mL) and dichloromethane (20 mL). The organic layer was collected, dried over anhydrous MgSO$_4$ and concentrated in vacuo. The residue then was lyophilized to give compound #1. MS (ES+)[M/2+H]$^+$ 420.3.

E. Isotopic Ion Channel Modulating Compounds

In general, an ion channel modulating compound may be modified by the substitution of one or more atoms in the ion channel modulating compound with a stable isotope thereof, wherein the stable isotope is stable over the time scale needed for compound synthesis, storage, and use. For instance, one or more hydrogen atoms may be replaced by one or more deuterium atoms to yield a deuterated analog of the ion channel modulating compound. The replacement of one or more atoms of an ion channel modulating compound with an isotope thereof yields what is referred to herein as an "isotopic ion channel modulating compound". An isotopic ion channel modulating compound may include an atom that is a heavier or lighter isotope than the standard isotope of the replaced atom or atoms (an "isotopic derivative").

Biological Significance of Isotopic Ion Channel Modulating Compounds

Sustained release of an ion channel modulating compound may be achieved by the replacement of one or more atoms of the ion channel modulating compound with a stable isotope thereof, wherein the stable isotope contains one or more additional neutron(s) than the normally abundant isotope of the atom in question (i.e., a "heavy atom"). An ion channel modulating compound may also be modified by the replacement of one or more atoms of the ion channel modulating compound with a stable isotope thereof, wherein the stable isotope contains fewer neutron(s) than the normally abundant isotope of the atom in question (i.e., a "light atom"). Incorporation of a heavy atom, particularly substitution of deuterium for hydrogen, can give rise to an isotope effect of the ion channel modulating compound that can alter its physiochemical properties, metabolism, pharmacodynamic response and pharmacokinetics. For instance, deuteration, as exemplified by deuterated Rapamycin (see U.S. Pat. No. 6,503,921), Cyclosporine (see U.S. Pat. No. 6,613,739) or Nifedipine (see U.S. Pat. No. 5,846,514) has been reported to alter the pharmacokinetics of a drug. Forster et al. (Isotechnica, AB) have shown that deuteration can enhance duration of action.

An ion channel modulating compound may be modified by the substitution of one or more atoms or a mixture of atoms with stable isotopes thereof. Although any atom in an ion channel modulating compound of the invention may be replaced with an isotopic derivative thereof, common isotope substitutions of C, N, O, and H make these atoms natural candidates for isotopic substitution in ion channel modulating compounds. Thus, in general, isotopic ion channel modulating compounds of the invention may comprise one or more or a mixture of heavy atom isotopes of C, N, O and H. Any isotope of an atom may be used to provide an isotopic ion channel modulating compound. Heavy atom isotopic analogs, light atom isotopic analogs, and an analog comprising a mixture of heavy and light atom isotopic derivatives are considered. Any ion channel modulating compound that is isotopically enriched may be considered an isotopic ion channel modulating compound.

An ion channel modulating compound of the invention may be deuterated by the substitution of any hydrogen in an ion channel modulating compound for deuterium. Monodeuterated (substitution of one deuterium atom for one hydrogen atom) isotopic analogs, polydeuterated (substitution of deuterium for more than one hydrogen) isotopic analogs, and perdeuterated (substitution of deuterium for all available hydrogen atoms) isotopic analogs are considered.

In one variation, a single moiety in an ion channel modulating compound may be replaced with a monodeuterated, polydeuterated, or perdeuterated moiety thereof. For instance, an isotopic ion channel modulating compound may comprise a —CH$_2$D, a —CD$_2$H or a —CD$_3$ moiety.

In an isotopic ion channel modulating compound, a single atom of an ion channel modulating compound may be substituted with an isotopic derivative thereof. In another variation, more than one of the same or different atoms of an ion channel modulating compound may be substituted with an isotopic derivative thereof. For instance, in one variation, a single hydrogen atom of an ion channel modulating compound may be replaced with a deuterium to provide a monodeuterated isotopic ion channel modulating compound. In another variation, hydrogen and at least one other atom of an ion channel modulating compound are replaced with corresponding stable isotopes thereof to provide an isotopic ion channel modulating compound. In still another variation, multiple hydrogen atoms in an ion channel modulating compound are replaced with deuterium atoms to yield a polydeuterated isotopic ion channel modulating compound. In yet another variation, all hydrogens in the ion channel modulating compound that may be replaced with a hydrogen isotope are replaced with deuterium to yield a perdeuterated isotopic ion channel modulating compound.

Any ion channel modulating compound described herein may be modified to provide an isotopic ion channel modulating compound. The ion channel modulating compound to be modified may increase or decrease ion channel activity. In some instances, the ion channel modulating compound may be used in the treatment of arrhythmia. In still other instances, the ion channel modulating compound may be used in the treatment of atrial fibrillation. Specific ion channel modulating compounds, which may be modified to provide isotopic ion channel modulating analogs are described throughout this specification, including compounds of formulae (I), (IA) or (IX), Compound A, polyethylene glycol derivatives of ion channel modulating compounds and ion channel modulating compounds conjugated to additional drug moieties, where such compounds may also be referred to as "antiarrhythmic compounds" or "antiarrhythmic agents." Each ion channel modulating compound, or derivative thereof, as listed or described throughout this specification may be modified to provide an isotopic ion channel modulating compound the same as if each and every ion channel modulating compound or derivative thereof were individually and specifically indicated for use as an isotopic ion channel modulating compound.

In one variation, an isotopic ion channel modulating compound is provided, wherein the compound comprises one or more standard atom replacements, and wherein the single isotopic replacement atom or multiple isotopic replacement atoms are non-radioactive. In another variation, an isotopic ion channel modulating compound is provided, where the compound comprises an atom selected from the group consisting of $^{13}C$, $^{15}N$, $^{18}O$, and $^{2}H$ (or D).

In another variation, an isotopic ion channel modulating compound is provided, wherein the compound is derived from an ion channel modulating compound as described herein, particularly a compound of formula (I), (IA), (IX) or Compound A. The compound may comprise one or more atoms selected from the group consisting of $^{13}C$, $^{15}N$, $^{18}O$, and $^{2}H$ (or D).

In another variation, an isotopic ion channel modulating compound is provided, wherein the compound comprises an aminocycloalkyl ether moiety. In a particular variation, an isotopic ion channel modulating compound of formula (XX) is provided, or a solvate, pharmaceutically acceptable salt, ester, amide, complex, chelate, stereoisomer, stereoisomeric mixture, geometric isomer, crystalline or amorphous form thereof, and mixtures thereof:

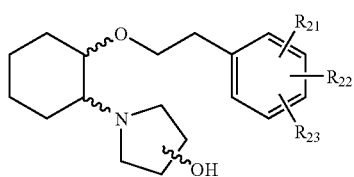

(XX)

wherein, $R_{21}$, $R_{22}$ and $R_{23}$ are independently selected from hydrogen, deuterium, $C_1$-$C_6$alkoxy, and a $C_1$-$C_6$ alkoxy comprising an isotopic derivative of a H, C or O atom, with the proviso that $R_{21}$, $R_{22}$ and $R_{23}$ cannot all be hydrogen, and wherein at least one of the atoms in formula (XX) is replaced with an isotopic derivative thereof. In another variation, a heavy ion channel modulating compound of formula (XX) is provided, wherein the compound comprises at least one atom of carbon-13 ($^{13}C$). In another variation, a heavy ion channel modulating compound of formula (XX) is provided, wherein the compound comprises at least one atom of nitrogen-15 ($^{15}N$). In another variation, a heavy ion channel modulating compound of formula (XX) is provided, wherein the compound comprises at least one atom of oxygen-18 ($^{18}O$). In another variation, an isotopic ion channel modulating compound of formula (XX) is provided, wherein the compound comprises at least one atom of deuterium ($^{2}H$ or D).

In another variation, an isotopic Compound A or its hydrochloride salt (shown below as the compound of formula (XXVIII)), or its solvates, other pharmaceutically acceptable salts, esters, amides, complexes, chelates, stereoisomers, stereoisomeric mixtures, geometric isomers, crystalline or amorphous forms thereof, and mixtures thereof is provided:

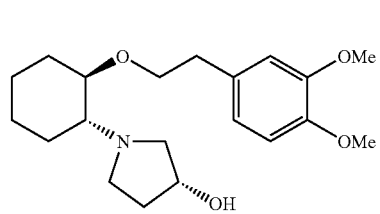

Compound A

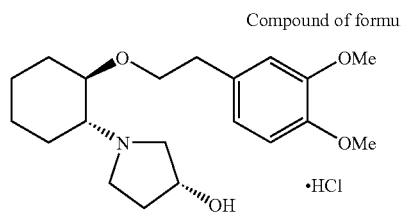

Compound of formula (XXVII)

wherein at least one of the atoms in Compound A or in the compound of formula (XXVII) is replaced with an isotopic derivative thereof. In another variation, an isotopic Compound A or an isotopic compound of formula (XXVII) is provided, wherein the compound comprises at least one atom of carbon-13. In another variation, an isotopic Compound A or an isotopic compound of formula (XXVII) is provided, wherein the compound comprises at least one atom of nitrogen-15. In another variation, an isotopic Compound A or an isotopic compound of formula (XXVII) is provided, wherein the compound comprises at least one atom of oxygen-18. In another variation, an isotopic Compound A or an isotopic compound of formula (XXVII) is provided, wherein the compound comprises at least one atom of deuterium.

In another variation, isotopic ion channel modulating compounds of formula (ID), or a solvate, pharmaceutically acceptable salt, ester, amide, complex, chelate, stereoisomer, stereoisomeric mixture, geometric isomer, crystalline or amorphous form thereof, are provided, wherein the hydrogen atoms of the methoxy group at 4-position of the phenyl ring of Compound A are substituted by deuterium as shown in formula (ID):

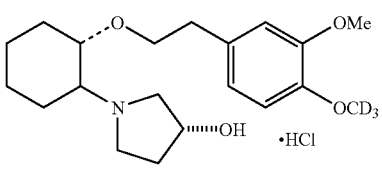

(ID)

In another variation, isotopic ion channel modulating compounds of formula (IID), or a solvate, pharmaceutically acceptable salt, ester, amide, complex, chelate, stereoisomer, stereoisomeric mixture, geometric isomer, crystalline or amorphous form thereof, are provided, wherein the hydrogen atoms of the two methoxy groups at 3- and 4-position of the phenyl ring are substituted by deuterium as shown in formula (IID):

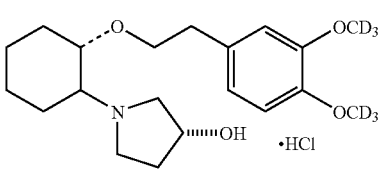

(IID)

In another variation, isotopic ion channel modulating compounds of formula (IIID) are provided, or a solvate, pharmaceutically acceptable salt, ester, amide, complex, chelate, stereoisomer, stereoisomeric mixture, geometric isomer, crystalline or amorphous form thereof, wherein the hydrogen atoms of the methoxy group at 4-position of the phenyl ring are substituted by deuterium as shown in formula (IIID):

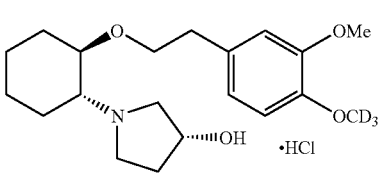

(IIID)

In another variation, isotopic ion channel modulating compounds of formula (IVD) are provided, or a solvate, pharmaceutically acceptable salt, ester, amide, complex, chelate, stereoisomer, stereoisomeric mixture, geometric isomer, crystalline or amorphous form thereof, wherein the hydrogen atoms of the two methoxy groups at 3- and 4-position of the phenyl ring are substituted by deuterium as shown in formula (IVD):

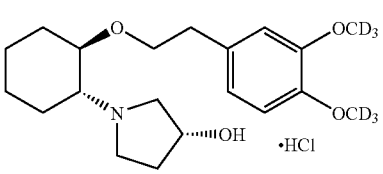

(IVD)

In another variation, isotopic ion channel modulating compounds of formula (VD), or a solvate, pharmaceutically acceptable salt, ester, amide, complex, chelate, stereoisomer, stereoisomeric mixture, geometric isomer, crystalline or amorphous form thereof, are provided, wherein the carbon atom of the methoxy group at 4-position of the phenyl ring is substituted by carbon-13 as shown in formula (VD):

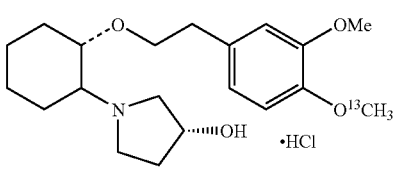

(VD)

In another variation, isotopic ion channel modulating compounds of formula (VID), or a solvate, pharmaceutically acceptable salt, ester, amide, complex, chelate, stereoisomer, stereoisomeric mixture, geometric isomer, crystalline or amorphous form thereof, are provided, wherein the carbon atoms of the two methoxy groups at 3- and 4-position of the phenyl ring are substituted by carbon-13 as shown in formula (VID):

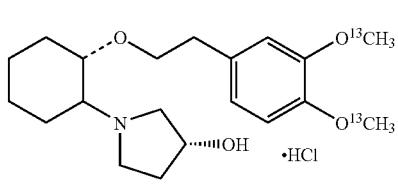

(VID)

In another aspect, isotopic ion channel modulating compounds of formula (VIID) are provided, or a solvate, pharmaceutically acceptable salt, ester, amide, complex, chelate, stereoisomer, stereoisomeric mixture, geometric isomer, crystalline or amorphous form thereof, wherein the carbon atom of the methoxy group at 4-position of the phenyl ring is substituted by carbon-13 as shown in formula (VIID):

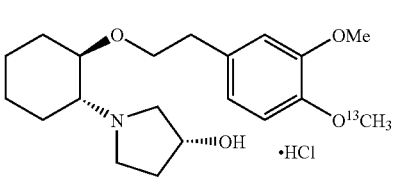

(VIID)

In another variation, isotopic ion channel modulating compounds of formula (VIIID) are provided, or a solvate, pharmaceutically acceptable salt, ester, amide, complex, chelate, stereoisomer, stereoisomeric mixture, geometric isomer, crystalline or amorphous form thereof, wherein the carbon atoms of the two methoxy groups at 3- and 4-position of the phenyl ring are substituted by carbon-13 as shown in formula (VIIID):

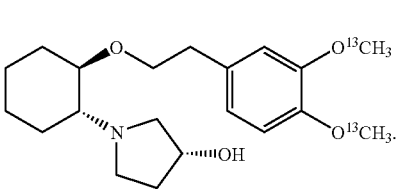

(VIIID)

Isotopic Ion Channel Modulating Compound Metabolites

Isotopic ion channel modulating compound metabolites are also described herein. That is, one or more atoms of a metabolite of an ion channel modulating compound may be substituted with an isotopic derivative thereof. Any metabolite of an ion channel modulating compound may be converted into an isotopic derivative by the substitution of any atom or atoms with an isotope thereof to provide an isotopic ion channel modulating compound metabolite. Any isotopic ion channel modulating compound may be broken down either in vivo, in vitro or ex vivo to its metabolites to provide an isotopic ion channel modulating compound metabolite. The metabolite pathway shown in FIG. I-1 depicts the major metabolites of one ion channel modulating compound, Compound A, or its HCl salt (compound of formula (XXVII)) in man. The metabolites result from (a) O-demethylation at the 4-position of the phenyl ring to form metabolite A (Phase I biotransformation), which may be followed by fast glucuronide formation to form metabolite I—C, wherein the glucuronide moiety is attached at the phenol moiety of metabolite B; and (b) glucuronide formation of metabolite C directly from the compound of formula (XXVII), wherein the glucuronide moiety is attached at the hydroxyl moiety on the pyrrolidinyl ring of the compound of formula (XXVII) (slow) (Phase II biotransformation).

Application No. 2005002693 for ion channel modulating compounds or antiarrhythmic compounds or agents. However, any effective dosage forms, routes of administration, and formulations of the isotopic ion channel modulating compounds may generally be used with any and all other aspects described in this patent. Examples of dosage forms, routes or administration, and formulations that may be used include but are not limited to those described in Remington's Pharmaceutical Sciences, Mack Publishing Company, Philadelphia, Pa., 17$^{th}$ ed. (1985). The isotopic ion channel modulating compounds may also be part of a modified ion channel modulating compound as described in other sections of this specification, such as isotopic compounds of PEGylated ion channel modulating compounds or isotopic compounds of drug conjugates comprising ion channel modulating compounds or the like.

Isotopic Atom Replacement Methods

Replacement of an atom with an isotopic derivative thereof may take place by methods known in the art, such as those described in U.S. Pat. No. 6,503,921, U.S. Pat. No. 6,613,739, U.S. Pat. No. 5,846,514, and the patents and publications referenced therein, all of which are herein incorporated by reference in their entirety. Additional experimental methods are described in the section immediately below.

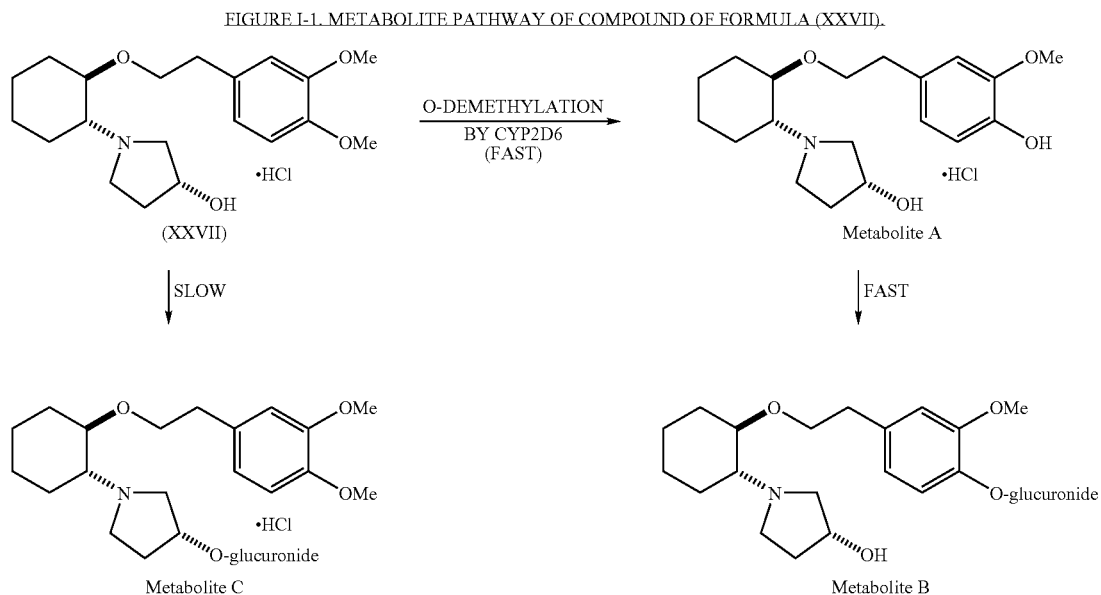

FIGURE I-1. METABOLITE PATHWAY OF COMPOUND OF FORMULA (XXVII).

Combination of Isotopic Ion Channel Modulating Compounds with other Variations

The isotopic ion channel modulating compounds described herein may be taken together with any other modification of the ion channel modulating compounds disclosed in this specification. Dosage forms, routes of administration, and formulations of the isotopic ion channel modulating compounds are the same as those described in any of the sections of this specification and, in particular, in PCT Published Patent Application No. WO 1999/50225; PCT Published Patent Application No. WO 2000/047547; PCT Published Patent Application No. WO 2004/098525; PCT Published Patent Application No. 2004/099137; PCT Published Patent Application No. 2005/018635; and U.S. Published Patent Preparation of Isotopic Ion Channel Modulating Compounds The aminoethers described in the present patent can be prepared from aminoalcohols and alcohols by following the general methods and specific experimental procedures described herein. The isotopic ion channel modulating compounds of the invention may be prepared as set forth in the following reaction schemes and examples.

Following the standard chemical literature description practice and as used in this patent, a full wedge bond means above the ring plane, and a dashed wedge bond means below the ring plane; one full bond and one dashed bond (i.e., - - - ) means a trans configuration, whereas two full bonds or two dashed bonds means a cis configuration.

Compounds of formula (ID) may be prepared according to the methods described below:

REACTION SCHEME I-1. PREPARATION OF COMPOUND (ID).

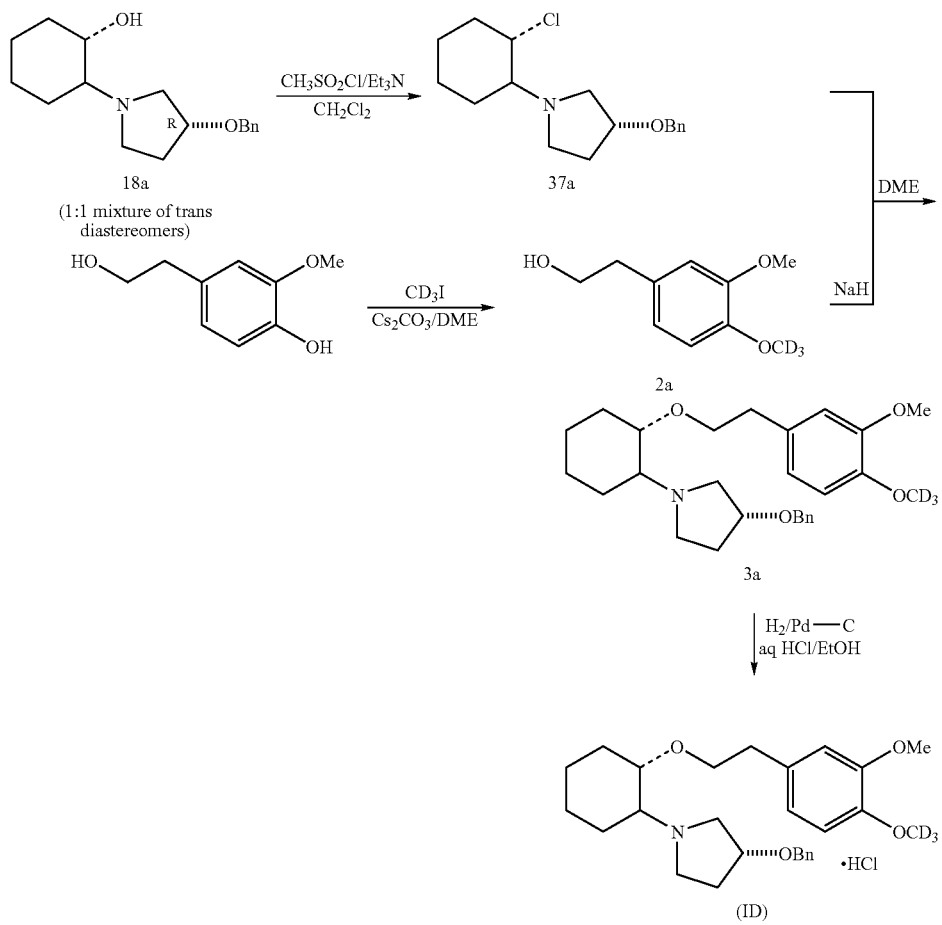

In the above Reaction Scheme, the Williamson ether synthesis (see Feuer, H.; Hooz, J. Methods of Formation of the Ether Linkage, In *Patai*, Wiley: New York, 1967; pp 445-492) between the activated chloride form (37a) of aminoalcohol (18a) with the alkoxide of the appropriate phenethyl alcohol, e.g., compound (2a), in a polar solvent such as DME (Reaction Scheme I-1) provided the corresponding aminoether, e.g., compound (3a), in high yield. Subsequent hydrogenolysis of compound (3a) provided compound (ID), as described in more detail below.

More specifically, homovanillyl alcohol may be reacted with deuterated methyl iodide in the presence of cesium carbonate in a solvent such as ethylene glycol dimethyl ether (DME) to provide intermediate (2a). Activation of (18a) via mesylation produces chloride (37a) as previously described herein. (37a) may then be reacted with the alkoxide of (2a) to provide (3a). Debenzylation of (3a) to (ID) can be carried out by hydrogenolysis in the presence of palladium on charcoal and concentrated HCl in a protic solvent such as EtOH.

Preparation of Compound of Formula (ID)

Homo vanillyl alcohol (1.0 g, 5.95 mmol) was dissolved in anhydrous DME (25 mL) followed by the addition of cesium carbonate (3.87 g, 11.89 mmol). The mixture was stirred under argon for 1 h and deuterium iodomethane (1.29 g, 8.92 mmol, 555 µL) was added. The reaction mixture was refluxed for 2.5 h and concentrated. The residue dissolved in ethyl acetate and washed with sat. NaHCO$_3$, water and dried over MgSO$_4$, filtered, concentrated to give a light yellow oil (2a) (1.03 g, 93%). $^1$H NMR (300 MHz, CDCl$_3$): δ 6.82-6.74 (m, 3H, aromatic), 3.86 (s, 3H, OCH$_3$), 3.82 (t, 2H), 2.79 (t, 2H), 1.47 (s, 1H).

To an oven dried round bottom flask (100 mL) charged with argon and cooled was added NaH (197 mg, 8.2 mmol). A solution of (2a) (690 mg, 4.09 mmol) in anhydrous DME (20 mL) was added slowly to the reaction mixture and stirred for 1 h, then a solution of (37a) (1.0 g, 3.41 mmol) in DME (20 mL) was added and the resultant mixture was heated to 80-85° C. for 18 h. To the cooled mixture was added, 2M NaHCO$_3$ (10 mL), water (30 mL) and ethyl acetate (40 mL). The organic layer was collected and washed with brine, dried over MgSO$_4$ and concentrated in vacuo to give (3a) (1.4 g, 93% yield).

To a solution of (3a) (1.3 g, 2.94 mmol) in absolute ethanol (40 mL) was added palladium, 10 wt. % activated carbon (520 mg), 6M HCl (2 mL). The resultant reaction mixture was stirred for 18 h under a positive hydrogen atmosphere. The reaction mixture was filtered through celite 545 and concentrated to give 1.06 g of (ID) (92.6%). $^1$H NMR (300 MHz, DMSO-d$_6$) δ 10.9-10.34 (m, 1H, NH), 6.86-6.73 (m, 3H), 5.49 (s, 1H), 4.33 (s, 1H), 4 (q, 1H), 3.73 (s, 3H, OCH$_3$), 3.57-3.02 (m, 6H), 2.78 (d, 2H, J 5.06), 2.18-1.62 (m, 6H), 1.39-1.05 (m, 4H); MS (ES+) [M+H]$^+$ 353.10.

Compound of formula (IID) may be prepared as described below:

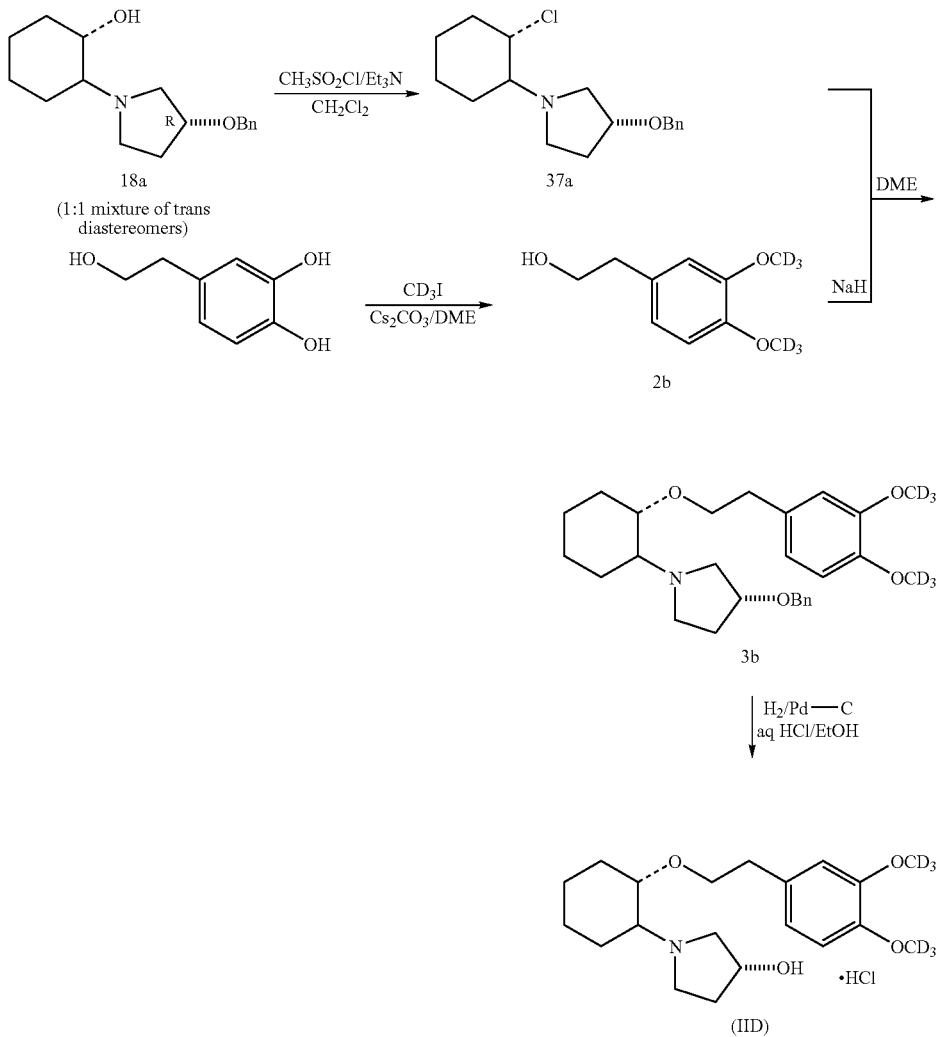

Compound (IID), as described above in Reaction Scheme I-2, follows the same synthetic methodology as Compound (ID) in Reaction Scheme I-1 except that 3,4-dihydroxyphenethyl alcohol is used as the starting material. Compound IID: $^1$H NMR (300 MHz, CDCl$_3$) δ 6.77-6.74 (m, 3H), 4.21-4.16 (m, 1H), 3.83-3.67 (m, 1H), 3.58-3.50 (m, 1H), 3.04-2.90 (m, 1H), 2.83-2.77 (m, 3H), 2.71-2.60 (m, 1H), 2.50-2.42 (m, 2H), 2.05-1.84 (m, 3H), 1.72-1.60 (m, 3H), 1.37-1.19 (m, 4H); $^{13}$C NMR (300 MHz, CDCl$_3$) δ 148.70 (+), 147.40 (+), 131.80 (+), 120.71 (−), 112.36 (−), 111.16 (−), 79.28/79.14 (−), 70.92/70.59 (−), 69.59/69.47 (+), 63.80/63.69 (−), 59.78/59.58 (+), 50.62 (−), 49.07/48.70 (+), 36.34 (+), 34.29/34.08 (+), 29.13 (+), 27.26/27.18 (+), 23.54 (+), 23.05 (+); MS (ES+) [M+H]$^+$ 356.2.

Similarly, compounds of formulae (VD) and (VID) may be synthesized according to Reaction Schemes I-3 and I-4, respectively.

Compounds of formula (VD) may be prepared as described below:
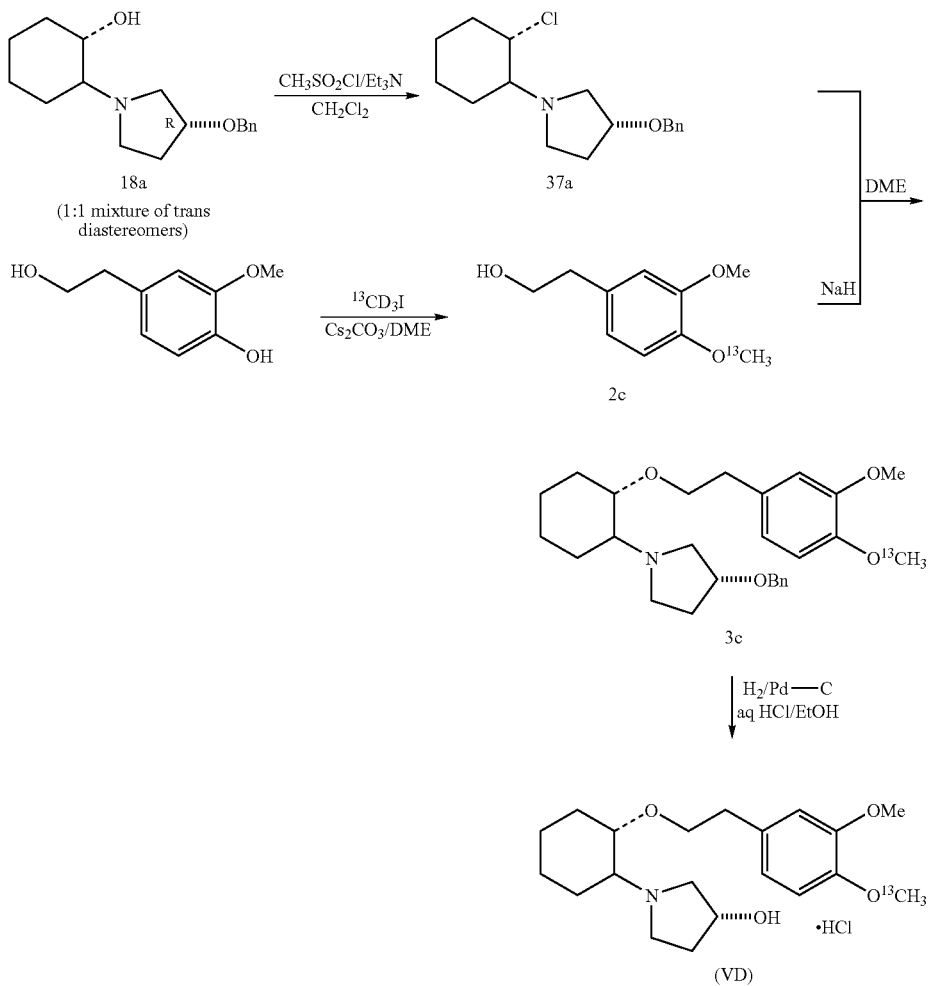
Compounds of formula (VID) may be prepared as described below:
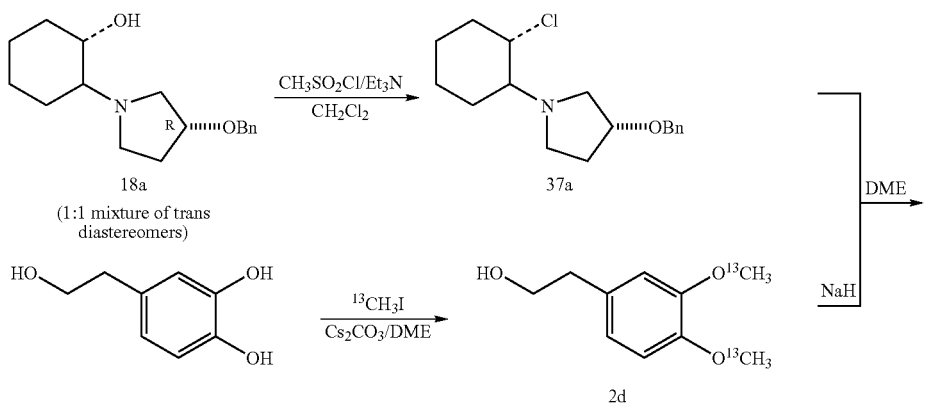

-continued

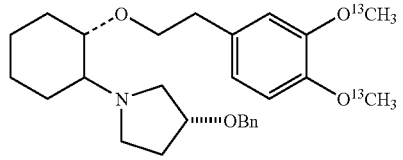

3d

H₂/Pd—C
aq HCl/EtOH

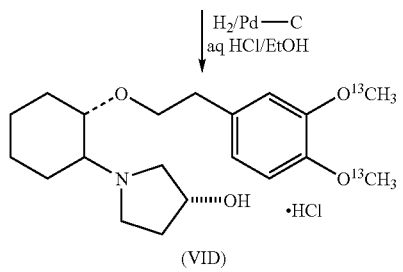

(VID)

Compounds (18a) and (37) may be prepared as described herein or by methods similar to those described in Published Patent Application No. WO 1999/50225; PCT Published Patent Application No. WO 2000/047547; PCT Published Patent Application No. WO 2004/098525; PCT Published Patent Application No. 2004/099137; PCT Published Patent Application No. 2005/018635; and U.S. Published Patent Application No. 2005002693.

Compound (IIID) and (IVD) may be isolated from compounds (ID) and (IID), respectively, by standard isolation techniques, by methods known to one skilled in the art or by the methods disclosed in PCT Published Patent Application WO 2004/099137. In a similar manner, Compounds (VIID) and (VIID) may be isolated from compounds (VD) and (VID), respectively, by standard isolation techniques, by methods known to one skilled in the art or by the methods disclosed in PCT Published Patent Application WO 2004/099137.

Compounds of formulae (VIIID), (IXD), (XD), (XID) and (XIID) may be prepared as described below:

REACTION SCHEME I-5. PREPARATION OF COMPOUND (XIID).

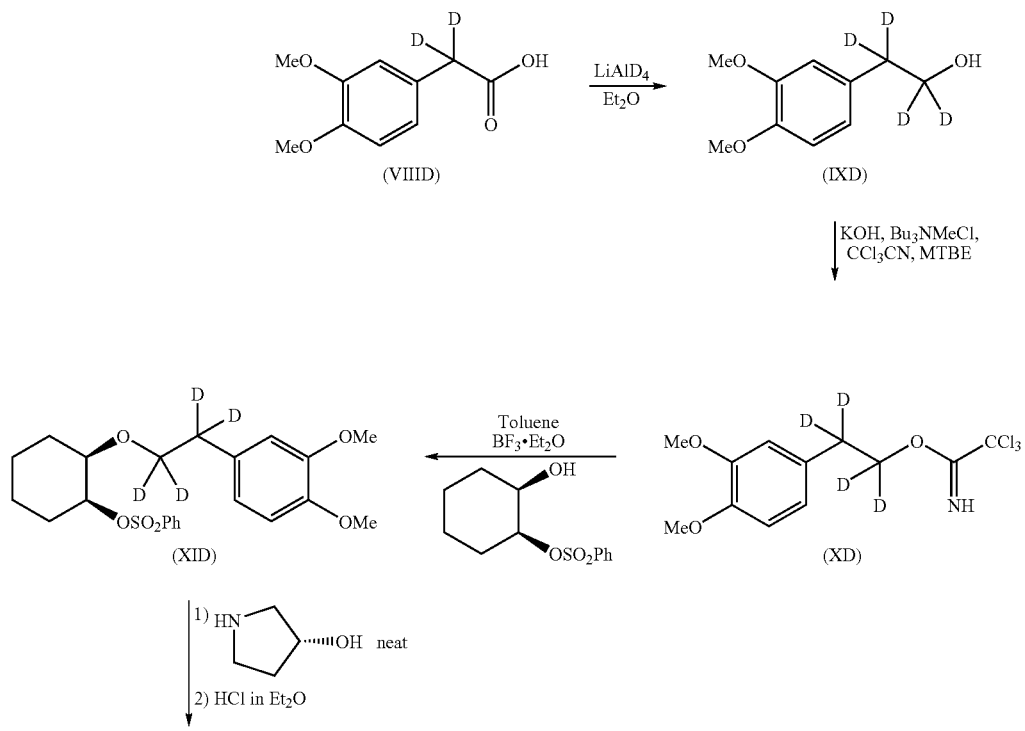

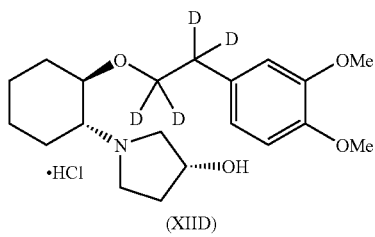

(XIIID)

Preparation of Compounds of Formula (VIIID) and (IXD)

To a one liter two necked round bottom flask was charged lithium aluminum deuteride (2.86 g, 68.1 mmol) and to this was slowly added anhydrous ether. A thermometer was placed in one neck to ensure the temperature remained steady. To this was added a solution of (3,4-dimethoxy-phenyl)-acetic acid-$d_2$ (6.00 g, 30.3 mmol, CDN Isotope, Cat #D-1941, Cas #19031-58-4) in anhydrous ether (300 mL) via addition funnel. The reaction mixture was allowed to stir at r.t. for 6 h. It was then quenched by adding water until bubbling had stopped. 5% HCl (75 mL) was then added. This mixture was allowed to stir at r.t. overnight. The mixture was then diluted with ethyl acetate, filtered and concentrated. The residue was then dissolved in ethyl acetate and washed successively with water and sodium bicarbonate. The aqueous layer was further extracted with ethyl acetate. The combined organic extract was dried over magnesium sulphonate, filtered and concentrated to afford a light yellow solid (4.01 g, 71.1% yield). TLC (EtOAc:Hexanes): compound of formula (VIIID) at $R_f$=0.20; compound of formula (IXD) at $R_f$=0.33; $^1$H-NMR (300 MHz, CDCl$_3$) δ: 6.71-6.80 (m, 3H), 3.83 (s, 3H), 3.81 (s, 3H); $^{13}$C-NMR (75 MHz, CDCl$_3$) δ: 148.95, 147.61, 130.91, 120.81, 112.21, 111.40, 62.76 (pentex, coupled to D), 55.84, 55.75, 37.73 (pentex, coupled to D). MS (ES): Calcd=186.24 [M]$^+$; Found=187.0 [M+H$_2$O]$^+$ Preparation of 2,2,3-Trichloro-acetimidic Acid 2-(3, 4-dimethoxy-phenyl)-ethyl ester-$d_4$ (XD)

To a two necked 500 mL round bottom flask connected with a thermometer and an additional funnel was charged 3,4-dimethoxyphenethyl alcohol-$d_4$ (IXD) (10.63 g, 57.1 mmol) and methyl tert-butyl ether [MTBE] (50 mL). The temperature was adjusted to 12° C. and then crushed solid potassium hydroxide (5.1 g, 91.0 mmol) and methyltributylammonium chloride (75% wt in water) (0.45 g, 1.24 mmol) were introduced to the flask. While stirring slowly, a solution of trichloroacetonitrile (10.25 g, 71.0 mmol) in MTBE (10 mL) was added through the addition funnel. The reaction was stirred at 12° C. until it was completed. Once completed, the reaction mixture was diluted with MTBE (10 mL) and cooled in an ice bath. The solution was washed successively with water (3×30 mL) and 0.4M KOH. The organic layer was dried over MgSO$_4$, filtered, and concentrated at a maximum bath temperature of 35° C. The residue was dissolved in ethanol (50 mL) and stirred for one hour at ambient temperature. The solution was left in the freezer overnight to allow crystallization. Water (50 mL) was added and allowed to stir at 0° C. for one hour. It was then filtered through a Buchner funnel and allowed to air dry for 30 minutes. The resulting crystals were transferred to a round bottom flask and dried under vacuum to afford off-white crystals (18.43 g, 97.7% yield). NMR spectral data suggested that this product was the E-isomer. TLC (EtOAc:Hexanes): Compound of formula (XD) at $R_f$=0.76

$^1$H-NMR (300 MHz, CDCl$_3$) δ: 8.24 (bs, 1H), 6.75-6.77 (m, 3H), 3.80-3.82 (m, 6H); $^{13}$C-NMR (75 MHz, CDCl$_3$) δ: 162.58, 148.71, 147.64, 130.02, 120.84, 112.32, 111.19, 91.32, 69.50 (pentex, coupled to D). 55.73, 55.66, 33.56 (pentex, coupled to D). MS(ES): Calcd=330.63 [M]$^+$; Found=330.9 [M]$^+$ Preparation of (1R,2S)-Benzenesulfonic acid 2-[2-(3, 4-dimethoxy-phenyl)-ethoxy-cyclohexyl ester-$d_4$ (XID)

To a 500 mL round bottom flask under nitrogen connected to an addition funnel was charged a solution of (1R,2S) diol monosulfonate (XD) (13.0 g, 51.0 mmol) in anhydrous toluene (25 mL). To this solution, borontriflouride etherate (7.3 g) was added. The reaction mixture was allowed to stir for half an hour at ambient temperature. A solution of DMPE Ester-$d_4$ (XD) (18 g, 54.4 mmol) in anhydrous toluene (25 mL) was added via the addition funnel and was then stirred at ambient temperature under nitrogen for 24 hours. The reaction mixture was then cooled to −10° C. in a salt/ice bath. The cooled solution was filtered through a Buchner funnel and washed with cold (−10° C.) toluene. NaOH (4%, 100 mL) was then added to the toluene solution and stirred at ambient temperature for one hour. The organic layer was then separated followed by addition of 8% NaOH (100 mL) and was allowed to stir for 3 hours at 40° C. The organic layer was then separated, dried over MgSO$_4$, filtered, and concentrated. The oil was then dried further under vacuum to afford brown oil which was then purified by column chromatography (Gradient elution, 4:1 to 8:1 hexanes:ethyl acetate). Yellow oil was obtained at (14.4 grams, 67% yield). TLC (EtOAc:Hexanes): (XID) at $R_f$=0.5; $^1$H-NMR (300 MHz, CDCl$_3$): δ1.2-1.77 (m, 6H), 2.00 (s, 1H), 2.65 (t, J=7 Hz, 2H), 3.48 (t, J=7 Hz, 3H), 3.82 (m, 7H), 4.68 (m, 1H), 6.72 (m, 3H), 7.53 (m, 3H), 7.89 (m, 2H); MS(ES): Calcd=424.24 [M]$^+$; Found=425.3 [M+H]$^+$ Preparation of (1R,2R)-2-[(3R)-Hydroxypyrrolidinyl]-1-(3,4-dimethoxyphen-ethoxy)cyclohexane-$d_4$, Hydrochloride Salt (XIID)

The toluene stock solution of (1R,2S) ether monosulfonate (XI) (13.5 g, 31.8 mmol) was concentrated under reduced pressure to dryness at a maximum bath temperature of 45° C. 3-(R)-pyrrolidinol (13.9 g, 159 mmol, 5.0 mole eq) was added to the flask and the pot contents were adjusted to 62° C. (60-64° C.). The reaction mixture was agitated at 62° C. (60-64° C.) until the reaction was judged complete by TLC analysis. The flask was kept under vacuum for the first 6 hours of reaction to remove all traces of toluene. Upon completion the reaction mixture was cooled to 40° C. (37-43° C.), then diluted with 3 M HCl solution (~30 ml, 3.5 mole eq). The aqueous solution was cooled to 22° C. (19-25° C.) and further diluted with 1M HCl solution (ca. 1 vol, 0.5 mole eq) until pH 3-4 by pH paper. The aqueous solution was washed 3 times with isopropyl acetate (3×30 ml) at 22° C. (19-25° C.). The acidic aqueous layer was neutralized with 12% NaOH solution (ca. 40 mL, 5.3 mole eq) until pH 12 (11.5-12.5) while maintaining the temperature at 22° C. (19-25° C.). The aqueous layer was extracted twice with isopropyl acetate (2×30 mL) at 22° C. (19-25° C.). The combined organic layer was dried over anhydrous sodium sulfate, filtered, and concentrated under reduced pressure to obtain a light brown syrup (5.8 g). The residue was dissolved in acetonitrile (anhydrous) and concentrated under reduced pressure to reduce the volume of acetonitrile. The content was charged with HCl/CH$_3$CN solution (20-30%) until the pH≈2-4 (pH paper) while keeping the temperature at <15° C. during the addition. The acetonitrile was removed and dried under high vacuum to obtain a beige gummy solid. To the gummy solid was charged CH$_3$CN and the solution was heated to 40° C. The flask was allowed to cool to ambient temperature without cooling medium. After cooling at −10° C. for 2 h, no slurry was observed and the content was left in the fridge (4-6° C.) for 24 h. This did not produce any slurry and the CH$_3$CN was removed under vacuum and dried high vacuum to obtain a hygroscopic beige solid. This solid was washed with acetone (15 mL) at 50-60° C. (i.e. agitate solid in acetone at 50-60° C. for 2-3 h). The contents were cooled to ambient temperature, filtered to obtain a non hygroscopic off-white solid (3.9 g, 33%). Purity: 96% by HPLC, 98.1 CE; $R_f$=0.50 (1:1, v/v, EtOAc:MeOH with 5% iPrNH$_2$); MS(ES): Calcd=353 [M]$^+$; Found=354.1 [M]$^+$, MS and NMR data suggested that 15-20% of the non-deuterated compound. Elemental analysis: Calcd for C$_{20}$H$_{29}$D$_4$ClNO$_4$, C, 61.60; N, 3.59; Cl, 9.09; H, 8.27. Found C, 61.25; N, 3.57; H, 8.02; Cl, 9.82.

Compounds of formula (XIIID) may be prepared as follows:

REACTION SCHEME I-6. PREPARATION OF COMPOUND (XIIID).

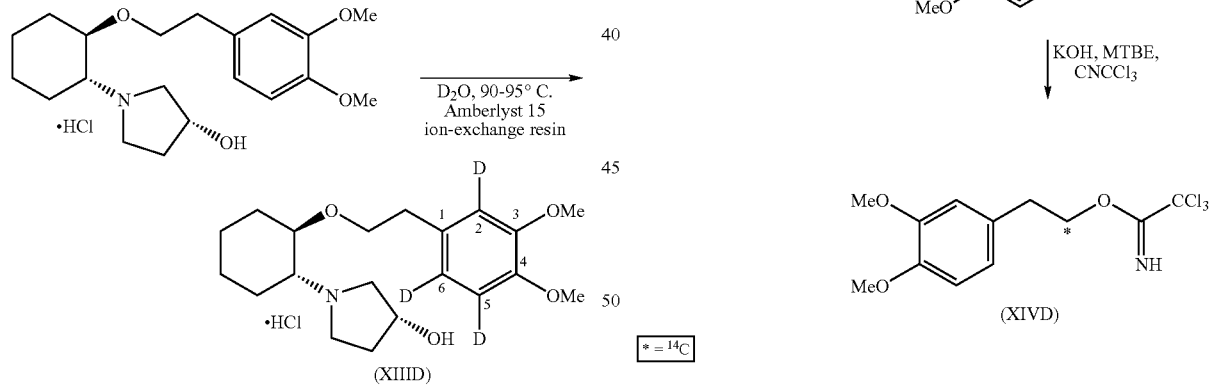

Preparation of 1R,2R)-2-[(3R)-Hydroxypyrrolidinyl]-1-(3,4 dimethoxyphenethoxy)cyclohexane-d$_3$ Hydrochloride Salt (XIID)

Compound (XIIID) was synthesized according to Reaction Scheme I-6 using the procedure of Tuck et al. (K. L. Tuck, Tan, H-W, Hayball, P. J.; *J. Labelled Cpd. Radiopharma.* 2000, 43, 817-823). To a solution of the starting compound (0.6 g, 1.6 mmol) in D$_2$O (2.0 mL, 99% D enrichment, Aldrich) was added Amberlyst 15 ion-exchange resin (0.6 g, Sigma-Aldrich, cas #39389-20-3). The mixture was heated in a sealed vessel for 24 h. On completion, the vessel was cooled, and the solution was filtered to remove the resin and washed with H$_2$O (2×5 mL). To the filtered solution was added a brine solution (15 mL) and the aqueous solution was extracted with CH$_2$Cl$_2$ (4×10 mL). The combined organic extracts were dried (MgSO$_4$), filtered, and concentrated under reduced pressure to obtain a foamy solid (0.5 g), which was further recrystallized from isopropyl alcohol to give a white solid (0.4 g). $R_f$=0.51 (1:1, v/v, EtOAc:MeOH with 5% iPrNH$_2$); MS (ES) Found=351.1 [M]$^+$, 352.1 [M]$^+$, 353.1 [M]$^+$ (ratio~66%:100%:33% by MS).

Compounds of formula (XIVD) may be prepared as follows:

REACTION SCHEME I-7. PREPARATION OF COMPOUND (XIVD).

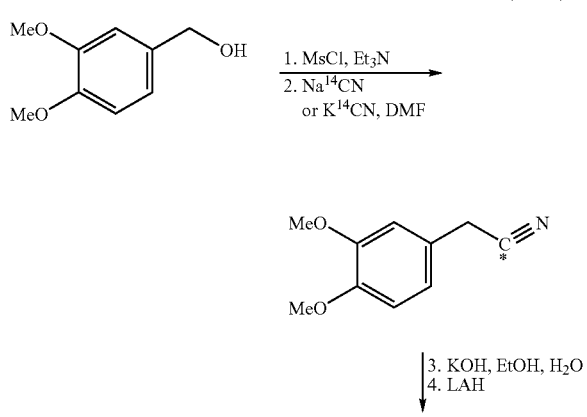

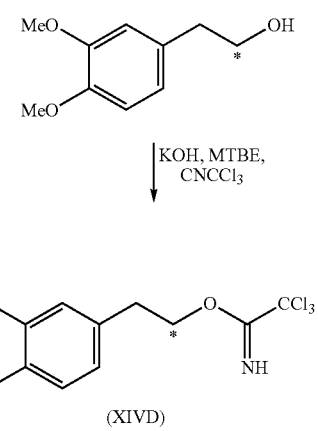

(XIVD)

* = $^{14}$C

To 3,4-dimethoxyphenyl)methanol was added either Na$^{14}$CN or K$^{14}$CN in DMF to give the $^{14}$C analog of the 2-(3,4-dimethoxyphenyl)acetonitrile. Reduction of the acetonitrile with LAH gave $^{14}$C labeled 2-(3,4-dimethoxyphenyl)ethanol.

A solution of $^{14}$C labeled 2-(3,4-dimethoxy-phenyl)-ethanol in CH$_2$Cl$_2$ was stirred for 45 min at RT and then cooled to 0° C. before drop-wise addition of trichloroacetonitrile. The reaction mixture was stirred until the reaction was judged to be complete by TLC and GC. Compound (XIV) may be isolated by standard isolation techniques, by methods known to one skilled in the art.

Compounds of formula (XVD) may be prepared as follows:

REACTION SCHEME I-8. PREPARATION OF COMPOUND (XVD).

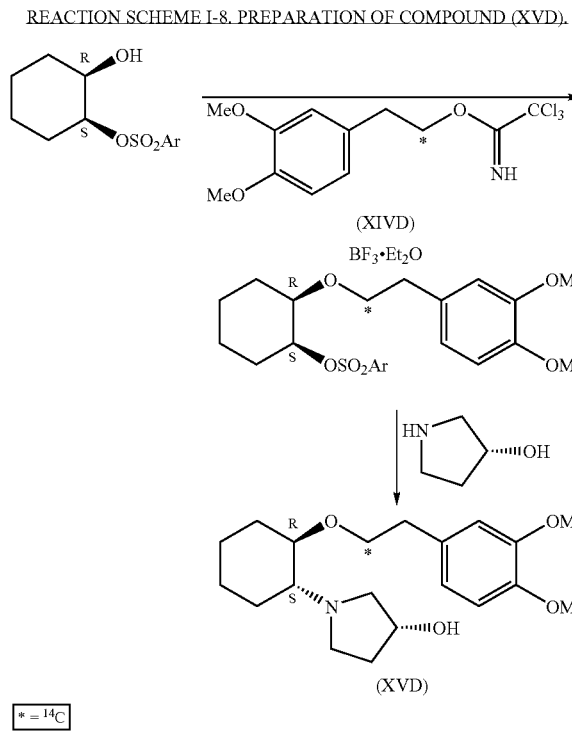

(XVD)

* = $^{14}C$ (1S,2R)-2-Hydroxycyclohexyl benzenesulfonate reacts with the $^{14}C$ labelled trichloroaetimidate (XIVD) derivative of 3,4-dimethoxyphenethyl alcohol under Lewis acid conditions to give the activated sulfonate. Nucleophilic displacement with 3-(R)-pyrrolidinol of the activated sulfonate will afford the $^{14}C$ labelled (XVD). Compound (XVD) may be isolated by standard isolation techniques, by methods known to one skilled in the art.

F. Preferred Embodiments of the Invention

As set forth above, certain embodiments of the invention are preferred.

One embodiment of the invention is a PEGylated derivative described herein wherein the PEG moiety is attached to the ion channel modulating compound via a linker.

Another embodiment of the invention is a PEGylated derivative described herein wherein the ion channel modulating compound is a compound of formula (I), or solvates or pharmaceutically acceptable salts thereof, as described above.

Of this embodiment, a further embodiment is a PEGylated derivative wherein the compound of formula (I) is attached to a PEG moiety by the substitution of any valency of the compound of formula (I) with a bond to the PEG moiety, wherein the bond to the PEG moiety is a direct bond from the compound of formula (I) to the PEG moiety or is a bond from the compound of formula (I) to a linker that is bound to the PEG moiety.

Another embodiment is a PEGylated derivative wherein the ion channel modulating compound is a compound of formula (IA), or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, as described above.

Of this embodiment, a further embodiment is a PEGylated derivative wherein the compound of formula (IA) is attached to a PEG moiety by the substitution of any valency of the compound of formula (IA) with a bond to the PEG moiety, wherein the bond to the PEG moiety is a direct bond from the compound of formula (IA) to the PEG moiety or is a bond from the compound of formula (IA) to a linker that is attached to the PEG moiety.

Of this embodiment, another embodiment is a PEGylated derivative wherein the compound of formula (IA) is Compound A, or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, as described above.

Of this particular embodiment, a further embodiment is wherein Compound A is attached to the PEG moiety by the substitution of any valency of Compound A with a bond to a PEG moiety, wherein the bond to a PEG moiety is a direct bond from Compound A or is a bond from a linker that is bound to the PEG moiety.

Of this particular embodiment, a further embodiment is wherein Compound A is attached to the PEG moiety by the substitution of the valency occupied by the hydrogen in the ......OH moiety in Compound A with a bond to the PEG moiety.

Of this particular embodiment, a further embodiment is wherein a second PEG moiety is attached to Compound A by the substitution of the valency occupied by one of the methyl groups of the —$OCH_3$ groups in Compound A with a bond to the second PEG moiety.

Another embodiment of the invention is a PEGylated derivative wherein the ion channel modulating compound is a compound of formula (IX), or solvates or pharmaceutically acceptable salts thereof, as described above.

Of this embodiment, a further embodiment is wherein the compound of formula (IX) is attached to a PEG moiety by the substitution of any valency of the compound of formula (IX) with a bond to the PEG moiety, wherein the bond to the PEG moiety is a direct bond from the compound of formula (IX) to the PEG moiety or is a bond from the compound of formula (IX) to a linker that is bound to the PEG moiety.

Another embodiment of the invention is a PEGylated derivative having the formula (PEGI), or a solvate or pharmaceutically acceptable salt thereof, as described above.

Another embodiment of the invention is a PEGylated derivative having the formula (PEGII), or a solvate or pharmaceutically acceptable salt thereof, as described above.

Another embodiment of the invention is a PEGylated derivative having the formula (PEGIII), or a solvate or pharmaceutically acceptable salt thereof, as described above.

Of the drug conjugates of the invention described herein, one embodiment is a drug conjugate further comprising a linker.

Of the drug conjugates of the invention described herein, one embodiment is wherein the ion channel modulating compound is a compound of formula (I), or solvates or pharmaceutically acceptable salts thereof, as described above.

Of the drug conjugates of the invention described herein, another embodiment is wherein the ion channel modulating compound is a compound of formula (IA), or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, as described above.

Of this embodiment, a further embodiment is wherein the compound of formula (IA) is Compound A, or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, as described herein.

Of the drug conjugates of the invention described herein, another embodiment is wherein the ion channel modulating compound is a compound of formula (IX), or solvates or pharmaceutically acceptable salts thereof, as described herein.

Another embodiment of the invention is a drug conjugate having the formula (DC-I), or a solvate or pharmaceutically acceptable salt thereof; as described above.

Another embodiment of the invention is a drug conjugate having the formula (DC-III), or a solvate or pharmaceutically acceptable salt thereof; as described above.

Another embodiment of the invention is a drug conjugate having the formula (DC-IV), or a solvate or pharmaceutically acceptable salt thereof; as described above.

Another embodiment of the invention is a drug conjugate wherein the additional drug moiety is selected from the group consisting of a cardiovascular agent, beta-blocker, ACE inhibitor, antihypertensive, diuretic, antipsychotic, anticoagulant (antiplatelet), antidepressant, inotrope, calcium sensitizer, calcium channel blocker, adrenergic blocking agent, angiotensin II receptor antagonist, xanthine oxidase Inhibitor (XOI), natriuretic peptide, metabolic modulator, lipid/cholesterol modulating agent, anti-inflammatory agent, vasodilator, anti-convulsant, antioxidant, antilipid, digitalis glycoside, rate control drug, antihistamine, antispasmodic, antibiotic, antirejection drug, immunomodulator, chemotherapeutic and antiarrhythmic.

Of the isotopic ion channel modulating compounds described herein, one embodiment are those compounds wherein the stable isotope is selected from a heavy atom isotope of C, N, O or H.

Of this embodiment, one preferred embodiment is wherein the stable isotope is $^2$H (deuterium).

Another preferred embodiment is wherein the isotopic ion channel modulating compound is perdeuterated.

Another preferred embodiment is wherein the isotopic ion channel modulating compound comprises a —CD$_3$ moiety.

Another preferred embodiment is wherein the isotopic ion channel modulating compound comprises a —OCD$_3$ moiety.

Of the isotopic ion channel modulating compounds described herein, another embodiment are those compounds wherein the stable isotope is $^{13}$C.

Of this embodiment, a preferred embodiment is wherein the compound comprises a —$^{13}$CH$_3$ moiety.

Another preferred embodiment is wherein the compound comprises a —O$^{13}$CH$_3$ moiety.

Of the isotopic ion channel modulating compounds described herein, one embodiment are those compounds of formula (XX), or a solvate, pharmaceutically acceptable salt, ester, amide, complex, chelate, stereoisomer, stereoisomeric mixture, geometric isomer, crystalline or amorphous form thereof, or mixtures thereof, as described above.

Of these compounds of formula (XX), one embodiment are those compounds comprising at least one $^{13}$C atom.

Of these compounds of formula (XX), another embodiment are those compounds comprising at least one $^{15}$N atom.

Of these compounds of formula (XX), another embodiment are those compounds comprising at least one $^{18}$O atom.

Of these compounds of formula (XX), another embodiment are those compounds comprising at least one $^2$H (deuterium) atom.

Of the isotopic ion channel modulating compounds described herein, other embodiment are those compounds of formula (ID), formula (IID), formula (IIID), formula (IVD), formula (VD), formula (VID), formula (VIID) or formula (VIIID), or solvates, pharmaceutically acceptable salts, esters, amides, complexes, chelates, stereoisomers, stereoisomeric mixtures, geometric isomers, crystalline or amorphous forms thereof, or mixtures thereof, as described above.

G. Pharmaceutical Compositions, Dosage Forms and Administration of the Compounds of the Invention The compounds of the invention as described herein, including PEGylated derivatives of ion channel modulating compounds; drug conjugates comprising ion channel modulating compounds and isotopic derivatives of ion channel modulating compounds, may be used in pharmaceutical compositions. Such pharmaceutical compositions include one or more compounds of the invention, selected from any of the compounds described herein, or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, described above, in combination with a pharmaceutically acceptable carrier, diluent or excipient. These pharmaceutical compositions may be prepared in a similar manner as described for compounds of formula (I), (IA), and (IX) and Compound A in Published Patent Application No. WO 1999/50225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US2005002693, the pertinent disclosures of which are incorporated in full by reference herein.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of the compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, pharmaceutical compositions of the invention include a compound of the present invention as described herein, in admixture with one or more carriers. The carrier(s) may be particulate, so that the compositions are, for example, in tablet or powder form. The carrier(s) may be liquid, with the pharmaceutical compositions being, for example, an oral syrup or injectable liquid. In addition, the carrier(s) may be gaseous, so as to provide an aerosol composition useful in, e.g., inhalatory administration.

When intended for oral administration, the pharmaceutical composition of the invention is preferably in either solid or liquid form, where semi-solid, semi-liquid, suspension and gel forms are included within the forms considered herein as either solid or liquid.

As a solid composition for oral administration, the pharmaceutical composition of the invention may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the pharmaceutical composition of the invention is in the form of a capsule, e.g., a gelatin capsule, it may contain, in addition to materials of the above type, a liquid carrier such as polyethylene glycol or a fatty oil.

The pharmaceutical composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred pharmaceutical compositions contain, in addition to the present compounds, one or more of a sweetening agent, thickening agent, preservative (e.g., alkyl p-hydroxybenzoate), dye/colorant and flavor enhancer (flavorant). In a pharmaceutical composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active aminocycloalkyl ether compound. Preferred compositions and preparations according to the present invention are prepared so that a parenteral dosage unit contains between 0.01 to 10% by weight of active compound.

The pharmaceutical composition of the invention may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the pharmaceutical composition of the invention may include a transdermal patch or iontophoresis device. Topical formulations may contain a concentration of the inventive compound of from about 0.1 to about 25% w/v (weight per unit volume).

The pharmaceutical composition of the invention may be intended for rectal administration, in the form, e.g., of a suppository which will melt in the rectum and release the drug. The pharmaceutical composition of the invention for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the aminocycloalkyl ether compound is dispersed homogeneously therein by stirring. The molten homogeneous mixture is then poured into convenient sized molds, allowed to cool and thereby solidify.

The pharmaceutical composition of the invention may include various materials which modify the physical form of a solid or liquid dosage unit. For example, the pharmaceutical composition of the invention may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The pharmaceutical compositions of the invention in solid or liquid form may include an agent which binds to the aminocycloalkyl ether compound and thereby assists in the delivery of the active components. Suitable agents which may act in this capacity include a monoclonal or polyclonal antibody, a protein or a liposome.

The pharmaceutical compositions of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical compositions of the present invention may contain one or more known pharmacological agents used in methods for either modulating ion channel activity in a warm-blooded animal or for modulating ion channel activity in vitro, or used in the treatment and/or prevention of arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g. diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, atrial contractile dysfunction, hypotension, Alzheimer's disease, dementia and other mental disorders, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer or other diseases. Other agents known to cause libido enhancement, analgesia or local anesthesia may be combined with compounds of the present invention.

The pharmaceutical compositions of the invention may be prepared by methodology well known in the pharmaceutical art. The aminocycloalkyl ether compounds of the present invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A pharmaceutical composition of the invention intended to be administered by injection can be prepared by combining the aminocycloalkyl ether compound of the present invention with water, and preferably buffering agents, so as to form a solution. The water is preferably sterile pyrogen-free water. A surfactant may be added to facilitate the formation of a homogeneous solution or suspension. Surfactants are compounds that non-covalently interact with the aminocycloalkyl ether compound so as to facilitate dissolution or homogeneous suspension of the aminocycloalkyl ether compound in the aqueous delivery system. Surfactants are desirably present in aqueous compositions of the invention because the aminocycloalkyl ether compounds according to the present invention may be hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

As used herein, "treating arrhythmia" refers to therapy for arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred for some treatments. The dosage amount and frequency are selected to create an effective level of the agent without harmful effects. It will generally range from a dosage of from about 0.01 to about 100 mg/kg/day, and typically from about 0.1 to 10 mg/kg where administered orally or intravenously for antiarrhythmic effect or other therapeutic application.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocycloalkyl ether compound of the invention may be co-administered with epinephrine in order to induce local anesthesia.

H. Utility and Testing of the Compounds of the Invention

The present invention provides one or more compounds, or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above, for use in methods for modulating ion channel activity in a warm-blooded animal or for modulating ion channel activity in vitro. In one version of this embodiment, the warm-blooded animal in which the ion channel activity is modulated is a mammal; in one version, the warm-blooded animal is a human; in one version, the warm-blooded animal is a farm animal. In one version of this embodiment, the method for modulating ion channel activity in vitro utilizes a compound of the invention to determine the desired activity.

As disclosed within the present invention, a variety of cardiac pathological conditions may be treated and/or prevented by the use of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above. These compounds of the present invention are ion channel modulating compounds that either singly or together with one or more additional compounds are able to selectively modulate certain ionic currents. The ion currents referred to herein are generally cardiac currents and more specifically, are the sodium currents and early repolarising currents.

Early repolarising currents correspond to those cardiac ionic currents which activate rapidly after depolarization of membrane voltage and which effect repolarisation of the cell. Many of these currents are potassium currents and may include, but are not limited to, the transient outward current $I_{to1}$ such as Kv4.2 and Kv4.3), and the ultrarapid delayed rectifier current ($I_{Kur}$) such as Kv1.5, Kv1.4 and Kv2.1). The ultrarapid delayed rectifier current ($I_{Kur}$) has also been described as $I_{sus}$. A second calcium dependent transient outward current ($I_{to2}$) has also been described.

The pathological conditions that may be treated and/or prevented by the present invention may include, but are not limited to, various cardiovascular diseases.

The cardiac pathological conditions that may be treated and/or prevented by the present invention may include, but are not limited to, arrhythmias such as the various types of atrial and ventricular arrhythmias, e.g. atrial fibrillation, atrial flutter, ventricular fibrillation, ventricular flutter.

In one embodiment, the present invention provides ion channel modulating compounds that can be used to selectively inhibit cardiac early repolarising currents and cardiac sodium currents.

In another embodiment, the present invention provides ion channel modulating compounds that can be used to selectively inhibit cardiac early repolarising currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation.

In other embodiments, the present invention provides a method for modulating ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for modulating ion channel activity in an in vitro setting comprising administering in vitro an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the activity/conductance of ion channel in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the activity/conductance of ion channel in an in vitro setting comprising administering in vitro an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for modulating potassium ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for modulating voltage-gated potassium ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, and mixtures thereof; or a composition or medicament that includes said compound or mixture comprising compounds as described above.

In other embodiments, the present invention provides a method for modulating cardiac sodium currents activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, and mixtures thereof; or a composition or medicament that includes said compound or mixture comprising compounds as described above.

In other embodiments, the present invention provides a method for modulating cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for blocking/inhibiting cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, and mixtures thereof; or a composition or medicament that includes said compound or mixture comprising compounds as described above.

In other embodiments, the present invention provides a method for blocking/inhibiting the cardiac ion channels responsible for cardiac early repolarising currents and cardiac sodium currents ion channel activity in a warm-blooded animal under conditions where an arrhythmogenic substrate is present in the heart of said warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, and mixtures thereof; or a composition or medicament that includes said compound or mixture comprising compounds as described above.

In other embodiments, the cardiac early repolarising currents referred to in the present invention comprise ionic currents which activate rapidly after depolarisation of membrane voltage and which effect repolarisation of the cell.

In other embodiments, the cardiac early repolarising currents referred to in the present invention comprise the cardiac transient outward potassium current (Ito) and/or the ultrarapid delayed rectifier current ($I_{Kur}$).

In other embodiments, the cardiac transient outward potassium current ($I_{to}$) and/or the ultrarapid delayed rectifier current ($I_{Kur}$) referred to in the present invention comprise at least one of the Kv4.2, Kv4.3, Kv2.1, Kv1.4 and Kv1.5 currents.

In other embodiments, the present invention provides a method for treating and/or preventing arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular arrhythmia in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial fibrillation in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular fibrillation in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In another embodiments, the present invention provides a method for treating and/or preventing atrial flutter in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

In other embodiments, the present invention provides a method for treating and/or preventing ventricular flutter in a warm-blooded animal comprising administering to a warm-blooded animal in need thereof, an effective amount of one or more compounds of the present invention or solvates, pharmaceutically acceptable salts, esters, amides, complexes, chelates, stereoisomers, stereoisomeric mixtures, geometric isomers, crystalline or amorphous forms, metabolites, metabolic precursors or prodrugs thereof, including isolated enantiomeric, diastereomeric and geometric isomers thereof, and mixtures thereof; or a composition or medicament that includes said compound or mixture comprising compounds as described above.

As noted above, the present invention provides for utilizing the compounds described above in in vitro and in vivo methods. In one embodiment, ion channels, such as cardiac potassium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating and/or preventing a variety of diseases or disorders caused by defective or inadequate function of the ion channels. The compounds of the invention are found to have significant activity in modulating various ion channel activity both in vivo and in vitro.

In one embodiment, the present invention provides a compound of the present invention or a composition containing said compound, for use in methods for either modulating ion channel activity in a warm-blooded animal or for modulating ion channel activity in vitro. Some of the ion channels to which the compounds, compositions and methods of the present invention have modulating effect are various potassium and sodium channels. These potassium and sodium ion channels may be voltage-activated (also known as voltage-gated) or ligand-activated (also known as ligand-gated), and may be present in cardiac and/or neuronal systems.

In one embodiment, the invention provides a compound of the present invention, or composition containing said compound, for use in methods for either modulating activity of ion channel(s) in a warm-blooded animal or for modulating activity of ion channel(s) in vitro, wherein said ion channel(s) correspond to some of the cardiac and/or neuronal ion channels that are responsible for one or more early repolarising currents comprising those which activate rapidly after membrane depolarisation and which effect repolarisation of the cells.

In another embodiment, of the present invention, the above-mentioned early repolarising currents comprise the transient outward potassium current ($I_{to}$ for cardiac or $I_A$ for neuronal) and/or the ultrarapid delayed rectifier current ($I_{Kur}$); and include at least one of the Kv4.2, Kv4.3, Kv2.1, Kv1.3, Kv1.4 and Kv1.5 currents.

In another embodiment, the present invention provides a compound of the present invention, or composition containing said compound, for use in methods for either modulating activity of ion channel(s) in a warm-blooded animal or for modulating activity of ion channel(s) in vitro, wherein said ion channel(s) correspond to either the cardiac or neuronal ion channel(s) that are responsible for Kv1.5 current.

In yet another embodiment, the present invention provides a compound of the present invention, or composition containing said compound, for use in methods for either modulating activity of ion channel(s) in a warm-blooded animal or for modulating activity of ion channel(s) in vitro, wherein said ion channel(s) correspond to the potassium channel that are responsible for Kv4.2 current.

Furthermore, the voltage-activated sodium ion channels comprise the $Na_v1$, $Na_v2$ or $Na_v3$ series and may be present in cardiac, neuronal, skeletal muscle, central nervous and/or peripheral nervous systems (e.g. hH1Na).

For cardiac sodium channels, in studies on ion channels in isolated human atrial myocytes, compounds of the present invention have been shown to produce frequency-dependent blockade of cardiac sodium channels. In these studies enhanced blockade of cardiac sodium channels was observed at faster rates of stimulation with sodium block increasing several-fold during rapid stimulation rates. These protocols have been designed to mimic the short recovery intervals during fibrillation.

As noted earlier, modulating the activity of an ion channel as used above may imply but does not limit to blocking or inhibiting the conductance of the current through the ion channel.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of the present invention, or a composition containing a compound of the present invention is administered to a warm-blooded animal in need thereof. Some of the diseases and conditions to which the compounds, compositions and methods of the present invention may be applied are as follows: arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g. diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, heart failure, atrial contractile dysfunction, hypotension, Alzheimer's disease, dementia and other mental disorder, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer.

Furthermore, the present invention provides a method for producing analgesia or local anesthesia in a warm-blooded animal which includes administering to a warm-blooded animal in need thereof an effective amount of a compound of the present invention or a pharmaceutical composition containing said compound. These methods may be used to relieve or forestall the sensation of pain in a warm-blooded animal.

The invention further provides a method for enhancing libido in a warm-blooded animal which includes administering to a warm-blooded animal in need thereof an effective amount of a compound of the present invention or a pharmaceutical composition containing said compound. These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

Furthermore, the present invention provides a method in an in vitro setting, wherein a preparation that contains ion channels is contacted with an effective amount of an aminocycloalkyl ether compound of the invention. Suitable preparations containing cardiac sodium channels and/or cardiac potassium channels include cells isolated from cardiac tissue as well as cultured cell lines. The step of contacting includes, for example, incubation of ion channels with a compound under conditions and for a time sufficient to permit modulation of the activity of the channels by the compound.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an aminocycloalkyl ether compound of the invention may be co-administered with epinephrine in order to induce local anesthesia.

In order to assess whether a compound has a desired pharmacological activity with the present invention, it may be subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous infusion every 5 minutes to a conscious rat. The effects of the compound on blood pressure, heart rate and the ECG are measured continuously. Increasing doses are given until a severe adverse event occurs. The drug related adverse event is identified as being of respiratory, central nervous system or cardiovascular system origin. This test gives an indication as to whether the compound is modulating the activity of sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

All of the foregoing tests may be performed using rat tissue. In order to ensure that a compound is not having effects which are only specific to rat tissue, further experiments may be performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, anesthetized monkeys (*Macaca fascicularis*). In this preparation, a blood pressure cannula and ECG electrodes are suitably placed in an anesthetized monkey. In addition, a stimulating electrode is placed onto the right atria and/or ventricle, together with monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23 G needle as applied to the shaved back of a guinea pig (Cavia porcellus) is assessed following subcutaneous administration of sufficient (50 µL, 10 mg/mL) solution in saline to raise a visible bleb on the skin. Each test is performed on the central area of the bleb and also on its periphery to check for diffusion of the test solution from the point of administration. If the test animal produces a flinch in response to the stimulus, this demonstrates the absence of blockade of pain sensation. Testing may be carried out at intervals for up to 8 hours or more post-administration. The sites of bleb formation are examined after 24 hours to check for skin abnormalities consequent to local administration of test substances or of the vehicle used for preparation of the test solutions.

Biological Example 1

Assessment of Antiarrhythmic Efficacy

Antiarrhythmic efficacy may be assessed by investigating the effect of a compound of the invention on the incidence of cardiac arrhythmias in anesthetized rats subjected to coronary artery occlusion. Rats weighing 200-300 gms are subjected to preparative surgery and assigned to groups in a random block design. In each case, the animal is anesthetized with pentobarbital during surgical preparation. The left carotid artery is cannulated for measurement of mean arterial blood pressure and withdrawal of blood samples. The left jugular vein is also cannulated for injection of drugs. The thoracic cavity is opened and a polyethylene occluder loosely placed around the left anterior descending coronary artery. The thoracic cavity is then closed. An ECG is recorded by insertion of electrodes placed along the anatomical axis of the heart. In a random and double-blind manner, an infusion of vehicle or the compound to be tested is given about 15 min post-surgery. After 5 minutes infusion, the occluder is pulled so as to produce a coronary artery occlusion. ECG, arrhythmias, blood pressure, heart rate and mortality are monitored for 15 minutes after occlusion. Arrhythmias are recorded as ventricular tachycardia (VT) and ventricular fibrillation (VF) and scored according to Curtis, M. J. and Walker, M. J. A., Cardiovasc. Res. 22:656 (1988).

Rats are excluded from the study if they do not exhibit pre-occlusion serum potassium concentrations within the range of 2.9-3.9 mM. Occlusion is associated with increases in R-wave height and "S-T" segment elevation; and an occluded zone (measured after death by cardiogreen dye perfusion) in the range of 25%-50% of total left-ventricular weight.

Results of the test compounds may be expressed as values of a given infusion rate in micromol/kg/min. ($ED_{50}AA$) which will reduce the arrhythmia score in treated animals to 50% of that shown by animals treated only with the vehicle in which the test compound(s) is dissolved.

Biological Example 2

Measurement of Cardiovascular and Behavioral Effects

Preparative surgery is performed in Sprague Dawley rats weighing 200-300 gm and anaesthetized with 65 mg/kg (i.p.) pentobarbital. The femoral artery and vein are cannulated using polyethylene (PE)-10 tubing. Prior to surgery, this PE-10 tubing had been annealed to a wider gauge (PE-50) tubing for externalization. The cannulated PE-10/PE-50 tubing is passed through a trocar and exteriorised together with three (lead II) limb ECG leads (see below). The trocar is threaded under the skin of the back and out through a small incision at the mid-scapular region. A ground ECG electrode is inserted subcutaneously using a 20 gauge needle with the lead wire threaded through it. To place the other ECG electrodes, a small incision is made in the anterior chest region over the heart and ECG leads are inserted into the subcutaneous muscle layer in the region of the heart using a 20 gauge needle. Other ECG leads are inserted into the subcutaneous muscle layer in the region near the base of the neck and shoulder (right side). The animal is returned to a clean recovery-cage with free access to food and water. The treatment and observational period for each animal commenced after a 24-hour recovery period.

A 15 min observational period is recorded followed by the intravenous infusion regime of the test compound at an initial dose of 2.0 µmol/kg/min (at 1 ml/hr). This rate is doubled every 5 minutes until one of the following effects is observed:

a) partial or complete convulsions b) severe arrhythmias c) bradycardia below 120 beats/min d) hypotension below 50 mmHg e) the dose exceeds 32 times the initial starting dose (i.e. 64 µmol/kg/min).

Blood pressure (BP), heart rate (HR) and ECG variables are continuously recorded while behavioral responses are also monitored and the total accumulative drug dose and drug infusion rate at which the response (such as convulsion, piloerection, ataxia, restlessness, compulsive chewing, lip-smacking, wet dog shake etc.) occurred are recorded.

Estimates of plasma concentrations of the test compound are determined by removing a 0.5 mL blood sample at the end of the experiment. Blood samples are centrifuged for 5 min at 4600×g and the plasma decanted. Brain tissue samples are also extracted and kept frozen (−20° C.) along with the plasma samples for chemical analysis.

Electrocardiograph (ECG) parameters: PR, QRS, $QT_1$ (peak of T-wave), $QT_2$ (midpoint of T-wave deflection) and hemodynamic parameters: BP and HR are analyzed using the automated analysis function in LabView (National Instruments) with a customized autoanalysis software (Nortran Pharmaceuticals). The infused dose producing 25% from control ($D_{25}$) for all recorded ECG variables is determined.

Results of the tests can be expressed as $D_{25}$ (micromol/kg) which are the doses required to produce a 25% increase in the ECG parameter measured. The increases in P-R interval and QRS interval indicate cardiac sodium channel blockade while the increase in Q-T interval indicates cardiac potassium channel blockade.

Biological Example 3

Electrophysiological Test (In Vivo)

Male Sprague-Dawley rats weighing between 250-350 g are used. They are randomly selected from a single group and anesthetized with pentobarbital (65 mg/kg, ip.) with additional anesthetic given if necessary.

The trachea is cannulated and the rat is artificially ventilated at a stroke volume of 10 mL/kg, 60 strokes/minute. The right external jugular vein and the left carotid artery are cannulated for intravenous injections of compounds and blood pressure (BP) recording, respectively.

Needle electrodes are subcutaneously inserted along the suspected anatomical axis (right atrium to apex) of the heart for ECG measurement. The superior electrode is placed at the level of the right clavicle about 0.5 cm from the midline, while the inferior electrode is placed on the left side of the thorax, 0.5 cm from the midline and at the level of the ninth rib.

Two Teflon-coated silver electrodes are inserted through the chest wall using 27 G needles as guides and implanted in the epicardium of left ventricle (4-5 mm apart). Square pulse stimulation is provided by a stimulator controlled by a computer. In-house programmed software is used to determine the following: threshold current (iT) for induction of extra systoles, maximum following frequency (MFF), effective refractory period (ERP) and ventricular flutter threshold (VTt). Briefly, iT is measured as the minimal current (in µA) of a square wave stimulus required to capture and pace the heart at a frequency of 7.5 Hz and a pulse width of 0.5 msec; ERP is the minimum delay (in msec) for a second stimulus required to cause an extra systole with the heart entrained at a frequency of 7.5 Hz (1.5×iT and 0.2 msec pulse width), MFF is the maximum stimulation frequency (in Hz) at which the heart is unable to follow stimulation (1.5×iT and 0.2 msec pulse width); VTt is the minimum pulse current (in µA) to evoke a sustained episode of VT (0.2 msec pulse width and 50 Hz) (Howard, P. G. and Walker, M. J. A., *Proc. West. Pharmacol. Soc.* 33:123-127 (1990)).

Blood pressure (BP) and electrocardiographic (ECG) parameters are recorded and analyzed using LabView (National Instruments) with a customized autoanalysis software (Nortran Pharmaceuticals Inc.) to calculate mean BP (mm Hg, $\frac{2}{3}$ diastolic+$\frac{1}{3}$ systolic blood pressure), HR (bpm, 60/R-R interval); PR (msec, the interval from the beginning of the P-wave to the peak of the R-wave), QRS (msec, the interval from the beginning of the R-wave due to lack of Q wave in rat ECG, to the peak of the S-wave), QT (msec, the interval from the beginning of the R-wave to the peak of the T-wave).

The initial infusion dose is chosen based on a previous toxicology study of the test compound in conscious rats. This is an infusion dose that did not produce a 10% change from pre-drug levels in haemodynamic or ECG parameters.

The animal is left to stabilize prior to the infusion treatment according to a predetermined random and blind table. The initial infusion treatment is started at a rate of 0.5 mL/hr/300 g (i.e., 0.5 µmol/kg/min). Each infusion dose is doubled (in rate) every 5 minutes. All experiments are terminated at 32 mL/hr/300 g (i.e., 32 µmol/kg/min). Electrical stimulation protocols are initiated during the last two minutes of each infusion level.

Responses to test compounds are calculated as percent changes from pre-infusion values; this normalization is used to reduce individual variation. The mean values of BP and ECG parameters at immediately before the electrical stimulation period (i.e., 3 min post-infusion) are used to construct cumulative dose-response curves. Data points are fit using lines of best fit with minimum residual sum of squares (least squares; SlideWrite program; Advanced Graphics Software, Inc.). $D_{25}$'s (infused dose that produced 25% change from pre-infusion value) are interpolated from individual cumulative dose-response curves and used as indicators for determining the potency of compounds of the present invention.

Biological Example 4

Absorption, Distribution, and Excretion of Radioactivity Following Oral or Intravenous Administration of [$^{14}$C]Compound A to Rats Sprague Dawley and Long Evans rats weighing between 150-275 g were used. They were randomly selected via computer generated random numbers for assignment of animal numbers and groups based on body weight.

The study design are shown in Table 1 below:

TABLE 1

STUDY DESIGN SHOWING GROUP DESIGNATIONS AND DOSE LEVELS

| Group | Number of Animals | | Strain | Dose Route | Target Dose Level (mg/kg) | Target Dose Volume (mL/kg) | Samples Collected |
|---|---|---|---|---|---|---|---|
| | Male | Female | | | | | |
| 1 | 8 | 8 | SD | Oral | 25 | 2 | Carcass for WBA |
| 2 | 6 | 0 | LE | Oral | 25 | 2 | Carcass for WBA |
| 3 | 3 | 3 | SD | Oral | 25 | 2 | Urine and Feces |
| 4 | 8 | 8 | SD | IV | 25 | 2 | Carcass for WBA |
| 5 | 6 | 0 | LE | IV | 25 | 2 | Carcass for WBA |

TABLE 1-continued

STUDY DESIGN SHOWING GROUP DESIGNATIONS AND DOSE LEVELS

| Group | Number of Animals | | Strain | Dose Route | Target Dose Level (mg/kg) | Target Dose Volume (mL/kg) | Samples Collected |
|---|---|---|---|---|---|---|---|
| | Male | Female | | | | | |
| 6 | 3 | 3 | SD | IV | 25 | 2 | Urine and Feces |

IV Intravenous
LE Long Evans
SD Sprague Dawley
WBA Whole-body autoradiography
Note:
Each animal will receive a target dose of approximately 100 μCi/kg The appropriate quantities of radiolabeled test article were combined in an appropriate vehicle to prepare the dose formulations. Predose and postdose samples of each radiolabeled dose formulation were taken at the time of dose administration to determine radioactivity concentration and homogeneity. Predose and postdose samples were stored at approximately −20° C. until analyzed.

The volume of radiolabeled dose formulation administered to each animal was calculated based on the body weight taken on the day of dose administration. The actual amount administered was determined by weighing the dose syringe before and after dose administration. Animals dosed orally were fasted overnight approximately 4 hours postdose. Animals dosed intravenously were not fasted. The oral dose was administered via a ball-tipped gauge needle. The intravenous dose was administered as a slow bolus injection via a tail vein. The dose apparatus was flushed with approximately 0.5 mL of dose vehicle. The dose and flush were administered over 2 minutes. After the dose and flush were administered, but before the needle was removed from the animal, a gauze pad was placed over the injection site and slight pressure was applied as the needle is removed. The gauze pad and dose apparatus were saved for radioanalysis.

For animals dosed intravenously (Groups 4 and 5), all postdose collections were based off the time from the end of the intravenous dose. For Groups 1 and 4, one animal/sex/time point was sacrificed via an overdose of halothane anesthesia at 0.25, 0.5, 2, 4, 8, 24, 72, and 168 hours postdose (Group 1) and at 0.083, 0.5, 2, 4, 8, 24, 72, and 168 hours postdose (Group 4). For Groups 2 and 5, one animal/time point was sacrificed via an overdose of halothane anesthesia at 0.25, 0.5, 2, 24, 72, and 168 hours postdose (Group 2) and at 0.083, 0.5, 2, 12, 72, and 168 hours postdose (Group 5). Blood (approximately 2 mL) was collected from the right jugular vein via syringe and needle and transferred into tubes containing sodium EDTA anticoagulant prior to sacrifice. Samples were maintained on wet ice, in a chilled Kryorack, or stored at approximately 5° C. until aliquoted and centrifuged to obtain plasma. Immediately after blood collection, the animals were prepared for WBA. The carcasses were immediately frozen in a hexane/dry ice bath for approximately 5 minutes. The carcasses were drained, blotted dry, and placed on dry ice or stored at approximately −70° C. for at least 2 hours. Each carcass was then be placed into an appropriately labeled bag and stored at approximately −20° C. The frozen carcasses were embedded in chilled carboxymethylcellulose and frozen into blocks. Embedded carcasses were stored at approximately −20° C. in preparation for autoradiographic analysis.

Urine and feces were collected (Groups 3 and 6). The following samples were collected for analysis of excretion of radioactivity. Urine was collected in plastic containers surrounded by dry ice at 0-8, 8-24, and at 24-hour intervals through 168 hours postdose. The weight of each sample was recorded. Feces were collected in plastic containers surrounded by dry ice at 24-hour intervals through 168 hours postdose. The weight of each sample was recorded. After the last excreta collections, cages were washed and wiped with a solution of 1% trisodium phosphate in water and gauze pads. The cage wash samples and gauze were collected into separate plastic containers and the weight of each cage wash sample was recorded. Animals were sacrificed via an overdose of halothane anesthesia and the residual carcass from each animal was retained for possible radioanalysis.

Samples were uniquely identified to indicate origin and collection time. All samples, except blood, were stored at approximately −20° C. before and after analysis. Blood was stored at approximately 5° C. until aliquoted and centrifuged. Plasma was harvested, aliquoted, and stored at approximately −20° C. The cellular fraction of the blood was discarded.

Samples were analyzed for content of radioactivity by liquid scintillation counting (LSC). Each sample was homogenized before radioanalysis, unless the entire sample was to be analyzed. All samples were analyzed in duplicate if sample size allows and counted for at least 5 minutes or 100,000 counts.

Quality control standards fortified with $^{14}C$ radioactivity were placed into the frozen block containing the carcass, and were used for monitoring the uniformity of section thickness. Using a Leica CM 3600 cryomicrotome, the appropriate sections were collected on adhesive tape. All of the major tissues, organs, and biological fluids were represented. After drying, a representative section from each level of interest was mounted and wrapped tightly with mylar film. Plastic embedded ARC autoradiographic standards purchased from American Radiolabeled Chemicals, Inc. were exposed with the sections to Amersham Biosciences phosphorimaging screens. The exposed screens were scanned using an Amersham Biosciences Storm. The autoradiographic standards were sampled using Imaging Research Inc. AIS software to create a calibrated standard curve. Using this standard curve, a lower limit of detection based on the lowest readable concentration was calculated (this was reported as the lower limit of quantitation based on the mean). Using AIS software, tissue concentrations were interpolated from each standard curve as nanocuries/g and then converted to pg equivalents/g (or ng equivalents/g, if appropriate) on the basis of the test article specific activity. The autoradiographs were annotated using Adobe Pagemaker software and printed on a FUJIX Pictrography 3000 digital image printer.

In addition to the foregoing assays, the compounds of the invention may be tested in any of the assays described in detail in PCT Published Patent Application No. WO 1999/050225; PCT Published Patent Application No. WO 2000/047547; PCT Published Patent Application No. WO 2004/098525; PCT Published Patent Application No. WO 2004/099137; PCT Published Patent Application No. WO 2005/018635; and U.S. Published Patent Application No. US 2005002693.

All of the U.S. patents, U.S. patent application publications, U.S. patent applications, foreign patents, foreign patent applications and non-patent publications referred to in this specification are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A drug conjugate comprising a drug moiety and an ion channel modulating compound, wherein the drug conjugate has the following formula (DC-I), or a pharmaceutically acceptable salt thereof:

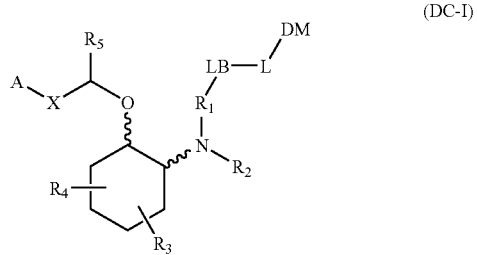

(DC-I)

wherein:
X is selected from a direct bond, —C($R_6$,$R_{14}$)—Y— and —C($R_{13}$)=CH—, with the proviso that when X is a direct bond and A is formula (III), then at least one of $R_7$, $R_8$ and $R_9$ is not hydrogen;
Y is selected from a direct bond, O, S and $C_1$-$C_4$alkylene;
$R_{13}$ is selected from hydrogen, $C_1$-$C_6$alkyl, $C_3$-$C_8$cycloalkyl, aryl and benzyl;
$R_1$ and $R_2$, taken together with the nitrogen atom to which they are directly attached in formula (DC-I), form a ring denoted by formula (DC-II-Z):

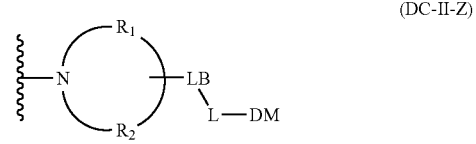

(DC-II-Z)

wherein the ring of formula (DC-II-Z) is formed from the nitrogen as shown as well as three to nine additional ring atoms independently selected from carbon, nitrogen, oxygen, and sulfur; where any two adjacent ring atoms may be joined together by single or double bonds, and where any one or more of the additional carbon ring atoms may be substituted with one or two substituents selected from hydrogen, hydroxy, $C_1$-$C_3$hydroxyalkyl, oxo, $C_2$-$C_4$acyl, $C_1$-$C_3$alkyl, $C_2$-$C_4$alkylcarboxy, $C_1$-$C_3$alkoxy, $C_1$-$C_{20}$alkanoyloxy, or may be substituted to form a spiro five- or six-membered heterocyclic ring containing one or two heteroatoms selected from oxygen and sulfur; and any two adjacent additional carbon ring atoms may be fused to a $C_3$-$C_8$-carbocyclic ring, and any one or more of the additional nitrogen ring atoms may be substituted with substituents selected from hydrogen, $C_1$-$C_6$alkyl, $C_2$-$C_4$acyl, $C_2$-$C_4$hydroxyalkyl and $C_3$-$C_8$alkoxyalkyl; or LB is a linkage group;
L is an optional linker;
DM is the drug moiety selected from;

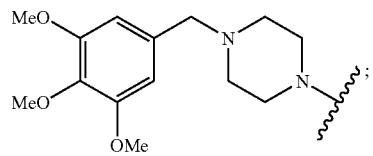

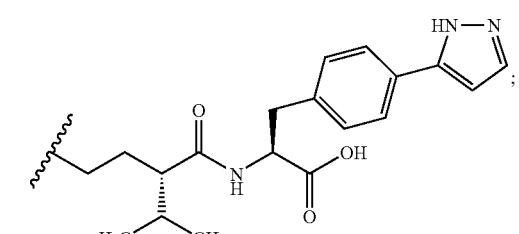

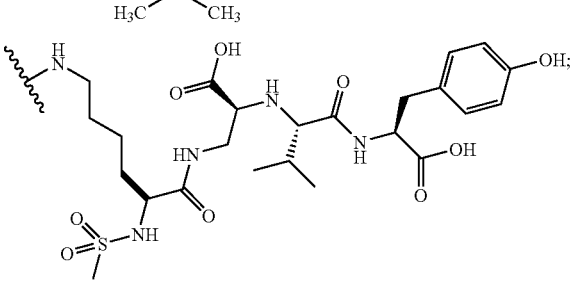

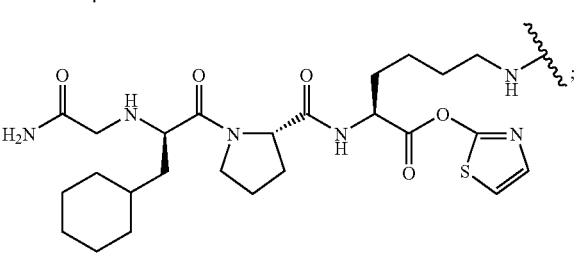

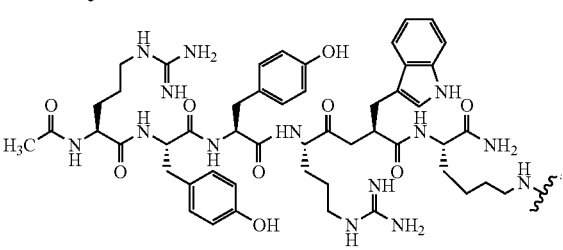

-continued
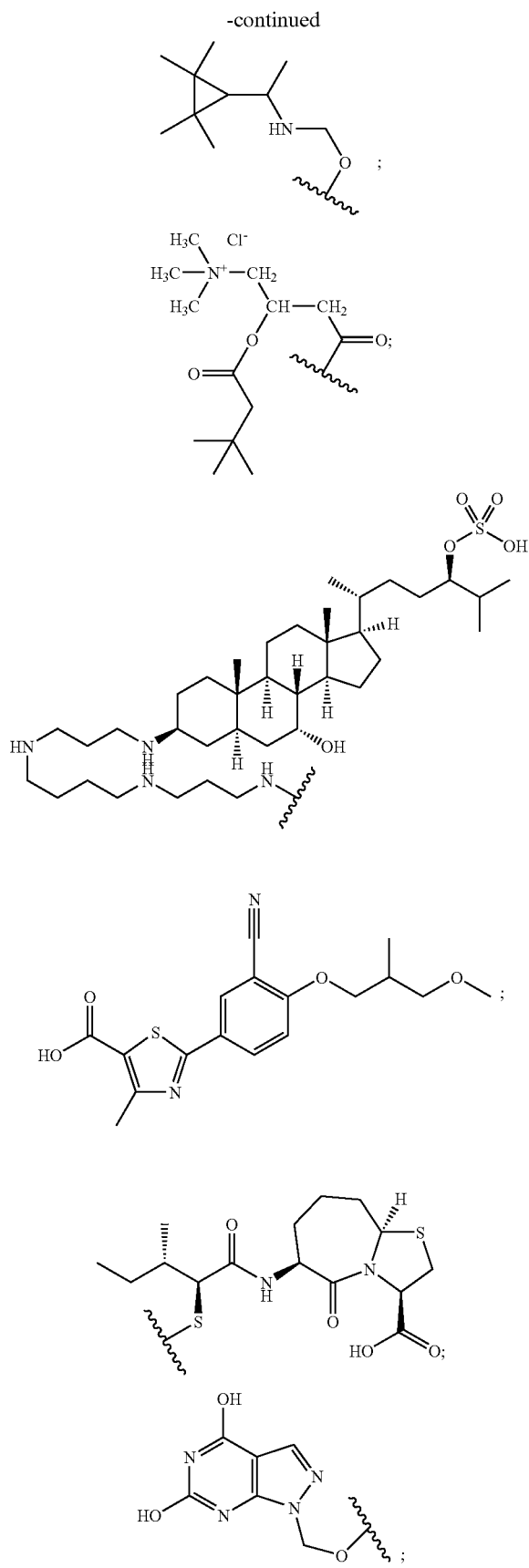
-continued
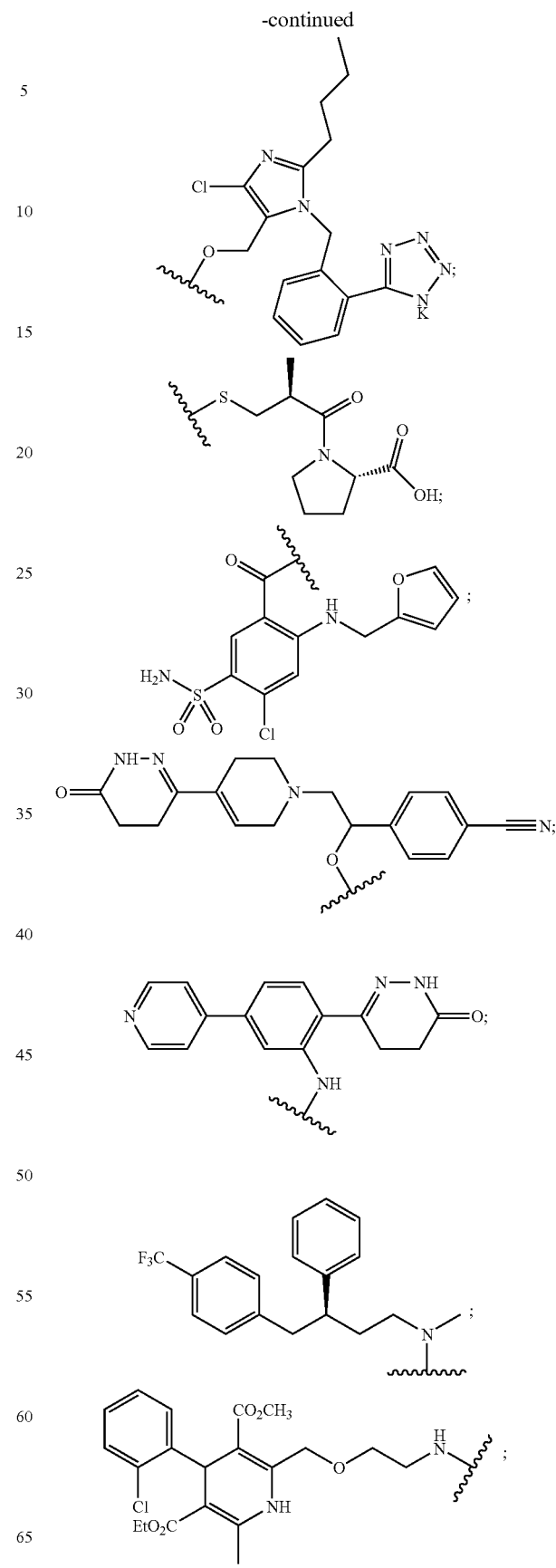

-continued

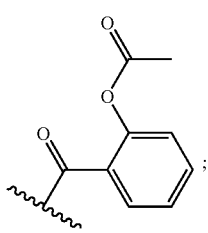

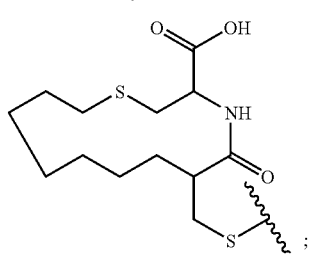

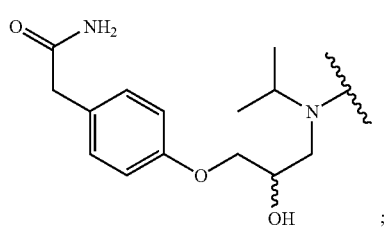

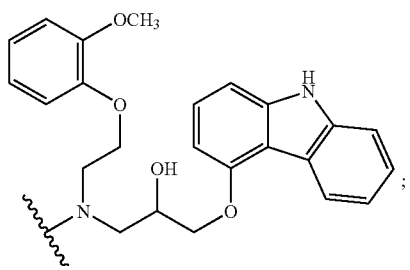

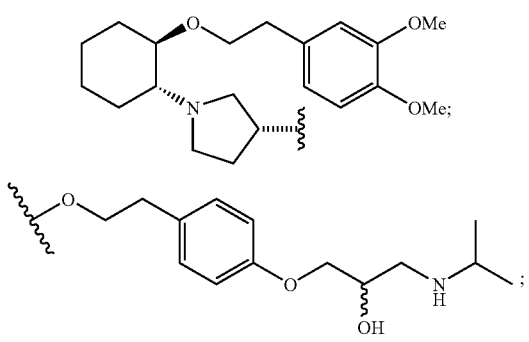

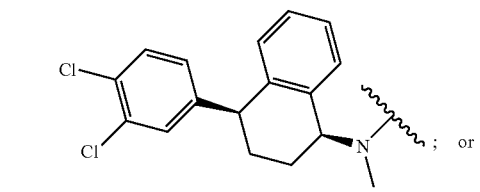

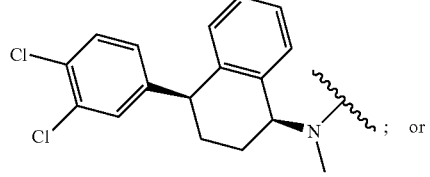

-continued

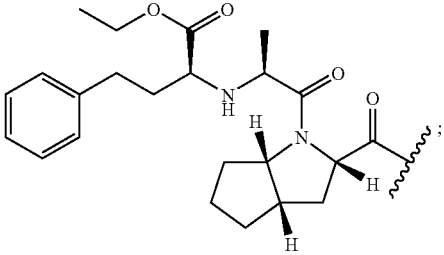

$R_3$ and $R_4$ are independently attached to the cyclohexane ring shown in formula (DC-I) at the 3-, 4-, 5- or 6-positions and are independently selected from hydrogen, hydroxy, $C_1$-$C_6$alkyl and $C_1$-$C_6$alkoxy, and, when both $R_3$ and $R_4$ are attached to the same cyclohexane ring atom, may together form a spiro five- or six-membered heterocyclic ring containing one or two heteroatoms selected from oxygen and sulfur;

$R_5$, $R_6$ and $R_{14}$ are independently selected from hydrogen, $C_1$-$C_6$alkyl, aryl and benzyl, or $R_6$ and $R_{14}$, when taken together with the carbon to which they are attached, may form a spiro $C_3$-$C_5$cycloalkyl;

A is selected from $C_5$-$C_{12}$alkyl, a $C_3$-$C_{13}$carbocyclic ring, and ring systems selected from formulae (III), (IV), (V), (VI), (VII) and (VIII):

(III)

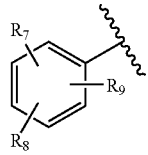

where $R_7$, $R_8$ and $R_9$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl and N($R_{15}$,$R_{16}$) where $R_{15}$ and $R_{16}$ are independently selected from hydrogen, acetyl, methanesulfonyl and $C_1$-$C_6$alkyl;

(IV)

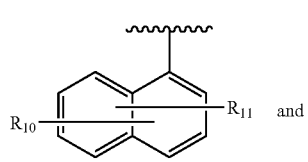 and (V)

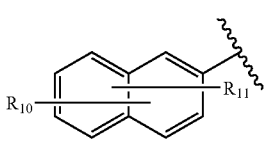

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and N($R_{15}$,$R_{16}$) where $R_{15}$ and $R_{16}$ are independently selected from hydrogen, acetyl, methanesulfonyl, and $C_1$-$C_6$alkyl;

(VI)

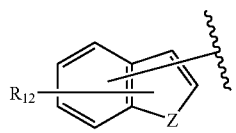

where $R_{12}$ is selected from bromine, chlorine, fluorine, carboxy, hydrogen, hydroxy, hydroxymethyl, methanesulfonamido, nitro, sulfamyl, trifluoromethyl, $C_2$-$C_7$alkanoyloxy, $C_1$-$C_6$alkyl, $C_1$-$C_6$alkoxy, $C_2$-$C_7$alkoxycarbonyl, $C_1$-$C_6$thioalkyl, and $N(R_{15},R_{16})$ where $R_{15}$ and $R_{16}$ are independently selected from hydrogen, acetyl, methanesulfonyl, and $C_1$-$C_6$alkyl; and Z is selected from CH, $CH_2$, O, N and S, where Z may be directly bonded to "X" as shown in formula (DC-I) when Z is CH or N, or Z may be directly bonded to $R_{17}$ when Z is N, and $R_{17}$ is selected from hydrogen, $C_1$-$C_6$alkyl, $C_3$-$C_8$cycloalkyl, aryl and benzyl;

(VII)

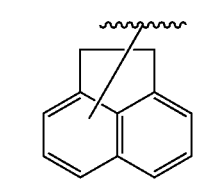

(VIII)

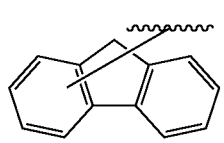

including isolated enantiomeric and diastereomeric isomers thereof, and mixtures thereof.

2. A pharmaceutical composition comprising the drug conjugate of claim 1 and a pharmaceutically acceptable excipient.

3. The drug conjugate of claim 1 selected from the group consisting of:

formula DC-5:

(DC-5)

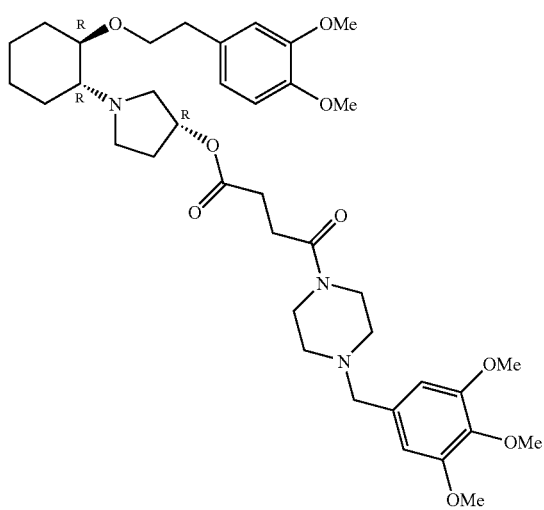

formula DC-7:

(DC-7)

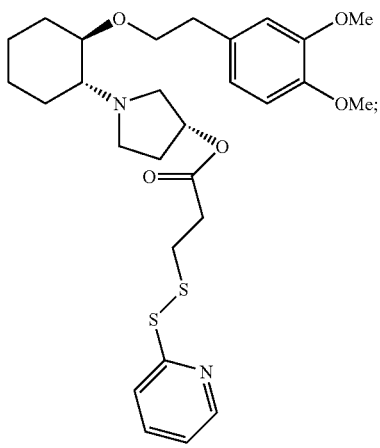

formula DC-9:

(DC-9)

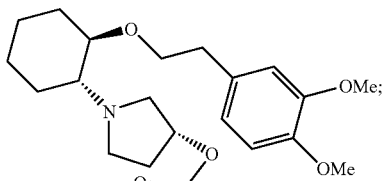
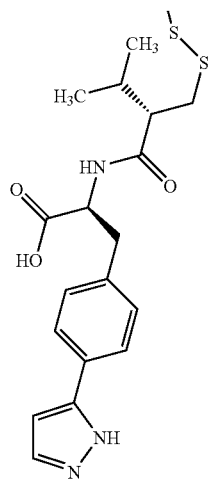

formula DC-11:
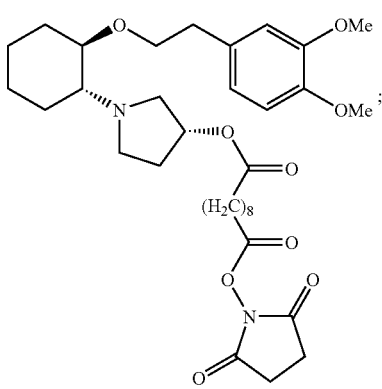
(DC-11)
formula DC-13:
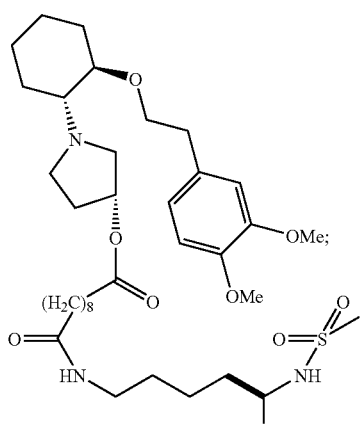
(DC-13)
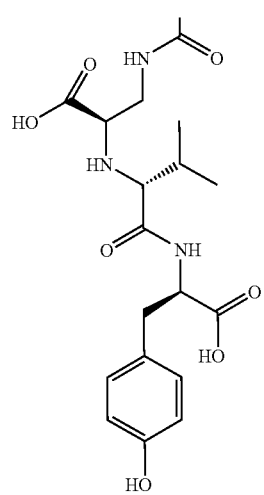
formula DC-15:
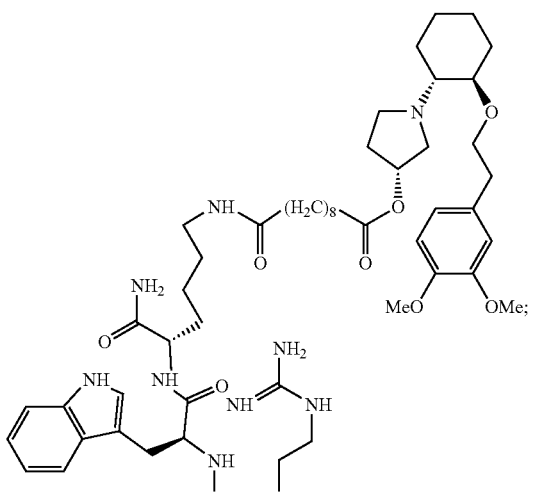
(DC-15)
formula DC-17:
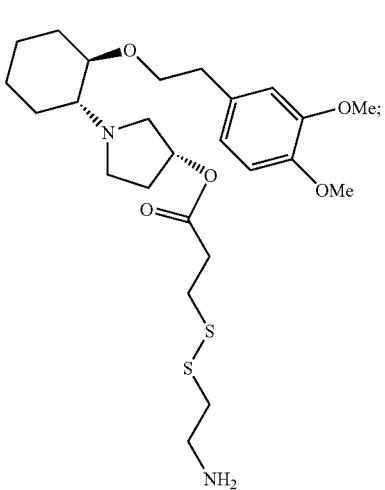
(DC-17)
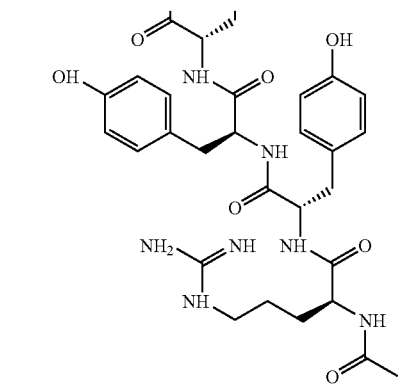

-continued
formula DC-19:
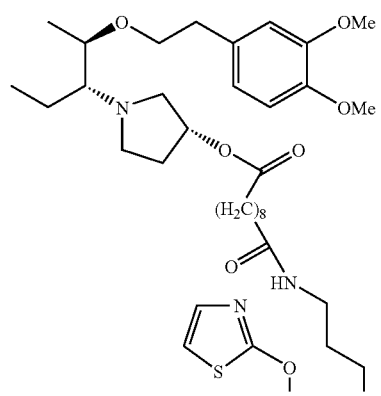
(DC-19)
formula DC-21:
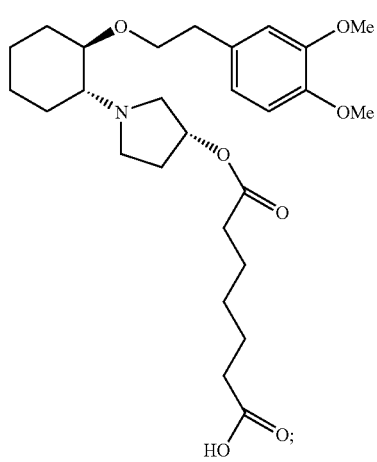
(DC-21)
-continued
formula DC-23:
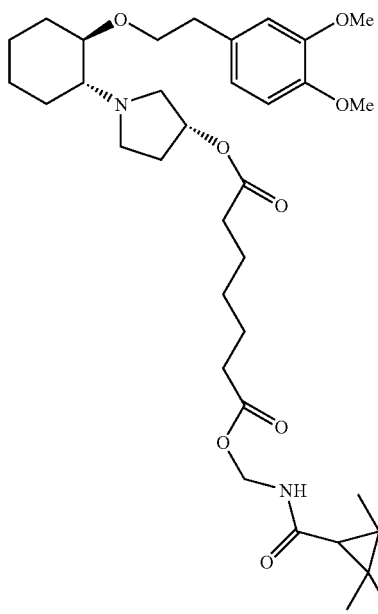
(DC-23)
formula DC-27:
(DC-27)
formula DC-29:
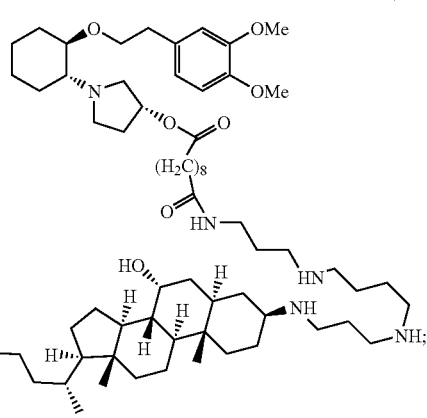
(DC-29)

formula DC-31:
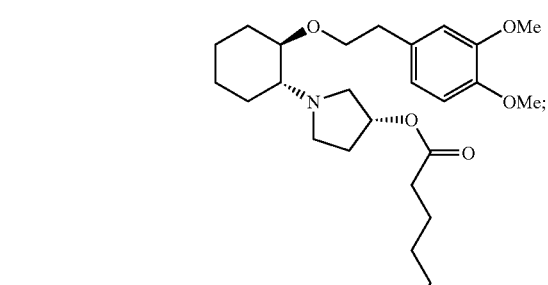
formula DC-33:
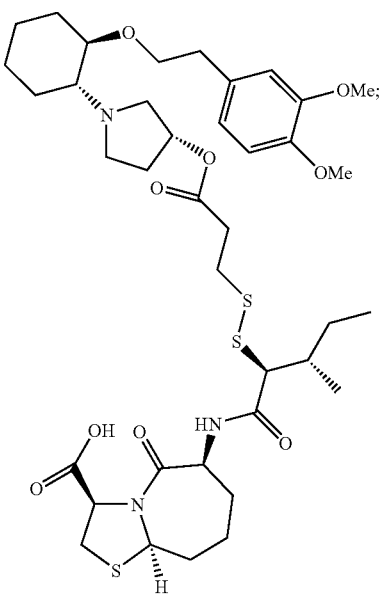
formula DC-35:
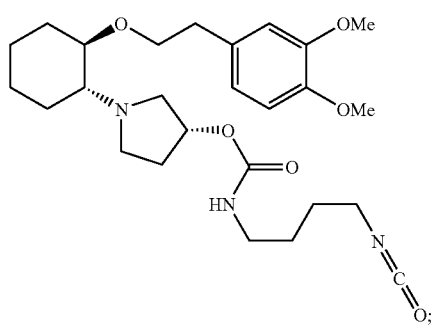
formula DC-37:
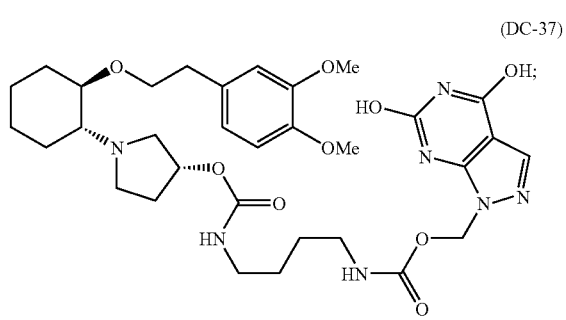
formula DC-39:
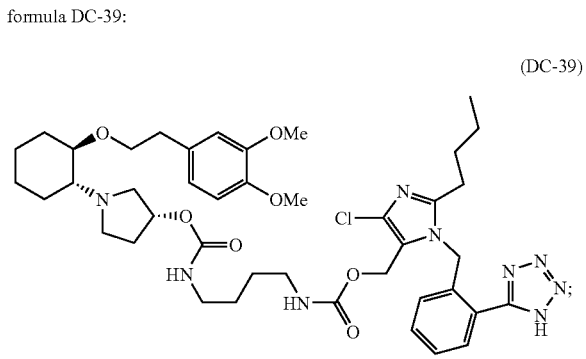
formula DC-41:
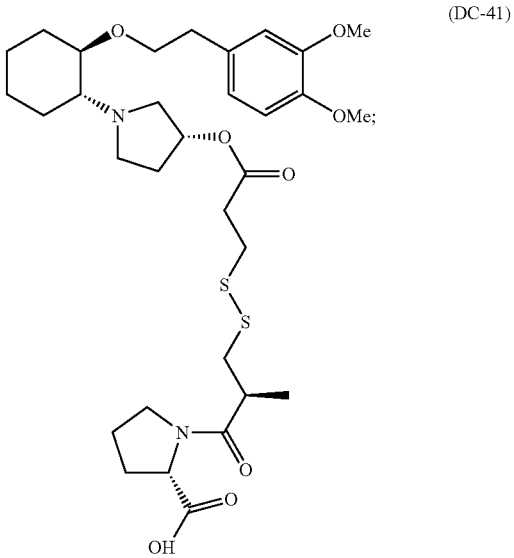
formula DC-43:
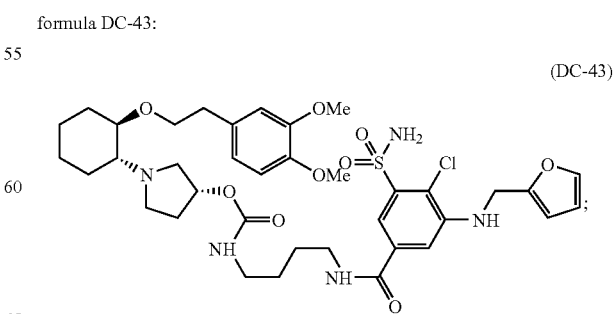

-continued
formula DC-45:
(DC-45)
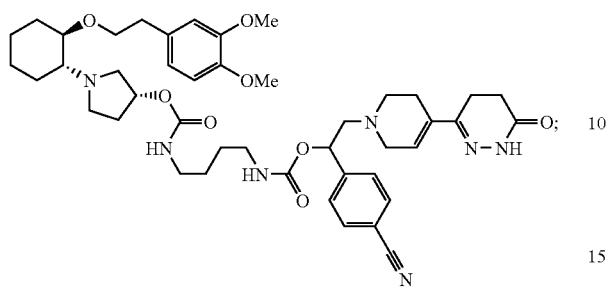
formula DC-47:
(DC-47)
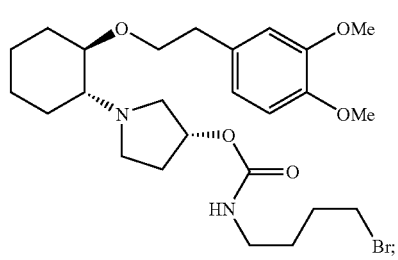
formula DC-49:
(DC-49)
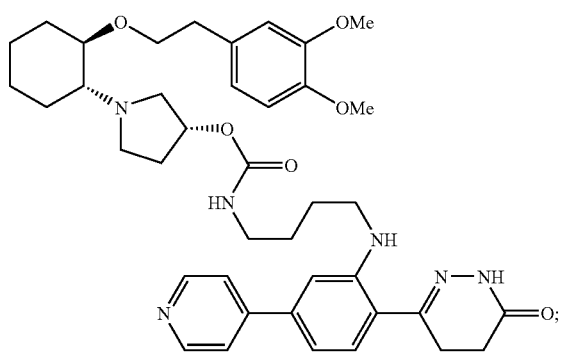
formula DC-51:
(DC-51)
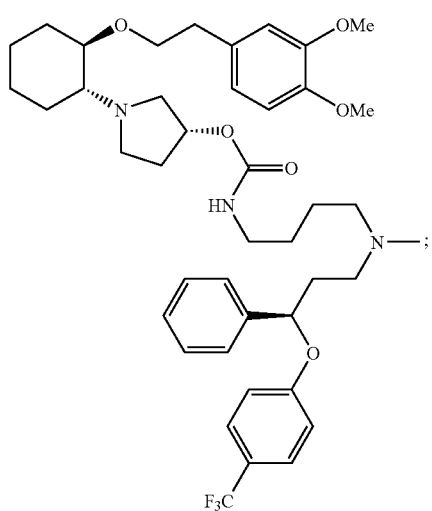
-continued
formula DC-53:
(DC-53)
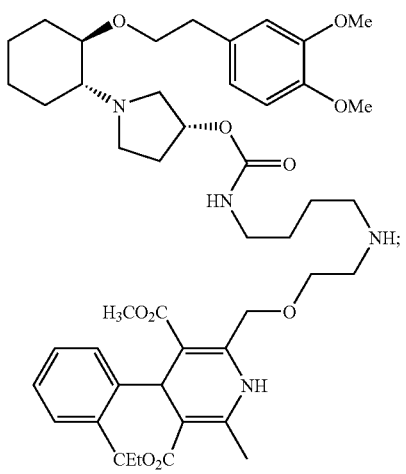
formula DC-55:
(DC-55)
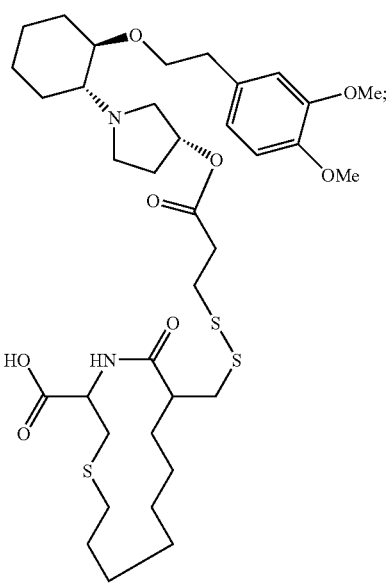
formula DC-67:
(DC-67)
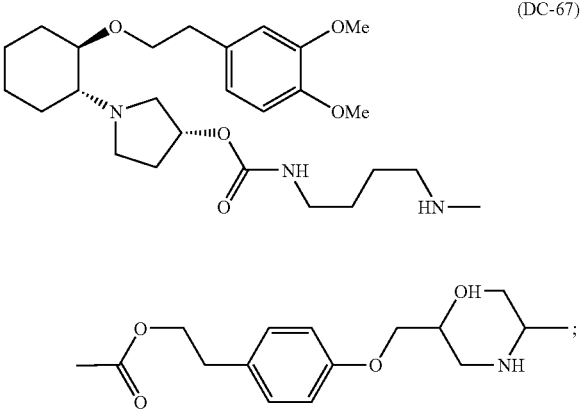

-continued
formula DC-69:
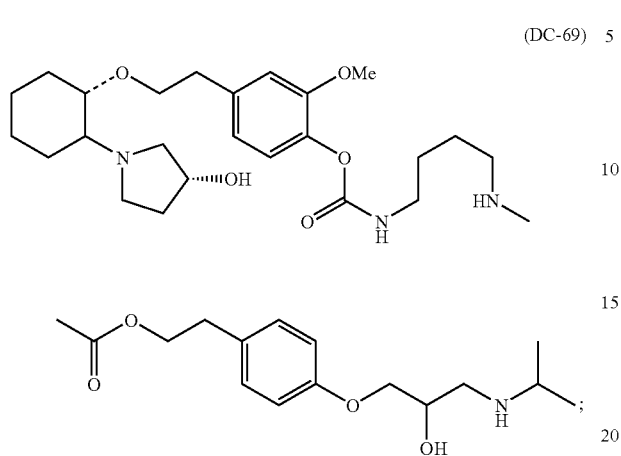
(DC-69)
formula DC-72, formula DC-73:
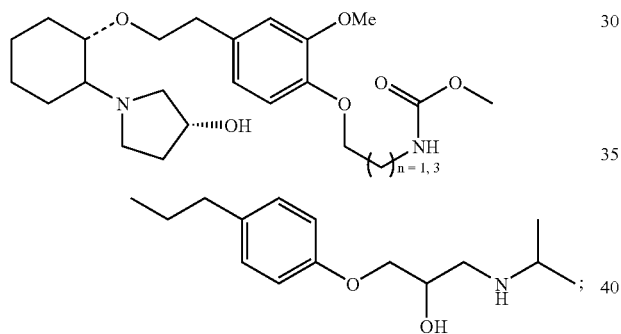
DC-72 (n = 1) DC-73 (n = 3)
formula DC-74:
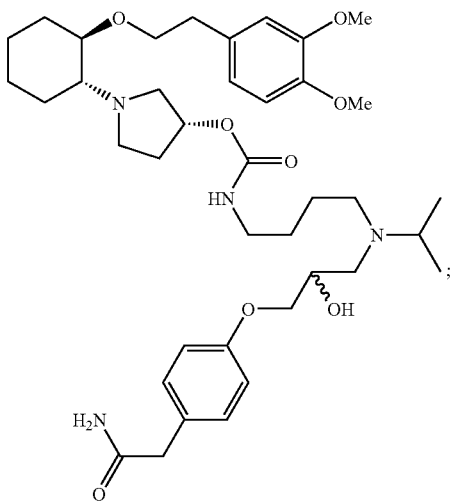
(DC-74)
-continued
formula DC-75:
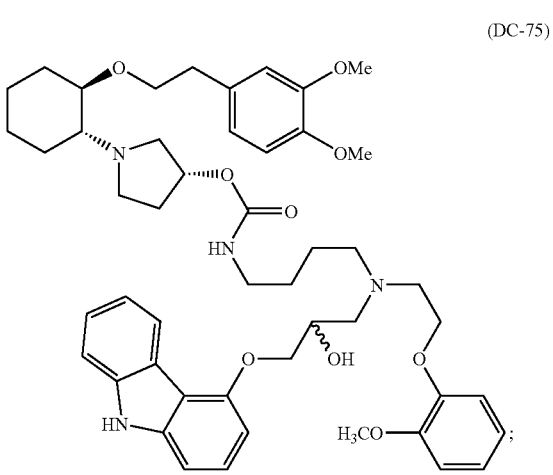
(DC-75)
formula DC-77:
(DC-77)
formula DC-78:
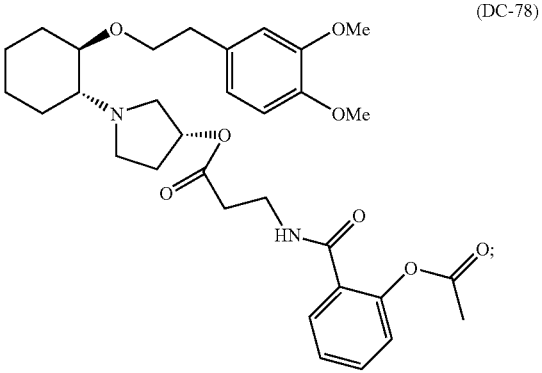
(DC-78)

formula DC-83:
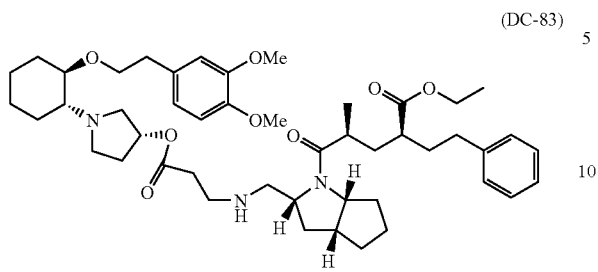
formula DC-84:
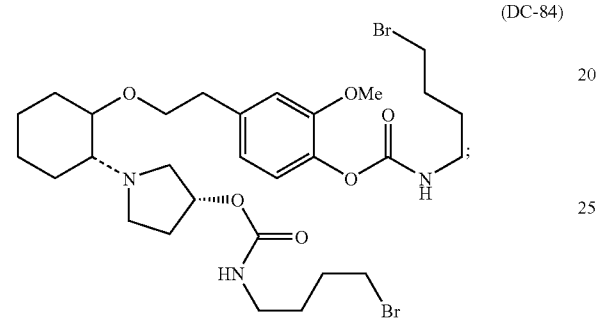
formula DC-85:
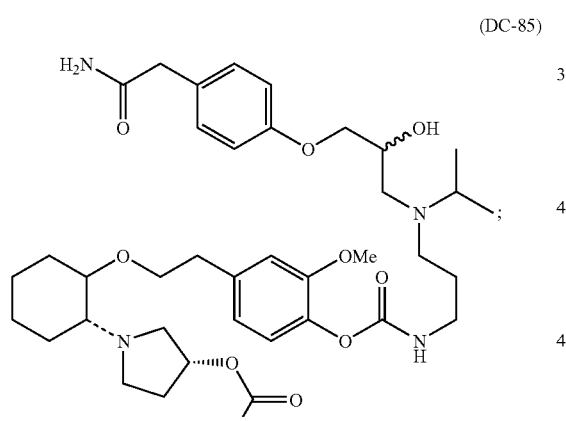
-continued
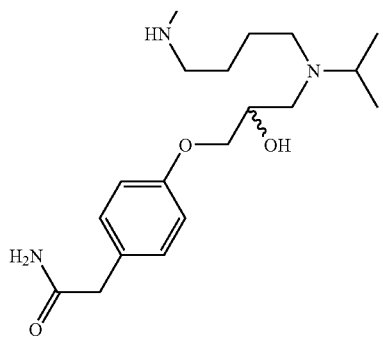
and formula DC-86:
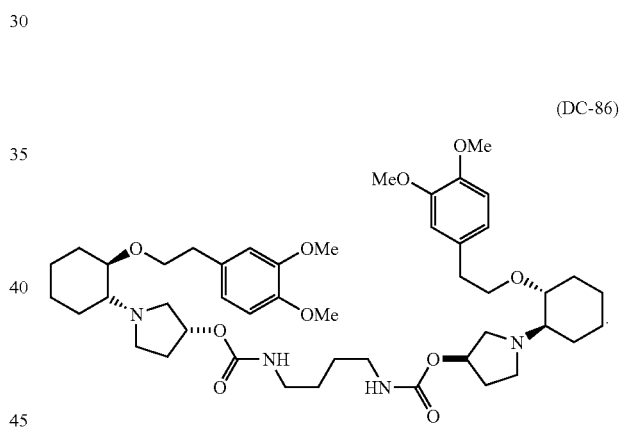
4. The drug conjugate of claim 1 wherein the drug conjugate is
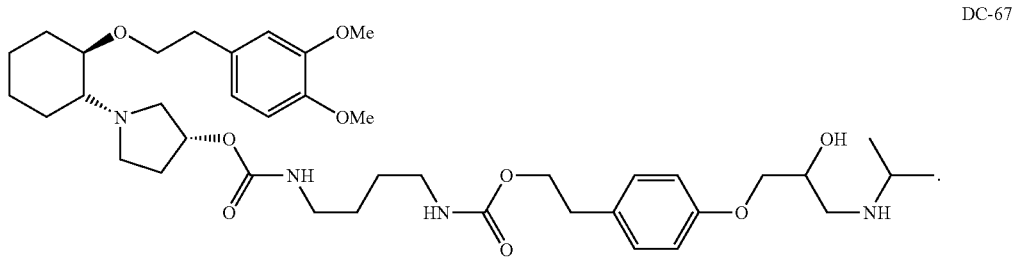

5. The drug conjugate of claim 1 wherein the ion channel modulating compound is a compound of formula (IA), or pharmaceutically acceptable salts thereof:

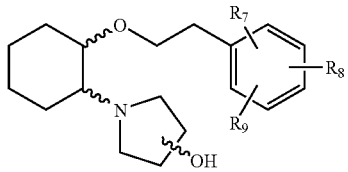

(IA)

wherein, $R_7$, $R_8$ and $R_9$ are independently selected from hydrogen, hydroxy and $C_1$-$C_6$alkoxy, including isolated enantiomeric and diastereomeric thereof, and mixtures thereof, with the proviso that $R_7$, $R_8$ and $R_9$ cannot all be hydrogen.

6. The drug conjugate of claim 5 wherein the compound of formula (IA) is Compound A:

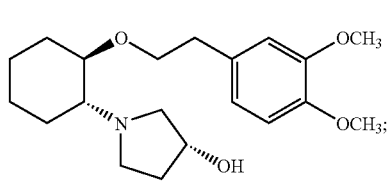

Compound A or pharmaceutically acceptable salts thereof.

* * * * *

UNITED STATES PATENT AND TRADEMARK OFFICE
CERTIFICATE OF CORRECTION

PATENT NO.       : 7,786,119 B2
APPLICATION NO.  : 11/547419
DATED            : August 31, 2010
INVENTOR(S)      : Elizabeth L. S. Cheu et al.

It is certified that error appears in the above-identified patent and that said Letters Patent is hereby corrected as shown below:

Title Page; Item (56):
"Kepler et al., "Synthesis of 5,5-Diphenylhydantoin-2,4,5-$^{13}C_3$," *J. Labelled Cpd.* X4): 683-687, 1974." should read, --Kepler et al., "Synthesis of 5,5-Diphenylhydantoin-2,4,5-$^{13}C_3$," *J. Labelled Cpd.* X(4):683-687, 1974.--.

Column 184, Lines 28-37:

Please delete the formula, " 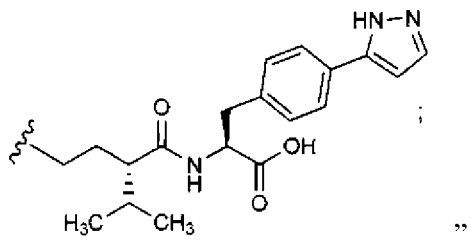 "

It should read, -- 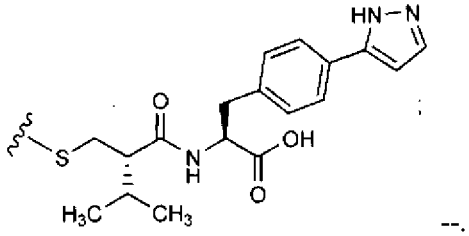 --.

Column 184, Lines 56-65:

Signed and Sealed this
Eighteenth Day of September, 2012

David J. Kappos
*Director of the United States Patent and Trademark Office*

CERTIFICATE OF CORRECTION (continued)
U.S. Pat. No. 7,786,119 B2

Please delete the formula, " 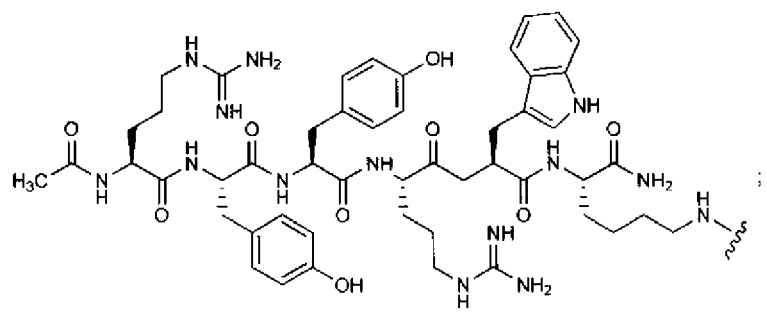 "

It should read, -- 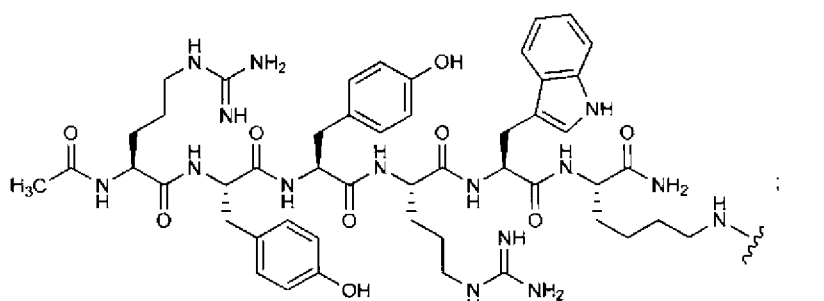 --.

Column 185, Lines 1-10:

Please delete the formula, " 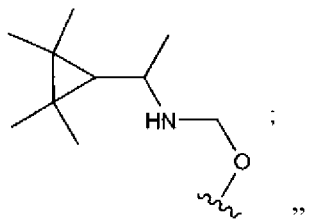 "

It should read, -- 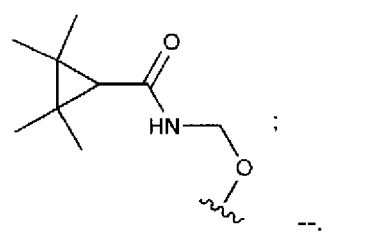 --.

Column 185, Lines 37-46:

Please delete the formula, " 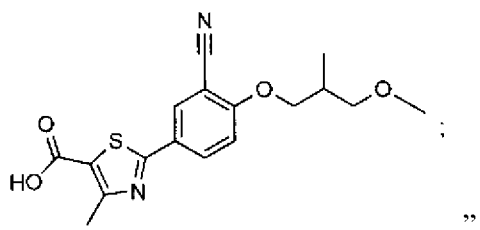 "

It should read, -- 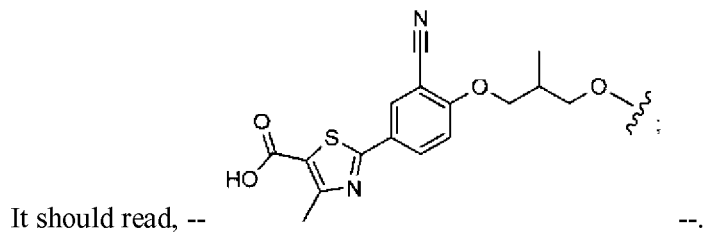 --.
Column 186, Lines 51-58:
Please delete the formula, " 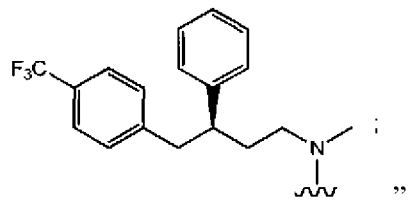 "
It should read, -- 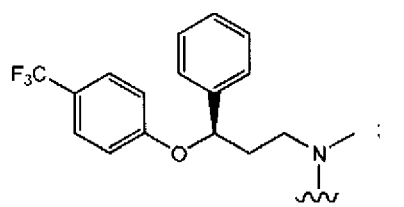 --.
Column 190, Lines 3-33:
The formula DC-7,
"formula DC-7:
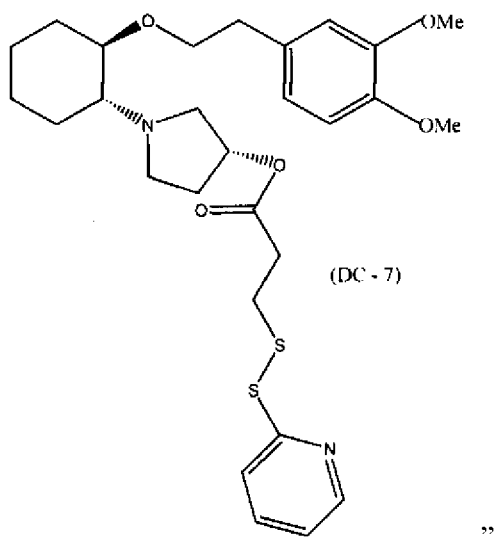
"
should be removed from the issued patent.

CERTIFICATE OF CORRECTION (continued)

Column 191, Lines 3-24:
The formula DC-11,

"formula DC-11

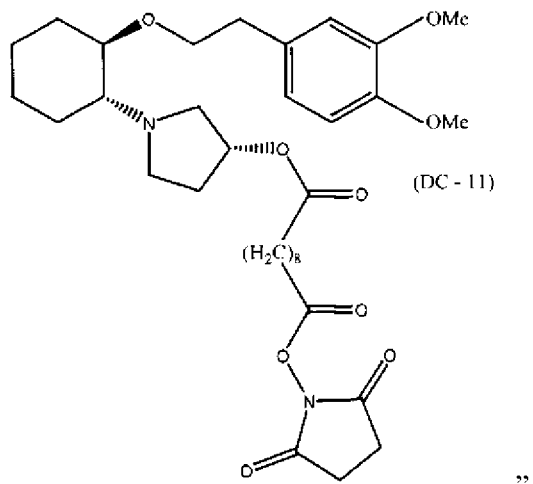

should be removed from the issued patent.

Column 191, Lines 28-66:
Please delete the formula DC-13,
formula DC-13:
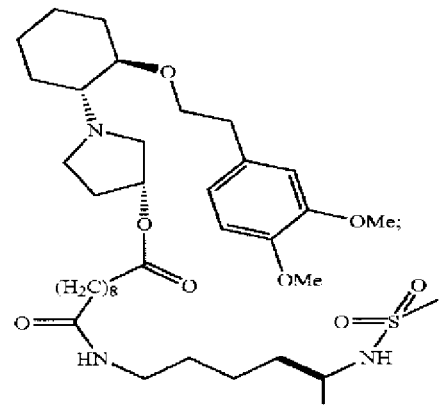
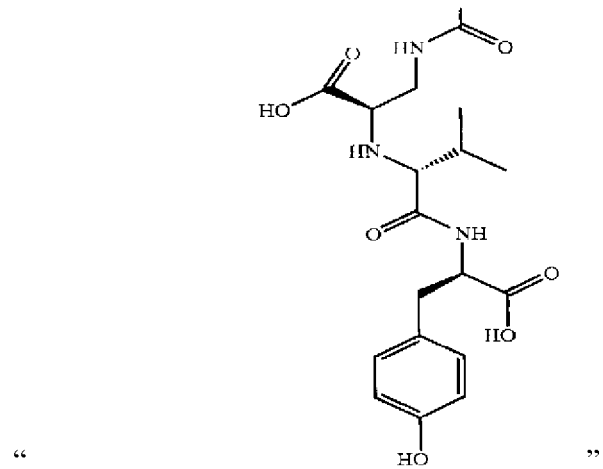
"          "

CERTIFICATE OF CORRECTION (continued)
U.S. Pat. No. 7,786,119 B2

Page 6 of 13

It should read, -- 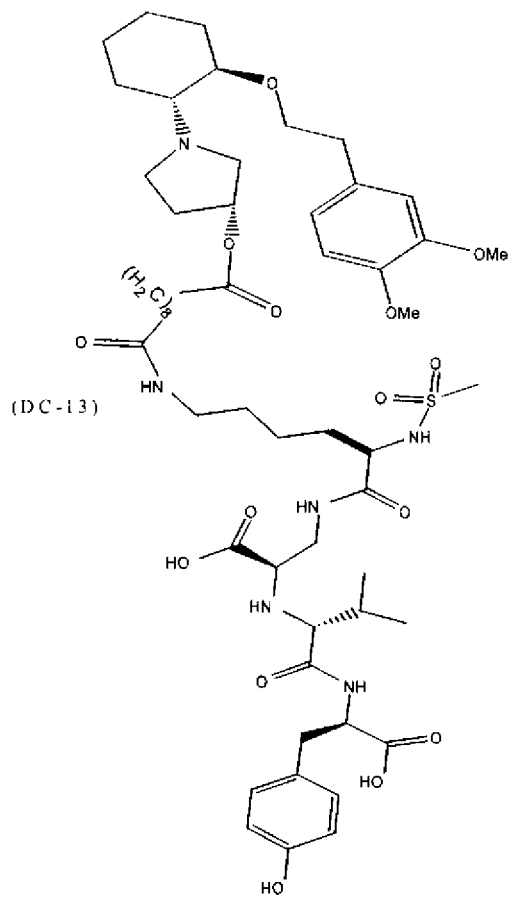 --.

Column 192, Lines 3-44:
Please delete the formula, " 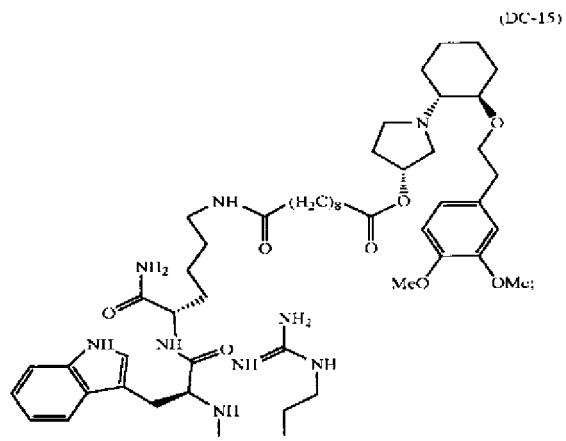 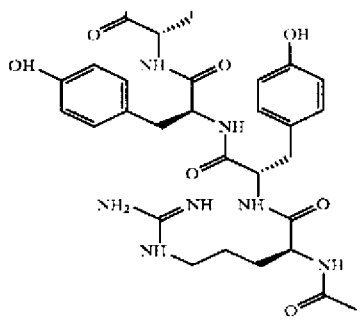 "
It should read, -- 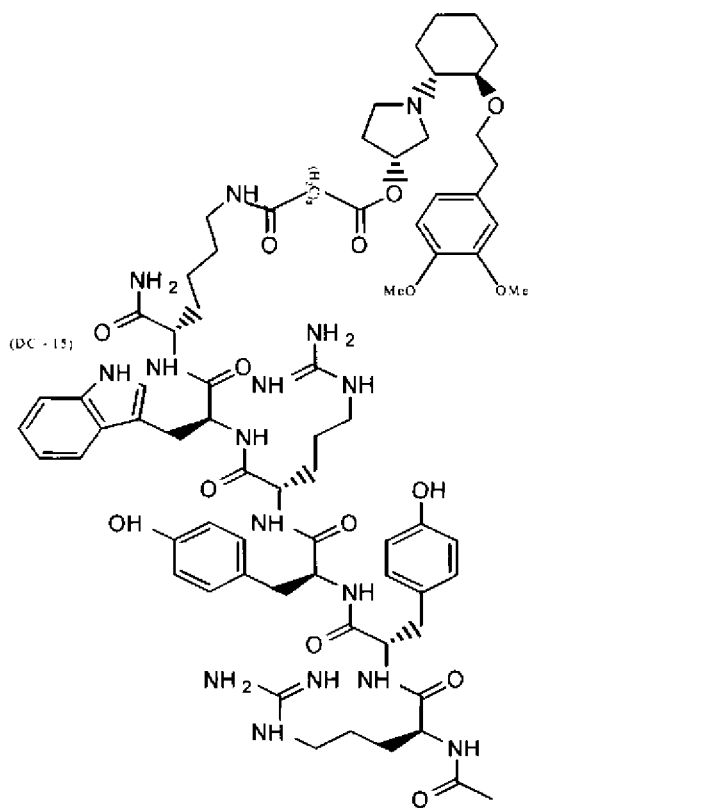 --.

CERTIFICATE OF CORRECTION (continued)
U.S. Pat. No. 7,786,119 B2

Column 192, Lines 45-70:
The formula DC-17,

"formula DC-17:

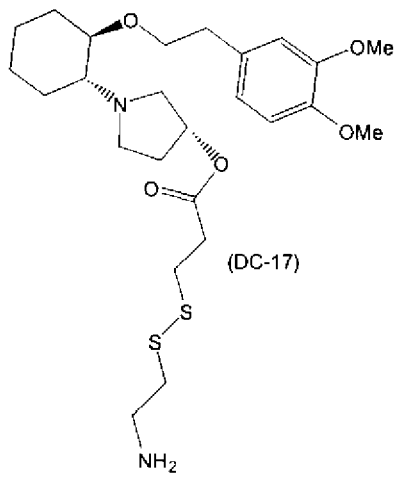

should be removed from the issued patent.

Column 193, Lines 3-40:

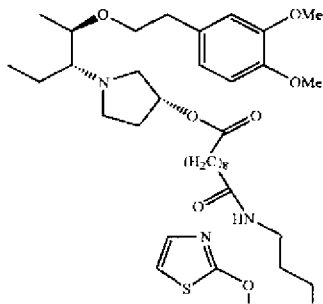

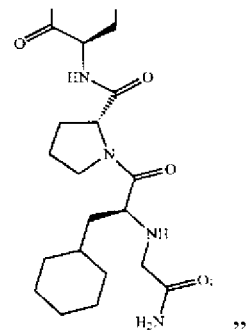

Please delete the formula DC-19, " "

CERTIFICATE OF CORRECTION (continued)
U.S. Pat. No. 7,786,119 B2

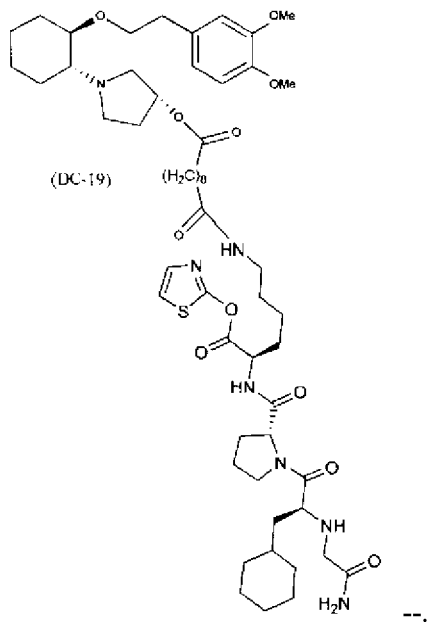

It should read, --  --.

Column 193, Lines 45-66:
The formula DC-21,

"formula DC-21:

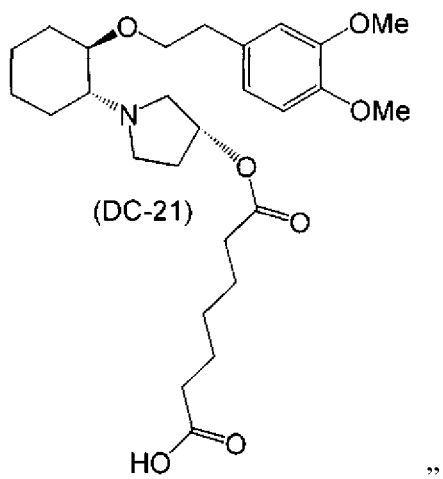

"

should be removed from the issued patent.

Column 195, Lines 51-66:
The formula DC-35,
"formula DC-35:
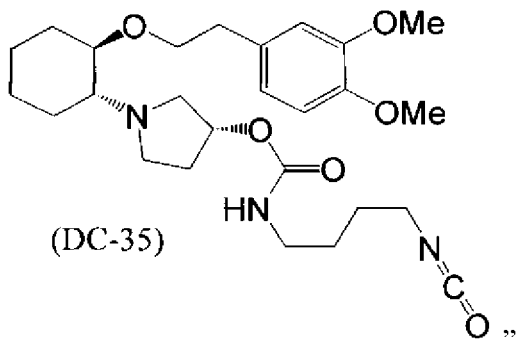
(DC-35)
"
should be removed from the issued patent.
Column 197, Lines 17-28:
The formula DC-47,
"formula DC-47:
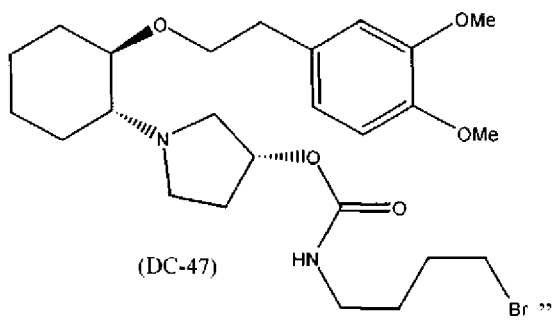
(DC-47)
"
should be removed from the issued patent.
Column 198, Lines 47-65:
Please delete the formula DC-67, "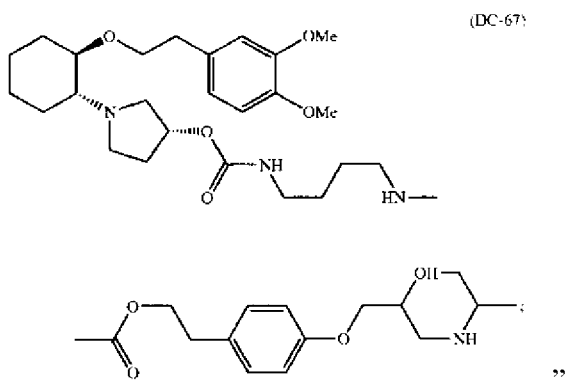"

CERTIFICATE OF CORRECTION (continued)
U.S. Pat. No. 7,786,119 B2

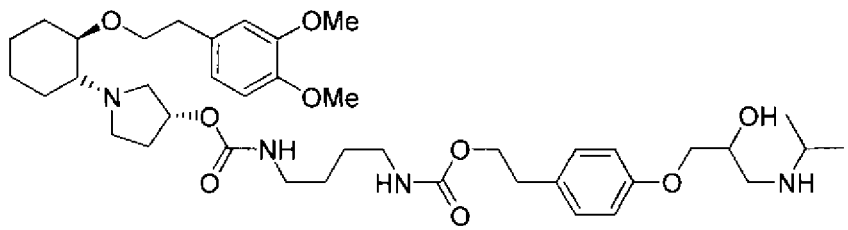

It should read, --                                                                                              --.

DC-67

Column 199, Lines 3-21:
The formula DC-69,

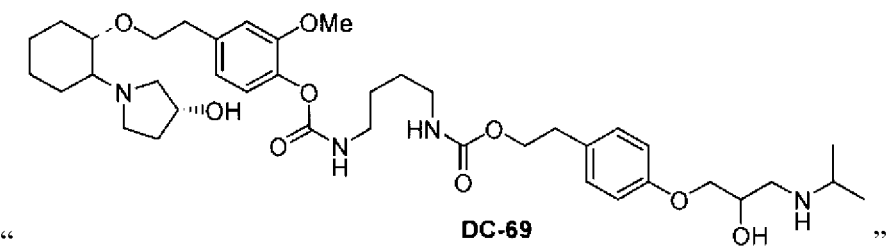

"                                              DC-69                                              "

should be removed from the issued patent.

Column 199, Lines 25-44:
The formulas DC-72 and DC-73,

"formula DC-72, formula DC-73:

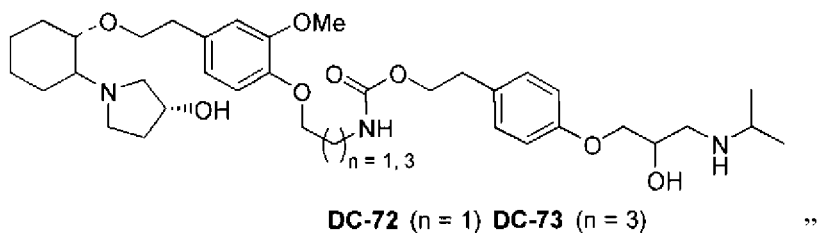

DC-72 (n = 1)  DC-73 (n = 3)                       "

should be removed from the issued patent.

CERTIFICATE OF CORRECTION (continued)
U.S. Pat. No. 7,786,119 B2

Column 201, Lines 3-13:

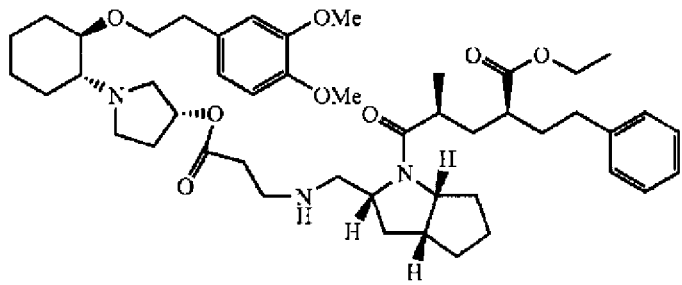

Please delete the formula DC-83, "

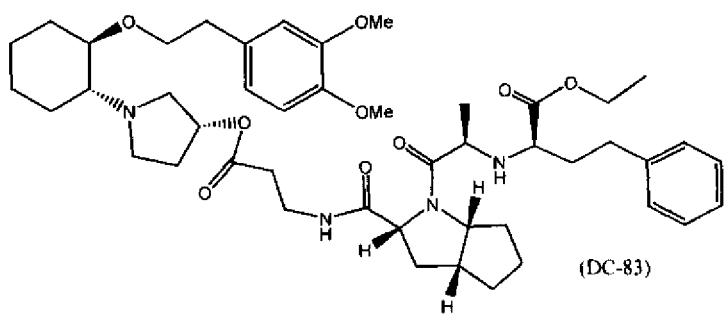

It should read, --                                                                                                --.

Column 201, Lines 14-30:
The formula DC-84,

"formula DC-84:

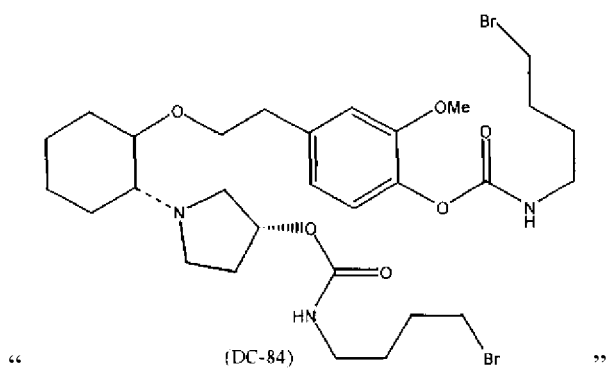

"                                                                                                "

should be removed from the issued patent.

CERTIFICATE OF CORRECTION (continued)
U.S. Pat. No. 7,786,119 B2

Column 201, Lines 31-48:
The formula DC-85,

"formula DC-85:

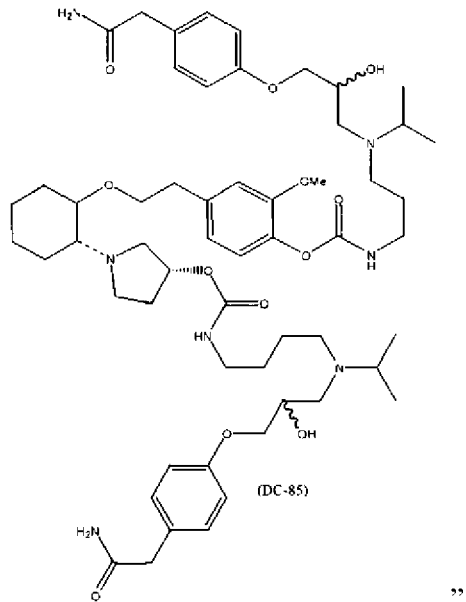

"

should be removed from the issued patent.